(12) United States Patent
Blais et al.

(10) Patent No.: US 10,947,280 B2
(45) Date of Patent: *Mar. 16, 2021

(54) USPA2 PROTEIN CONSTRUCTS AND USES THEREOF

(71) Applicant: GLAXOSMITHKLINE BIOLOGICALS SA, Rixensart (BE)

(72) Inventors: Normand Blais, Laval (CA); Cindy Castado, Rixensart (BE); Patrick Chomez, Rixensart (BE); Marianne Dewerchin, Rixensart (BE)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/914,750

(22) Filed: Jun. 29, 2020

(65) Prior Publication Data

US 2020/0325184 A1 Oct. 15, 2020

Related U.S. Application Data

(60) Continuation of application No. 16/023,164, filed on Jun. 29, 2018, now Pat. No. 10,745,449, which is a division of application No. 15/119,220, filed as application No. PCT/IB2015/051308 on Feb. 20, 2015, now Pat. No. 10,040,832.

(60) Provisional application No. 61/946,937, filed on Mar. 3, 2014, provisional application No. 61/946,932, filed on Mar. 3, 2014, provisional application No. 61/943,909, filed on Feb. 24, 2014.

(51) Int. Cl.

| | |
|---|---|
| *A61K 39/00* | (2006.01) |
| *A61K 39/02* | (2006.01) |
| *A61K 39/102* | (2006.01) |
| *C07K 14/21* | (2006.01) |
| *A61K 39/104* | (2006.01) |
| *C07K 16/12* | (2006.01) |

(52) U.S. Cl.
CPC ............ *C07K 14/212* (2013.01); *A61K 39/00* (2013.01); *A61K 39/102* (2013.01); *A61K 39/1045* (2013.01); *C07K 16/1217* (2013.01); *A61K 2039/55505* (2013.01); *A61K 2039/55566* (2013.01); *A61K 2039/55572* (2013.01); *A61K 2039/55577* (2013.01); *A61K 2039/70* (2013.01)

(58) Field of Classification Search
CPC ....... A61K 39/00; A61K 39/02; A61K 39/102
USPC ...... 424/9.1, 9.2, 184.1, 185.1, 234.1, 251.1
See application file for complete search history.

(56) References Cited

U.S. PATENT DOCUMENTS

| | | | |
|---|---|---|---|
| 8,323,667 B2 | 12/2012 | Forsgren et al. | |
| 10,040,832 B2 * | 8/2018 | Blais | A61P 37/04 |

FOREIGN PATENT DOCUMENTS

| | | |
|---|---|---|
| WO | 98/28333 A2 | 7/1998 |
| WO | 02/083710 A2 | 10/2002 |
| WO | 2007/018463 A2 | 2/2007 |
| WO | 2007/084053 A1 | 7/2007 |

OTHER PUBLICATIONS

Cheng, et al., "Effects of His-tag on cholesterol oxidase expression in *Escherichia coli*." Industrial Microbiology, vol. 42, No. 5, pp. 29-34 (2012)—English Abstract on p. 34.
International Search Report for PCT/IB2015/051308 dated Jul. 6, 2015.
Written Opinion for PCT/IB2015/051308.
Nov. 1, 1999 "SubName: Full=Ubiquitous surface protein A2 {ECO:0000313 EMBL:AGH27427.1}; SubName: Full=UspA2 {ECO:0000313 EMBL:AAD43466.1};" XP002739304, retrieved from EBI accession No. UniProt:Q9XD55 Database accession No. Q9XD55 sequence.
McMichael, et al., "Isolation and Characterization of Two Proteins from Moraxella catarrhalis That Bear a Common Epitope" Infection and Immunity; 1998; pp. 4374-4381; vol. 66, Issue 9.
Svensson, et al. "Histidine tag fusion increases expression levels of active recombinant amelogenin in *Escherichia coli*." Protein Expression and Purification, vol. 48, pp. 134-141 (2006).
Yu-Ching, et al., "Impact of sequence diversity in the Moraxella catarrhalis UspA2/UspA2H head domain on vitronectin binding and antigenic variation"; Microbes & Infection; 2013; pp. 375-387; vol. 15(5).
Parent U.S. Appl. No. 16/023,164, filed Jun. 29, 2018, Publication No. 2008-0354996, Dec. 13, 2018.
U.S. Appl. No. 15/119,220, filed Aug. 16, 2016, Publication No. 2017-0008932, Jan. 12, 2017.
U.S. Appl. No. 12/063,408, filed Feb. 8, 2008, U.S. Pat. No. 8,092,811, Publication No. 2010-0062027, Mar. 10, 2010.
U.S. Appl. No. 13/314,727, filed Dec. 8, 2011, U.S. Pat. No. 8,323,667, Publication No. 2012-0148614, Jun. 14, 2012.
U.S. Appl. No. 13/666,941, filed Nov. 1, 2012, U.S. Pat. No. 8,895,030, Publication No. 2013-0129763, May 23, 2013.
U.S. Appl. No. 14/110,857, filed Oct. 9, 2013, U.S. Pat. No. 8,945,577, Publication No. 2014-0056934, Feb. 27, 2014.
U.S. Appl. No. 14/508,033, filed Oct. 7, 2014, U.S. Pat. No. 9,255,127, Publication No. 2015-0140026, May 21, 2015.

(Continued)

Primary Examiner — Rodney P Swartz
(74) Attorney, Agent, or Firm — Barbara J. Carter

(57) ABSTRACT

The present invention relates to compositions comprising *Moraxella catarrhalis* (*M. catarrhalis*) Ubiquitous surface protein A2 (UspA2). More particularly, the present application relates to UspA2 protein constructs and immunogenic compositions comprising the constructs, vaccines comprising such immunogenic compositions and therapeutic uses of the same. The invention further relates to compositions comprising UspA2 in combination with at least one antigen from *Haemophilus influenzae*, immunogenic compositions comprising the antigens, vaccines comprising such immunogenic compositions and therapeutic uses of the same.

12 Claims, 37 Drawing Sheets

Specification includes a Sequence Listing.

(56) References Cited

OTHER PUBLICATIONS

U.S. Appl. No. 14/571,546, filed Dec 16, 2014, U.S. Pat. No. 9,296,794, Publication No. 2015-0166613, Jun. 18, 2015.
U.S. Appl. No. 14/571,807, filed Dec 16, 2014, U.S. Pat. No. 9,409,957, Publication No. 2015-0175670, Jun. 25, 2015.
U.S. Appl. No. 14/986,104, filed Dec. 31, 2015 U.S. Pat. No. 9,657,067 Publication No. 2016-0318979, Nov. 3, 2016.
U.S. Appl. No. 15/046,908, filed Feb. 18, 2016, Publication No. 2016-0250313, Sep. 1, 2016.
U.S. Appl. No. 15/197,952, filed Jun. 30, 2016, Publication No. 2017-0029472, Feb. 2, 2017.
U.S. Appl. No. 15/486,513, filed Apr. 13, 2017, Publication No. 2017-0281746, Oct. 5, 2017.
U.S. Appl. No. 15/861,789, filed Jan. 4, 2018.

\* cited by examiner

MOLECULAR WEIGHT DISTRIBUTION OF PURIFIED MC-005 DETERMINED BY SEDIMENTATION VELOCITY ANALYTICAL ULTRACENTRIFUGATION. THE MAJORITY OF PROTEIN IS FOUND AS A TRIMER, WITH A SMALL PROPORTION OF A HIGHER MOLECULAR WEIGHT OLIGMER THAT MAY CORRESPOND TO DIMER OF TRIMER. MW = MOLECULAR WEIGHT. kDa = KILODALTON.

FIG. 6 MOLECULAR WEIGHT DISTRIBUTION OF PURIFIED MC-001 DETERMINED BY SEDIMENTATION VELOCITY ANALYTICAL ULTRACENTRIFUGATION. THE SAMPLE PRESENTS MULTIPLE SPECIES AND IS HIGHLY POLYDISPERSE. THE SEDIMENTATION COEFFICIENT OF THE MAJOR SPECIES DETECTED DOESN'T CORRESPOND TO THE ONE OF THE TRIMERS NORMALLY DETECTED IN THE OTHER LOTS.

EFFECT OF THE TETRAVALENT PD/ PEPIIA/ UspA2/ AS01E VACCINE FORMULATION ON MOUSE LUNGS PRE-SENSITIZED WITH HEAT INACTIVATED M. cat. - PERIVASCULARITIS AND PERIBRONCHI

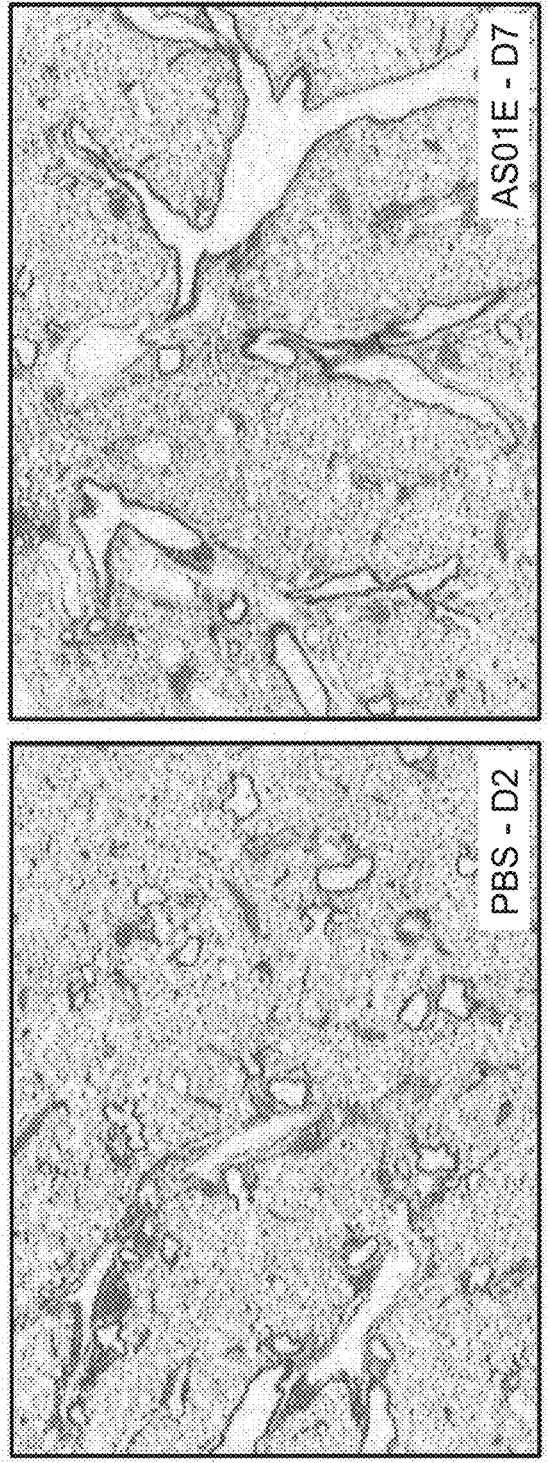
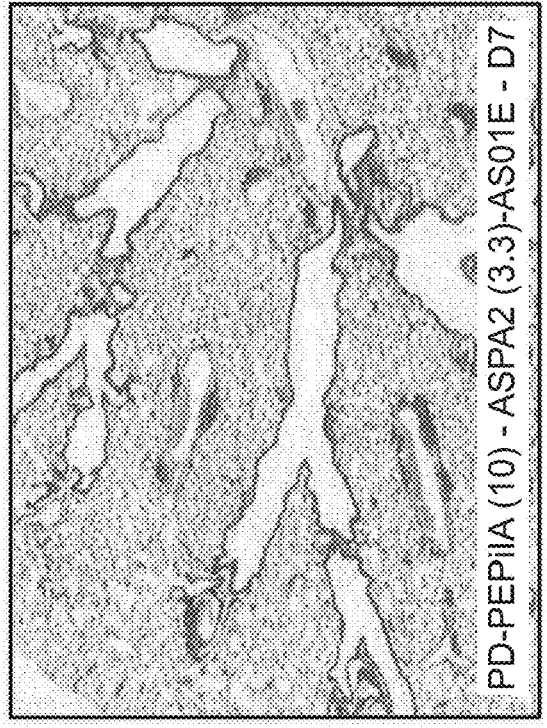
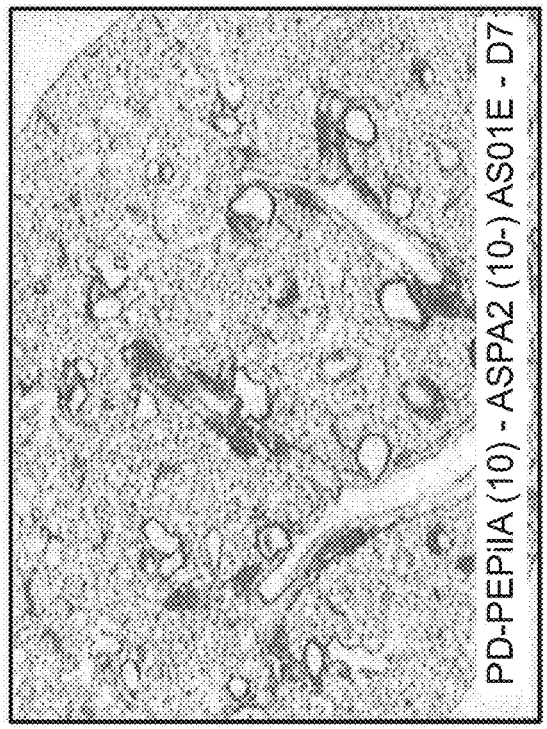
FIG. 27
EFFECT OF THE TETRAVALENT PD/ PEPIIA/ UspA2/ AS01E VACCINE FORMULATION ON MOUSE LUNGS PRE-SENSITIZED WITH HEAT INACTIVATED M. cat. - DAY 7 POST-I EFFECT OF THE TETRAVALENT PD/ PEPIIA/ UspA2/ AS01E VACCINE FORMULATION ON MOUSE LUNGS PRE-SENSITIZED WITH HEAT INACTIVATED M. cat. - DAY 14 POST-IMMUNIZATION
FIG. 28
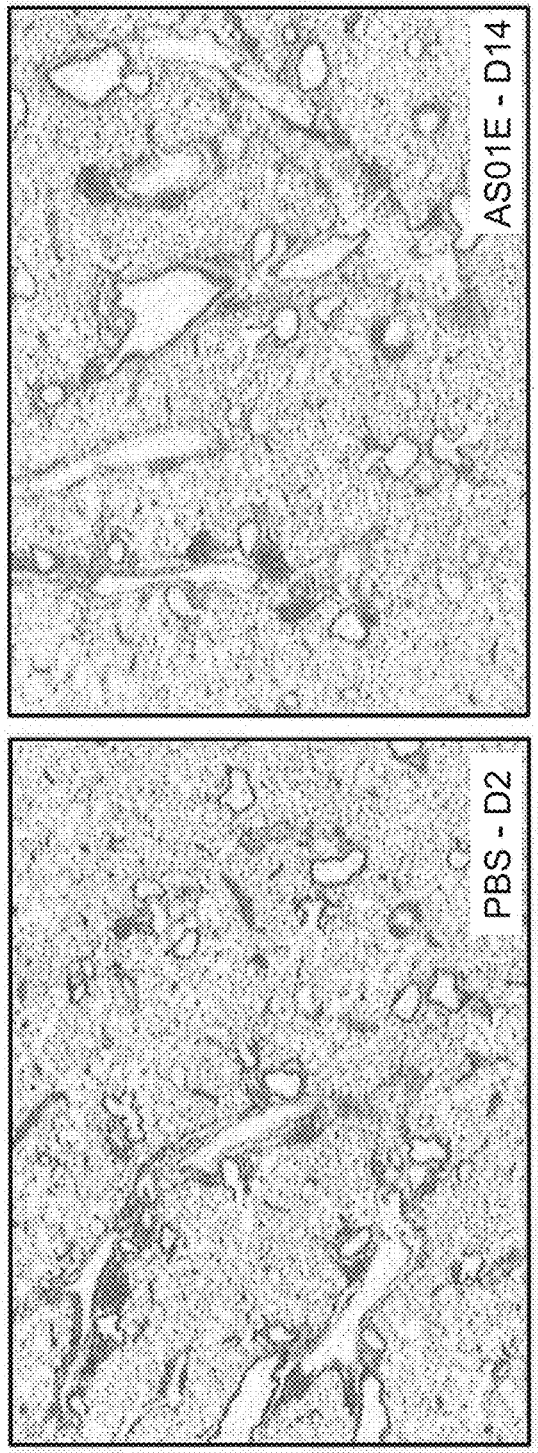

FIG. 29

EFFECT OF THE TETRAVALENT PD/ PEPIA/ PEplIA/ UspA2/ AS01E VACCINE FORMULATION ON MOUSE LUNGS PRE-SENSITIZED WITH HEAT INACTIVATED M. cat. - DETAILED RESULTS

| | AN. # | PERIVASCULITIS/PERIBRONCHIOLITIS | | | | |
|---|---|---|---|---|---|---|
| | | 1 | 2 | 3 | 4 | 5 |
| D2 | PBS | 3F<br>L+M | 3D<br>L+M | 3D<br>L+M | 3D<br>L+M | A |
| | PD-PE-PIIA-USPA2 (10) | 2D<br>L+M | 2-3D<br>L+M | 3D<br>L+M | 2-3D<br>L+M | 3D<br>L+M |
| | PD-PE-PIIA-USPA2 (3.3) | 2-3D<br>L+M | 2-3D<br>L+M | 2-3D<br>L+M | 3D<br>L+M | 3D<br>L+M |
| | AS01E-3 | 3D<br>L+M | 3D<br>L+M | 3D<br>L+M | 3D<br>L+M | 3D<br>L+M |
| D7 | PD-PE-PIIA-USPA2 (10) | 2-3D<br>L+M | 2-3D<br>L+M | 2-3D<br>L+M | 2-3D<br>L+M | 2-3D<br>L+M |
| | PD-PE-PIIA-USPA2 (3.3) | 3D<br>L+M | 3D<br>L+M | 3D<br>L+M | 2-3D<br>L+M | 2-3D<br>L+M |
| | AS01E-3 | 3D<br>L+M | 2-3D<br>L+M | 2-3D<br>L+M | 2-3D<br>L+M | 2-3D<br>L+M |
| D14 | PD-PE-PIIA-USPA2 (10) | 2D<br>L+M | 2D<br>L+M | 2-3D<br>L+M | 2-3D<br>L+M | A |
| | PD-PE-PIIA-USPA2 (3.3) | 2-3D<br>L+M | 2-3D<br>L+M | 2-3D<br>L+M | 2-3D<br>L+M | A |
| | AS01E-3 | 2D<br>L+M | 2-3D<br>L+M | 2-3D<br>L+M | 2-3D<br>L+M | 2D<br>L+M |

LEGEND:
- THE FIRST LINE IN EACH BOX GIVES INFORMATION ABOUT THE INFLAMMATION SEVERITY: A = ABSENT; 1 = MINIMAL; 2 = SLIGHT; 3 = MODERATE; 4 = MARKED; 5 = SEVERE, AND THE ALTERATION DISTRIBUTION: F = FOCAL; M = MULTIFOCAL; D = DIFFUSE.
- THE SECOND LINE REFERS TO THE NATURE OF THE CELLS OBSERVED: L = LYMPHOCYTES; M = MACROPHAGES.

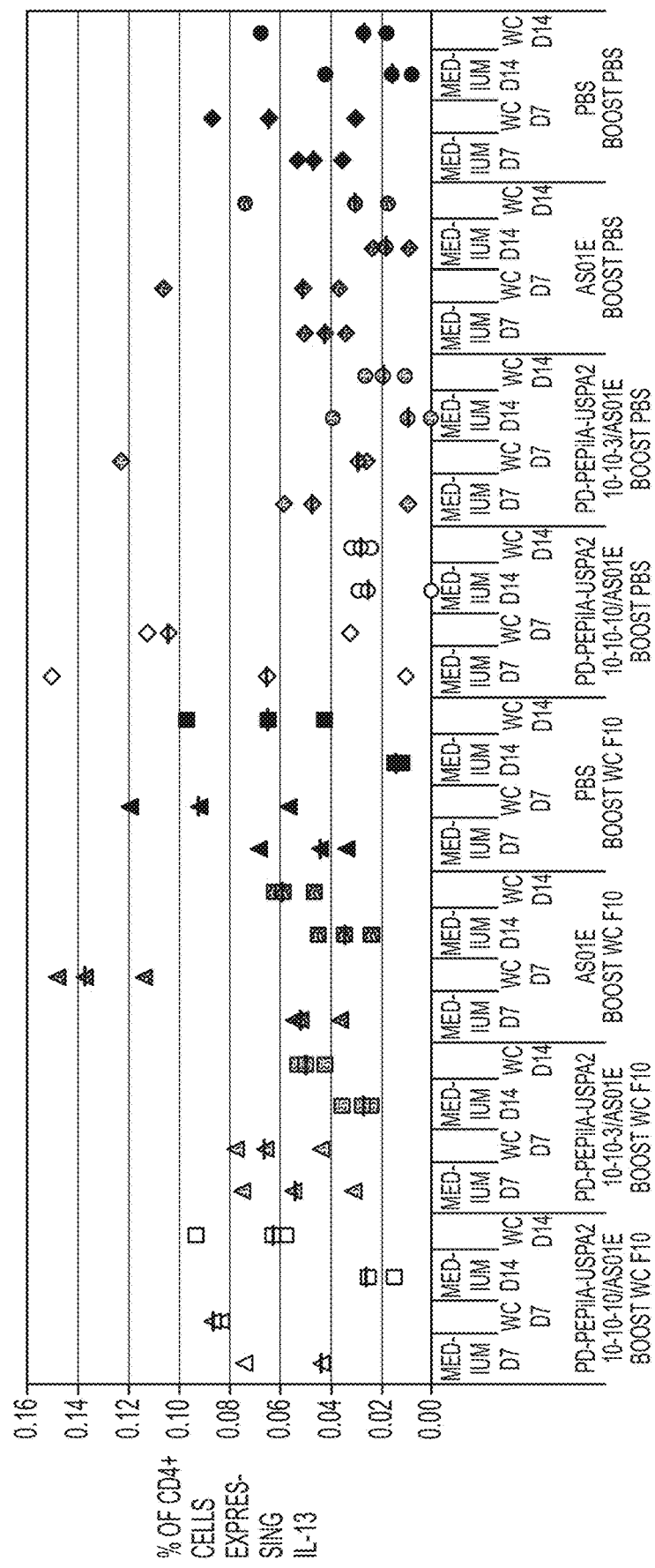

USPA2 PROTEIN CONSTRUCTS AND USES THEREOF

CROSS-REFERENCE TO RELATED APPLICATIONS

This application is a continuation application of U.S. patent application Ser. No. 16/023,164 filed Jun. 29, 2018 (allowed), which is a divisional application of U.S. patent application Ser. No. 15/119,220 filed Aug. 16, 2016, (now U.S. Pat. No. 10,040,832, issued Aug. 7, 2018), which was filed pursuant to 35 U.S.C. § 371 as a United States National Phase Application of International Application No. PCT/IB2015/051308 filed Feb. 20, 2015 which claims priority from U.S. Application Ser. No. 61/946,932 filed Mar. 3, 3014, U.S. Application Ser. No. 61/946,937 filed Mar. 3, 2014, and U.S. Application Ser. No. 61/943,909 filed Feb. 24, 2014, each of which is hereby incorporated by reference in their entirety.

SEQUENCE LISTING

A sequence listing filed herewith, entitled "VR65032C1_US_SEQLIST", prepared Jun. 29, 2020, 344 KB in size, is hereby incorporated by reference herein.

FIELD OF THE INVENTION

The present invention relates to compositions comprising *Moraxella catarrhalis* (*M. catarrhalis, M. cat.*) Ubiquitous surface protein A2 (UspA2). More particularly, the present application relates to UspA2 protein constructs and immunogenic compositions comprising the constructs, vaccines comprising such immunogenic compositions and therapeutic uses of the same.

BACKGROUND OF THE INVENTION

Ubiquitous surface protein A2 (UspA2) is a trimeric autotransporter that appears as a lollipop-shared structure in electron micrographs (Hoiczyk et al. EMBO J. 19: 5989-5999 (2000)). It is composed of a N-terminal head, followed by a stalk which ends by an amphipathic helix and a C-terminal membrane domain. (Hoiczyk et al. EMBO J. 19: 5989-5999 (2000)). UspA2 contains a very well conserved domain (Aebi et al., Infection & Immunity 65(11) 4367-4377 (1997)), which is recognized by a monoclonal antibody that was shown protective upon passive transfer in a mouse *Moraxella catarrhalis* challenge model (Helminnen et al. J Infect Dis. 170(4): 867-72 (1994)).

UspA2 has been shown to interact with host structures and extracellular matrix proteins like fibronectin (Tan et al., J Infect Dis. 192(6): 1029-38 (2005)) and laminin (Tan et al., J Infect Dis. 194(4): 493-7 (2006)), suggesting it can play a role at an early stage of *Moraxella catarrhalis* infection.

UspA2 also seems to be involved in the ability of *Moraxella catarrhalis* to resist the bactericidal activity of normal human serum. (Attia A S et al. Infect Immun 73(4): 2400-2410 (2005)). It (i) binds the complement inhibitor C4 bp, enabling *Moraxella catarrhalis* to inhibit the classical complement system, (ii) prevents activation of the alternative complement pathway by absorbing C3 from serum and (iii) interferes with the terminal stages of the complement system, the Membrane Attack Complex (MAC), by binding the complement regulator protein vitronectin. (de Vries et al., Microbiol Mol Biol Rev. 73(3): 389-406 (2009)).

*Moraxella catarrhalis* is an important and common respiratory pathogen that has been associated with increased risk of exacerbations in chronic obstructive pulmonary disease (COPD) in adults. (Sateesh et al., Journal of Chronic Obstructive Pulmonary Disease 3:109-115 (2006)).

A need for vaccines for *Moraxella catarrhalis* exists.

BRIEF SUMMARY OF THE INVENTION

As a first aspect, the present invention provides the proteins of formula (I).

$$A\text{-}(R_1)_m\text{-}(B)_n \qquad \text{(formula I)}$$

wherein:
A is UspA2 from *Moraxella catarrhalis* or an immunogenic fragment thereof;
$R_1$ is an amino acid;
m is 0, 1 or 2;
B is histidine; and
n is 0, 1, 2, 3, 4, 5 or 6.

As a second aspect, the present invention provides immunogenic compositions comprising proteins of formula (I) and proteins of the invention. The composition may further comprise a pharmaceutically acceptable adjuvant. The composition may comprise an excipient.

In a third aspect, the present invention provides a method for the treatment or prevention of a condition or disease caused wholly or in part by *Moraxella catarrhalis*. The method comprises administering to a subject in need thereof a therapeutically effective amount of a protein of formula (I) or a protein of the invention.

In a fourth aspect, the present invention provides a method for the treatment or prevention of otitis media. The method comprises administering to a subject in need thereof a therapeutically effective amount of a protein of formula (I) or a protein of the invention.

In a fifth aspect, the present invention provides a method for the treatment or prevention of exacerbations in chronic obstructive pulmonary disease. The method comprises administering to a subject in need thereof a therapeutically effective amount of a protein of formula (I) or a protein of the invention.

In a sixth aspect, the present invention provides a method for the treatment or prevention of pneumonia. The method comprises administering to a subject in need thereof a therapeutically effective amount of a protein of formula (I) or a protein of the invention.

In a seventh aspect, the present invention provides a pharmaceutical composition comprising a protein of formula (I) or a protein of the invention for use in the treatment or prevention of a condition or disease caused wholly or in part by *Moraxella catarrhalis*. Pharmaceutical compositions may further comprise a pharmaceutically acceptable adjuvant.

In an eighth aspect, the present invention provides nucleic acids encoding the proteins of the invention.

In a ninth aspect, the present invention provides a process of producing nucleic acids of the invention.

In a tenth aspect, the present invention provides a composition comprising at least one antigen from *Moraxella catarrhalis* and at least one antigen from *Haemophilus influenzae*. The composition may further comprise a pharmaceutically acceptable adjuvant. The composition may comprise an excipient.

In an additional aspect, the present invention provides a method for the treatment or prevention of a condition or disease caused wholly or in part by *Moraxella catarrhalis* and/or *Haemophilus influenzae*. The method comprises administering to a subject in need thereof a therapeutically effective amount of a protein of formula (I) or a protein of the invention.

In a further aspect, the present invention provides a method for the treatment or prevention of exacerbations in chronic obstructive pulmonary disease. The method comprises administering to a subject in need thereof a therapeutically effective amount of a protein of formula (I) or a protein of the invention and a therapeutically effective amount of at least one antigen from *Haemophilus influenzae*.

The present invention also provides a pharmaceutical composition comprising a protein of formula (I) or a protein of the invention for use in the treatment or prevention of a condition or disease caused wholly or in part by *Moraxella catarrhalis* in combination with at least one antigen from *Haemophilus influenzae*. Pharmaceutical compositions may further comprise a pharmaceutically acceptable adjuvant.

Further aspects of the present invention are described in the detailed description of particular embodiments, examples and claims which follow.

BRIEF DESCRIPTION OF THE DRAWINGS

FIG. 27: Effect of the tetravalent PD/PEPilA/UspA2/$AS01_E$ vaccine formulation on mouse lungs pre-sensitized with heat inactivated *M. cat.*—Day 7 post-immunization.

FIG. 28: Effect of the tetravalent PD/PEPilA/UspA2/$AS01_E$ vaccine formulation on mouse lungs pre-sensitized with heat inactivated *M. cat.*—Day 14 post-immunization.

FIG. 29: Effect of the tetravalent PD/PEPilA/UspA2/$AS01_E$ vaccine formulation on mouse lungs pre-sensitized with heat inactivated *M. cat.*—Detailed results.

FIG. 37: Post-challenge lung CD4 T cell responses upon *M. cat*. WC re-stimulation. Lung CD4 cells expressing IL13. Restimulated with heat-inactivated *M. cat*. whole cells (WC) or medium.

DETAILED DESCRIPTION OF THE INVENTION

Figure 1:
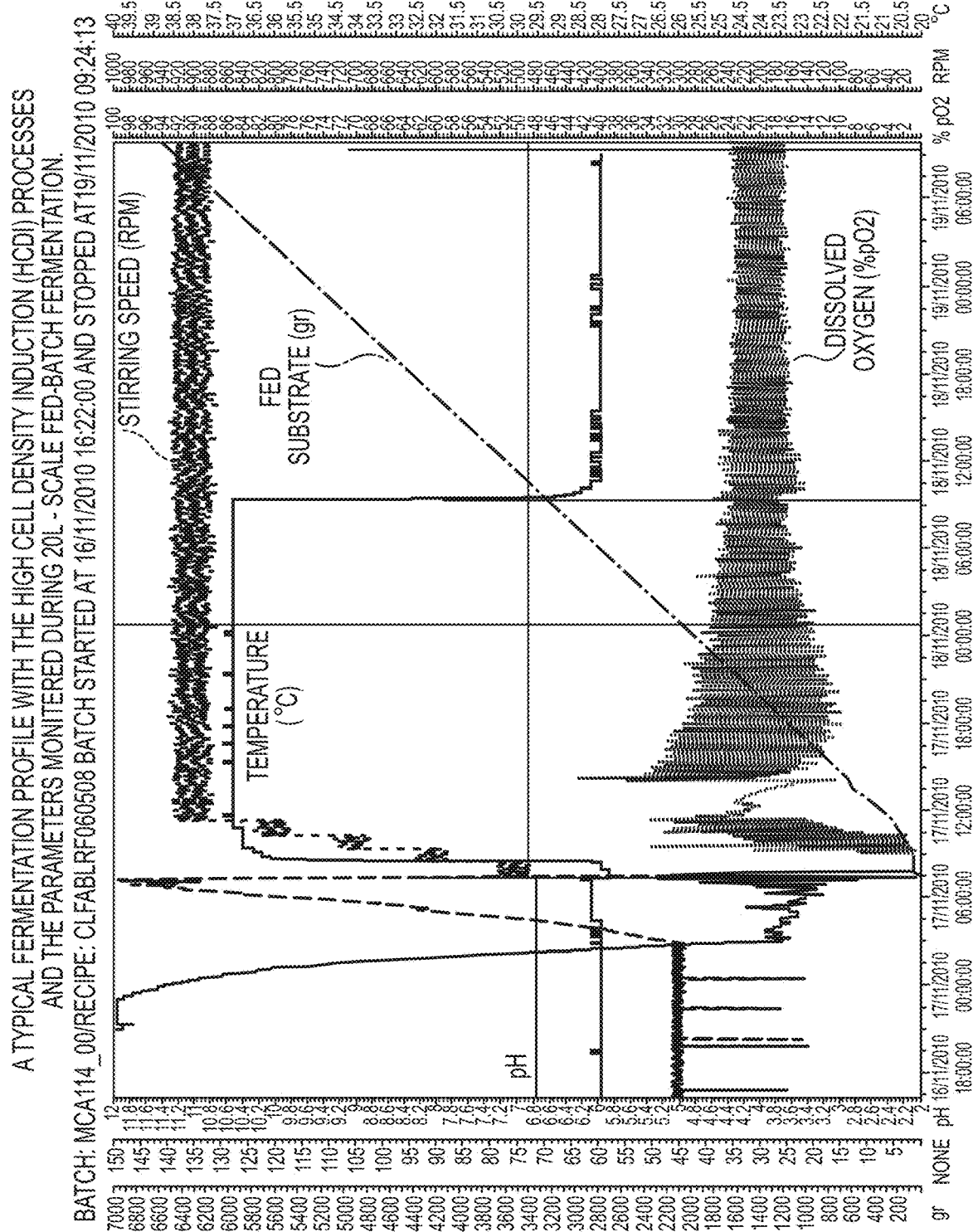
FIG. 1: A typical fermentation profile with the High Cell Density Induction (HCDI) processes and the parameters monitored during 20 L-scale fed-batch fermentation.

Unless otherwise explained or defined herein, all technical and scientific terms used herein have the same meaning as commonly understood by one of ordinary skill in the art to which this disclosure belongs. For example, definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen may be approximate. Thus, where a concentration is indicated to be (for example) approximately 200 μg, it is intended that the concentration includes values slightly more or slightly less than ("about" or "~") 200 μg.

Although methods and materials similar or equivalent to those described herein can be used in the practice or testing of this disclosure, suitable methods and materials are described below.

The term "comprises" means "includes". Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of terms are provided. Additional terms and explanations are provided in the context of this disclosure.

A "subject" as used herein is a mammal, including humans, non-human primates, and non-primate mammals such as members of the rodent genus (including but not limited to mice and rats) and members of the order Lagomorpha (including but not limited to rabbits).

As used herein "UspA2" means Ubiquitous surface protein A2 from *Moraxella catarrhalis*. UspA2 may consist of or comprise the amino acid sequence of SEQ ID NO: 1 from ATCC 25238.

(SEQ ID NO: 1)
MKTMKLLPLKIAVTSAMIIGLGAASTANAQAKNDITLEDLPYLIKKIDQ

NELEADIGDITALEKYLALSQYGNILALEELNKALEELDEDVGWNQNDI

ANLEDDVETLTKNQNALAEQGEAIKEDLQGLADFVEGQEGKILQNETSI

KKNTQRNLVNGFEIEKNKDAIAKNNESIEDLYDFGHEVAESIGEIHAHN

EAQNETLKGLITNSIENTNNITKNKADIQALENNVVEELFNLSGRLIDQ

KADIDNNINNIYELAQQQDQHSSDIKTLKKNVEEGLLELSGHLIDQKTD

IAQNQANIQDLATYNELQDQYAQKQTEAIDALNKASSENTQNIEDLAAY

NELQDAYAKQQTEAIDALNKASSENTQNIEDLAAYNELQDAYAKQQTEA

IDALNKASSENTQNIAKNQADIANNINNIYELAQQQDQHSSDIKTLAKA

SAANTDRIAKNKADADASFETLTKNQNTLIEKDKEHDKLITANKTAIDA

NKASADTKFAATADAITKNGNAITKNAKSITDLGTKVDGFDSRVTALDT

KVNAFDGRITALDSKVENGMAAQAALSGLFQPYSVGKFNATAALGGYGS

KSAVAIGAGYRVNPNLAFKAGAAINTSGNKKGSYNIGVNYEF as well as sequences with at least or exactly 63%, 66%, 70%, 72%, 74%, 75%, 77%, 80%, 84%, 85%, 90%, 95%, 96%, 97%, 98%, 99% or 100% identity, over the entire length, to SEQ ID NO: 1. Comparison of 38 sequences of UspA2 from *Moraxella catarrhalis* (Table 1, SEQ ID NO: 1-SEQ ID NO: 38) demonstrated approximately 63% to approximately 100% identity to UspA2 as set forth in SEQ ID NO. 1.

UspA2 as described in SEQ ID NO: 1 contains a signal peptide (for example, amino acids 1 to 29 of SEQ ID NO: 1), a laminin binding domain (for example, amino acids 30 to 177 of SEQ ID NO: 1), a fibronectin binding domain (for example, amino acids 165 to 318 of SEQ ID NO: 1) (Tan et al. JID 192: 1029-38 (2005)), a C3 binding domain (for example, amino acids 30 to 539 of SEQ ID NO: 1 (WO2007/018463), or a fragment of amino acids 30 to 539 of SEQ ID NO: 1, for example, amino acids 165 to 318 of SEQ ID NO: 1 (Hallström T et al. *J. Immunol*. 186: 3120-3129 (2011)), an amphipathic helix (for example, amino acids 519 to 564 of SEQ ID NO: 1 or amino acids 520-559 of SEQ ID NO:1, identified using different prediction methods) and a C terminal anchor domain (for example, amino acids 576 to 630 amino acids of SEQ ID NO: 1 (Brooks et al., *Infection & Immunity*, 76(11), 5330-5340 (2008)).

UspA2 amino acid differences have been described for various *Moraxella catarrhalis* species. See for example, J Bacteriology 181(13):4026-34 (1999), *Infection and Immunity* 76(11):5330-40 (2008) and *PLoS One* 7(9):e45452 (2012).

UspA2 may consist of or comprise an amino acid sequence that differs from SEQ ID NO. 1 at any one or more amino acid selected from the group consisting of: AA (amino acid) 30 to 298, AA 299 to 302, AA 303 to 333, AA 334 to 339, AA 349, AA 352 to 354, AA 368 to 403, AA 441, AA 451 to 471, AA 472, AA474 to 483, AA 487, AA 490, AA 493, AA 529, AA 532 or AA 543. UspA2 may consist of or comprise an amino acid sequence that differs from SEQ ID NO: 1 in that it contains at least one amino acid insertion in comparison to SEQ ID NO. 1. UspA2 may consists of or comprise an amino acid sequence that differs from SEQ ID NO. 1 at any one of the amino acid differences in SEQ ID NO: 2 through SEQ ID NO: 38. For example, SEQ ID NO. 1 may contain K instead of Q at amino acid 70, Q instead of G at amino acid 135 and/or D instead of N at amino acid 216.

TABLE 1

UspA2 amino acid sequences from 38 strains of *Moraxalla catarrhalis* (SEQ ID NO: 1 - SEQ ID NO: 38).

| Strain | UspA2 sequences |
|---|---|
| ATCC 25238 (SEQ ID NO: 1) | MKTMKLLPLKIAVISAMIIGLGAASTANAQAKNDITLEDLPYLIKKIDQNELEADIGDITALEK YLALSQYGNILALEELNKALEELDEDVGWNQNDIANLEDDVETLIKNQNALAEQGEAIKEDLQG LADFVEGQEGKILQNETSIKKNIQRNLVNGFEIEKNKDAIAKNNESIEDLYDFGHEVAESIGEI HAHNEAQNETLKGLITNSIENTNNITKNKADIQALENNVVEELFNLSGRLIDQKADIDNNINNI YELAQQQDQHSSDIKTLKKNVEEGLLELSGHLIDQKTDIAQNQANIQDLATYNELQDQYAQKQT EAIDALNKASSENTQNIEDLAAYNELQDAYAKQQTEAIDALNKASSENTQNIEDLAAYNELQDA YAKQQTEAIDALNKASSENTQNIAKNQADIANNINNIYELAQQQDQHSSDIKTLAKASAANTDR IAKNKADADASFETLTKNQNTLIEKDKEHDKLITANKTAIDANKASADTKFAATADAITKNGNA ITKNAKSITDLGTKVDGFDSRVTALDTKVNAFDGRITALDSKVENGMAAQAALSGLFQPYSVGK FNATAALGGYGSKSAVAIGAGYRVNPNLAFKAGAAINTSGNKKGSYNIGVNYEF (630 aa) |
| American 2933 (SEQ ID NO: 2) | MKTMKLLPLKIAVISAMIIGLGAASTANAQSRDRSLEDIQDSISKLVQDDINTLKQDQQKMNKY LLLNQLANTLITDELNNNVIKNTNSIEALGDEIGWLENDIADLEEGVEELTKNQNTLIEKDEEH DRLIAQNQADIQTLENNVVEELFNLSGRLIDQEADIAKNNASIEELYDFDNEVAERIGEIHAYT EEVNKTLENLITNSVKNTDNIDKNKADIDNNINHIYELAQQQDQHSSDIKTLKNNVEEGLLELS GHLIDQKADLTKDIKALESNVEEGLLDLSGRLLDQKADLTKDIKALESNVEEGLLDLSGRLLDQ KADIAQNQTDIQDLAAYNELQDQYAQKQTEAIDALNKASSENTQNIEDLAAYNELQDAYAKQQT EAIDALNKASSENTQNIAKNQADIANNINNIYELAQQQDQHSSDIKTLAKASAANTNRIATAEL GIAENKKDAQIAKAQANANKTAIDENKASADTKFAATADAITKNGNAITKNAKSITDLGTKVDG FDGRVTALDTKVNAFDGRITALDSKVENGMAAQAALSGLFQPYSVGKFNATAALGGYGSKSAVA IGAGYRVNPNLAFKAGAAINTSGNKKGSYNIGVNYEF (613 aa) |
| American 2912 (SEQ ID NO: 3) | MKTMKLLPLKIAVTSALIIGLGAASTANAQQQLQTETFLPNFLSNDNYDLTDPFYHNMILGDTA LLDKQDGSQPQLKFYSNDKDSVPDSLLFSKLLHEQQLNGFKKGDTIIPLDKDGKPVYQVDYKLD GKGKKQKRRQVYSVTTKTATDDDVNSAYSRGILGKVDDLDDEMNFLNHDITSLYDVTANQQDAI KDLKKGVKGLNKELKELDKEVGVLSRDIGSLNDDVAQNNESIEDLYDFSQEVADSIGEIHAHNK AQNETLQDLITNSVENTNNITKNKADIQALENNVVEELFNLSGRLIDQKADLTKDIKTLESNVE EGLLELSGHLIDQKADIAKNQADIAQNQANIQDLAAYNELQDAYAKQQTEAIDALNKASSENTQ NIEDLAAYNELQDAYAKQQTEAIDALNKASSENTQNIAKNQADIANNINNIYELAQQQDQHSSD IKTLAKASAANTDRIAKNKADADASFETLIKNQNTLIEKDKEHDKLITANKTAIDENKASADTK FAATADAITKNGNAITKNAKSITDLGTKVDGFDSRVTALDTKVNAFDGRITALDSKVENGMAAQ AALSGLFQPYSVGKFNATAALGGYGSKSAVAIGAGYRVNPNLAFKAGAAINTSGNKKGSYNIGV NYEF (644 aa) |
| American 2908 (SEQ ID NO: 4) | MKTMKLLPLKIAVTSALIVGLGAASTANAQLVERFFPNIFLDKPLAKQHYHNVVVGDISIVSDL QSNSDQLKFYSDDEGLVPDSLLFNKMLHEQLLNGFKEGDTIIPLDENGKPVYKVDYKLDGKEPR KVYSVTTKIATAEDVATSSYANGIQKDIDDLYDFDHQVTERLTQHGKTIYRNGERILANEESVQ YLNKEVQNNIEHIYELAQQQDQHSSDIKTLESNVEKGLLELSGHLIDQKADLTKDIKTLESNVE EGLLDLSGRLIDQKADLTKDIKTLESNVEEGLLDLSGRLIDQKADIAQNQANIQDLAAYNELQD QYAQKQTEAIDALNKASSENTQNIEDLAAYNELQDAYAKQQTEAIDALNKASSENTQNIAKNQA DIANNINNIYELAQQQDQHSSDIKTLAKASAANTNRIATAELGIAENKKDAQIAKAQANANKTA IDENKASADTKFAATADAITKNGNAITKNAKSITDLGTKVDGFDSRVTALDTKVNAFDGRITAL DSKVENGMAAQAALSGLFQPYSVGKFNATAALGGYGSKSAVAIGAGYRVNPNLAFKAGAAINTS GNKKGSYNIGVNYEF (591 aa) |
| Finnish 307 (SEQ ID NO: 5) | MKTMKLLPLKIAVTSAMIIGLGAASTANAQQQQQQQQQQQSRTEIFFPNIFFNENHDELDDAYH NIILGDTALLDKQDGSQPQLKFYSNDKDSVPDSLLFSKLLHEQQLNGFKKGDTIIPLDKDGKPV YQVDYKLDGKGKKQKRRQVYSVTTKTATDDDVNSAYSRGILGKVDDLDDEMNFLNHDITSLYDV TANQQDAIKGLKKGVKGLNKELKELDKEVGVLSRDIGSLNDDVAQNNESIEDLYDFSQEVADSI GEIHAHNKAQNETLQDLITNSVENTNNITKNKADIQALENNVVEELFNLSGRLIDQKADLTKDI KTLESNVEEGLLELSGHLIDQKADIAKNQADIAQNQANIQDLAAYNELQDAYAKQQTEAIDALN KASSENTQNIEDLAAYNELQDAYAKQQTEAIDALNKASSENTQNIEDLAAYNELQDAYAKQQTE AIDALNKASSENTQNIAKNQADIANNINNIYELAQQQDQHSSDIKTLAKASAANTDRIAKNKAD ADASFETLIKNQNTLIEKDKEHDKLITANKTAIDENKASADTKFAATADAITKNGNAITKNAKS ITDLGTKVDAFDGRVTALDTKVNAFDGRITALDSKVENGMAAQAALSGLFQPYSVGKFNATAAL GGYGSKSAVAIGAGYRVNPNLAFKAGAAINTSGNKKGSYNIGVNYEF (687 aa) |
| Finnish 353 (SEQ ID NO: 6) | MKTMKLLPLKIAVTSAMIVGLGMASTANAQQQKSPKTETFLPNIFFNEYADDLDTLYHNMILGD TAITHDDQYKFYADDATEVPDSLFFNKILHDQLLYGFKEGDKIIPLDENGKPVYKLDKRLENGV QKTVYSVTTKTATADDVNSAYSRGIQGDIDDLYEANKENVNRLIEHGDKIFANEESVQYLNREV QNNIENIHELAQQQDQHSSDIKTLKKNVEKDLLDSGRLIAQKEDIAQNQTDIQDLATYNELQD QYAQKQTEAIDALNKASSENTQNIAKNSNHIKTLENNIEEGLLELSGHLIDQKADLTKDIKALE SNVEEGLLDLSGRLIDQKADIAQNQANIQDLAAYNELQDAYAKQQTEAIDALNKASSENTQNIE DLAAYNELQDAYAKQQTEAIDALNKASSENTQNIEDLAAYNELQDAYAKQQTEAIDALNKASSE |

TABLE 1-continued

UspA2 amino acid sequences from 38 strains of *Moraxalla catarrhalis*
(SEQ ID NO: 1 - SEQ ID NO: 38).

| Strain | UspA2 sequences |
|---|---|
| | NTQNIAKNQADIANNINNIYELAQQQDQHSSDIKTLAKASAANTDRIAKNKADADASFETLYKN QNTLIEKDKEHDKLITANKTAIDANKASADTKFAATADAITKNGNAITKNAKSITDLGTKVDGF DGRVTALDTKVNALDTKVNAFDGRITALDSKVENGMAAQAALSGLFQPYSVGKFNATAALGGYG SKSAVAIGAGYRVNPNLAFKAGAAINTSGNKKGSYNIGVNYEF (683 amino acids) |
| Finnish 358 (SEQ ID NO: 7) | MKTMKLLPLKIAVTSAMMVGLGMASTANAQQQKSPKTEIFLPNLFDNDNTELTDPLYHNMILGN TALLTQENQYKFYADDGNGVPDSLLFNKILHDQLLHGFKEGGTIIPLDENGKPVYKLDSIVEQG KTKTVYSVTTKTATADDVNSAYSRGIQGDIDDLYEANKENVNRLIEHGDKIFANEESVQYLNRE VQNNIENIHELAQQQDQHSSDIKTLKKNVEKDLLDLSGRLIAQKEDIAQNQTDIQDLATYNELQ DQYAQKQTEAIDALNKASSENTQNIAKNSNHIKTLENNIEEGLLELSGHLIDQKADLTKDIKAL ESNVEEGLLDLSGRLIDQKADIAQNQANIQDLAAYNELQDAYAKQQTEAIDALNKASSENTQNI EDLAAYNELQDAYAKQQTEAIDALNKASSENTQNIEDLAAYNELQDAYAKQQTEAIDALNKASS ENTQNIAKNQADIANNINNIYELAQQQDQHSSDIKTLAKASAANTDRIAKNKADADASFETLTK NQNTLIEKDKEHDKLITANKTAIDANKASADTKFAATADAITKNGNAITKNAKSITDLGTKVDG FDGRVTALDTKVNALDTKVNAFDGRITALDSKVENGMAAQAALSGLFQPYSVGKFNATAALGGY GSKSAVAIGAGYRVNPNLAFKAGAAINTSGNKKGSYNIGVNYEF (684 amino acids) |
| Finnish 216 (SEQ ID NO: 8) | MKTMKLLPLKIAVTSAMIIGLGAASTANAQQQQKTKTEVFLPNLFDNDYYDLTDPLYHSMILGD TATLFDQQDNSKSQLKFYSNDKDSVPDSLLFSKLLHEQQLNGFKAGDTIIPLDKDGKPVYTQDT RTKDGKVETVYSVTTKIATQDDVEQSAYSRGIQGDIDDLYDINREVNEYLKATHDYNERQTEAI DALNKASSANTDRIDTAEERIDKNEYDIKALESNVGKDLLDLSGRLIAQKEDIDNNINHIYELA QQQDQHSSDIKTLKNNVEEGLLELSGHLIDQKADLTKDIKTLENNIEEGLLELSGHLIDQKADL TKDIKTLENNIEEGLLELSGHLIDQKADIAQNQANIQDLAAYNELQDQYAQKQTEAIDALNKAS SENTQNIEDLAAYNELQDAYAKQQTEAIDALNKASSENTQNIEDLAAYNELQDAYAKQQTEAID ALNKASSENTQNIAKNQADIANNINNIYELAQQQDQHSSDIKTLAKVSAANTDRIAKNKADADA SFETLTKNQNTLIEKDKEHDKLITANKTAIDANKASADTKFAATADAITKNGNAITKNAKSITD LGTKVDGFDGRVTALDTKVNAFDGRITALDSKVENGMAAQAALSGLFQPYSVGKFNATAALGGY GSKSAVAIGAGYRVNPNLAFKAGAAINTSGNKKGSYNIGVNYEF (684 amino acids) |
| Dutch H2 (SEQ ID NO: 9) | MKTMKLLPLKIAVTSAMMVGLGMASTANAQQQKSPKTEIFLPNLFDNDNTELTDPLYHNMILGN TALLTQENQYKFYADDGNGVPDSLLFNKILHDQLLHGFKKGDTIIPLDENGKPVYKLDSIVEQG KTKTVYSVTTKTATADDVNSAYSRGIQGDIDDLYEANKENVNRLIEHGDKIFANEESVQYLNRE VQNNIENIYELVQQQDQHSSDIKTLKKNVEKDLLDLSGRLIAQKEDIAQNQTDIQDLATYNELQ DQYAQKQTEAIDALNKASSENTQNIAKNSNHIKTLENNIEEGLLELSGHLIDQKADLTKDIKAL ESNVEEGLLDLSGRLIDQKADIAQNQANIQDLAAYNELQDAYAKQQTEAIDALNKASSENTQNI EDLAAYNELQDAYAKQQTEAIDALNKASSENTQNIEDLAAYNELQDAYAKQQTEAIDALNKASS ENTQNIAKNQADIANNINNIYELAQQQDQHSSDIKTLAKASAANTDRIAKNKADADASFETLTK NQNTLIEKDKEHDKLITANKTAIDANKASADTKFAATADAITKNGNAITKNAKSITDLGTKVDG FDGRVTALDTKVNALDTKVNAFDGRITALDSKVENGMAAQAALSGLFQPYSVGKFNATAALGGY GSKSAVAIGAGYRVNPNLAFKAGAAINTSGNKKGSYNIGVNYEF (684 amino acids) |
| Dutch F10 (SEQ ID NO: 10) | MKTMKLLPLKIAVTSAMIIGLGAASTANAQLAEQFFPNIFSNHAPVKQHYHNVVVGDTSIVENL QDSDDTQLKFYSNDEYSVPDSLLFNKMLHEQQLNGFKKGDTIIPLDENGKPVYKVDYKLDGQEP RRVYSVTTKIATQDDVDNSPYSRGIQGDIDDLYEANKENVNRLIEHGDKIFANEESVQYLNKEV QNNIENIYELAQQQDQHSSDIKTLKKNVEEGLLELSGHLIDQKADLTKDIKTLESNVEEGLLEL SGHLIDQKADIAKNQADIAQNQANIQDLAAYNELQDAYAKQQTEAIDALNKASSENTQNIEDLA AYNELQDAYAKQQTEAIDALNKASSENTQNIAKNQADIANNINNIYELAQQQDQHSSDIKTLAK ASAANTDRIAKNKADADASFETLTKNQNTLIEKDKEHDKLITANKTAIDANKASADTKFAATAD AITKNGNAITKNAKSITDLGTKVDAFDGRVTALDTKVNALDTKVNAFDGRITALDSKVENGMAAQAALSGL FQPYSVGKFNATAALGGYGSKSAVAIGAGYRVNPNLAFKAGAAINTSGNKKGSYNIGVNYEF (574 amino acids) |
| Norwegian 1 (SEQ ID NO: 11) | MKTMKLLPLKIAVTSALIVGLGAASTANAQQQPQTETFFPNIFFNENHDALDDVYHNMILGDTA ITQDNQYKFYADAISEVPDSLLFNKILHDQQLNGFKEGDTIIPLDENGKPVYKLDEKVENGVKK SVYSVTTKTATRADVEQSAYSRGIQGDIDDLYEANKENVNRLIEHGDKIFANEESVQYLNKEVQ NNIENIHELAQQQDQHSSDIKTLKKNVEEGLLELSGHLIDQKADLTKDIKTLESNVEEGLLDLS GRLLDQKADIAQNQANIQDLAAYNELQDAYAKQQTEAIDALNKASSENTQNIEDLAAYNELQDA YAKQQTEAIDALNKASSENTQNIEDLAAYNELQDAYAKQQTEAIDALNKASSENTQNIEDLAAY NELQDAYAKQQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQNTLI EKDKEHDKLITANKTAIDANKASADTKFAATADAITKNGNAITKNAKSITDLGTKVDAFDGRVT ALDTKVNALDTKVNAFDGRITALDSKVENGMAAQAALSGLFQPYSVGKFNATAALGGYGSKSAV AIGAGYRVNPNLAFKAGAAINTSGNKKGSYNIGVNYEF (678 amino acids) |
| Norwegian 13 (SEQ ID NO: 12) | MKTMKLLPLKIAVTSAMIVGLGAASTANAQQQQQPRTETFFPNIFFNENHDALDDVYHNMILGD TAITQDNQYKFYADAISEVPDSLLFNKILHDQQLNGFKEGDTIIPLDENGKPVYKLDEKVENGV KKSVYSVTTKTATRADVEQSAYSRGIQGDIDDLYEANKENVNRLIEHGDKIFANEESVQYLNRE VQNNIENIHELAQQQDQHSSDIKTLKKNVEKDLLDLSGRLIAQKEDIAQNQTDIQDLATYNELQ DQYAQKQTEAIDALNKASSENTQNIAKNSNHIKTLENNIEEGLLELSGHLIDQKADLTKDIKTL ENNIEEGLLELSGHLIDQKADLTKDIKALESNVEEGLLDLSGRLIDQKADIAQNQANIQDLAAY NELQDQYAQKQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQNTLI EKDKEHDKLITANKTAIDTNKASADTKFAATADAITKNGNAITKNAKSITDLGTKVDGFDGRVT ALDTKVNALDTKVNAFDGRITALDSKVENGMAAQAALSGLFQPYSVGKFNATAALGGYGSKSAV AIGAGYRVNPNLAFKAGAAINTSGNKKGSYNIGVNYEF (678 amino acids) |

TABLE 1-continued

UspA2 amino acid sequences from 38 strains of *Moraxalla catarrhalis*
(SEQ ID NO: 1 - SEQ ID NO: 38).

| Strain | UspA2 sequences |
|---|---|
| Norwegian 20 (SEQ ID NO: 13) | MKTMKLLPLKIAVTSALIVGLGAASTANAQLVERFFPNIFLDKPLAKQHYHNVVVGDTSIVSDL QSNSDQLKFYSDDEGLVPDSLLFNKMLHEQLLNGFKEGDTIIPLDENGKPVYKVDYKLDGKEPR KVYSVTTKIATAEDVATSSYANGIQKDIDDLYDFDHQVTERLTQHGKTIYRNGERILANEESVQ YLNKEVQNNIEHIYELAQQQDQHSSDIKTLESNVEKGLLELSGHLIDQKADLTKDIKTLENNVE EGLLDLSGRLIDQKADIAQNQANIQDLAAYNELQDYAQKQTEAIDALNKASSENTQNIEDLAA YNELQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDINKASADTKFAATADA ITKNGNAITKNAKSITDLGTKVDGFDSRVTALDTKVNALDTKVNALDTKVNAFDGRITALDSKV ENGMAAQAALSGLFQPYSVGKFNATAALGGYGSKSAVAIGAGYRVNPNLAFKAGAAINTSGNKK GSYNIGVNYEF (587 amino acids) |
| Norwegian 25 (SEQ ID NO: 14) | MKTMKLLPLKIAVTSAMIVGLGAASTANAQQQQQPRTETFFPNIFFNENHDALDDVYHNMILGD TAITQDNQYKFYADAISEVPDSLLFNKILHDQQLNGFKEGDTIIPLDENGKPVYKLDEKVENGV KKSVYSVTTKTATRADVEQSAYSRGIQGDIDDLYEANKENVNRLIEHGDKIFANEESVQYLNRE VQNNIENIHELAQQQDQHSSDIKTLKKNVEKDLLDLSGRLIAQKADIAQNQTDIQDLATYNELQ DQYAQKQTEAIDALNKASSENTQNIAKNSNHIKTLENNIEEGLLELSGHLIDQKADLTKDIKTL ENNIEEGLLELSGHLIDQKADLIKDIKALESNVEEGLLDLSGRLLDQKADIAQNQANIQDLAAY NELQDYAQKQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQNTLI EKDKEHDKLITANKTAIDTNKASADTKFAATADAITKNGNAITKNAKSITDLGTKVDGFDGRVT ALDTKVNALDTKVNAFDGRITALDSKVENGMAAQAALSGLFQPYSVGKFNATAALGGYGSKSAV AIGAGYRVNPNLAFKAGAAINTSGNKKGSYNIGVNYEF (678 amino acids) |
| Norwegian 27 (SEQ ID NO: 15) | MKTMKLLPLKIAVTSALIVGLGAASTANAQVRDKSLEDIEALLGKIDISKLEKEKKQQTELQKY LLLSQYANVLTMEELNKNVEKNTNSIEALGYEIGWLENDIADLEEGVEELTKNQNTLIEKDEEH DRLIAQNQADIKTLENNVVEELFNLSDRLIDQEADIAKNNASIEELYDFDNEVAERIGEIHAYT EEVNKTLEKLITNSVKNTDNIDKNKADIQALENNVEEGLLELSGHLIDQKADLTKDIKALESNV EEGLLDLSGRLLDQKADIAKNQADIAQNQTDIQDLAAYNELQDYAQKQTEAIDALNKASSENT QNIEDLAAYNELQDAYAKQQTEAIDALNKASSENTQNIEDLAAYNELQDAYAKQQTEAIDALNK ASSENTQNIAKNQADIANNINNIYELAQQQDQHSSDIKTLAKVSAANTDRIAKNKADADASFET LTKNQNTLIEKDKEHDKLITANKTAIDANKASADTKFAATADAITKNGNAITKNAKSITDLGTK VDGFDSRVTALDTKVNAFDGRITALDSKVENGMAAQAALSGLFQPYSVGKFNATAALGGYGSKS AVAIGAGYRVNPNLAFKAGAAINTSGNKKGSYNIGVNYEF (616 amino acids) |
| Norwegian 36 (SEQ ID NO: 16) | MKTMKLLPLKIAVTSALIVGLGAASTANAQATETFLPNLFDNDYTETTDPLYHGMILGNTAITQ DTQYKFYAENGNEVPDSLFFNKILHDQQLNGFKEGDTIIPLDENGKPVYKLDEITENGVKRKVY SVTTKTATREDVEQSAYSRGIQGDIDDLYEANKENVNRLIEHGDKIFANEESVQYLNKEVQNNI ENIHELAQQQDQHSSDIKTLKKNVEEGLLELSGHLIDQKADLTKDIKALESNVEEGLLDLSGHL IDQKADLTKDIKALESNVEEGLLDLSGRLLDQKADIAKNQADIAQNQTDIQDLAAYNELQDQYA QKQTEAIDALNKASSENTQNIEDLAAYNELQDQYAQKQTEAIDALNKASSENTQNIEDLAAYNE LQDQYAQKQTEAIDALNKASSENTQNIEDLAAYNELQDQYAQKQTEAIDALNKASSENTQNIAK NQADIANNINNIYELAQQQDQHSSDIKTLAKASAANTDRIAKNKADADASFETLTKNQNTLIEK DKEHDKLITANKTAIDANKASADTKFAATADAITKNGNAITKNAKSITDLGTKVDGFDGRVTAL DTKVNALDTKVNAFDGRITALDSKVENGMAAQAALSGLFQPYSVGKFNATAALGGYGSKSAVAI GAGYRVNPNLAFKAGAAINTSGNKKGSYNIGVNYEF (676 amino acids) |
| BC5SV (SEQ ID NO: 17) | MKTMKLLPLKIAVTSALIVGLGAASTANAQNGTSTKLKNLKEYAQYLDNYAQYLDDDIDDL DKEVGELSQNIAKNQANIKDLNKKLSRDIDSLREDVYDNQYEIVNNQADIEKNQDDIKELE NNVGKELLNLSGRLLDQKADIDNNINNIYELAQQQDQHSSDIKTLKKNVEEGLLELSGHLI DQKSDIAQNQTDIQDLATYNELQDQYAQKQTEAIDALNKASSENTQNIEDLAAYNELQDAY AKQQTEAIDALNKASSENTQNIQDLAAYNELQDAYAKQQTEAIDALNKASSENTQNIEDLA AYNELQDAYAKQQTEAIDALNKASSENTQNIEDLAAYNELQDAYAKQQTEAIDALNKASSE NTQNIEDLAAYNELQDAYAKQQTEAIDALNKASSENTQNIAKNQADIANNINNIYELAQQQ DQHSSDIKTLAKASAANTDRIAKNKADADASFETLTKNQNTLIEKDKEHDKLITANKTAID ANKASADTKFAATADAITKNGNAITKNAKSITDLGTKVDAFDGRVTALDTKVNAFDGRITA LDSKVENGMAAQAALSGLFQPYSVGKFNATAALGGYGSKSAVAIGAGYRVNPNLAFKAGAA INTSGNKKGSYNIGVNYEF (629 amino acids) |
| Norwegian 14 (SEQ ID NO: 18) | MKTMKLLPLKIAVTSAMIVGLGMASTANAQQQRSPKTETFLPNIFFNEYADDLDTLYHNMI LGDTAITHDDQYKFYADDATEVPDSLFFNKILHDQLLYGFKEGDKIIPLDENGKPVYKLDK RLDNGVQKTVYSVTTKTATADDVNSAYSRGIQGDIDDLYEANKENVNRLIEHGDKIFANEE SVQYLNKEVQNNIENIHELAQQQDQHSSDIKTLKKNVEEGLLELSGHLIDQKTDIAQNQTD IQDLATYNELQDQYAQKQTEAIDALNKASSENTQNIAKNSNRIKALENNIEEGLLELSGHL IDQKADLTKDIKALESNVEEGLLDLSGRLIDQKADIAQNQANIQDLAAYNELQDAYAKQQT EAIDALNKASSENTQNIEDLAAYNELQDAYAKQQTEAIDALNKASSENTQNIEDLAAYNEL QDAYAKQQTEAIDALNKASSENTQNIAKNQADIANNINNIYELAQQQDQHSSDIKTLAKAS AANTDRIAKNKADADASFETLTKNQNTLIEKDKEHDKLITANKTAIDANKASADTKFAATA DAITKNGNAITKNAKSITDLGTKVDGFDGRVTALDTKVNALDTKVNAFDGRITALDSKVEN GMAAQAALSGLFQPYSVGKFNATAALGGYGSKSAVAIGAGYRVNPNLAFKAGAAINTSGNK KGSYNIGVNYEF (683 amino acids) |

TABLE 1-continued

UspA2 amino acid sequences from 38 strains of *Moraxalla catarrhalis*
(SEQ ID NO: 1 - SEQ ID NO: 38).

| Strain | UspA2 sequences |
|---|---|
| Norwegian 3 (SEQ ID NO: 19) | MKTMKLLPLKIAVTSAMIVGLGAASTANAQAQSNRSLDQVQALLRGIDETKIKKEIQQSQQ PELNKYLTFNQLANALNIEELNNNVQKNTQRLDSAATLYGDLSKTVPKSIKENKESIKENK ESIKENKESIKENKESIKENKESIKENKESITTLTRKSFQNQVDIVRNNASIEDLYAYGQE VAKSIGEIHAYTEEVNKTLENLITNSVENTNNITKNKADIQALENNVVEELFNLSGRLIDQ KADIDNNINNIYELAQQQDQHSSDIKTLKKNVEEGLLELSGHLIDQKADLTKDIKTLESNV EEGLLDLSGRLLDQKADIAQNQANIQDLAAYNELQDAYAKQQTEAIDALNKASSENTQNIE DLAAYNELQDAYAKQQTEAIDALNKASSENTQNIEDLAAYNELQDAYAKQQTEAIDALNKA SSENTQNIEDLAAYNELQDAYAKQQTEAIDALNKASSENTQNIAKNQADIANNINNIYELA QQQDQHSSDIKTLAKASAANTDRIAKNKADADASFETLTKNQNTLIEKDKEHDKLITANKT VIDANKASADTKFAATADAITKNGNAITKNAKSITDLGTKVDGFDGRVTALDTKVNALDTK VNAFDGRITALDSKVENGMAAQAALSGLFQPYSVGKFNATAALGGYGSKSAVAIGAGYRVN PNLAFKAGAAINTSGNKKGSYNIGVNYEF (700 amino acids) |
| Finnish 414 (SEQ ID NO: 20) | MKTMKLLPLKIAVTSALIVGLGAASTANAQATETFLPNLFDNDYIETTDPLYHGMILGNTA ITQDTQYKFYAENGNEVPDSLFFNKILHDQQLNGFKEGDTIIPLDENGKPVYKLDEITENG VKRKVYSVTTKTATREDVEQSAYSRGIQGDIDDLYEANKENVNRLIEHGDKIFANEESVQY LNKEVQNNIENIHELAQQQDQHSSDIKTLKKNVEEGLLELSGHLIDQKADLTKDIKTLENN VEEGLLELSGHLIDQKADLTKDIKALESNVEEGLLDLSGRLLDQKADIAKNQADIAQNQTD IQDLAAYNELQDQYAQKQTEAIDALNKASSENTQNIEDLAAYNELQDQYAQKQTEAIDALN KASSENTQNIEDLAAYNELQDQYAQKQTEAIDALNKASSENTQNIEDLAAYNELQDQYAQK QTEAIDALNKASSENTQNIAKNQADIANNINNIYELAQQQDQHSSDIKTLAKASAANTDRI AKNKADADASFETLTKNQNTLIEKDKEHDKLITANKTAIDANKASADTKFAATADAITKNG NAITKNAKSITDLGTKVDGFDGRVTALDTKVNALDTKVNAFDGRITALDSKVENGMAAQAA LSGLFQPYSVGKFNATAALGGYGSKSAVAIGAGYRVNPNLAFKAGAAINTSGNKKGSYNIG VNYEF (676 amino acids) |
| Japanese Z7476 (SEQ ID NO: 21) | MKTMKLLPLKIAVTSAMIIGLGAASTANAQLAEQFFPNIFSNHAPVKQHYHNVVVGDTSIV ENLQDSDDTQLKFYSNDEYSVPDSLLFNKMLHEQQLNGFKKGDTIIPLDENGKPVYKVDYK LDGQEPRRVYSVTTKIATQDDVDNSPYSRGIQGDIDDLYEANKENVNRLIEHGDKIFANEE SVQYLNKEVQNNIENIYELAQQQDQHSSDIKTLKKNVEEGLLELSGRLIDQKADIAQNQAN IQDLAAYNELQDAYAKQQTEAIDALNKASSENTQNIEDLAAYNELQDAYAKQQTEAIDALN KASSENTQNIEDLAAYNELQDAYAKQQTEAIDALNKASSENTQNIEDLAAYNELQDAYAKQ QTEAIDALNKASSENTQNIEDLAAYNELQDAYAKQQTEAIDALNKASSENTQNIEDLAAYN ELQDAYAKQQTEAIDALNKASSENTQNIAKNQADIANNINNIYELAQQQDQHSSDIKTLAK VSAANTDRIAKNKADADASFETLTKNQNTLIEKDKEHDKLITANKTAIDANKASADTKFAA TADAITKNGNAITKNAKSITDLGTKVDGFDGRVTALDTKVNAFDGRITALDSKVENGMAAQ AALSGLFQPYSVGKFNATAALGGYGSKSAVAIGAGYRVNPNLAFKAGAAINTSGNKKGSYN IGVNYEF (678 amino acids) |
| Belgian Z7530 (SEQ ID NO: 22) | MKTMKLLPLKIAVTSAMIIGLGAASTANAQSRDRSLEDIQDSISKLVQDDINTLKQDQQKM NKYLLLNQLANTLITDELNNNVIKNTNSIEALGDEIGWLENDIADLEEGVEELTKNQNTLI EKDEEHDRLIAQNQADIQTLENNVVEELFNLSGRLIDQEADIAKNNASIEELYDFDNEVAE RIGEIHAYTEEVNKTLENLITNSVKNTDNIDKNKADIDNNINHIYELAQQQDQHSSDIKTL KNNVEEGLLELSGHLIDQKADLTKDIKALESNVEEGLLDLSGRLLDQKADLTKDIKALESN VEEGLLDLSGRLLDQKADIAQNQTDIQDLAAYNELQDQYAQKQTEAIDALNKASSENTQNI EDLAAYNELQDAYAKQQTEAIDALNKASSENTQNIAKNQADIANNINNIYELAQQQDQHSS DIKTLAKASAANTNRIATAELGIAENKKDAQIAKAQANANKTAIDENKASADTKFAATADA ITKNGNAITKNAKSITDLGTKVDGFDGRVTALDTKVNAFDGRITALDSKVENGMAAQAALS GLFQPYSVGKFNATAALGGYGSKSAVAIGAGYRVNPNLAFKAGAAINTSGNKKGSYNIGVN YEF (613 amino acids) |
| German Z8063 (SEQ ID NO: 23) | MKTMKLLPLKIAVTSALIVGLGAASTANAQATNKDITLEDVLKSIEEIDPYELRDYIEYPT AIERFLLLSQYGNTLTLEEFDNDIELLDQDVEDLEESVTELAKNQNSLIEQGEAIKEDLQG LADFVERQEDKILQNETSIKKNTQRNLVNGFEIEKNKDAIAKNNESIEDLYDFGHEVAKSI GEIHAHNEAQNETLKDLITNSVKNTDNITKNKADIQALESNVEKGLLELSGHLIDQKADID NNINNIHELAQQQDQHSSDIKTLKKNVEEGLLELSGHLIDQKSDIAQNQANIQDLATYNEL QDQYAQKQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQN TLIEKDKEHDKLITANKTAIDANKASADTKFAATADAITKNGNAITKNAKSITDLGTKVDG FDSRVTALDTKVNAFDGRITALDSKVENGMAAQAALSGLFQPYSVGKFNATAALGGYGSKS AVAIGAGYRVNPNLAFKAGAAINTSGNKKGSYNIGVNYEF (589 amino acids) |
| American O12E (SEQ ID NO: 24) | MKTMKLLPLKIAVTSAMMVGLGMASTANAQQQKSPKTEIFLPNLFDNDNTELTDPLYHNMI LGNTALLTQENQYKFYADDGNGVPDSLFFNKILHDQLLHGFKEGDTIIPLDENGKPVYKLD SIVEQGKTKTVYSVTTKTATADDVNSAYSRGIQGDIDDLYEANKENVNRLIEHGDKIFANE ESVQYLNREVQNNIENIHELAQQQDQHSSDIKTLKKNVEKDLLDLSGRLIAQKEDIAQNQT DIQDLATYNELQDQYAQKQTEAIDALNKASSENTQNIAKNSNHIKTLENNIEEGLLELSGH LIDQKADLTKDIKALESNVEEGLLDLSGRLIDQKADIAQNQANIQDLAAYNELQDAYAKQQ TEAIDALNKASSENTQNIEDLAAYNELQDAYAKQQTEAIDALNKASSENTQNIEDLAAYNE LQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDANKASADTKFAAT ADAITKNGNAITKNAKSITDLGTKVDGFDGRVTALDTKVNALDTKVNAFDGRITALDSKVE NGMAAQAALSGLFQPYSVGKFNATAALGGYGSKSAVAIGAGYRVNPNLAFKAGAAINTSGN KKGSYNIGVNYEF (684 amino acids) |

TABLE 1-continued

UspA2 amino acid sequences from 38 strains of Moraxalla catarrhalis
(SEQ ID NO: 1 - SEQ ID NO: 38).

| Strain | UspA2 sequences |
|---|---|
| Greek MC317 (SEQ ID NO: 25) | MKTMKLLPLKIAVTSALIVGLGAASTANAQQQQKTKTEVFLPNLFYNDYIEETDLLYHNMI LGDTAALVDRQNYSNSQLKFYSNDEESVPDSLLFSKMLNNQQLNGFKAGDIIIPVDANGQV IYQKDTRVEGGKTRTVLSVTTKIATQQDVDSAYSRGIQGKVNDLDDEMNFLNHDITSLYDV TANQQDDIKGLKKGVKDLKKGVKGLNKELKELDKEVGVLSRDIGSLNDDVAQNNESIEDLY DFSQEVADSIGEIHAHNKAQNETLQDLITNSVENTNNITKNKADIQALENNVVEELFNLSG RLIDQKADLTKDIKTLESNVEEGLLELSGHLIDQKADIAKNQADIAQNQANIQDLAAYNEL QDAYAKQQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQN TLIEKDKEHDKLITANKTAIDENKASADTKFAATADAITKNGNAITKNAKSITDLGTKVDG FDGRVTALDTKVNAFDGRITALDSKVENGMAAQAALSGLFQPYSVGKFNATAALGGYGSKS AVAIGAGYRVNPNLAFKAGAAINTSGNKKGSYNIGVNYEF (650 amino acids) |
| American V1122 (SEQ ID NO: 26) | MKTMKLLPLKIAVTSALIVGLGAVSTTNAQAQSRSLDQIQTKLADLAGKIAAGKNGGGQNN QNNQNDINKYLFLSQYANILTMEELNNNVVKNSSSIETLETDFGWLENDVADLEDGVEELT KNQNTLIEKDEEHDRLIAQNQADIQTLENNVVEELFNLSDRLIDQKADIAKNQADIAQNNE SIEELYDFDNEVAEKIGEIHAYTEEVNKTLQDLITNSVKNTDNIDKNKADIDNNINHIYEL AQQQDQHSSDIKTLKNNVEEGLLELSGHLIDQKADLTKDIKTLENNVEEGLLDLSGRLIDQ KADIAKNQADIAQNQTDIQDLAAYNELQDYAQKQTEAIDALNKASSENTQNIEDLAAYNE LQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDENKASADTKFAAT ADAITKNGNAITKNAKSITDLGTKVDGFDGRVTALDTKVNAFDGRITALDSKVENGMAAQA ALSGLFQPYSVGKFNATAALGGYGSKSAVAIGAGYRVNPNLAFKAGAAINTSGNKKGSYNI GVNYEF (616 amino acids) |
| American P44 (SEQ ID NO: 27) | MKTMKLLPLKIAVTSALIVGLGTASTANAQVASPANQKIQQKIKKVRKELRQDIKSLRNDI DSNTADIGSLNDDVADNQDDILDNQADIAKNQDDIEKNQADIKELDKEVGVLSREIGSLND DIADNYTDIIDNYTDIIDNQANIAKNQDDIEKNQADIKELDKEVGVLSREIGSLNDDVADN QDDIAKNQADIQTLENNVEEGLLELSGHLLDQKADIDNNINNIYELAQQQDQHSSDIKTLK KNVEEGLLELSGHLIDQKTDIAQNQANIQDLATYNELQDQYAQEQTEAIDALNKASSENTQ NIAKNSNRIKALESNVEEGLLELSGHLIDQKADLTKDIKALESNVEEGLLELSGHLIDQKA DIAQNQANIQDLAAYNELQDQYAKQTEAIDALNKASSENTQNIEDLAAYNELQDAYAKQQ TEAIDALNKASSENTQNIAKNQADIANNINNIYELAQQQDQHSSDIKTLAKASAANTDRIA KNKADADASFETLTKNQNTLIEKDKEHDKLITANKTAIDANKVSADTKFAATADAITKGN AITKNAKSITDLGTKVDAFDSRVTALDTKVNAFDGRITALDSKVENGMAAQAALSGLFQPY SVGKFNATAALGGYGSKSAVAIGAGYRVNPNLAFKAGAAINTSGNKKGSYNIGVNYEF (668 amino acids) |
| American V1171 (SEQ ID NO: 28) | MKTMKLLPLKIAVTSAMIVGLGATSTVNAQVVEQFFPNIFFNENHDELDDAYHNMILGDTA IVSNSQDNSTQLKFYSNDEDSVPDSLLFSKLLHEQQLNGFKAGDTIIPLDKDGKPVYTKDT RTKDGKVETVYSVTTKIATQDDVEQSAYSRGIQGDIDDLYDINREVNEYLKATHDYNERQT EAIDALNKASSANTDRIDTAEERIDKNEYDIKALESNVEEGLLELSGHLIDQKADLTKDIK ALESNVEEGLLELSGHLIDQKADLTKDIKALESNVEEGLLDLSGRLIDQKADIAQNQANIQ DLAAYNELQDAYAKQQTEAIDALNKASSENTQNIEDLAAYNELQDAYAKQQTEAIDALNKA SSENTQNIEDLAAYNELQDAYAKQQTEAIDALNKASSENTQNIEDLAAYNELQDAYAKQQT EAIDALNKASSENTQNIAKNQADIANNINNIYELAQQQDQHSSDIKTLAKASAANTDRIAK NKADADASFETLTKNQNTLIEKDKEHDKLITANKTAIDANKASADTKFAATADAITKNGNA ITKNAKSITDLGTKVDGFDGRVTALDTKVNALDTKVNAFDGRITALDSKVENGMAAQAALS GLFQPYSVGKFNATAALGGYGSKSAVAIGAGYRVNPNLAFKAGAAINTSGNKKGSYNIGVN YEF (674 amino acids) |
| American TTA24 (SEQ ID NO: 29) | MKTMKLLPLKIAVTSAMIIGLGAASTANAQSRDRSLEDIQDSISKLVQDDIDTLKQDQQKM NKYLLLNQLANTLITDELNNNVIKNTNSIEALGDEIGWLENDIADLEEGVEELTKNQNTLI EKDEEHDRLIAQNQADIQTLENNVVEELFNLSGRLIDQEADIAKNNASIEELYDFDNEVAE RIGEIHAYTEEVNKTLENLITNSVKNTDNIDKNKADIDNNINHIYELAQQQDQHSSDIKTL KNNVEEGLLELSGHLIDQKADLTKDIKALESNVEEGLLDLSGRLLDQKADLTKDIKALESN VEEGLLDLSGRLLDQKADIAQNQTDIQDLAAYNELQDQYAQKQTEAIDALNKASSENTQNI EDLAAYNELQDAYAKQQTEAIDALNKASSENTQNIAKNQADIANNINNIYELAQQQDQHSS DIKTLAKASAANTNRIATAELGIAENKKDAQIAKAQANANKTAIDENKASADTKFAATADA ITKNGNAITKNAKSITDLGTKVDGFDGRVTALDTKVNAFDGRITALDSKVENGMAAQAALS GLFQPYSVGKFNATAALGGYGSKSAVAIGAGYRVNPNLAFKAGAAINTSGNKKGSYNIGVN YEF (613 amino acids) |
| American O35E (SEQ ID NO: 30) | MKTMKLLPLKIAVTSAMIVGLGATSTVNAQVVEQFFPNIFFNENHDELDDAYHNMILGDTA IVSNSQDNSTQLKFYSNDEDSVPDSLLFSKLLHEQQLNGFKAGDTIIPLDKDGKPVYTKDT RTKDGKVETVYSVTTKIATQDDVEQSAYSRGIQGDIDDLYDINREVNEYLKATHDYNERQT EAIDALNKASSANTDRIDTAEERIDKNEYDIKALESNVEEGLLELSGHLIDQKADLTKDIK ALESNVEEGLLELSGHLIDQKADLTKDIKALESNVEEGLLDLSGRLLDQKADIAKNQADIA QNQTDIQDLAAYNELQDAYAKQQTEAIDALNKASSENTQNIAKNQADIANNINNIYELAQQ QDQHSSDIKTLAKASAANTDRIAKNKADADASFETLTKNQNTLIEKDKEHDKLITANKTAI DANKASADTKFAATADAITKNGNAITKNAKSITDLGTKVDGFDGRVTALDTKVNALDTKVN AFDGRITALDSKVENGMAAQAALSGLFQPYSVGKFNATAALGGYGSKSAVAIGAGYRVNPN LAFKAGAAINTSGNKKGSYNIGVNYEF (576 amino acids) |

TABLE 1-continued

UspA2 amino acid sequences from 38 strains of *Moraxalla catarrhalis* (SEQ ID NO: 1 - SEQ ID NO: 38).

| Strain | UspA2 sequences |
|---|---|
| American SP12-6 (SEQ ID NO: 31) | MKTMKLLPLKIAVTSAMMVGLGMASTANAQQQKSPKTEIFLPNLFDNDNTELTDPLYHNMI LGNTALLTQENQYKFYADDGNGVPDSLLFNKILHDQLLHGFKEGDTIIPLDENGKPVYKLD SIVEQGKTKTVYSVTTKTATADDVNSAYSRGIQGDIDDLYEANKENVNRLIEHGDKIFANE ESVQYLNREVQNNIENIHELAQQQDQHSSDIKTLKKNVEKDLLDLSGRLIAQKEDIAQNQT DIQDLATYNELQDQYAQKQTEAIDALNKASSENTQNIAKNSNHIKTLENNIEEGLLELSGH LLIDQKADLTKDIKALESNVEEGLLDLSGRLIDQKADIAQNQANIQDLAAYNELQDAYAKQQ TEAIDALNKASSENTQNIEDLAAYNELQDAYAKQQTEAIDALNKASSENTQNIEDLAAYNE LQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDANKASADTKFAAT ADAITKNGNAITKNAKSITDLGTKVDGFDGRVTALDTKVNALDTKVNAFDGRITALDSKVE NGMAAQAALSGLFQPYSVGKFNATAALGGYGSKSAVAIGAGYRVNPNLAFKAGAAINTSGN KKGSYNIGVNYEF (684 amino acids) |
| American SP12-5 (SEQ ID NO: 32) | MKTMKLLPLKIAVTSAMIIGLGAASTANAQATETFLPNLFDNDYTETTDPLYHGMILGNTA ITQDTQYKFYAENGNEVPDSLFFNKILHDQQLNGFKEGDTIIPLDENGKPVYKLDEITENG VKRKVYSVTTKTATREDVEQSAYSRGIQGDIDDLYEANKENVNRLIEHGDKIFANEESVQY LNKEVQNNIENIHELAQQQDQHSSDIKTLKKNVEEGLLELSGRLIAQKEDIAQNQTDIQDL ATYNELQDQYAQKQTEAIDALNKASSENTQNIAKNSNHIKTLENNIEEGLLELSGHLIDQK ADLTKDIKALESNVEEGLLDLSGRLLDQKADIAKNQADIAQNQTDIQDLAAYNELQDQYAQ KQTEAIDALNKASSENTQNIEDLAAYNELQDAYAKQQTEAIDALNKASSENTQNIEDLAAY NELQDAYAKQQTEAIDALNKASSENTQNIAKNQADIANNINNIYELAQQQDQHSSDIKTLA KASAANTDRIAKNKADADASFETLTKNQNTLIEKDKEHDKLITANKTAIDANKASADTKFA ATADAITKNGNAITKNAKSITDLGTKVDGFDGRVTALDTKVNALDTKVNAFDGRITALDSK VENGMAAQAALSGLFQPYSVGKFNATAALGGYGSKSAVAIGAGYRVNPNLAFKAGAAINTS GNKKGSYNIGVNYEF (686 amino acids) |
| Swedish BC5 (SEQ ID NO: 33) | MKTMKLLPLKIAVTSAMIIGLGAASTANAQAKNDITLEDLPYLIKKIDQNELEADIGDITALEK YLALSQYGNILALEELNKALEELDEDVGWNQNDIANLEDDVETLTKNQNALAEQGEAIKEDLQG LADFVEGQEGKILQNETSIKKNTQRNLVNGFEIEKNKDAIAKNNESIEDLYDFGHEVAESIGEI HAHNEAQNETLKGLITNSIENTNNITKNKADIQALENNVVEELFNLSGRLIDQKADIDNNINNI YELAQQQDQHSSDIKTLKKNVEEGLLELSGHLIDQKTDIAQNQANIQDLATYNELQDQYAQKQT EAIDALNKASSENTQNIEDLAAYNELQDAYAKQQTEAIDALNKASSENTQNIEDLAAYNELQDA YAKQQTEAIDALNKASSENTQNIAKNQADIANNINNIYELAQQQDQHSSDIKTLAKASAANTDR IAKNKADADASFETLTKNQNTLIEKDKEHDKLITANKTAIDANKASADTKFAATADAITKNGNA ITKNAKSITDLGTKVDGFDSRVTALDTKVNAFDGRITALDSKVENGMAAQAALSGLFQPYSVGK FNATAALGGYGSKSAVAIGAGYRVNPNLAFKAGAAINTSGNKKGSYNIGVNYEF (630 amino acids) |
| American 7169 (SEQ ID NO: 34) | MKTMKLLPLKIAVTSALIVGLGAASTANAQAQDRSLEQIQDKLANLVEKIEQAKSQNGQSQ KDINQYLLLSQYANVLTMEELNNNVVKNSSSIETLDNDIAWLNDDLIDLDKEVGVLSRDIG SLHDDVAQNQADIKTLKNNVVEELFNLSDRLIDQEADIAQNNESIEDLYDFGREVAESIGE IHAHNEAQNETLKDLITNSVKNTDNITKNKADIQALENDVGKELLNLSGRLIDQKADIDNN INHIYELAQQQDQHSSDIKTLKNNVEEGLLELSGHLIDQKADLTKDIKALESNVEEGLLDL SGRLLDQKADIAQNQANIQDLAAYNELQDAYAKQQTEAIDALNKASSENTQNIEDLAAYNE LQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDANKASADTKFAAT ADAITKNGNAITKNAKSITDLGTKVDGFDSRVTALDTKVNAFDGRITALDSKVENGMAAQA ALSGLFQPYSVGKFNATAALGGYGSKSAVAIGAGYRVNPNLAFKAGAAINTSGNKKGSYNI GVNYEF (616 amino acids) |
| Finnish FIN2344 (SEQ ID NO: 35) | MKTMKLLPLKIAVTSAMIIGLGATSTVNAQVVEQFFPNIFFNENHDELDDAYHNMILGDTA IVSNSQDNSTQLKFYSNDEDSVPDSLLFSKLLHEQQLNGFKAGDTIIPLDKDGKPVYTKDT RTKDGKVETVYSVTTKIATQDDVEQSAYSRGIQGDIDDLYDINREVNEYLKATHDYNERQT EAIDALNKASSANTDRIDTAEERIDKNEYDIKALESNVGKDLLDLSGRLIAQKEDIDNNIN HIYELAQQQDQHSSDIKTLKNNVEEGLLELSGHLIDQKADLTKDIKTLESNVEEGLLDLSG RLIDQKADIAQNQANIQDLAAYNELQDQYAQKQTEAIDALNKASSENTQNIEDLAAYNELQ DAYAKQQTEAIDALNKASSENTQNIAKNQADIANNINNIYELAQQQDQHSSDIKTLAKVSA ANTDRIAKNKADADASFETLTKNQNTLIEKDKEHDKLITANKTAIDANKASADTKFAATAD AITKNGNAITKNAKSITDLGTKVDGFDGRVTALDTKVNAFDGRITALDSKVENGMAAQAAL SGLFQPYSVGKFNATAALGGYGSKSAVAIGAGYRVNPNLAFKAGAAINTSGNKKGSYNIGV NYEF (614 amino acids) |
| American V1118 (SEQ ID NO: 36) | MKTMKLPPLKIAVTSAMIIGLGAASTANAQTTETFLPNLFDNDYTETTDPLYHGMILGDTA ITQDTQYKFYAENGNEVPDSLFFNKILHDQLLNGFKAGDTIIPLDENGKPVYKLDERTENG VKRKVYSVTTKTATQADVEQSAYSRGIQGDIDDLYEANKENVNRLIEHGDKIFANEESVQY LNREVQNNIENIHELAQQQDQHSSDIKTLKKNVEKDLLDLSGRLIAQKEDIAQNQTDIQDL ATYNELQDQYAQKQTEAIDALNKASSENTQNIAKNSNHIKTLENNIEECLLELSGHLIDQK ADLTKDIKALESNVEEGLLDLSGRLIDQKADIAQNQANIQDLAAYNELQDAYAKQQTEAID ALNKASSENTQNIEDLAAYNELQDAYAKQQTEAIDALNKASSENTQNIEDLAAYNELQDAY AKQQTEAIDALNKASSENTQNIAKNQADIANNINNIYELAQQQDQHSSDIKTLAKASAANT DRIAKNKADADASFETLTKNQNTLIEKDKEHDKLITANKTAIDANKASADTKFAATADAIT KNGNAITKNAKSITDLGTKVDGFDGRVTALDTKVNALDTKVNAFDGRITALDSKVENGMAA QAALSGLFQPYSVGKFNATAALGGYGSKSAVAIGAGYRVNPNLAFKAGAAINTSGNKKGSY NIGVNYEF (679 amino acids) |

TABLE 1-continued

UspA2 amino acid sequences from 38 strains of *Moraxalla catarrhalis*
(SEQ ID NO: 1 - SEQ ID NO: 38).

| Strain | UspA2 sequences |
|---|---|
| American V1145 (SEQ ID NO: 37) | MKTMKLLPLKIAVTSALIVGLGAASTANAQETLEEVLESIKQINEQDLQDDIGYNSALDRY LVLSQYGNLLIAKELNENVEKNSNSIAKNSNSIADLEADVGYLAENQNTLIEQNETINQEL EGITHELESFIAYAHAQDQKNLVNEFEIEKNKDAIAKNNESIEDLYDFGHEVAESIGEIHA YTEEVNKTLENLITNSVKNTDNITKNKADIQALESNVEKELLNLSGRLIDQKADIDNNINH IYELAQQQDQHSSDIKTLKKNVEEGLLELSGHLIDQKSDIAQNQTDIQDLATYNELQDQYA QKQTEAIDALNKASSENTQNIEDLAAYNELQDAYAKQQTEAIDALNKASSENTQNIEDLAA YNELQDAYAKQQTEAIDALNKASSENTQNIEDLAAYNELQDAYAKQQTEAIDALNKASSEN TQNIEDLAAYNELQDAYAKQQTEAIDALNKASSENTQNIEDLAAYNELQDAYAKQQTEAID ALNKASSENTQNIAKNQADIANNINNIYELAQQQDQHSSDIKTLAKASAANTDRIAKNKAD ADASFETLTKNQNTLIEKDKEHDKLITANKTAIDANKASADTKFAATADAITKNGNAITKN AKSITDLGTKVDGFDSRVTALDTKVNAFDGRITALDSKVENGMAAQAALSGLFQPYSVGKF NATAALGGYGSKSAVAIGAGYRVNPNLAFKAGAAINTSGNKKGSYNIGVNYEF (724 amino acids) |
| American V1156 (SEQ ID NO: 38) | MKTMKLLPLKIAVTSALIVGLGAASTANAQAQARDRSLEDIQALIGNIDVDKIRSQKQKNP EIFQYLLLNQLSNTLITDELNNNVIKNTNSIETLDNDIAWLNDDLIDLDKEVGVLSRDIGS LHDDVAQNQADIKTLENNVVEELFNLSDRLIDQEAEIAQNNESIEDLYDFGREVAESIGEI HAHNEAQNETLKDLITNSVKNTDNIDKNKADIQALENNVEEGLLELSGHLIDQKADLTKDI KALESNVEEGLLDLSGRLLDQKADIAKNQADIAQNQTDIQDLAAYNELQDQYAQKQTEAID ALNKASSENTQNIEDLAAYNELQDAYAKQQTEAIDALNKASSENTQNIEDLAAYNELQDAY AKQQTEAIDALNKASSENTQNIAKNQADIANNINNIYELAQQQDQHSSDIKTLAKVSAANT DRIAKNKADADASFETLTKNQNTLIEKDKEHDKLITANKTAIDANKASADTKFAATADAIT KNGNAITKNAKSITDLGTKVDGFDSRVTALDTKVNAFDGRITALDSKVENGMAAQAALSGL FQPYSVGKFNATAALGGYGSKSAVAIGAGYRVNPNLAFKAGAAINTSGNKKGSYNIGVNYE F (611 amino acids) |

UspA2 may be UspA2 from *M. catarrhalis* strain ATCC (a US registered trademark) 25238™, American 2933. American 2912, American 2908, Finnish 307, Finnish 353, Finnish 358, Finnish 216, Dutch H2, Dutch F10, Norwegian 1, Norwegian 13, Norwegian 20, Norwegian 25, Norwegian 27, Norwegian 36, BC5SV, Norwegian 14, Norwegian 3, Finish 414, Japanese Z7476, Belgium Z7530, German Z8063, American O12E, Greek MC317, American V1122, American P44, American V1171, American TTA24, American O35E, American SP12-6, American SP12-5, Swedish BC5, American 7169, Finnish FIN2344, American V1118, American V1145 or American V1156. UspA2 may be UspA2 as set forth in any of SEQ ID NO: 1-SEQ ID NO: 38. UspA2 may be UspA2 from another source which corresponds to the sequence of UspA2 in any one of SEQ ID NO: 1-SEQ ID NO: 38. Corresponding UspA2 sequences may be determined by one skilled in the art using various algorithms. For example, the Gap program or the Needle program may be used to determine UspA2 sequences corresponding to any one of SEQ ID NO: 1-SEQ ID NO: 38.

UspA2 may be a sequence with at least 95% identity, over the entire length, to any of SEQ ID NO: 1-SEQ ID NO: 38.

Immunogenic fragments of UspA2 comprise immunogenic fragments of at least 450 contiguous amino acids of SEQ ID NO: 1, 490 contiguous amino acids of SEQ ID NO: 1 (for example, the UspA2 fragment of MC-004 or MC-005), 511 contiguous amino acids of SEQ ID NO: 1 (for example, the UspA2 fragment of construct MC-001, MC-002, MC-003 or MC-004), 534 contiguous amino acids of SEQ ID NO: 1 (for example, the UspA2 fragment of MC-009 or MC-011) or 535 contiguous amino acids of SEQ ID NO: 1 (for example, the UspA2 fragment of MC-007, MC-008 or MC-010). The immunogenic fragments may elicit antibodies which can bind SEQ ID NO: 1.

Immunogenic fragments of UspA2 may comprise immunogenic fragments of at least 450, 490, 511, 534 or 535 contiguous amino acids of any of SEQ ID NO: 1-SEQ ID NO: 38. Immunogenic fragments of UspA2 may comprise immunogenic fragments of UspA2 from any of SEQ ID NO: 2-SEQ ID NO: 38 which correspond to the UspA2 fragment of SEQ ID NO: 1 in any of the UspA2 constructs MC-001, MC-002, MC-003, MC-004, MC-005, MC-006, MC-007, MC-008, MC-009, MC-010 or MC-011. The immunogenic fragments may elicit antibodies which can bind the full length sequence from which the fragment is derived.

Alignments between polypeptides pairs may be calculated by various programs. For example, the Needle program from the EMBOSS package (Free software; EMBOSS: The European Molecular Biology Open Software Suite (2000). *Trends in Genetics* 16(6): 276-277) and the Gap program from the GCG (a US registered trademark) package (Accelrys Inc.) may be used.

The Gap and Needle programs are an implementation of the Needleman-Wunsch algorithm described in: Needleman, S. B. and Wunsch, C. D. (1970) J. Mol. Biol. 48, 443-453. These programs are using frequently the BLOSUM62 scoring matrix (Steven Henikoft and Jorja G. Henikoft (1992), "Amino acid substitution matrices from protein blocks"), Proc. Natl. Acad. Sci. USA 89 (Biochemistry): 10915-10919) with gap open and extension penalties of, respectively, 8 and 2. Sometimes, the PAM250 scoring matrix (Dayhoft et al., (1978), "A model of evolutionary changes in proteins", In "Atlas of Protein sequence and structure" 5(3) M. O. Dayhoft (ed.), 345-352, National Biomedical Research Foundation, Washington) is also used.

Scoring matrices are describing by numbers the tendency of each amino acid to mutate in another, or to be conserved. These numbers are generally computed from statistics of mutations observed in faithful pairwise or multiple alignments, or even in fragments of multiple alignments. Generally, in these tables, if a high positive number is associated with a pair of identical amino acids, it is indicating that this residue has a low tendency for mutation. At the opposite, a high positive number associated with a pair of different amino acids is indicating a high tendency of mutation between these two. And this is called a "conservative substitution".

Looking at a pairwise alignment, aligned identical residues ("identities") between the two sequences can be observed. A percentage of identity can be computed by multiplying by 100 (1) the quotient between the number of identities and the length of the alignment (for example, in the Needle program output), or (2) the quotient between the number of identities and the length of the longest sequence, or (3) the quotient between the number of identities and the length of the shortest sequence, or (4) the quotient between the number of identities and the number of aligned residues (for example, in the Gap program output).

The percentage of identities of Table 8 have been calculated according the definition (3) of the previous paragraph, using the pairwise alignments computed by the Gap software.

As used herein, "adjuvant" means a compound or substance that, when administered to a subject in conjunction with a vaccine, immunotherapeutic, or other antigen- or immunogen-containing composition, increases or enhances the subject's immune response to the administered antigen or immunogen (as compared to the immune response that would be obtained in the absence of adjuvant). This is to be distinguished from "adjuvant therapy", defined by the National Cancer Institute of the United States Institutes of Health in the context of cancer treatment as additional treatment given after the primary treatment, to lower the risk that the cancer will recur.

The invention further provides proteins of formula (I) containing conservative amino acid substitutions. For example, the proteins of formula (I) may contain a conservative substitution of any amino acid from UspA2 of Moraxella catarrahlis as described in any of the sequences set forth herein (for example, any UspA2 sequence set forth in SEQ ID NO. 1-SEQ ID NO. 38).

As used herein "signal peptide" refers to a short (less than 60 amino acids, for example, 3 to 60 amino acids) polypeptide present on precursor proteins (typically at the N terminus), and which is typically absent from the mature protein. The signal peptide (sp) is typically rich in hydrophobic amino acids. The signal peptide directs the transport and/or secretion of the translated protein through the membrane. Signal peptides may also be called targeting signals, transit peptides, localization signals, or signal sequences. For example, the signal sequence may be a co-translational or post-translational signal peptide.

A heterologous signal peptide may be cleaved from a protein construct by signal peptide peptidases during or after protein transportation or secretion. For example, the signal peptide peptidase is signal peptide peptidase I. A "heterologous" signal peptide is one which is not associated with the protein as it exists in nature.

As used herein "treatment" means the prevention of occurrence of symptoms of the condition or disease in a subject, the prevention of recurrence of symptoms of the condition or disease in a subject, the delay of recurrence of symptoms of the condition or disease in a subject, the decrease in severity or frequency of symptoms of the condition or disease in a subject, slowing or eliminating the progression of the condition and the partial or total elimination of symptoms of the disease or condition in a subject.

As used herein, "optionally" means that the subsequently described event(s) may or may not occur, and includes both event(s) that occur and events that do not occur.

Otitis media is a major cause of morbidity in 80% of all children less than 3 years of age. (Expert Rev. Vaccines 5:517-534 (2006)). More than 90% of children develop otitis media before age 7 (Current Opinion in Investigational Drugs 4:953-958 (2003)). In 2000, there were 16 million visits made to office-based physicians for otitis media in the United States and approximately 13 million antibacterial prescriptions dispensed. (Pediatrics 113:1451-1465 (2004)). In European countries, the reported acute otitis media rates range between 0.125 to 1.24 per child-year. (Expert Review of Vaccines 8:1479-1500 (2009)). Otitis media is a costly infection and the most common reason children receive antibiotics. (Current Infectious Disease Reports 11:177-182 (2009)). Bacteria are responsible for approximately 70% of cases of acute otitis media, with Streptococcus pneumoniae, non-typeable Haemophilus influenzae (NTHi), and Moraxella catarrhalis predominating as the causative agents (Expert Review of Vaccines 5:517-534 (2006)). A subset of children experience recurrent and chronic otitis media and these otitis prone children have protracted middle-ear effusions that are associated with hearing loss and delays in speech and language development. (Current Infectious Disease Reports 11:177-182 (2009)). Recent antibiotic pressure and vaccination with the pneumococcal conjugate vaccine have resulted in the emergence of β-lactamase-producing Haemophilus influenzae and Moraxella catarrhalis as the leading organisms causing acute otitis media in North America, followed by Streptococcus pneumoniae (Pediatr Clin N Am 60 (2013) 391-407).

Since otitis media is a multifactorial disease, the feasibility of preventing otitis media using a vaccination strategy has been questioned. (Current Infectious Disease Reports 11:177-182 (2009)).

The chinchilla model is a robust and validated animal model of otitis media and its prevention (Expert Review of Vaccines 8:1063-1082 (2009)). While the chinchilla model may mimic the natural course of human infection, others have suggested that results in the chinchilla model may vary from one laboratory to the next. (Current Opinion in Investigational Drugs 4:953-958 (2003)).

Various other rodents have also been used for the induction of otitis media and are summarized in Vaccine 26:1501-1524 (2008). The murine animal model is often studied in otitis media research.

The presence of bactericidal antibody is associated with protection from otitis media due to non-typeable H. influenzae. (Current Opinion in Infectious Disease 16:129-134 (2003)). However, an immune response need not be bactericidal to be effective against NTHi. Antibodies that merely react with NTHi surface adhesins can reduce or eliminate otitis media in the chinchilla. (Current Opinion in Investigational Drugs 4:953-958 (2003)).

Chronic obstructive pulmonary disease is a chronic inflammatory disease of the lungs and a major cause of morbidity and mortality worldwide. Approximately one in 20 deaths in 2005 in the US had COPD as the underlying cause. (Drugs and Aging 26:985-999 (2009)). It is projected that in 2020 COPD will rise to the fifth leading cause of disability adjusted life years, chronic invalidating diseases, and to the third most important cause of mortality (Lancet 349:1498-1504 (1997)).

The course of COPD is characterized by progressive worsening of airflow limitation and a decline in pulmonary function. COPD may be complicated by frequent and recurrent acute exacerbations (AE), which are associated with enormous health care expenditure and high morbidity. (Proceedings of the American Thoracic Society 4:554-564 (2007)). One study suggests that approximately 50% of acute exacerbations of symptoms in COPD are caused by non-typeable Haemophilus influenzae, Moraxella catarrhalis, Streptococcus pneumoniae, and Pseudomonas aeruginosa. (Drugs and Aging 26:985-999 (2009)). *Haemophilus influenzae* (*H. influenzae*) is found in 20-30% of exacerbations of COPD; *Streptococcus pneumoniae*, in 10-15% of exacerbations of COPD; and *Moraxella catarrhalis*, in 10-15% of exacerbations of COPD. (*New England Journal of Medicine* 359:2355-2365 (2008)). *Haemophilus influenzae, Streptococcus pneumoniae*, and *Moraxella catarrhalis* have been shown to be the primary pathogens in acute exacerbations of bronchitis in Hong Kong, South Korea, and the Phillipines, while *Klebsiella* spp., *Pseudomonas aeruginosa* and *Acinetobacter* spp. constitute a large proportion of pathogens in other Asian countries/regions including Indonesia, Thailand, Malaysia and Taiwan (Respirology, (2011) 16, 532-539; doi:10.1111/j.1440.1843.2011.01943.x). In Bangladesh, 20% of patients with COPD showed positive sputum culture for *Pseudomonas, Klebsiella, Streptococcus pneumoniae* and *Haemophilus influenzae*, while 65% of patients with AECOPD (acute exacerbation of COPD) showed positive cultures for *Pseudomonas, Klebsiella, Acinetobacter, Enterobacter, Moraxella catarrhalis* and combinations thereof. (Mymensingh Medical Journal 19:576-585 (2010)). However, it has been suggested that the two most important measures to prevent COPD exacerbation are active immunizations and chronic maintenance of pharmacotherapy. (Proceedings of the American Thoracic Society 4:554-564 (2007)).

Community-acquired pneumonia (CAP) has been described as the leading cause of death from infectious disease and the six-ranked cause of death overall in the United States. *Moraxella catarrhalis* is one of the pathogens associated with CAP in North America (Clin Chest Med 26 (2005) 37-55) and is one of the pathogens associated with moderate to severe community acquired pneumonia in Japan (*J Infect Chemother.* 2014 Nov. 20. pii: S1341-321X (14) 00396-1. doi: 10.1016/j.jiac.2014.11.006. [Epub ahead of print]).

There is a need for effective vaccines against *M. catarrhalis*.

The present invention relates to proteins of formula (I).

$$A\text{-}(R_1)_m\text{-}(B)_n \qquad \text{(formula I)}$$

wherein:
A is UspA2 from *Moraxella catarrhalis* or an immunogenic fragment thereof;
$R_1$ is an amino acid;
m is 0 or 2;
B is histidine; and
n is 0, 1, 2, 3, 4, 5 or 6.

In one particular embodiment, $R_1$ and m are defined wherein $(R_1)_m$ is AS (alanine serine). In another embodiment, $R_1$ is non-native amino acids.

In one embodiment, the proteins of formula (I) and proteins of the invention are defined wherein m is 0. In one embodiment, when m is 0, n is 2. In another embodiment of the invention, when m is 0, n is not 0.

In one embodiment, m is 2.

In one particular embodiment, n is selected from the group consisting of 1, 2 and 6. In another embodiment, n is selected from the group consisting of 2 and 6. In one particular embodiment, n is 2. In another embodiment, n is 6.

In one embodiment, n is selected from the group consisting of 0, 1, 2, and 6, or any subset thereof.

In one embodiment n is 0. In another embodiment, when n is 0, m is 2.

In one embodiment, n is 1. In one embodiment, n is 3. In one embodiment, n is 4. In one embodiment, n is 5.

In one embodiment, the proteins of formula (I) further contain a methionine (M) at the amino terminus; a protein with the following formula: methionine-A-$(R_1)_m$-$(B)_n$. These are included within proteins of the invention. In one particular embodiment, when m is 0 and n is 0, the proteins of formula (I) and proteins of the invention are non-native proteins.

In one embodiment, the proteins of formula (I) and proteins of the invention are non-native proteins.

In one embodiment, the proteins of formula (I) are defined wherein A is UspA2 from *M. catarrhalis*. In another embodiment, the proteins of formula (I) are defined wherein A is UspA2 as set forth in an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37 and SEQ ID NO: 38 or any subset of SEQ ID NO: 1 through SEQ ID NO:38. In another embodiment, the proteins of formula (I) are defined wherein A is UspA2, wherein UspA2 is at least 63%, 66%, 70%, 72%, 74%, 75%, 77%, 80%, 84%, 85%, 90%, 95%, 96%, 97%, 98%, 99% or 100% identical, over the entire length, to SEQ ID NO: 1. In another embodiment, the proteins of formula (I) are defined wherein A is UspA2, wherein UspA2 is approximately 75% to 100% identical to the UspA2 amino acid sequence set forth in SEQ ID NO: 1. In another embodiment, A is UspA2 wherein UspA2 is approximately 90% to 100% identical to the UspA2 amino acid sequence set forth in SEQ ID NO: 1. In another embodiment, A is UspA2 wherein UspA2 is at least 95% identical to the UspA2 amino acid sequence set forth in SEQ ID NO: 1. In another embodiment, the proteins of formula (I) are defined wherein A is UspA2, wherein UspA2 is approximately 75% to 100% identical to the UspA2 amino acid sequence set forth in any one of SEQ ID NO: 1-SEQ ID NO: 38. In another embodiment, A is UspA2 wherein UspA2 is approximately 90% to 100% identical to the UspA2 amino acid sequence set forth in any one of SEQ ID NO: 1-SEQ ID NO: 38. In additional embodiment, A is UspA2 wherein UspA2 is at least 95% identical to UspA2 as set forth in any of SEQ ID NO: 1-SEQ ID NO: 38. In a particular embodiment, A is UspA2 having the amino acid sequence set forth in SEQ ID NO. 1.

In another embodiment, the proteins of formula (I) are defined wherein A is an immunogenic fragment of UspA2 from *M. catarrhalis*. In another embodiment, A is an immunogenic fragment of UspA2 wherein UspA2 has an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37 and SEQ ID NO: 38 or any subset of SEQ ID NO: 1 through SEQ ID NO: 38. In another embodiment, A is an immunogenic fragment of UspA2, wherein UspA2 is approximately 75% to 100% identical to the amino acid sequence set forth in SEQ ID NO: 1. In another embodiment, A is an immunogenic fragment of UspA2, wherein UspA2 is approximately 90% to 100% identical to SEQ ID NO. 1. In an another embodiment, A is an immunogenic fragment of UspA2, wherein UspA2 is at least 95% identical to SEQ ID NO: 1. In another embodiment, A is an immunogenic fragment of UspA2, wherein UspA2 is approximately 75% to 100% identical to the amino acid sequence set forth in any one of SEQ ID NO: 1-SEQ ID NO: 38. In another embodiment, A is an immunogenic fragment of UspA2, wherein UspA2 is approximately 90% to 100% identical to any one of SEQ ID NO: 1-SEQ ID NO: 38. In an additional embodiment, A is an immunogenic fragment of UspA2, wherein UspA2 is at least 95% identical to any of SEQ ID NO: 1-SEQ ID NO: 38. In a particular embodiment, A is an immunogenic fragment of UspA2 wherein UspA2 has the amino acid sequence set forth in SEQ ID NO: 1.

In another embodiment, A is an immunogenic fragment of UspA2 from M. catarrhalis selected from the group consisting of amino acids 30-540 of SEQ ID NO. 1 (SEQ ID NO: 39), amino acids 31-540 of SEQ ID NO: 1 (SEQ ID NO: 40), amino acids 30-519 of SEQ ID NO: 1 (SEQ ID NO: 41), amino acids 30-564 of SEQ ID NO: 1 (SEQ ID NO: 42) and amino acids 31-564 of SEQ ID NO: 1 (SEQ ID NO: 43). More specifically, in one embodiment, A is SEQ ID NO: 43, amino acids 31-564 of SEQ ID NO: 1. In an additional embodiment, A is SEQ ID NO: 42, amino acids 30-564 of SEQ ID NO: 1. In another embodiment, A is an immunogenic fragment of UspA2 from M. catarrhalis selected from the group consisting of amino acids 30-540 of SEQ ID NO. 1 (SEQ ID NO:39), amino acids 31-540 of SEQ ID NO. 1 (SEQ ID NO: 40) and amino acids 30-519 of SEQ ID NO. 1 (SEQ ID NO: 41). In another embodiment, A is an immunogenic fragment of UspA2 with at least 52% (American 2908), 55% (Norwegian 25), 57% (Japanese Z7476), 62% (Finnish FIN2344), 64% (American 2912), 69% (American P44), 73% (American 7169), 76% (Norwegian 27), 81% (American V1145), 88% (German Z8063) or 100% (Swedish BC5) identity to SEQ ID NO. 39. In another embodiment, A is an immunogenic fragment of UspA2 with at least 52% (American 2908), 57% (Dutch F10), 62% (American 2933), 65% (Greek MC317), 67% (American V1122), 70% (American P44), 73% (American 7169), 76% (Norwegian 3), 81% (German Z8063), 100% (Swedish BC5) identical to SEQ ID NO. 43.

In another embodiment, A is an immunogenic fragment of UspA2 from M. catarrhalis from SEQ ID NO: 2 through SEQ ID NO: 38 where the fragment comprises the amino acids that align with amino acids 30-540 of SEQ ID NO. 1 (SEQ ID NO: 39), amino acids 31-540 of SEQ ID NO: 1 (SEQ ID NO: 40), amino acids 30-519 of SEQ ID NO: 1 (SEQ ID NO: 41), amino acids 30-564 of SEQ ID NO: 1 (SEQ ID NO: 42) or amino acids 31-564 of SEQ ID NO: 1 (SEQ ID NO: 43). In one embodiment, the Gap program (from the GCG package), or the Needle program (from the EMBOSS package), implementing the Needleman-Wunsch algorithm, may be used to align the sequences.

```
UspA2
                                                        SEQ ID NO: 1
MKTMKLLPLKIAVTSAMIIGLGAASTANAQAKNDITLEDLPYLIKKIDQNELEADIGDIT

ALEKYLALSQYGNILALEELNKALEELDEDVGWNQNDIANLEDDVETLTKNQNALAEQGE

AIKEDLQGLADFVEGQEGKILQNETSIKKNTQRNLVNGFEIEKNKDAIAKNNESIEDLYD

FGHEVAESIGEIHAHNEAQNETLKGLITNSIENTNNITKNKADIQALENNVVEELFNLSG

RLIDQKADIDNNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAYAKQQTEAIDA

LNKASSENTQNIEDLAAYNELQDAYAKQQTEAIDALNKASSENTQNIAKNQADIANNINN

IYELAQQQDQHSSDIKTLAKASAANTDRIAKNKADADASFETLTKNQNTLIEKDKEHDKL

ITANKTAIDANKASADTKFAATADAITKNGNAITKNAKSITDLGTKVDGFDSRVTALDTK

VNAFDGRITALDSKVENGMAAQAALSGLFQPYSVGKFNATAALGGYGSKSAVAIGAGYRV

NPNLAFKAGAAINTSGNKKGSYNIGVNYEF

Amino acids 30-540 of UspA2 from SEQ ID NO: 1,
                                                        SEQ ID NO: 39
QAKNDITLEDLPYLIKKIDQNELEADIGDIT

ALEKYLALSQYGNILALEELNKALEELDEDVGWNQNDIANLEDDVETLTKNQNALAEQGE

AIKEDLQGLADFVEGQEGKILQNETSIKKNTQRNLVNGFEIEKNKDAIAKNNESIEDLYD

FGHEVAESIGEIHAHNEAQNETLKGLITNSIENTNNITKNKADIQALENNVVEELFNLSG

RLIDQKADIDNNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAYAKQQTEAIDA

LNKASSENTQNIEDLAAYNELQDAYAKQQTEAIDALNKASSENTQNIAKNQADIANNINN

IYELAQQQDQHSSDIKTLAKASAANTDRIAKNKADADASFETLTKNQNTLIEKDKEHDKL

ITANKTAIDANKASADTKFAATADAITKNGNAITKNAKSITDLGTKVDGFDSRVTALDTK
```

Amino acids 31-540 of UspA2 from SEQ ID NO: 1,
SEQ ID NO: 40
AKNDITLEDLPYLIKKIDQNELEADIGDIT

ALEKYLALSQYGNILALEELNKALEELDEDVGWNQNDIANLEDDVETLTKNQNALAEQGE

AIKEDLQGLADFVEGQEGKILQNETSIKKNTQRNLVNGFEIEKNKDAIAKNNESIEDLYD

FGHEVAESIGEIHAHNEAQNETLKGLITNSIENTNNITKNKADIQALENNVVEELFNLSG

RLIDQKADIDNNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAYAKQQTEAIDA

LNKASSENTQNIEDLAAYNELQDAYAKQQTEAIDALNKASSENTQNIAKNQADIANNINN

IYELAQQQDQHSSDIKTLAKASAANTDRIAKNKADADASFETLTKNQNTLIEKDKEHDKL

ITANKTAIDANKASADTKFAATADAITKNGNAITKNAKSITDLGTKVDGFDSRVTALDTK

Amino acids 30-519 of UspA2 from SEQ ID NO: 1,
SEQ ID NO: 41
QAKNDITLEDLPYLIKKIDQNELEADIGDIT

ALEKYLALSQYGNILALEELNKALEELDEDVGWNQNDIANLEDDVETLTKNQNALAEQGE

AIKEDLQGLADFVEGQEGKILQNETSIKKNTQRNLVNGFEIEKNKDAIAKNNESIEDLYD

FGHEVAESIGEIHAHNEAQNETLKGLITNSIENTNNITKNKADIQALENNVVEELFNLSG

RLIDQKADIDNNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAYAKQQTEAIDA

SENTQNIEDLAAYNELQDAYAKQQTEAIDALNKASSENTQNIAKNQADIANNINN

IYELAQQQDQHSSDIKTLAKASAANTDRIAKNKADADASFETLTKNQNTLIEKDKEHDKL

ITANKTAIDANKASADTKFAATADAITKNGNAITKNAKS

Amino acids 30-564 of UspA2 from SEQ ID NO: 1,
SEQ ID NO: 42
QAKNDITLEDLPYLIKKIDQNELEADIGDIT

ALEKYLALSQYGNILALEELNKALEELDEDVGWNQNDIANLEDDVETLTKNQNALAEQGE

AIKEDLQGLADFVEGQEGKILQNETSIKKNTQRNLVNGFEIEKNKDAIAKNNESIEDLYD

FGHEVAESIGEIHAHNEAQNETLKGLITNSIENTNNITKNKADIQALENNVVEELFNLSG

RLIDQKADIDNNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAYAKQQTEAIDA

LNKASSENTQNIEDLAAYNELQDAYAKQQTEAIDALNKASSENTQNIAKNQADIANNINN

IYELAQQQDQHSSDIKTLAKASAANTDRIAKNKADADASFETLTKNQNTLIEKDKEHDKL

ITANKTAIDANKASADTKFAATADAITKNGNAITKNAKSITDLGTKVDGFDSRVTALDTK

VNAFDGRITALDSKVENGMAAQAA

Amino acids 31-564 of UspA2 from SEQ ID NO: 1,
SEQ ID NO: 43
AKNDITLEDLPYLIKKIDQNELEADIGDIT

ALEKYLALSQYGNILALEELNKALEELDEDVGWNQNDIANLEDDVETLTKNQNALAEQGE

AIKEDLQGLADFVEGQEGKILQNETSIKKNTQRNLVNGFEIEKNKDAIAKNNESIEDLYD

FGHEVAESIGEIHAHNEAQNETLKGLITNSIENTNNITKNKADIQALENNVVEELFNLSG

RLIDQKADIDNNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAYAKQQTEAIDA

LNKASSENTQNIEDLAAYNELQDAYAKQQTEAIDALNKASSENTQNIAKNQADIANNINN

```
-continued
IYELAQQQDQHSSDIKTLAKASAANTDRIAKNKADADASFETLTKNQNTLIEKDKEHDKL

ITANKTAIDANKASADTKFAATADAITKNGNAITKNAKSITDLGTKVDGFDSRVTALDTK

VNAFDGRITALDSKVENGMAAQAA
```

In another embodiment, A is an immunogenic fragment of UspA2 from *M. catarrhalis* that differs from SEQ ID NO: 1 in one or more of the following amino acids: AA (amino acid) 30 to 298, AA 299 to 302, AA 303 to 333, AA 334 to 339, AA 349, AA 352 to 354, AA 368 to 403, AA 441, AA 451 to 471, AA 472, AA 474 to 483, AA 487, AA 490, AA 493, AA 529, AA 532 or AA 543. In another embodiment, A is an immunogenic fragment of UspA2 from *M. catarrhalis* that differs from SEQ ID NO: 1 in that it contains at least one amino acid insertion in comparison to SEQ ID NO. 1.

In another embodiment, A is an immunogenic fragment of UspA2 that contains a laminin binding domain and a fibronectin binding domain.

In an additional embodiment, A is an immunogenic fragment of UspA2 that contains a laminin binding domain, a fibronectin binding domain and a C3 binding domain.

In a further embodiment, A is an immunogenic fragment of UspA2 that contains a laminin binding domain, a fibronectin binding domain, a C3 binding domain and an amphipathic helix.

The laminin binding domain, fibronectin binding domain, C3 binding domain or amphipathic helix may be as defined for SEQ ID NO: 1 or may be the corresponding sequence in any one of SEQ ID NO: 2 through SEQ ID NO: 38.

Proteins of formula (I) and proteins of the invention are useful as immunogens in subjects such as mammals, particularly humans. In particular, the proteins of formula (I) and proteins of the invention are useful in inducing an immune response against *M. catarrhalis* in subjects, particularly humans. The proteins of formula (I) and proteins of the invention are useful in the treatment or prevention of *M. catarrhalis* infection or disease. More specifically, the proteins of formula (I) and proteins of the invention are useful in the treatment or prevention of otitis media and/or COPD and/or AECOPD and/or pneumonia.

The present invention relates to immunogenic compositions comprising UspA2 from *M. catarrhalis* or an immunogenic fragment thereof. The present invention also relates to vaccines comprising such immunogenic compositions and therapeutic uses of the same. Immunogenic compositions and vaccines of the present invention are useful in the treatment or prevention of *M. catarrhalis* infection or disease. More specifically, immunogenic compositions and vaccines described herein are useful in the treatment or prevention of otitis media and/or COPD and/or AECOPD and/or pneumonia.

In one embodiment, the immunogenic composition comprises UspA2 from *M. catarrhalis*. UspA2 may be any one of SEQ ID NO: 1 through SEQ ID NO: 38 or a UspA2 sequence at least 75%, 80%, 85%, 90%, 95%, 96%, 97%, 98% or 99% identical to any one of SEQ ID NO: 1 through SEQ ID NO: 38. UspA2 may also be a UspA2 sequence at least 63% (American 2908), 66% (Japanese Z7476), 70% (Dutch F10), 72% (Finnish 358), 74% (American P44), 77% (Finnish 307), 80% (Norwegian 3), 84% (American V1145), 90% (German Z8063) or 100% (Swedish BC5) identical to that of SEQ ID NO. 1.

In another embodiment, the immunogenic composition comprises an immunogenic fragment of UspA2. The immunogenic fragment of UspA2 may be SEQ ID NO: 39, SEQ ID NO: 40, SEQ ID NO: 41, SEQ ID NO: 42 or SEQ ID NO.43, or a sequence having at least 90%, 95%, 96%, 97%, 98%, 99% sequence identity to any one of SEQ ID NO: 39, SEQ ID NO: 40, SEQ ID NO: 41, SEQ ID NO: 42 or SEQ ID NO.43. The immunogenic fragment of UspA2 may be a UspA2 sequence at least 52% (American 2908), 55% (Norwegian 25), 57% (Japanese Z7476), 62% (Finnish FIN2344), 64% (American 2912), 69% (American P44), 73% (American 7169), 76% (Norwegian 27), 81% (American V1145), 88% (German Z8063) or 100% (Swedish BC5) identical to SEQ ID NO. 39. The immunogenic fragment of UspA2 may also be a UspA2 sequence at least 52% (American 2908), 57% (Dutch F10), 62% (American 2933), 65% (Greek MC317), 67% (American V1122), 70% (American P44), 73% (American 7169), 76% (Norwegian 3), 81% (German Z8063), 100% (Swedish BC5) identical to SEQ ID NO. 43. Amino acid differences have been described in UspA2 from various *Moraxella catarrhalis* species.

UspA2 contains a laminin binding domain (for example, amino acids 30-177 of SEQ ID NO: 1, SEQ ID NO: 44). In one embodiment, the fragment of UspA2 comprises the laminin binding region of SEQ ID NO: 1. In an additional embodiment, the fragment of UspA2 comprises the laminin binding region of any one of SEQ ID NO: 2-SEQ ID NO: 38.

```
Amino acids 30-177 of SEQ ID NO: 1, SEQ ID NO: 44:
QAKNDITLEDLPYLIKKIDQNELEADIGDITALEKYLALSQYGNILALEE

LNKALEELDEDVGWNQNDIANLEDDVETLTKNQNALAEQGEAIKEDLQGL

ADFVEGQEGKILQNETSIKKNTQRNLVNGFEIEKNKDAIAKNNESIED.
```

UspA2 contains a fibronectin binding domain (for example, amino acids 165-318 of SEQ ID NO: 1, SEQ ID NO: 45). In one embodiment, the fragment of UspA2 comprises the fibronectin binding region of SEQ ID NO: 1. In an additional embodiment, the fragment of UspA2 comprises the fibronectin binding region of any one of SEQ ID NO: 2-SEQ ID NO:38. The fibronectin binding domain of SEQ ID NO: 45 also has C3 binding properties.

```
Amino acids 165-318 of SEQ ID NO: 1,
SEQ ID NO: 45:
KDAIAKNNESIEDLYD

FGHEVAESIGEIHAHNEAQNETLKGLITNSIENTNNITKNKADIQALENN

VVEELFNLSGRLIDQKADIDNNINNIYELAQQQDQHSSDIKTLKKNVEEG

LLELSGHLIDQKTDIAQNQANIQDLATYNELQDQYAQK.
```

UspA2 contains a complement component 3 (C3) binding domain (for example, amino acids 30-539 of SEQ ID NO: 1, SEQ ID NO: 46, or amino acids 165-318 of SEQ ID NO: 1, SEQ ID NO: 45). In one embodiment, the fragment of UspA2 comprises the C3 binding region of SEQ ID NO: 1. In an additional embodiment, the fragment of UspA2 comprises a C3 binding domain of any one of SEQ ID NO: 2-SEQ ID NO: 38.

Amino acids 30-539 of SEQ ID NO: 1, SEQ ID NO: 46:
QAKNDITLEDLPYLIKKIDQNELEADIGDIT

ALEKYLALSQYGNILALEELNKALEELDEDVGWNQNDIANLEDDVETLTK

NQNALAEQGEAIKEDLQGLADFVEGQEGKILQNETSIKKNTQRNLVNGFE

IEKNKDAIAKNNESIEDLYDFGHEVAESIGEIHAHNEAQNETLKGLITNS

IENTNNITKNKADIQALENNVVEELFNLSGRLIDQKADIDNNINNIYELA

QQQDQHSSDIKTLKKNVEEGLLELSGHLIDQKTDIAQNQANIQDLATYNE

LQDQYAQKQTEAIDALNKASSENTQNIEDLAAYNELQDAYAKQQTEAIDA

LNKASSENTQNIEDLAAYNELQDAYAKQQTEAIDALNKASSENTQNIAKN

QADIANNINNIYELAQQQDQHSSDIKTLAKASAANTDRIAKNKADADASF

ETLTKNQNTLIEKDKEHDKLITANKTAIDANKASADTKFAATADAITKNG

NAITKNAKSITDLGTKVDGFDSRVTALDT

UspA2 contains an amphipathic helix (for example, amino acids 519-564 of SEQ ID NO: 1 or or amino acids 520-559 of SEQ ID NO:1). In one embodiment, the fragment of UspA2 comprises amino acids 519-564 of SEQ ID NO: 1. In another embodiment, the fragment of UspA2 comprises amino acids 520-559 of SEQ ID NO:1. In an additional embodiment, the fragment of UspA2 comprises an amphipathic helix of any one of SEQ ID NO: 2-SEQ ID NO:38.

In one embodiment, the immunogenic composition comprises a protein of formula (I) wherein A is an immunogenic fragment of UspA2 that comprises a laminin binding domain and a fibronectin binding domain.

In an additional embodiment, the immunogenic composition comprises a protein of formula (I) wherein A is an immunogenic fragment of UspA2 that comprises a laminin binding domain, a fibronectin binding domain and a C3 binding domain.

In a further embodiment, the immunogenic composition comprises a protein of formula (I) wherein A is an immunogenic fragment of UspA2 that comprises a laminin binding domain, a fibronectin binding domain, a C3 binding domain and an amphipathic helix.

In another embodiment, the immunogenic composition comprises a protein as defined by formula (I). The immunogenic composition may contain, for example, a protein of formula (I) with an additional methionine at the amino terminus.

In one embodiment, the present immunogenic compositions may be administered with other antigens. For example, the present immunogenic composition may be administered with antigens from *H. influenzae*. For example, the protein of formula (I) may be administered with Protein D (PD) from *H. influenzae*. Protein D may be as described in WO91/18926. The present immunogenic composition may be administered with Protein E (PE) and Pilin A (PilA) from *H. Influenzae*. Protein E and Pilin A may be as described in WO2012/139225; the contents of which are incorporated herein by reference. Protein E and Pilin A may be presented as a fusion protein.

In another embodiment, the immunogenic compositions of the invention may be administered with additional antigens from other bacterial species also known to cause otitis media, COPD, AECOPD or pneumonia.

The amount of the immunogenic composition which is required to achieve the desired therapeutic or biological effect will depend on a number of factors such as the use for which it is intended, the means of administration, the recipient and the type and severity of the condition being treated, and will be ultimately at the discretion of the attendant physician or veterinarian. In general, a typical dose for the treatment of a condition caused in whole or in part by *M. catarrhalis* in a human, for instance, may be expected to lie in the range of from about 0.001 mg-0.120 mg. More specifically, a typical dose for the treatment of a condition caused wholly or in part by *M. catarrhalis* in a human may lie in the range of from about 0.003 mg to about 0.03 mg of protein. The present invention provides an immunogenic composition comprising a protein of formula (I) or a protein of the invention for use in the treatment or prevention of a condition or disease caused wholly or in part by *M. catarrhalis*. The immunogenic composition may contain additional antigens; a typical dose for the treatment of a condition caused wholly or in part by *H. influenzae* in a human may lie in the range of from about 0.005 mg to about 0.05 mg for each additional antigen. This dose may be administered as a single unit dose. Several separate unit doses may also be administered. For example, separate unit doses may be administered as separate priming doses within the first year of life or as separate booster doses given at regular intervals (for example, every 1, 5 or 10 years). The present invention also provides an immunogenic composition comprising a protein of formula (I) or a protein of the invention for use in the treatment or prevention of a condition or disease caused wholly or in part by *Moraxella catarrhalis* in combination with at least one antigen from *Haemophilus influenzae*.

Formulations comprising the immunogenic compositions of the invention may be adapted for administration by an appropriate route, for example, by the intramuscular, sublingual, transcutaneous, intradermal or intranasal route. Such formulations may be prepared by any method known in the art.

The immunogenic compositions of the present invention may additionally comprise an adjuvant. When the term "adjuvant" is used in this specification, it refers to a substance that is administered in conjunction with the immunogenic composition to boost the patient's immune response to the immunogenic component of the composition.

Suitable adjuvants include an aluminum salt such as aluminum hydroxide gel or aluminum phosphate or alum, but may also be a salt of calcium, magnesium, iron or zinc, or may be an insoluble suspension of acylated tyrosine, or acylated sugars, cationically or anionically derivatized saccharides, or polyphosphazenes. In one embodiment, the protein may be adsorbed onto aluminium phosphate. In another embodiment, the protein may be adsorbed onto aluminium hydroxide. In a third embodiment, alum may be used as an adjuvant.

Suitable adjuvant systems which promote a predominantly Th1 response include: non-toxic derivatives of lipid A, Monophosphoryl lipid A (MPL) or a derivative thereof, particularly 3-de-O-acylated monophosphoryl lipid A (3D-MPL) (for its preparation see GB 2220211 A); and a combination of monophosphoryl lipid A, preferably 3-de-O-acylated monophosphoryl lipid A, together with either an aluminum salt (for instance aluminum phosphate or aluminum hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen (Thoelen et al. *Vaccine* (1998) 16:708-14; EP 689454-B1).

AS01 is an Adjuvant System containing MPL (3-O-desacyl-4'-monophosphoryl lipid A), QS21 ((*Quillaja saponaria* Molina, fraction 21) Antigenics, New York, N.Y., USA) and liposomes. AS01B is an Adjuvant System containing MPL, QS21 and liposomes (50 μg MPL and 50 μg QS21). AS01E is an Adjuvant System containing MPL, QS21 and liposomes (25 μg MPL and 25 μg QS21). In one embodiment, the immunogenic composition or vaccine comprises AS01. In another embodiment, the immunogenic composition or vaccine comprises AS01B or AS01E. In a particular embodiment, the immunogenic composition or vaccine comprises AS01E.

AS02 is an Adjuvant System containing MPL and QS21 in an oil/water emulsion. AS02V is an Adjuvant System containing MPL and QS21 in an oil/water emulsion (50 μg MPL and 50 μg Q521).

AS03 is an Adjuvant System containing α-Tocopherol and squalene in an oil/water (o/w) emulsion. $AS03_A$ is an Adjuvant System containing α-Tocopherol and squalene in an o/w emulsion (11.86 mg tocopherol). $AS03_B$ is an Adjuvant System containing α-Tocopherol and squalene in an o/w emulsion (5.93 mg tocopherol). $AS03_C$ is an Adjuvant System containing α-Tocopherol and squalene in an o/w emulsion (2.97 mg tocopherol). In one embodiment, the immunogenic composition or vaccine comprises AS03.

AS04 is an Adjuvant System containing MPL (50 μg MPL) adsorbed on an aluminum salt (500 μg $Al^{3+}$). In one embodiment, the immunogenic composition or vaccine comprises AS04.

A system involving the use of QS21 and 3D-MPL is disclosed in WO 94/00153. A composition wherein the QS21 is quenched with cholesterol is disclosed in WO 96/33739. An additional adjuvant formulation involving QS21, 3D-MPL and tocopherol in an oil in water emulsion is described in WO 95/17210. In one embodiment the immunogenic composition additionally comprises a saponin, which may be QS21. The formulation may also comprise an oil in water emulsion and tocopherol (WO 95/17210). Unmethylated CpG containing oligonucleotides (WO 96/02555) and other immunomodulatory oligonucleotides (WO 0226757 and WO 03507822) are also preferential inducers of a TH1 response and are suitable for use in the present invention.

Additional adjuvants are those selected from the group of metal salts, oil in water emulsions, Toll like receptor agonists, (in particular Toll like receptor 2 agonist, Toll like receptor 3 agonist, Toll like receptor 4 agonist, Toll like receptor 7 agonist, Toll like receptor 8 agonist and Toll like receptor 9 agonist), saponins or combinations thereof.

The present invention provides a process for preparing an immunogenic composition comprising combining a protein of formula (I) or a protein of the invention with an adjuvant.

The present invention further provides a vaccine containing an immunogenic composition of the invention and a pharmaceutically acceptable adjuvant.

Possible excipients include arginine, pluronic acid and/or polysorbate. In a preferred embodiment, polysorbate 80 (for example, TWEEN (a US registered trademark) 80) is used. In a further embodiment, a final concentration of about 0.03% to about 0.06% is used. Specifically, a final concentration of about 0.03%, 0.04%, 0.05% or 0.06% polysorbate 80 (w/v) may be used.

The present invention provides a process for preparing an immunogenic composition or vaccine comprising combining a protein of formula (I) or protein of the invention with a pharmaceutically acceptable excipient.

The present invention also provides nucleic acids encoding the proteins of the invention. The term "nucleic acid" refers to a polymeric form of nucleotides. Nucleotides can be ribonucleotides, deoxyribonucleotides, or modified forms of either ribonucleotides or deoxyribonucleotides. The term includes single and double forms of DNA. The nucleic acids are preferably substantially free from other nucleic acids.

The present invention provides a process of producing nucleic acids of the invention. Nucleic acids of the invention may be prepared by methods known by those skilled in the art. For example, the nucleic acids of the invention may be synthesized in part or in whole. The nucleic acids may be prepared by digesting longer amino acids or joining shorter amino acids.

The present invention provides a method for the treatment or prevention of otitis media. The method comprises administering to a subject in need thereof a therapeutically effective amount of a protein of formula (I) or a protein of the invention.

The present invention provides a method for the treatment or prevention of exacerbations in chronic obstructive pulmonary disease. The exacerbation of COPD may be an acute exacerbation. The method comprises administering to a subject in need thereof a therapeutically effective amount of the protein of formula (I) or a protein of the invention.

The present invention provides a method for the treatment or prevention of pneumonia. The method comprises administering to a subject in need thereof a therapeutically effective amount of the protein of formula (I) or a protein of the invention.

The present invention provides a pharmaceutical composition comprising a protein of formula (I) or a protein of the invention for use in the treatment or prevention of a condition or disease caused wholly or in part by *Moraxella catarrhalis*. Pharmaceutical compositions may further comprise a pharmaceutically acceptable adjuvant.

The present invention provides use of (a) proteins of formula (I) and proteins of the invention, (b) an immunogenic composition comprising a protein of formula (I) or protein of the invention or (c) a vaccine comprising (c1) a protein of formula (I) or protein of the invention or (c2) immunogenic composition comprising a protein of formula (I) or protein of the invention for the manufacture of a medicament for treating or preventing *M. catarrhalis* infection or disease.

The present invention provides use of (a) proteins of formula (I) and proteins of the invention, (b) an immunogenic composition comprising a protein of formula (I) or protein of the invention or (c) a vaccine comprising (c1) a protein of formula (I) or protein of the invention or (c2) immunogenic composition comprising a protein of formula (I) or protein of the invention for the manufacture of a medicament for treating or preventing otitis media.

The present invention provides use of (a) proteins of formula (I) and proteins of the invention, (b) an immunogenic composition comprising a protein of formula (I) or protein of the invention or (c) a vaccine comprising (c1) a protein of formula (I) or protein of the invention or (c2) immunogenic composition comprising a protein of formula (I) or protein of the invention for the manufacture of a medicament for treating or preventing acute exacerbations of chronic obstructive pulmonary disease (AECOPD).

The present invention provides a use of (a) proteins of formula (I) and proteins of the invention, (b) an immunogenic composition comprising a protein of formula (I) or protein of the invention or (c) a vaccine comprising (c1) a protein of formula (I) or protein of the invention or (c2)

immunogenic composition comprising a protein of formula (I) or protein of the invention for the manufacture of a medicament for treating or preventing pneumonia.

The following examples are intended for illustration only and are not intended to limit the scope of the invention in any way.

In the examples, the following terms have the designated meaning:
6×his=six histidines;
xg=centrifugal force (number gravities)
AS=alanine serine
BSA=bovine serum albumin;
° C.=degrees Celsius;
$CaCl_2$=calcium chloride;
CD=circular dichroism;
$CHCl_3$=chloroform;
$CH_3CN$=acetonitrile;
$CO_2$=carbon dioxide;
Da=dalton;
DNA=deoxyribonucleic acid;
DO=dissolved oxygen;
DSC=differential scanning calorimetry;
EDTA=ethylenediaminetetraacetic acid;
h=hour;
$H_2O$=water;
$H_2O_2$=hydrogen peroxide;
HCDI=high cell density induction;
HCl=hydrogen chloride;
His=his=histidine;
IMAC=immobilized metal affinity chromatography;
IPTG=isopropyl β-D-1-thiogalactopyranoside;
kVolts=kilovolts
L=liter;
LB=Luria-Bertani;
LCD=low cell density induction;
MeOH=methanol;
ml=milliliter;
NaCl=sodium chloride;
RPM=rpm=revolutions per minute;
min=minute;
mM=millimolar;
=microgram;
µL=microliter;
MW=molecular weight;
m/z=mass/charge;
NaCl=sodium chloride;
$NaPO_4$=sodium phosphate;
ng=nanogram;
$NH_4OH$=ammonium hydroxide;
nm=nanometer;
O.D.=optical density;
PBS=phosphate buffered saline;
PCR=polymerase chain reaction;
psi=pounds per square inch;
PVDF=polyvinylidene diluoride;
SDS-PAGE=sodium dodecyl sulphate polyacrylamide gel electrophoresis;
TFA=trifluoroacetic acid
Tm=melting point;
$Tm_1$=first melting point;
$Tm_2$=second melting point;
w/v=weight/volume.

EXAMPLES

Example 1: Protein Constructs

Protein constructs were produced with different fragments of UspA2 with and without additional amino acids. The following table describes protein constructs made.

TABLE 2

Protein constructs containing UspA2 protein.

| Construct ID | Description | N-terminal | | C-Terminal |
|---|---|---|---|---|
| MC-001 | UspA2 + ½ helix + 6His | UspA2 fragment (A.A.: 30-540 of SEQ ID NO: 1, SEQ ID NO: 47) | | ASHHHHHH |
| | A.A. | 30 | 540 | 541   548 |
| MC-002 | UspA2 + ½ helix | UspA2 fragment (A.A.: 30-540 of SEQ ID NO: 1, SEQ ID NO: 47) | | |
| | A.A. | 30 | 540 | |
| MC-003 | UspA2 + ½ helix + 1His | UspA2 fragment (A.A.: 30-540 of SEQ ID NO:. 1, SEQ ID NO: 47) | | H |
| | A.A. | 30 | 540 | 541 |
| MC-004 | UspA2 + ½ helix + 2His | UspA2 fragment (A.A.: 30-540 of SEQ ID NO: 1, SEQ ID NO: 47) | | HH |
| | A.A. | 30 | 540 | 541   542 |
| MC-005 | UspA2 Δhelix + 6His | UspA2 fragment (A.A.: 30-519 of SEQ ID NO: 1, SEQ ID NO: 48) | | ASHHHHHH |
| | A.A. | 30 | 519 | 520   527 |
| MC-006 | UspA2 Δhelix | UspA2 fragment (A.A.: 30-519 of SEQ ID NO: 1, SEQ ID NO: 48) | | |
| | A.A. | 30 | 519 | |
| MC-007 | UspA2 + helix + 6His | UspA2 fragment (A.A.: 30-564 of SEQ ID NO: 1, SEQ ID NO: 49) | | ASHHHHHH |
| | A.A. | 30 | 564 | 565   572 |
| MC-008 | UspA2 + helix + 2His | UspA2 fragment (A.A.: 30-564 of SEQ ID NO: 1, SEQ ID NO: 49) | | HH |
| | A.A. | 30 | 564 | 565   566 |

TABLE 2-continued

Protein constructs containing UspA2 protein.

| Construct ID | Description | N-terminal------------------------------------C-Terminal | | |
|---|---|---|---|---|
| MC-009 | UspA2 + helix + 2HisΔQ | UspA2 fragment (A.A.: 31-564 of SEQ ID NO: 1, SEQ ID NO: 50) | | HH |
| | A.A. | 31 | | 564 565 566 |
| MC-010 | UspA2 + helix | UspA2 fragment (A.A.: 30-564 of SEQ ID NO: 1, SEQ ID NO: 49) | | |
| | A.A. | 30 | | 564 |
| MC-011 | UspA2 + ½ helix + 6HisΔQ | UspA2 fragment (A.A.: 31-540 of SEQ ID NO: 1, SEQ ID NO: 51) | | ASHHHHHH |
| | A.A. | 31 | | 540 541  548 |

A.A. = amino acid

The DNA and amino acid sequences for each protein constructs listed in Table 2 are set forth below.
Protein Construct Sequences:

MC-001 (DNA)

SEQ ID NO: 52

```
ATGCAGGCCAAAAATGATATTACCCTGGAAGATCTGCCGTATCTGATCAAAAAAATCGATCAG

AACGAACTGGAAGCCGATATTGGTGATATTACCGCACTGGAAAAATATCTGGCACTGAGCCAG

TATGGAAATATTCTGGCCCTGGAAGAACTGAATAAAGCTCTGGAAGAGCTGGATGAAGATGTG

GGTTGGAATCAGAATGATATCGCCAATCTGGAAGATGATGTTGAAACCCTGACCAAAAATCAG

AATGCACTGGCAGAACAGGGTGAAGCAATTAAAGAAGATCTGCAGGGTCTGGCAGATTTTGTT

GAAGGTCAGGAAGGCAAAATTCTGCAGAACGAAACCAGCATCAAAAAAAACACCCAGCGTAAT

CTGGTGAATGGCTTTGAAATTGAAAAAAACAAAGATGCCATTGCCAAAAACAACGAAAGCATT

GAAGATCTGTATGATTTTGGTCATGAAGTTGCCGAAAGCATTGGTGAAATTCATGCACATAAC

GAAGCACAGAATGAAACCCTGAAAGGTCTGATTACCAACAGCATCGAAAATACCAATAACATT

ACCAAAAACAAAGCAGATATTCAGGCGCTGGAAAATAATGTTGTGGAAGAACTGTTTAATCTG

AGCGGTCGTCTGATTGATCAGAAAGCCGATATCGATAATAACATTAACAACATTTATGACTG

GCACAGCAGCAGGATCAGCATAGCAGCGATATCAAAACCCTGAAAAAAAACGTTGAAGAAGGT

CTGCTGGAACTGTCTGGTCACCTGATCGATCAGAAAACTGATATTGCCCAGAATCAGGCAAAT

ATTCAGGATCTGGCCACCTATAATGACTGCAGGATCAGTATGCACAGAAACAGACCGAAGCA

ATTGATGCCCTGAATAAAGCGAGCAGCGAAAACACCCAGAATATCGAAGATCTGGCAGCATAC

AACGAACTGCAGGATGCCTATGCAAAACAGCAGACTGAAGCCATCGACGCACTGAACAAGGCA

AGCTCTGAAAACACGCAGAACATTGAAGATCTGGCTGCCTATAATGAATTACAGGATGCGTAT

GCCAAACAGCAGACCGAAGCGATTGATGCGCTGAACAAAGCCTCTTCTGAAAATACACAGAAT

ATCGCCAAAAATCAGGCCGATATTGCCAACAATATCAATAATATCTATGAACTGGCCCAGCAG

CAGGATCAGCACTCTTCTGATATCAAAACACTGGCAAAAGCAAGCGCAGCAAATACCGATCGT

ATTGCGAAAACAAAGCCGATGCAGATGCAAGCTTTGAAACACTGACGAAAAACCAGAACACC

CTGATTGAAAAGATAAAGAACATGATAAACTGATCACCGCCAATAAAACCGCAATTGATGCA

AATAAAGCCAGCGCAGATACCAAATTTGCAGCAACCGCAGATGCAATTACCAAAAATGGCAAT

GCCATCACCAAAAATGCCAAAAGCATTACCGATCTGGGCACCAAAGTTGATGGTTTTGATAGC

CGTGTGACCGCACTGGATACCAAAGCAAGCCATCATCATCACCACCACTAA
```

MC-001 (protein)-(M)(UspA2 amino acids 30-540)(ASHHHHHH)
SEQ ID NO: 53

MQAKNDITLEDLPYLIKKIDQNELEADIGDITALEKYLALSQYGNILALEELNKALEELDEDV

GWNQNDIANLEDDVETLTKNQNALAEQGEAIKEDLQGLADFVEGQEGKILQNETSIKKNTQRN

LVNGFEIEKNKDAIAKNNESIEDLYDFGHEVAESIGEIHAHNEAQNETLKGLITNSIENTNNI

TKNKADIQALENNVVEELFNLSGRLIDQKADIDNNINNIYELAQQQDQHSSDIKTLKKNVEEG

LLELSGHLIDQKTDIAQNQANIQDLATYNELQDQYAQKQTEAIDALNKASSENTQNIEDLAAY

NELQDAYAKQQTEAIDALNKASSENTQNIEDLAAYNELQDAYAKQQTEAIDALNKASSENTQN

IAKNQADIANNINNIYELAQQQDQHSSDIKTLAKASAANTDRIAKNKADADASFETLTKNQNT

LIEKDKEHDKLITANKTAIDANKASADTKFAATADAITKNGNAITKNAKSITDLGTKVDGFDS

RVTALDTKASHHHHHH

MC-002 (DNA)
SEQ ID NO: 54

ATGCAGGCCAAAAATGATATTACCCTGGAAGATCTGCCGTATCTGATCAAAAAAATCGATCAG

AACGAACTGGAAGCCGATATTGGTGATATTACCGCACTGGAAAAATATCTGGCACTGAGCCAG

TATGGAAATATTCTGGCCCTGGAAGAACTGAATAAAGCTCTGGAAGAGCTGGATGAAGATGTG

GGTTGGAATCAGAATGATATCGCCAATCTGGAAGATGATGTTGAAACCCTGACCAAAAATCAG

AATGCACTGGCAGAACAGGGTGAAGCAATTAAAGAAGATCTGCAGGGTCTGGCAGATTTTGTT

GAAGGTCAGGAAGGCAAAATTCTGCAGAACGAAACCAGCATCAAAAAAAACACCCAGCGTAAT

CTGGTGAATGGCTTTGAAATTGAAAAAAACAAAGATGCCATTGCCAAAAACAACGAAAGCATT

GAAGATCTGTATGATTTTGGTCATGAAGTTGCCGAAAGCATTGGTGAAATTCATGCACATAAC

GAAGCACAGAATGAAACCCTGAAAGGTCTGATTACCAACAGCATCGAAAATACCAATAACATT

ACCAAAAACAAAGCAGATATTCAGGCGCTGGAAAATAATGTTGTGGAAGAACTGTTTAATCTG

AGCGGTCGTCTGATTGATCAGAAAGCCGATATCGATAATAACATTAACAACATTTATGAACTG

GCACAGCAGCAGGATCAGCATAGCAGCGATATCAAAACCCTGAAAAAAAACGTTGAAGAAGGT

CTGCTGGAACTGTCTGGTCACCTGATCGATCAGAAAACTGATATTGCCCAGAATCAGGCAAAT

ATTCAGGATCTGGCCACCTATAATGAACTGCAGGATCAGTATGCACAGAAACAGACCGAAGCA

ATTGATGCCCTGAATAAAGCGAGCAGCGAAAACACCCAGAATATCGAAGATCTGGCAGCATAC

AACGAACTGCAGGATGCCTATGCAAAACAGCAGACTGAAGCCATCGACGCACTGAACAAGGCA

AGCTCTGAAAACACGCAGAACATTGAAGATCTGGCTGCCTATAATGAATTACAGGATGCGTAT

GCCAAACAGCAGACCGAAGCGATTGATGCGCTGAACAAAGCCTCTTCTGAAAATACACAGAAT

ATCGCCAAAAATCAGGCCGATATTGCCAACAATATCAATAATATCTATGAACTGGCCCAGCAG

CAGGATCAGCACTCTTCTGATATCAAAACACTGGCAAAAGCAAGCGCAGCAAATACCGATCGT

ATTGCGAAAAACAAAGCCGATGCAGATGCAAGCTTTGAAACACTGACGAAAAACCAGAACACC

CTGATTGAAAAAGATAAAGAACATGATAAACTGATCACCGCCAATAAAACCGCAATTGATGCA

AATAAAGCCAGCGCAGATACCAAATTTGCAGCAACCGCAGATGCAATTACCAAAAATGGCAAT

GCCATCACCAAAAATGCCAAAAGCATTACCGATCTGGGCACCAAAGTTGATGGTTTTGATAGC

CGTGTGACCGCACTGGATACCAAATAA

MC-002 (Protein)-(M)(UspA2 amino acids 30-540)
SEQ ID NO: 55

MQAKNDITLEDLPYLIKKIDQNELEADIGDITALEKYLALSQYGNILALEELNKALEELDEDV

GWNQNDIANLEDDVETLTKNQNALAEQGEAIKEDLQGLADFVEGQEGKILQNETSIKKNTQRN

LVNGFEIEKNKDAIAKNNESIEDLYDFGHEVAESIGEIHAHNEAQNETLKGLITNSIENTNNI

TKNKADIQALENNVVEELFNLSGRLIDQKADIDNNINNIYELAQQQDQHSSDIKTLKKNVEEG

-continued

LLELSGHLIDQKTDIAQNQANIQDLATYNELQDQYAQKQTEAIDALNKASSENTQNIEDLAAY

NELQD

AYAKQQTEAIDALNKASSENTQNIEDLAAYNELQDAYAKQQTEAIDALNKASSENTQNIAKNQ

ADIANNINNIYELAQQQDQHSSDIKTLAKASAANTDRIAKNKADADASFETLTKNQNTLIEKD

KEHDKLITANKTAIDANKASADTKFAATADAITKNGNAITKNAKSITDLGTKVDGFDSRVTAL

DTK

SEQ ID NO: 56
ATGCAGGCCAAAAATGATATTACCCTGGAAGATCTGCCGTATCTGATCAAAAAAATCGATCAG

AACGAACTGGAAGCCGATATTGGTGATATTACCGCACTGGAAAAATATCTGGCACTGAGCCAG

TATGGAAATATTCTGGCCCTGGAAGAACTGAATAAAGCTCTGGAAGAGCTGGATGAAGATGTG

GGTTGGAATCAGAATGATATCGCCAATCTGGAAGATGATGTTGAAACCCTGACCAAAAATCAG

AATGCACTGGCAGAACAGGGTGAAGCAATTAAAGAAGATCTGCAGGGTCTGGCAGATTTTGTT

GAAGGTCAGGAAGGCAAAATTCTGCAGAACGAAACCAGCATCAAAAAAAACACCCAGCGTAAT

CTGGTGAATGGCTTTGAAATTGAAAAAAACAAAGATGCCATTGCCAAAAACAACGAAAGCATT

GAAGATCTGTATGATTTTGGTCATGAAGTTGCCGAAAGCATTGGTGAAATTCATGCACATAAC

GAAGCACAGAATGAAACCCTGAAAGGTCTGATTACCAACAGCATCGAAAATACCAATAACATT

ACCAAAAACAAAGCAGATATTCAGGCGCTGGAAAATAATGTTGTGGAAGAACTGTTTAATCTG

AGCGGTCGTCTGATTGATCAGAAAGCCGATATCGATAATAACATTAACAACATTTATGAACTG

GCACAGCAGCAGGATCAGCATAGCAGCGATATCAAAACCCTGAAAAAAAACGTTGAAGAAGGT

CTGCTGGAACTGTCTGGTCACCTGATCGATCAGAAAACTGATATTGCCCAGAATCAGGCAAAT

ATTCAGGATCTGGCCACCTATAATGAACTGCAGGATCAGTATGCACAGAAACAGACCGAAGCA

ATTGATGCCCTGAATAAAGCGAGCAGCGAAAACACCCAGAATATCGAAGATCTGGCAGCATAC

AACGAACTGCAGGATGCCTATGCAAAACAGCAGACTGAAGCCATCGACGCACTGAACAAGGCA

AGCTCTGAAAACACGCAGAACATTGAAGATCTGGCTGCCTATAATGAATTACAGGATGCGTAT

GCCAAACAGCAGACCGAAGCGATTGATGCGCTGAACAAAGCCTCTTCTGAAAATACACAGAAT

ATCGCCAAAAATCAGGCCGATATTGCCAACAATATCAATAATATCTATGAACTGGCCCAGCAG

CAGGATCAGCACTCTTCTGATATCAAAACACTGGCAAAGCAAGCGCAGCAAATACCGATCGT

ATTGCGAAAAACAAAGCCGATGCAGATGCAAGCTTTGAAACACTGACGAAAAACCAGAACACC

CTGATTGAAAAAGATAAAGAACATGATAAACTGATCACCGCCAATAAAACCGCAATTGATGCA

AATAAAGCCAGCGCAGATACCAAATTTGCAGCAACCGCAGATGCAATTACCAAAAATGGCAAT

GCCATCACCAAAAATGCCAAAAGCATTACCGATCTGGGCACCAAAGTTGATGGTTTTGATAGC

CGTGTGACCGCACTGGATACCAAAGTTAATGCATTTGATGGTCGTATTACCGCTCTGGATAGT

AAAGTTGAAAATGGAATGGCAGCACAAGCAGCACACTAA

SEQ ID NO: 57
MQAKNDITLEDLPYLIKKIDQNELEADIGDITALEKYLALSQYGNILALEELNKALEELDEDV

GWNQNDIANLEDDVETLTKNQNALAEQGEAIKEDLQGLADFVEGQEGKILQNETSIKKNTQRN

LVNGFEIEKNKDAIAKNNESIEDLYDFGHEVAESIGEIHAHNEAQNETLKGLITNSIENTNNI

TKNKADIQALENNVVEELFNLSGRLIDQKADIDNNINNIYELAQQQDQHSSDIKTLKKNVEEG

LLELSGHLIDQKTDIAQNQANIQDLATYNELQDQYAQKQTEAIDALNKASSENTQNIEDLAAY

NELQDAYAKQQTEAIDALNKASSENTQNIEDLAAYNELQDAYAKQQTEAIDALNKASSENTQN

IAKNQADIANNINNIYELAQQQDQHSSDIKTLAKASAANTDRIAKNKADADASFETLTKNQNT

-continued

LIEKDKEHDKLITANKTAIDANKASADTKFAATADAITKNGNAITKNAKSITDLGTKVDGFDS

RVTALDTKVNAFDGRITALDSKVENGMAAQAAH

MC-003 (DNA)
SEQ ID NO: 87
ATGCAGGCCAAAAATGATATTACCCTGGAAGATCTGCCGTATCTGATCAAAAAAATCGATCAG

AACGAACTGGAAGCCGATATTGGTGATATTACCGCACTGGAAAAATATCTGGCACTGAGCCAG

TATGGAAATATTCTGGCCCTGGAAGAACTGAATAAAGCTCTGGAAGAGCTGGATGAAGATGTG

GGTTGGAATCAGAATGATATCGCCAATCTGGAAGATGATGTTGAAACCCTGACCAAAAATCAG

AATGCACTGGCAGAACAGGGTGAAGCAATTAAAGAAGATCTGCAGGGTCTGGCAGATTTTGTT

GAAGGTCAGGAAGGCAAAATTCTGCAGAACGAAACCAGCATCAAAAAAAACACCCAGCGTAAT

CTGGTGAATGGCTTTGAAATTGAAAAAAACAAAGATGCCATTGCCAAAAACAACGAAAGCATT

GAAGATCTGTATGATTTTGGTCATGAAGTTGCCGAAAGCATTGGTGAAATTCATGCACATAAC

GAAGCACAGAATGAAACCCTGAAAGGTCTGATTACCAACAGCATCGAAAATACCAATAACATT

ACCAAAAACAAAGCAGATATTCAGGCGCTGGAAAATAATGTTGTGGAAGAACTGTTTAATCTG

AGCGGTCGTCTGATTGATCAGAAAGCCGATATCGATAATAACATTAACAACATTTATGAACTG

GCACAGCAGCAGGATCAGCATAGCAGCGATATCAAAACCCTGAAAAAAAACGTTGAAGAAGGT

CTGCTGGAACTGTCTGGTCACCTGATCGATCAGAAAACTGATATTGCCCAGAATCAGGCAAAT

ATTCAGGATCTGGCCACCTATAATGAACTGCAGGATCAGTATGCACAGAAACAGACCGAAGCA

ATTGATGCCCTGAATAAAGCGAGCAGCGAAAACACCCAGAATATCGAAGATCTGGCAGCATAC

AACGAACTGCAGGATGCCTATGCAAAACAGCAGACTGAAGCCATCGACGCACTGAACAAGGCA

AGCTCTGAAAACACGCAGAACATTGAAGATCTGGCTGCCTATAATGAATTACAGGATGCGTAT

GCCAAACAGCAGACCGAAGCGATTGATGCGCTGAACAAAGCCTCTTCTGAAAATACACAGAAT

ATCGCCAAAAATCAGGCCGATATTGCCAACAATATCAATAATATCTATGAACTGGCCCAGCAG

CAGGATCAGCACTCTTCTGATATCAAAACACTGGCAAAGCAAGCGCAGCAAATACCGATCGT

ATTGCGAAAACAAAGCCGATGCAGATGCAAGCTTTGAAACACTGACGAAAAACCAGAACACC

CTGATTGAAAAAGATAAAGAACATGATAAACTGATCACCGCCAATAAAACCGCAATTGATGCA

AATAAAGCCAGCGCAGATACCAAATTTGCAGCAACCGCAGATGCAATTACCAAAAATGGCAAT

GCCATCACCAAAAATGCCAAAAGCATTACCGATCTGGGCACCAAAGTTGATGGTTTTGATAGC

CGTGTGACCGCACTGGATACCAAACACTAA

MC-003 (Protein)-(M)(UspA2 amino acids 30-540)(H)
SEQ ID NO: 88
MQAKNDITLEDLPYLIKKIDQNELEADIGDITALEKYLALSQYGNILALEELNKALEELDEDV

GWNQNDIANLEDDVETLTKNQNALAEQGEAIKEDLQGLADFVEGQEGKILQNETSIKKNTQRN

LVNGFEIEKNKDAIAKNNESIEDLYDFGHEVAESIGEIHAHNEAQNETLKGLITNSIENTNNI

TKNKADIQALENNVVEELFNLSGRLIDQKADIDNNINNIYELAQQQDQHSSDIKTLKKNVEEG

LLELSGHLIDQKTDIAQNQANIQDLATYNELQDQYAQKQTEAIDALNKASSENTQNIEDLAAY

NELQDAYAKQQTEAIDALNKASSENTQNIEDLAAYNELQDAYAKQQTEAIDALNKASSENTQN

IAKNQADIANNINNIYELAQQQDQHSSDIKTLAKASAANTDRIAKNKADADASFETLTKNQNT

LIEKDKEHDKLITANKTAIDANKASADTKFAATADAITKNGNAITKNAKSITDLGTKVDGFDS

RVTALDTKH

MC-004 (DNA)
SEQ ID NO: 58
ATGCAGGCCAAAAATGATATTACCCTGGAAGATCTGCCGTATCTGATCAAAAAAATCGATCAG

AACGAACTGGAAGCCGATATTGGTGATATTACCGCACTGGAAAAATATCTGGCACTGAGCCAG

-continued

```
TATGGAAATATTCTGGCCCTGGAAGAACTGAATAAAGCTCTGGAAGAGCTGGATGAAGATGTG

GGTTGGAATCAGAATGATATCGCCAATCTGGAAGATGATGTTGAAACCCTGACCAAAAATCAG

AATGCACTGGCAGAACAGGGTGAAGCAATTAAAGAAGATCTGCAGGGTCTGGCAGATTTTGTT

GAAGGTCAGGAAGGCAAAATTCTGCAGAACGAAACCAGCATCAAAAAAAACACCCAGCGTAAT

CTGGTGAATGGCTTTGAAATTGAAAAAAACAAAGATGCCATTGCCAAAAACAACGAAAGCATT

GAAGATCTGTATGATTTTGGTCATGAAGTTGCCGAAAGCATTGGTGAAATTCATGCACATAAC

GAAGCACAGAATGAAACCCTGAAAGGTCTGATTACCAACAGCATCGAAAATACCAATAACATT

ACCAAAAACAAAGCAGATATTCAGGCGCTGGAAAATAATGTTGTGGAAGAACTGTTTAATCTG

AGCGGTCGTCTGATTGATCAGAAAGCCGATATCGATAATAACATTAACAACATTTATGAACTG

GCACAGCAGCAGGATCAGCATAGCAGCGATATCAAAACCCTGAAAAAAAACGTTGAAGAAGGT

CTGCTGGAACTGTCTGGTCACCTGATCGATCAGAAAACTGATATTGCCCAGAATCAGGCAAAT

ATTCAGGATCTGGCCACCTATAATGAACTGCAGGATCAGTATGCACAGAAACAGACCGAAGCA

ATTGATGCCCTGAATAAAGCGAGCAGCGAAAACACCCAGAATATCGAAGATCTGGCAGCATAC

AACGAACTGCAGGATGCCTATGCAAAACAGCAGACTGAAGCCATCGACGCACTGAACAAGGCA

AGCTCTGAAAACACGCAGAACATTGAAGATCTGGCTGCCTATAATGAATTACAGGATGCGTAT

GCCAAACAGCAGACCGAAGCGATTGATGCGCTGAACAAAGCCTCTTCTGAAAATACACAGAAT

ATCGCCAAAAATCAGGCCGATATTGCCAACAATATCAATAATATCTATGAACTGGCCCAGCAG

CAGGATCAGCACTCTTCTGATATCAAAACACTGGCAAAAGCAAGCGCAGCAAATACCGATCGT

ATTGCGAAAAACAAAGCCGATGCAGATGCAAGCTTTGAAACACTGACGAAAAACCAGAACACC

CTGATTGAAAAAGATAAAGAACATGATAAACTGATCACCGCCAATAAAACCGCAATTGATGCA

AATAAAGCCAGCGCAGATACCAAATTTGCAGCAACCGCAGATGCAATTACCAAAAATGGCAAT

GCCATCACCAAAAATGCCAAAAGCATTACCGATCTGGGCACCAAAGTTGATGGTTTTGATAGC

CGTGTGACCGCACTGGATACCAAACATCATTAA
```

MC-004 (Protein)-(M)(UspA2 amino acids 30-540)(HH)
SEQ ID NO: 59

```
MQAKNDITLEDLPYLIKKIDQNELEADIGDITALEKYLALSQYGNILALEELNKALEELDEDV

GWNQNDIANLEDDVETLTKNQNALAEQGEAIKEDLQGLADFVEGQEGKILQNETSIKKNTQRN

LVNGFEIEKNKDAIAKNNESIEDLYDFGHEVAESIGEIHAHNEAQNETLKGLITNSIENTNNI

TKNKADIQALENNVVEELFNLSGRLIDQKADIDNNINNIYELAQQQDQHSSDIKTLKKNVEEG

LLELSGHLIDQKTDIAQNQANIQDLATYNELQDQYAQKQTEAIDALNKASSENTQNIEDLAAY

NELQDAYAKQQTEAIDALNKASSENTQNIEDLAAYNELQDAYAKQQTEAIDALNKASSENTQN

IAKNQADIANNINNIYELAQQQDQHSSDIKTLAKASAANTDRIAKNKADADASFETLTKNQNT

LIEKDKEHDKLITANKTAIDANKASADTKFAATADAITKNGNAITKNAKSITDLGTKVDGFDS

RVTALDTKHH
```

MC-005 (DNA)
SEQ ID NO: 60

```
ATGCAGGCCAAAAATGATATTACCCTGGAAGATCTGCCGTATCTGATCAAAAAAATCGATCAG

AACGAACTGGAAGCCGATATTGGTGATATTACCGCACTGGAAAAATATCTGGCACTGAGCCAG

TATGGAAATATTCTGGCCCTGGAAGAACTGAATAAAGCTCTGGAAGAGCTGGATGAAGATGTG

GGTTGGAATCAGAATGATATCGCCAATCTGGAAGATGATGTTGAAACCCTGACCAAAAATCAG

AATGCACTGGCAGAACAGGGTGAAGCAATTAAAGAAGATCTGCAGGGTCTGGCAGATTTTGTT

GAAGGTCAGGAAGGCAAAATTCTGCAGAACGAAACCAGCATCAAAAAAAACACCCAGCGTAAT
```

```
CTGGTGAATGGCTTTGAAATTGAAAAAAACAAAGATGCCATTGCCAAAAACAACGAAAGCATT
GAAGATCTGTATGATTTTGGTCATGAAGTTGCCGAAAGCATTGGTGAAATTCATGCACATAAC
GAAGCACAGAATGAAACCCTGAAAGGTCTGATTACCAACAGCATCGAAAATACCAATAACATT
ACCAAAAACAAAGCAGATATTCAGGCGCTGGAAAATAATGTTGTGGAAGAACTGTTTAATCTG
AGCGGTCGTCTGATTGATCAGAAAGCCGATATCGATAATAACATTAACAACATTTATGAACTG
GCACAGCAGCAGGATCAGCATAGCAGCGATATCAAACCCTGAAAACGTTGAAAAAAAAGAAGGT
CTGCTGGAACTGTCTGGTCACCTGATCGATCAGAAAACTGATATTGCCCAGAATCAGGCAAAT
ATTCAGGATCTGGCCACCTATAATGAACTGCAGGATCAGTATGCACAGAAACAGACCGAAGCA
ATTGATGCCCTGAATAAAGCGAGCAGCGAAAACACCCAGAATATCGAAGATCTGGCAGCATAC
AACGAACTGCAGGATGCCTATGCAAAACAGCAGACTGAAGCCATCGACGCACTGAACAAGGCA
AGCTCTGAAAACACGCAGAACATTGAAGATCTGGCTGCCTATAATGAATTACAGGATGCGTAT
GCCAAACAGCAGACCGAAGCGATTGATGCGCTGAACAAAGCCTCTTCTGAAAATACACAGAAT
ATCGCCAAAAATCAGGCCGATATTGCCAACAATATCAATAATATCTATGAACTGGCCCAGCAG
CAGGATCAGCACTCTTCTGATATCAAAACACTGGCAAAAGCAAGCGCAGCAAATACCGATCGT
ATTGCGAAAAACAAAGCCGATGCAGATGCAAGCTTTGAAACACTGACGAAAAACCAGAACACC
CTGATTGAAAAAGATAAAGAACATGATAAACTGATCACCGCCAATAAAACCGCAATTGATGCA
AATAAAGCCAGCGCAGATACCAAATTTGCAGCAACCGCAGATGCAATTACCAAAAATGGCAAT
GCCATCACCAAAAATGCCAAAAGCGCAAGCCATCATCATCACCACCACTAA
```

MC-005 (Protein)-(M)(UspA2 amino acids 30-519)(ASHHHHHH)

SEQ ID NO: 61

```
MQAKNDITLEDLPYLIKKIDQNELEADIGDITALEKYLALSQYGNILALEELNKALEELDEDV
GWNQNDIANLEDDVETLTKNQNALAEQGEAIKEDLQGLADFVEGQEGKILQNETSIKKNTQRN
LVNGFEIEKNKDAIAKNNESIEDLYDFGHEVAESIGEIHAHNEAQNETLKGLITNSIENTNNI
TKNKADIQALENNVVEELFNLSGRLIDQKADIDNNINNIYELAQQQDQHSSDIKTLKKNVEEG
LLELSGHLIDQKTDIAQNQANIQDLATYNELQDQYAQKQTEAIDALNKASSENTQNIEDLAAY
NELQDAYAKQQTEAIDALNKASSENTQNIEDLAAYNELQDAYAKQQTEAIDALNKASSENTQN
IAKNQADIANNINNIYELAQQQDQHSSDIKTLAKASAANTDRIAKNKADADASFETLTKNQNT
LIEKDKEHDKLITANKTAIDANKASADTKFAATADAITKNGNAITKNAKSASHHHHHH
```

MC-006 (DNA)

SEQ ID NO: 62

```
ATGCAGGCCAAAAATGATATTACCCTGGAAGATCTGCCGTATCTGATCAAAAAAATCGATCAG
AACGAACTGGAAGCCGATATTGGTGATATTACCGCACTGGAAAAATATCTGGCACTGAGCCAG
TATGGAAATATTCTGGCCCTGGAAGAACTGAATAAAGCTCTGGAAGAGCTGGATGAAGATGTG
GGTTGGAATCAGAATGATATCGCCAATCTGGAAGATGATGTTGAAACCCTGACCAAAAATCAG
AATGCACTGGCAGAACAGGGTGAAGCAATTAAAGAAGATCTGCAGGGTCTGGCAGATTTTGTT
GAAGGTCAGGAAGGCAAAATTCTGCAGAACGAAACCAGCATCAAAAAAAACACCCAGCGTAAT
CTGGTGAATGGCTTTGAAATTGAAAAAAACAAAGATGCCATTGCCAAAAACAACGAAAGCATT
GAAGATCTGTATGATTTTGGTCATGAAGTTGCCGAAAGCATTGGTGAAATTCATGCACATAAC
GAAGCACAGAATGAAACCCTGAAAGGTCTGATTACCAACAGCATCGAAAATACCAATAACATT
ACCAAAAACAAAGCAGATATTCAGGCGCTGGAAAATAATGTTGTGGAAGAACTGTTTAATCTG
AGCGGTCGTCTGATTGATCAGAAAGCCGATATCGATAATAACATTAACAACATTTATGAACTG
GCACAGCAGCAGGATCAGCATAGCAGCGATATCAAACCCTGAAAAAAAACGTTGAAGAAGGT
CTGCTGGAACTGTCTGGTCACCTGATCGATCAGAAAACTGATATTGCCCAGAATCAGGCAAAT
```

-continued

```
ATTCAGGATCTGGCCACCTATAATGAACTGCAGGATCAGTATGCACAGAAACAGACCGAAGCA

ATTGATGCCCTGAATAAAGCGAGCAGCGAAAACACCCAGAATATCGAAGATCTGGCAGCATAC

AACGAACTGCAGGATGCCTATGCAAAACAGCAGACTGAAGCCATCGACGCACTGAACAAGGCA

AGCTCTGAAAACACGCAGAACATTGAAGATCTGGCTGCCTATAATGAATTACAGGATGCGTAT

GCCAAACAGCAGACCGAAGCGATTGATGCGCTGAACAAAGCCTCTTCTGAAAATACACAGAAT

ATCGCCAAAAATCAGGCCGATATTGCCAACAATATCAATAATATCTATGAACTGGCCCAGCAG

CAGGATCAGCACTCTTCTGATATCAAAACACTGGCAAAAGCAAGCGCAGCAAATACCGATCGT

ATTGCGAAAAACAAAGCCGATGCAGATGCAAGCTTTGAAACACTGACGAAAAACCAGAACACC

CTGATTGAAAAAGATAAAGAACATGATAAACTGATCACCGCCAATAAAACCGCAATTGATGCA

AATAAAGCCAGCGCAGATACCAAATTTGCAGCAACCGCAGATGCAATTACCAAAAATGGCAAT

GCCATCACCAAAAATGCCAAAAGCTAA
```

MC-006 (Protein)-(M)(UspA2 amino acids 30-519)

SEQ ID NO: 63

```
MQAKNDITLEDLPYLIKKIDQNELEADIGDITALEKYLALSQYGNILALEELNKALEELDEDV

GWNQNDIANLEDDVETLTKNQNALAEQGEAIKEDLQGLADFVEGQEGKILQNETSIKKNTQRN

LVNGFEIEKNKDAIAKNNESIEDLYDFGHEVAESIGEIHAHNEAQNETLKGLITNSIENTNNI

TKNKADIQALENNVVEELFNLSGRLIDQKADIDNNINNIYELAQQQDQHSSDIKTLKKNVEEG

LLELSGHLIDQKTDIAQNQANIQDLATYNELQDQYAQKQTEAIDALNKASSENTQNIEDLAAY

NELQDAYAKQQTEAIDALNKASSENTQNIEDLAAYNELQDAYAKQQTEAIDALNKASSENTQN

IAKNQADIANNINNIYELAQQQDQHSSDIKTLAKASAANTDRIAKNKADADASFETLTKNQNT

LIEKDKEHDKLITANKTAIDANKASADTKFAATADAITKNGNAITKNAKS
```

MC-007 (DNA)

SEQ ID NO: 64

```
ATGCAGGCCAAAAATGATATTACCCTGGAAGATCTGCCGTATCTGATCAAAAAAATCGATCAG

AACGAACTGGAAGCCGATATTGGTGATATTACCGCACTGGAAAAATATCTGGCACTGAGCCAG

TATGGAAATATTCTGGCCCTGGAAGAACTGAATAAAGCTCTGGAAGAGCTGGATGAAGATGTG

GGTTGGAATCAGAATGATATCGCCAATCTGGAAGATGATGTTGAAACCCTGACCAAAAATCAG

AATGCACTGGCAGAACAGGGTGAAGCAATTAAAGAAGATCTGCAGGGTCTGGCAGATTTTGTT

GAAGGTCAGGAAGGCAAAATTCTGCAGAACGAAACCAGCATCAAAAAAAACACCCAGCGTAAT

CTGGTGAATGGCTTTGAAATTGAAAAAAACAAAGATGCCATTGCCAAAAACAACGAAAGCATT

GAAGATCTGTATGATTTTGGTCATGAAGTTGCCGAAAGCATTGGTGAAATTCATGCACATAAC

GAAGCACAGAATGAAACCCTGAAAGGTCTGATTACCAACAGCATCGAAAATACCAATAACATT

ACCAAAAACAAAGCAGATATTCAGGCGCTGGAAAATAATGTTGTGGAAGAACTGTTTAATCTG

AGCGGTCGTCTGATTGATCAGAAAGCCGATATCGATAATAACATTAACAACATTTATGAACTG

GCACAGCAGCAGGATCAGCATAGCAGCGATATCAAAACCCTGAAAAAAAACGTTGAAGAAGGT

CTGCTGGAACTGTCTGGTCACCTGATCGATCAGAAAACTGATATTGCCCAGAATCAGGCAAAT

ATTCAGGATCTGGCCACCTATAATGAACTGCAGGATCAGTATGCACAGAAACAGACCGAAGCA

ATTGATGCCCTGAATAAAGCGAGCAGCGAAAACACCCAGAATATCGAAGATCTGGCAGCATAC

AACGAACTGCAGGATGCCTATGCAAAACAGCAGACTGAAGCCATCGACGCACTGAACAAGGCA

AGCTCTGAAAACACGCAGAACATTGAAGATCTGGCTGCCTATAATGAATTACAGGATGCGTAT

GCCAAACAGCAGACCGAAGCGATTGATGCGCTGAACAAAGCCTCTTCTGAAAATACACAGAAT

ATCGCCAAAAATCAGGCCGATATTGCCAACAATATCAATAATATCTATGAACTGGCCCAGCAG
```

-continued

```
CAGGATCAGCACTCTTCTGATATCAAAACACTGGCAAAAGCAAGCGCAGCAAATACCGATCGT

ATTGCGAAAAACAAAGCCGATGCAGATGCAAGCTTTGAAACACTGACGAAAAACCAGAACACC

CTGATTGAAAAAGATAAAGAACATGATAAACTGATCACCGCCAATAAAACCGCAATTGATGCA

AATAAAGCCAGCGCAGATACCAAATTTGCAGCAACCGCAGATGCAATTACCAAAAATGGCAAT

GCCATCACCAAAAATGCCAAAAGCATTACCGATCTGGGCACCAAAGTTGATGGTTTTGATAGC

CGTGTGACCGCACTGGATACCAAAGTTAATGCATTTGATGGTCGTATTACCGCTCTGGATAGT

AAAGTTGAATGGTATGGCAGCACAGGCAGCAGCAAGCCATCATCATCACCACCACTAA
```

MC-007 (Protein)-(M)(UspA2 amino acids 30-564)(ASHHHHHH)

SEQ ID NO: 65

```
MQAKNDITLEDLPYLIKKIDQNELEADIGDITALEKYLALSQYGNILALEELNKALEELDEDV

GWNQNDIANLEDDVETLTKNQNALAEQGEAIKEDLQGLADFVEGQEGKILQNETSIKKNTQRN

LVNGFEIEKNKDAIAKNNESIEDLYDFGHEVAESIGEIHAHNEAQNETLKGLITNSIENTNNI

TKNKADIQALENNVVEELFNLSGRLIDQKADIDNNINNIYELAQQQDQHSSDIKTLKKNVEEG

LLELSGHLIDQKTDIAQNQANIQDLATYNELQDQYAQKQTEAIDALNKASSENTQNIEDLAAY

NELQDAYAKQQTEAIDALNKASSENTQNIEDLAAYNELQDAYAKQQTEAIDALNKASSENTQN

IAKNQADIANNINNIYELAQQQDQHSSDIKTLAKASAANTDRIAKNKADADASFETLTKNQNT

LIEKDKEHDKLITANKTAIDANKASADTKFAATADAITKNGNAITKNAKSITDLGTKVDGFDS

RVTALDTKVNAFDGRITALDSKVENGMAAQAAASHHHHHH
```

MC-008 (DNA)

SEQ ID NO: 66

```
ATGCAGGCCAAAAATGATATTACCCTGGAAGATCTGCCGTATCTGATCAAAAAAATCGATCAG

AACGAACTGGAAGCCGATATTGGTGATATTACCGCACTGGAAAAATATCTGGCACTGAGCCAG

TATGGAAATATTCTGGCCCTGGAAGAACTGAATAAAGCTCTGGAAGAGCTGGATGAAGATGTG

GGTTGGAATCAGAATGATATCGCCAATCTGGAAGATGATGTTGAAACCCTGACCAAAAATCAG

AATGCACTGGCAGAACAGGGTGAAGCAATTAAAGAAGATCTGCAGGGTCTGGCAGATTTTGTT

GAAGGTCAGGAAGGCAAAATTCTGCAGAACGAAACCAGCATCAAAAAAAACACCCAGCGTAAT

CTGGTGAATGGCTTTGAAATTGAAAAAAACAAAGATGCCATTGCCAAAAACAACGAAAGCATT

GAAGATCTGTATGATTTTGGTCATGAAGTTGCCGAAAGCATTGGTGAAATTCATGCACATAAC

GAAGCACAGAATGAAACCCTGAAAGGTCTGATTACCAACAGCATCGAAAATACCAATAACATT

ACCAAAAACAAAGCAGATATTCAGGCGCTGGAAAATAATGTTGTGGAAGAACTGTTTAATCTG

AGCGGTCGTCTGATTGATCAGAAAGCCGATATCGATAATAACATTAACAACATTTATGAACTG

GCACAGCAGCAGGATCAGCATAGCAGCGATATCAAAACCCTGAAAAAAAACGTTGAAGAAGGT

CTGCTGGAACTGTCTGGTCACCTGATCGATCAGAAAACTGATATTGCCCAGAATCAGGCAAAT

ATTCAGGATCTGGCCACCTATAATGAACTGCAGGATCAGTATGCACAGAAACAGACCGAAGCA

ATTGATGCCCTGAATAAAGCGAGCAGCGAAAACACCCAGAATATCGAAGATCTGGCAGCATAC

AACGAACTGCAGGATGCCTATGCAAAACAGCAGACTGAAGCCATCGACGCACTGAACAAGGCA

AGCTCTGAAAACACGCAGAACATTGAAGATCTGGCTGCCTATAATGAATTACAGGATGCGTAT

GCCAAACAGCAGACCGAAGCGATTGATGCGCTGAACAAAGCCTCTTCTGAAAATACACAGAAT

ATCGCCAAAAATCAGGCCGATATTGCCAACAATATCAATAATATCTATGAACTGGCCCAGCAG

CAGGATCAGCACTCTTCTGATATCAAAACACTGGCAAAAGCAAGCGCAGCAAATACCGATCGT

ATTGCGAAAAACAAAGCCGATGCAGATGCAAGCTTTGAAACACTGACGAAAAACCAGAACACC

CTGATTGAAAAAGATAAAGAACATGATAAACTGATCACCGCCAATAAAACCGCAATTGATGCA

AATAAAGCCAGCGCAGATACCAAATTTGCAGCAACCGCAGATGCAATTACCAAAAATGGCAAT
```

```
GCCATCACCAAAAATGCCAAAAGCATTACCGATCTGGGCACCAAAGTTGATGGTTTTGATAGC

CGTGTGACCGCACTGGATACCAAAGTTAATGCATTTGATGGTCGTATTACCGCTCTGGATAGT

AAAGTTGAAAATGGTATGGCAGCACAGGCAGCACACCACTAA
```

MC-008 (Protein)-(M)(UspA2 30-564)(HH)
                                          SEQ ID NO: 67

```
MQAKNDITLEDLPYLIKKIDQNELEADIGDITALEKYLALSQYGNILALEELNKALEELDEDV

GWNQNDIANLEDDVETLTKNQNALAEQGEAIKEDLQGLADFVEGQEGKILQNETSIKKNTQRN

LVNGFEIEKNKDAIAKNNESIEDLYDFGHEVAESIGEIHAHNEAQNETLKGLITNSIENTNNI

TKNKADIQALENNVVEELFNLSGRLIDQKADIDNNINNIYELAQQQDQHSSDIKTLKKNVEEG

LLELSGHLIDQKTDIAQNQANIQDLATYNELQDQYAQKQTEAIDALNKASSENTQNIEDLAAY

NELQDAYAKQQTEAIDALNKASSENTQNIEDLAAYNELQDAYAKQQTEAIDALNKASSENTQN

IAKNQADIANNINNIYELAQQQDQHSSDIKTLAKASAANTDRIAKNKADADASFETLTKNQNT

LIEKDKEHDKLITANKTAIDANKASADTKFAATADAITKNGNAITKNAKSITDLGTKVDGFDS

RVTALDTKVNAFDGRITALDSKVENGMAAQAAHH
```

MC-009 (DNA)
                                          SEQ ID NO: 68

```
ATGGCGAAAAATGATATTACCCTGGAAGATCTGCCGTATCTGATCAAAAAAATCGATCAGAAC

GAACTGGAAGCCGATATTGGTGATATTACCGCACTGGAAAAATATCTGGCACTGAGCCAGTAT

GGAAATATTCTGGCCCTGGAAGAACTGAATAAAGCTCTGGAAGAGCTGGATGAAGATGTGGGT

TGGAATCAGAATGATATCGCCAATCTGGAAGATGATGTTGAAACCCTGACCAAAAATCAGAAT

GCACTGGCAGAACAGGGTGAAGCAATTAAAGAAGATCTGCAGGGTCTGGCAGATTTTGTTGAA

GGTCAGGAAGGCAAAATTCTGCAGAACGAAACCAGCATCAAAAAAAACACCCAGCGTAATCTG

GTGAATGGCTTTGAAATTGAAAAAAACAAAGATGCCATTGCCAAAAACAACGAAAGCATTGAA

GATCTGTATGATTTTGGTCATGAAGTTGCCGAAAGCATTGGTGAAATTCATGCACATAACGAA

GCACAGAATGAAACCCTGAAAGGTCTGATTACCAACAGCATCGAAAATACCAATAACATTACC

AAAAACAAAGCAGATATTCAGGCGCTGGAAAATAATGTTGTGGAAGAACTGTTTAATCTGAGC

GGTCGTCTGATTGATCAGAAAGCCGATATCGATAATAACATTAACAACATTTATGAACTGGCA

CAGCAGCAGGATCAGCATAGCAGCGATATCAAAACCCTGAAAAAAAACGTTGAAGAAGGTCTG

CTGGAACTGTCTGGTCACCTGATCGATCAGAAAACTGATATTGCCCAGAATCAGGCAAATATT

CAGGATCTGGCCACCTATAATGAACTGCAGGATCAGTATGCACAGAAACAGACCGAAGCAATT

GATGCCCTGAATAAAGCGAGCAGCGAAAACACCCAGAATATCGAAGATCTGGCAGCATACAAC

GAACTGCAGGATGCCTATGCAAAACAGCAGACTGAAGCCATCGACGCACTGAACAAGGCAAGC

TCTGAAAACACGCAGAACATTGAAGATCTGGCTGCCTATAATGAATTACAGGATGCGTATGCC

AAACAGCAGACCGAAGCGATTGATGCGCTGAACAAAGCCTCTTCTGAAAATACACAGAATATC

GCCAAAAATCAGGCCGATATTGCCAACAATATCAATAATATCTATGAACTGGCCCAGCAGCAG

GATCAGCACTCTTCTGATATCAAAACACTGGCAAAAGCAAGCGCAGCAAATACCGATCGTATT

GCGAAAAACAAAGCCGATGCAGATGCAAGCTTTGAAACACTGACGAAAAACCAGAACACCCTG

ATTGAAAAGATAAAGAACATGATAAACTGATCACCGCCAATAAAACCGCAATTGATGCAAAT

AAAGCCAGCGCAGATACCAAATTTGCAGCAACCGCAGATGCAATTACCAAAAATGGCAATGCC

ATCACCAAAAATGCCAAAAGCATTACCGATCTGGGCACCAAAGTTGATGGTTTTGATAGCCGT

GTGACCGCACTGGATACCAAAGTTAATGCATTTGATGGTCGTATTACCGCTCTGGATAGTAAA

GTTGAAAATGGTATGGCAGCACAGGCAGCACACCACTAA
```

MC-009 (Protein)-(M)(UspA2 31-564)(HH)
SEQ ID NO: 69

MAKNDITLEDLPYLIKKIDQNELEADIGDITALEKYLALSQYGNILALEELNKALEELDEDVG
WNQNDIANLEDDVETLTKNQNALAEQGEAIKEDLQGLADFVEGQEGKILQNETSIKKNTQRNL
VNGFEIEKNKDAIAKNNESIEDLYDFGHEVAESIGEIHAHNEAQNETLKGLITNSIENTNNIT
KNKADIQALENNVVEELFNLSGRLIDQKADIDNNINNIYELAQQQDQHSSDIKTLKKNVEEGL
LELSGHLIDQKTDIAQNQANIQDLATYNELQDQYAQKQTEAIDALNKASSENTQNIEDLAAYN
ELQDAYAKQQTEAIDALNKASSENTQNIEDLAAYNELQDAYAKQQTEAIDALNKASSENTQNI
AKNQADIANNINNIYELAQQQDQHSSDIKTLAKASAANTDRIAKNKADADASFETLTKNQNTL
IEKDKEHDKLITANKTAIDANKASADTKFAATADAITKNGNAITKNAKSITDLGTKVDGFDSR
VTALDTKVNAFDGRITALDSKVENGMAAQAAHH

MC-010 (DNA)
SEQ ID NO: 70

ATGCAGGCCAAAAATGATATTACCCTGGAAGATCTGCCGTATCTGATCAAAAAAATCGATCAG
AACGAACTGGAAGCCGATATTGGTGATATTACCGCACTGGAAAAATATCTGGCACTGAGCCAG
TATGGAAATATTCTGGCCCTGGAAGAACTGAATAAAGCTCTGGAAGAGCTGGATGAAGATGTG
GGTTGGAATCAGAATGATATCGCCAATCTGGAAGATGATGTTGAAACCCTGACCAAAAATCAG
AATGCACTGGCAGAACAGGGTGAAGCAATTAAAGAAGATCTGCAGGGTCTGGCAGATTTTGTT
GAAGGTCAGGAAGGCAAAATTCTGCAGAACGAAACCAGCATCAAAAAAAACACCCAGCGTAAT
CTGGTGAATGGCTTTGAAATTGAAAAAAACAAAGATGCCATTGCCAAAAACAACGAAAGCATT
GAAGATCTGTATGATTTTGGTCATGAAGTTGCCGAAAGCATTGGTGAAATTCATGCACATAAC
GAAGCACAGAATGAAACCCTGAAAGGTCTGATTACCAACAGCATCGAAAATACCAATAACATT
ACCAAAAACAAAGCAGATATTCAGGCGCTGGAAAATAATGTTGTGGAAGAACTGTTTAATCTG
AGCGGTCGTCTGATTGATCAGAAAGCCGATATCGATAATAACATTAACAACATTTATGAACTG
GCACAGCAGCAGGATCAGCATAGCAGCGATATCAAAACCCTGAAAAAAAACGTTGAAGAAGGT
CTGCTGGAACTGTCTGGTCACCTGATCGATCAGAAAACTGATATTGCCCAGAATCAGGCAAAT
ATTCAGGATCTGGCCACCTATAATGAACTGCAGGATCAGTATGCACAGAAAACAGACCGAAGCA
ATTGATGCCCTGAATAAAGCGAGCAGCGAAAACACCCAGAATATCGAAGATCTGGCAGCATAC
AACGAACTGCAGGATGCCTATGCAAAACAGCAGACTGAAGCCATCGACGCACTGAACAAGGCA
AGCTCTGAAAACACGCAGAACATTGAAGATCTGGCTGCCTATAATGAATTACAGGATGCGTAT
GCCAAACAGCAGACCGAAGCGATTGATGCGCTGAACAAAGCCTCTTCTGAAAATACACAGAAT
ATCGCCAAAAATCAGGCCGATATTGCCAACAATATCAATAATATCTATGAACTGGCCCAGCAG
CAGGATCAGCACTCTTCTGATATCAAAACACTGGCAAAAGCAAGCGCAGCAAATACCGATCGT
ATTGCGAAAAACAAAGCCGATGCAGATGCAAGCTTTGAAACACTGACGAAAAACCAGAACACC
CTGATTGAAAAAGATAAAGAACATGATAAACTGATCACCGCCAATAAAACCGCAATTGATGCA
AATAAAGCCAGCGCAGATACCAAATTTGCAGCAACCGCAGATGCAATTACCAAAAATGGCAAT
GCCATCACCAAAAATGCCAAAAGCATTACCGATCTGGGCACCAAAGTTGATGGTTTTGATAGC
CGTGTGACCGCACTGGATACCAAAGTTAATGCATTTGATGGTCGTATTACCGCTCTGGATAGT
AAAGTTGAAAATGGTATGGCAGCACAGGCAGCATAA

MC-010 (Protein)-(M)(UspA2 amino acids 30-564)
SEQ ID NO: 71

MQAKNDITLEDLPYLIKKIDQNELEADIGDITALEKYLALSQYGNILALEELNKALEELDEDV
GWNQNDIANLEDDVETLTKNQNALAEQGEAIKEDLQGLADFVEGQEGKILQNETSIKKNTQRN
LVNGFEIEKNKDAIAKNNESIEDLYDFGHEVAESIGEIHAHNEAQNETLKGLITNSIENTNNI

-continued

TKNKADIQALENNVVEELFNLSGRLIDQKADIDNNINNIYELAQQQDQHSSDIKTLKKNVEEG

LLELSGHLIDQKTDIAQNQANIQDLATYNELQDQYAQKQTEAIDALNKASSENTQNIEDLAAY

NELQDAYAKQQTEAIDALNKASSENTQNIEDLAAYNELQDAYAKQQTEAIDALNKASSENTQN

IAKNQADIANNINNIYELAQQQDQHSSDIKTLAKASAANTDRIAKNKADADASFETLTKNQNT

LIEKDKEHDKLITANKTAIDANKASADTKFAATADAITKNGNAITKNAKSITDLGTKVDGFDS

RVTALDTKVNAFDGRITALDSKVENGMAAQAA

MC-011 (DNA)

SEQ ID NO: 72

ATGGCGAAAAATGATATTACCCTGGAAGATCTGCCGTATCTGATCAAAAAAATCGATCAGAAC

GAACTGGAAGCCGATATTGGTGATATTACCGCACTGGAAAAATATCTGGCACTGAGCCAGTAT

GGAAATATTCTGGCCCTGGAAGAACTGAATAAAGCTCTGGAAGAGCTGGATGAAGATGTGGGT

TGGAATCAGAATGATATCGCCAATCTGGAAGATGATGTTGAAACCCTGACCAAAAATCAGAAT

GCACTGGCAGAACAGGGTGAAGCAATTAAAGAAGATCTGCAGGGTCTGGCAGATTTTGTTGAA

GGTCAGGAAGGCAAAATTCTGCAGAACGAAACCAGCATCAAAAAAAACACCCAGCGTAATCTG

GTGAATGGCTTTGAAATTGAAAAAAACAAAGATGCCATTGCCAAAAACAACGAAAGCATTGAA

GATCTGTATGATTTTGGTCATGAAGTTGCCGAAAGCATTGGTGAAATTCATGCACATAACGAA

GCACAGAATGAAACCCTGAAAGGTCTGATTACCAACAGCATCGAAAATACCAATAACATTACC

AAAAACAAAGCAGATATTCAGGCGCTGGAAAATAATGTTGTGGAAGAACTGTTTAATCTGAGC

GGTCGTCTGATTGATCAGAAAGCCGATATCGATAATAACATTAACAACATTTATGAACTGGCA

CAGCAGCAGGATCAGCATAGCAGCGATATCAAAACCCTGAAAAAAAACGTTGAAGAAGGTCTG

CTGGAACTGTCTGGTCACCTGATCGATCAGAAAACTGATATTGCCCAGAATCAGGCAAATATT

CAGGATCTGGCCACCTATAATGAACTGCAGGATCAGTATGCACAGAAACAGACCGAAGCAATT

GATGCCCTGAATAAAGCGAGCAGCGAAAACACCCAGAATATCGAAGATCTGGCAGCATACAAC

GAACTGCAGGATGCCTATGCAAAACAGCAGACTGAAGCCATCGACGCACTGAACAAGGCAAGC

TCTGAAAACACGCAGAACATTGAAGATCTGGCTGCCTATAATGAATTACAGGATGCGTATGCC

AAACAGCAGACCGAAGCGATTGATGCGCTGAACAAAGCCTCTTCTGAAAATACACAGAATATC

GCCAAAAATCAGGCCGATATTGCCAACAATATCAATAATATCTATGAACTGGCCCAGCAGCAG

GATCAGCACTCTTCTGATATCAAAACACTGGCAAAAGCAAGCGCAGCAAATACCGATCGTATT

GCGAAAAACAAAGCCGATGCAGATGCAAGCTTTGAAACACTGACGAAAAACCAGAACACCCTG

ATTGAAAAAGATAAAGAACATGATAAACTGATCACCGCCAATAAAACCGCAATTGATGCAAAT

AAAGCCAGCGCAGATACCAAATTTGCAGCAACCGCAGATGCAATTACCAAAAATGGCAATGCC

ATCACCAAAAATGCCAAAAGCATTACCGATCTGGGCACCAAAGTTGATGGTTTTGATAGCCGT

GTGACCGCACTGGATACCAAAGCAAGCCATCATCATCACCACCACTAA

MC-011 (Protein)-(M)(UspA2 amino acids 31-540)(ASHHHHHH)

SEQ ID NO: 73

MAKNDITLEDLPYLIKKIDQNELEADIGDITALEKYLALSQYGNILALEELNKALEELDEDVG

WNQNDIANLEDDVETLTKNQNALAEQGEAIKEDLQGLADFVEGQEGKILQNETSIKKNTQRNL

VNGFEIEKNKDAIAKNNESIEDLYDFGHEVAESIGEIHAHNEAQNETLKGLITNSIENTNNIT

KNKADIQALENNVVEELFNLSGRLIDQKADIDNNINNIYELAQQQDQHSSDIKTLKKNVEEGL

LELSGHLIDQKTDIAQNQANIQDLATYNELQDQYAQKQTEAIDALNKASSENTQNIEDLAAYN

ELQDAYAKQQTEAIDALNKASSENTQNIEDLAAYNELQDAYAKQQTEAIDALNKASSENTQNI

-continued

```
AKNQADIANNINNIYELAQQQDQHSSDIKTLAKASAANTDRIAKNKADADASFETLTKNQNTL

IEKDKEHDKLITANKTAIDANKASADTKFAATADAITKNGNAITKNAKSITDLGTKVDGFDSR

VTALDTKASHHHHHH
```

Vector Construction and Transformation

```
DNA Sequence for UspA2 from strain ATCC 25238
                                                         SEQ ID NO: 74
ATGAAAACCATGAAACTTCTCCCTCTAAAAATCGCTGTAACCAGTGCCATGATTATTGGCTTGGGTG

CGGCATCTACTGCGAATGCGCAGGCTAAAAATGATATAACTTTAGAGGATTTACCATATTTAATAAA

AAAGATTGACCAAAATGAATTGGAAGCAGATATCGGAGATATTACTGCTCTTGAAAAGTATCTAGCA

CTTAGCCAGTATGGCAATATTTTAGCTCTAGAAGAGCTCAACAAGGCTCTAGAAGAGCTCGACGAG

GATGTTGGATGGAATCAGAATGATATTGCAAACTTGGAAGATGATGTTGAAACGCTCACCAAAAAT

CAAAATGCTTTGGCTGAACAAGGTGAGGCAATTAAAGAAGATCTTCAAGGGCTTGCAGATTTTGTA

GAAGGGCAAGAGGGTAAAATTCTACAAAATGAAACTTCAATTAAAAAAAATACTCAGAGAAACCTTG

TCAATGGGTTTGAGATTGAGAAAAATAAAGATGCTATTGCTAAAAACAATGAGTCTATCGAAGATCT

TTATGATTTTGGTCATGAGGTTGCAGAAAGTATAGGCGAGATACATGCTCATAATGAAGCGCAAAA

TGAAACTCTTAAAGGCTTGATAACAAACAGTATTGAGAATACTAATAATATTACCAAAAACAAAGCT

GACATCCAAGCACTTGAAAACAATGTCGTAGAAGAACTATTCAATCTAAGCGGTCGCCTAATTGAT

CAAAAAGCAGATATTGATAATAACATCAACAATATCTATGAGCTGGCACAACAGCAAGATCAGCATA

GCTCTGATATCAAAACACTTAAAAAAAATGTCGAAGAAGGTTTGTTGGAGCTAAGCGGTCACCTAAT

TGATCAAAAAACAGATATTGCTCAAAACCAAGCTAACATCCAAGATCTGGCCACTTACAACGAGCTA

CAAGACCAGTATGCTCAAAAGCAAACCGAAGCGATTGACGCTCTAAATAAAGCAAGCTCTGAGAAT

ACACAAAACATCGAAGATCTGGCCGCTTACAACGAGCTACAAGATGCCTATGCCAAACAGCAAACC

GAAGCAATTGACGCTCTAAATAAAGCAAGCTCTGAGAATACACAAAACATCGAAGATCTGGCCGCT

TACAACGAGCTACAAGATGCCTATGCCAAACAGCAAACCGAAGCCATTGACGCTCTAAATAAAGCA

AGCTCTGAGAATACACAAAACATTGCTAAAAACCAAGCGGATATTGCTAATAACATCAACAATATCT

ATGAGCTGGCACAACAGCAAGATCAGCATAGCTCTGATATCAAAACCTTGGCAAAAGCAAGTGCTG

CCAATACTGATCGTATTGCTAAAAACAAAGCCGATGCTGATGCAAGTTTTGAAACGCTCACCAAAAA

TCAAAATACTTTGATTGAAAAAGATAAAGAGCATGACAAATTAATTACTGCAAACAAAACTGCGATT

GATGCCAATAAAGCATCTGCGGATACCAAGTTTGCAGCGACAGCAGACGCCATTACCAAAAATGG

AAATGCTATCACTAAAAACGCAAAATCTATCACTGATTTGGGCACTAAAGTGGATGGTTTTGACAGT

CGTGTAACTGCATTAGACACCAAAGTCAATGCCTTTGATGGTCGTATCACAGCTTTAGACAGTAAA

GTTGAAAACGGTATGGCTGCCCAAGCTGCCCTAAGTGGTCTATTCCAGCCTTATAGCGTTGGTAAG

TTTAATGCGACCGCTGCACTTGGTGGCTATGGCTCAAAATCTGCGGTTGCTATCGGTGCTGGCTAT

CGTGTGAATCCAAATCTGGCGTTTAAAGCTGGTGCGGCGATTAATACCAGTGGTAATAAAAAAGGC

TCTTATAACATCGGTGTGAATTACGAGTTCTAA.
```

Protein Sequence for UspA2 from Strain ATCC 25238.—SEQ ID NO. 1 as Described Above.

Vector Construction

To generate the construct MC-001, DNA fragment coding for an UspA2 gene fragment (amino acids 30 to 540 from strain ATCC 25238) including the NdeI/XhoI restriction sites to facilitate the cloning (the starting methionine is encoded by NdeI site) and the DNA sequence corresponding to the AS (alanine serine) amino acids linker and 6×his amino acids was codon-optimized (non-native) and synthesized by GENEART (a US registered trademark). Codon-optimized means that the nucleotide sequence was changed from the native sequence without changing the amino acid sequence in order to better fit with the codon usage in Escherichia coli for optimal expression. The UspA2 fragment was cloned according to standard methods into the pET-26b expression vector using the NdeI/XhoI restriction sites.

To generate MC-002, MC-003, and MC-004 constructs, a polymerase chain reaction was performed to amplify the UspA2 gene fragment (amino acids 30-540 from strain ATCC 25238) using the MC-001 construct as a template, the primer UspA2Nde opt (which contains the methionine start codon), and the primer UspA2opt delta His, A2opt 1His delta AS, and A2opt 2His delta AS, respectively. The UspA2 fragment was cloned according to standard methods into the pET-26b expression vector using the NdeI/XhoI restriction sites.

To generate the construct MC-005, a polymerase chain reaction was performed to amplify the UspA2 gene fragment (amino acids 30-519 from strain ATCC 25238) using the MC-001 vector as a template with the primers UspA2Nde opt (which contains the methionine start codon) and R delta hairpin A2opt His. DNA sequence corresponding to NdeI restriction site was incorporated into the 5' primer and XhoI restriction site was incorporated into the 3' primer. In addition, DNA sequence corresponding to the AS amino acids linker and 6×his amino acids was incorporated into the 3' primer. The generated PCR product was then inserted into the pET-26b(+) cloning vector (NOVAGEN (a US registered trademark)).

To generate the construct MC-006, a polymerase chain reaction was performed to amplify the UspA2 gene fragment (amino acids 30-519 from strain ATCC 25238) using the MC-005 construct as a template with the primers UspA2Nde opt (which contains the methionine start codon) and delta His delta helice. DNA sequence corresponding to NdeI restriction site was incorporated into the 5' primer and XhoI restriction site was incorporated into the 3' primer. The generated PCR product was then inserted into the pET-26b(+) cloning vector (NOVAGEN (a US registered trademark)).

To generate the construct MC-007, DNA fragment coding for an UspA2 gene fragment (amino acids 30 to 564 from strain ATCC 25238) including the NdeI/XhoI restriction sites to facilitate the cloning (starting methionine is encoded by NdeI site) and the DNA sequence corresponding to the AS amino acids linker and 6×his amino acids was codon-optimized and synthesized by GENEART (a US registered trademark) (plasmid: 1026399). The UspA2 fragment was cloned according to standard methods into the pET-26b expression vector using the NdeI/XhoI restriction sites.

To generate the construct MC-008, a polymerase chain reaction was performed to amplify the UspA2 gene fragment (amino acids 30-564 from strain ATCC 25238) using the MC-007 construct as a template with the primers UspA2Nde opt (which contains the methionine start codon) and 2His helice deltaAS. DNA sequence corresponding to NdeI restriction site was incorporated into the 5' primer and XhoI restriction site was incorporated into the 3' primer. The generated PCR product was then inserted into the pET-26b(+) cloning vector (NOVAGEN (a US registered trademark)).

To generate the construct MC-009, a polymerase chain reaction was performed to amplify the UspA2 gene fragment (amino acids 31-564 from strain ATCC 25238) using the 1026399 plasmid as the template and the primers N-term cyto Abis (which contains the methionine start codon) and 2His helice deltaAS. DNA sequence corresponding to NdeI restriction site was incorporated in the 5' primer including the glutamine deletion and XhoI restriction site was incorporated into the 3' primer including two histidine residues. The generated PCR product was then inserted into the pET-26b(+) cloning vector (NOVAGEN (a US registered trademark)). DNA sequencing of the final construct was performed to confirm the correct sequence.

To generate the construct MC-010, a polymerase chain reaction was performed to amplify the UspA2 gene fragment (amino acids 30-564 from strain ATCC 25238) using the MC-007 construct as a template with the primers UspA2 Nde opt (which contains the methionine start codon) and cyto helice dHis dAS. DNA sequence corresponding to NdeI restriction site was incorporated into the 5' primer and XhoI restriction site was incorporated into the 3' primer. The generated PCR product was then inserted into the pET-26b (+) cloning vector (NOVAGEN (a US registered trademark)).

To generate the construct MC-011, a polymerase chain reaction was performed to amplify the UspA2 gene fragment (amino acids 31-540 from strain ATCC 25238) using the MC-001 construct as a template with the primers N-term cyto Abis (which contains the methionine start codon) and N-term reverse. DNA sequence corresponding to NdeI restriction site was incorporated into the 5' primer and XhoI restriction site was incorporated into the 3' primer. The generated PCR product was then inserted into the pET-26b (+) cloning vector (NOVAGEN (a US registered trademark)).

A detailed list of PCR primer sequences used for amplifications is illustrated in Table 3. The polymerase chain reaction was performed using Expand High Fidelity PCR System kit (Roche) according to manufacturer's recommendations. Ligation was performed using Rapid DNA Ligation Kit (Roche) according to manufacturer's recommendations.

TABLE 3

| PCR primer sequences used for UspA2 amplifications | |
|---|---|
| Primer ID | DNA Sequence 5'-3' |
| UspA2Nde opt | GAATTCTTAATTAACATATGCAGGCCAAAAAT GATATTACCCTG (SEQ ID NO: 75) |
| UspA2opt delta His | GGCGCGCCTCGAGTTATTATTTGGTATCCAGT GCGGTCACACG (SEQ ID NO: 76) |
| UspA2opt 1His delta AS | GGCGCGCCTCGAGTTAGTGTTTGGTATCCAGT GCGGTCACACG (SEQ ID NO: 77) |
| UspA2opt 2His delta AS | GGCGCGCCTCGAGTTAGTGGTGTTTGGTATCC AGTGCGGTCACACG (SEQ ID NO: 78) |
| R delta hairpin A2opt His | GGCGCGCCTCGAGTTAGTGGTGGTGATGATGA TGGCTTGCGCTTTTGGCATTTTTGGTGATGGC AT (SEQ ID NO: 79) |
| Delta His delta hélice | CCGCTCGAGCTAGCTTTTGGCATTTTTGGTGA TGGC (SEQ ID NO: 80) |
| N term cytoAbis | GGAATTCCATATGGCGAAAAATGATATTACCC TGGAAGATCTG (SEQ ID NO: 81) |
| 2His hélice delta AS | GGCGCGCCTCGAGTTAGTGGTGTGCTGCCTGT GCTGCCATACCATT (SEQ ID NO: 82) |
| Cyto hélice dHis dAS | GGCGCGCCTCGAGTTATGCTGCCTGTGCTGCC ATACCATT (SEQ ID NO: 83) |
| N term reverse | CAGTTCATTATAGGTGGCCAGATCCTG (SEQ ID NO: 84) |

Transformation

*Escherichia coli* (*E. coli*) BLR (DE3), modified BLR (DE3) or B834(DE3) cells were transformed with plasmid DNA according to standard methods with CaCl$_2$-treated cells (Hanahan D. «Plasmid transformation by Simanis.» In Glover, D. M. (Ed), DNA cloning. IRL Press London. (1985): p. 109-135). Briefly, BLR (DE3) competent cells were gently thawed on ice. Approximately 4 µl of plasmid (10-100 ng) were mixed using 50-100 µl competent cells. Thereafter, this formulation was incubated on ice for 5 min. To perform the transformation reaction, the formulation was heat pulsed at 42° C. for 30 seconds then incubated on ice for 2 minutes. Approximately 0.5 ml of SOC medium (Super Optimal broth with Catabolite repression) was added to the transformed cells and the cell culture was incubated at 37° C. for one hour before plating on Luria-Bertani (LB) agar with 50 ug/ml kanamycin. Around 150 µl of transformed cell culture was plated and incubated overnight at 37° C.

BLR (DE3): BLR is a recA⁻derivative of BL21 (F– ompT hsdSB(rB– mB–) gal dcm (DE3). This $E.$ $coli$ strain used for expression of recombinant proteins improves plasmid monomer yields and may help stabilize target plasmids containing repetitive sequences or whose products may cause the loss of the DE3 prophage (Studier, F. W. (1991) J. Mol. Biol. 219: 37-44). The detailed genotype of $E.$ $coli$ BLR (DE3) has been published by NOVAGEN (a US registered trademark). (F– ompT hsdSB (rB– mB–) gal dcm Δ(srl-recA)306::Tn10 (TetR) (DE3).

B834 (DE3) is the parental strain for BL21. These hosts are methionine auxotrophs and allow high specific activity labeling of target proteins with 35S-methionine and selenomethionine for crystallography. The detailed genotype of $E.$ $coli$ B834 (DE3) has been published by NOVAGEN (a US registered trademark): F⁻ ompT hsdS$_B$(r$_B$– m$_B$–) gal dcm met (DE3).

Modified BLR (DE3): In order to prevent (phospho) gluconoylation, Pgl gene was inserted in the biotin locus located in the BLR (DE3) genome. In addition, to prevent the Ile-Val substitutions, the C219Y mutation in the threonine deaminase gene was corrected.

Genotype: (F– ompT hsdSB (rB– mB–) gal dcm Δ(srl-recA)306::Tn10 (TetR); Δ(bioA-bioD)::Pgi; TD+ (C21919 (DE3).

Example 2: Protein Expression Usinci Shake Flask $Escherichia$ $coli$ strains transformed with recombinant plasmid were used to inoculate 100 ml of LB broth (Becton, Dickinson and Company) ±1% (weight/volume, w/v) glucose (Laboratoire MAT, catalogue number: GR-0101) and 50 µg/ml kanamycin (Sigma). This preculture was generally grown overnight at 37° C. Twelve ml of the preculture is used to inoculate 500 ml LB broth+50 µg/ml kanamycine. Cultures were incubated at 37° C. with agitation of 150 RPM to reach an O.D.$_{600nm}$ of ~0.6.

At an O.D.$_{600nm}$ ~0.6, the BLR (DE3) cultures were induced for the expression of the recombinant protein by addition of 1 mM isopropyl β-D-1-thiogalactopyranoside (IPTG; EMD Chemicals Inc., catalogue number: 5815) and incubated overnight at 23° C. with agitation of 150 RPM. After the induction period, the cultures were centrifuged at 6370 g for 20 minutes and the pellets from 350 ml culture were frozen at –20° C. separately.

Example 3: Protein Purification Using Phosphate Buffer (MC-001 Construct and MC-011 Construct)

Each bacterial pellet obtained after induction in shake flask was resuspended in 30 ml 20 mM potassium phosphate buffer (pH 8.0) containing 10 mM NaCl and Roche COMPLETE (a US registered trademark) Protease Inhibitor Cocktail (1 tablet/50 ml ml buffer). Cell lysis is performed by 3× French Press extractions (20 000 psi) and clarification is performed by 30 minutes centrifugation at 23700 g. Supernatant is harvested and filtrated on 0.22 µm.

6×His tagged-proteins were purified on immobilized metal affinity chromatography (IMAC) using XK16 column and 20 ml NiNTA resin (Qiagen) previously equilibrated with 20 mM potassium phosphate buffer (pH 8.0) containing 10 mM NaCl or PBS buffer pH 8.0 containing 500 mM arginine. The soluble components were loaded on at up to 4 ml/min (producing a "flow through fraction"). After loading on the column, the column was washed with 60 ml of 20 mM potassium phosphate buffer (pH 8.0) containing 10 mM NaCl at a rate of 4 ml/min producing a "wash fraction #1. A second wash using same buffer+10 mM imidazole was performed, producing a "wash fraction #2. Elution was performed using same buffer containing 200 or/and 500 mM imidazole.

Samples from elution fractions were analyzed by sodium dodecyl sulfate polyacrylamide gel electrophoresis (SDS-PAGE). Samples containing the protein were dialyzed against 5 liters of 20 mM potassium phosphate buffer (pH 8.0) containing 10 mM NaCl. Protein concentration was determined using Lowry method.

Example 4: Protein Purification Using Arginine Containing Buffer (MC-001, MC-005 and MC-007)

Each bacterial pellet obtained after induction in shake flask (Example 3) or fermenter (Example 5) was resuspended in 30 ml PBS buffer+500 mM arginine pH8.0 and Roche COMPLETE (a US registered trademark) Protease Inhibitor Cocktail (1 tablet/50 ml buffer). Alternatively, fermentation cell paste (≈7 g) was resuspended in 90 ml PBS buffer containing 500 mM arginine pH8.0 and Roche COMPLETE (a US registered trademark) Protease Inhibitor Cocktail (1 tablet/50 ml buffer).

Cell lysis was performed by 2 or 3× French Press extractions (20 000 psi) and clarification was performed by 30 minutes centrifugation at 23 700 g 4° C. Supernatant was harvested and filtrated on 0.22 µm. 6×His tagged-proteins were purified on immobilized metal affinity chromatography (IMAC) using XK16 column and 80 ml NiNTA resin (Qiagen) previously equilibrated with PBS buffer+500 mM arginine pH 8.0. The soluble components were loaded on at up to 4 ml/min (producing a "flow through fraction"). After loading on the column, the column was washed with the same buffer, then with 20 mM potassium phosphate buffer (pH 8.0) containing 10 mM NaCl at a rate of 4-6 ml/min producing a "wash fraction #1." A second wash using same buffer+10 mM imidazole was performed, producing a "wash fraction #2." Elution was performed using same buffer+200 mM imidazole or 500 mM imidazole. In further elution vials, 5 mM EDTA final concentration was added.

Samples from elution fractions were analyzed by sodium dodecyl sulfate polyacrylamide gel electrophoresis (SDS-PAGE). Samples containing the proteins were dialyzed against 5 liters of 20 mM potassium phosphate buffer (pH 8.0) containing 10 mM NaCl and 5 mM EDTA. Protein concentration was determined using Lowry method.

This protocol may be used with other 6×His tagged-proteins.

Example 5: Fermentation

The following fermentation procedure may be used:
Working seeds are frozen aliquots of flask-grown $Escherichia$ $coli$ BLR(DE3) or BLR(DE3)-derived strains transformed with a pET26b derivative containing a sequence coding for a specific antigen candidate recombinant protein construct.

A working seed (WS) is removed from frozen storage, thawed and used to inoculate an Erlenmeyer flask containing pre-culture media. Manipulation of the seed and flask culture are performed aseptically under a Laminar Air Flow (LAF) Hood or Biological Safety Cabinet (BSC). The pre-culture flask is incubated typically between 30° C.-37° C. under 200 RPM agitation speed for the time needed to reach an Optical Density at 650 nm ($OD_{650nm}$) between 1.0 and 3.0, typically between 4-6 hrs.

A 20 L fermentor is prepared by Clean-In-Place followed by an automated steam sterilisation sequence. Starting medium is transferred aseptically into the fermentor. A bottle filled with $NH_4OH$ 25% is aseptically connected to the fermentor for automatic pH control. The initial pH of the starting medium is adjusted to target pH by addition of $NH_4OH$ solution. Irradiated antifoam is added using a syringe through a septum in the head-plate. A bottle filled with Feed medium is aseptically connected to the fermentor. Feed addition is controlled by either a pO2-cascade (control dissolved oxygen) to or a pre-programmed feed-curve. Agitation is controlled either by a pO2-cascade or a pre-programmed agitation-curve.

Initial fermentor parameters are typically as follows:
Temperature: 28° C.-32° C.
Pressure: 0.5 barg (7 psi)
Air flow rate: 2 VVM (Vessel Volumes per Minute)
pH: Regulated at 6.8 by addition of $NH_4OH$ 25%.

An aliquot of this pre-culture (typically between 5 ml-50 ml) is used to inoculate the starting fermentor media by syringe addition through a septum on the fermentor head-plate. The phases of Fermentation Culture are:

Batch Phase: Biomass is accumulated using carbon source in starting media.

Fed-batch Phase: Feed media is introduced either according to pO2-cascade control or pre-programmed feed curve. Biomass accumulation continues on carbon source in feed media.

Induction Phase: Expression of the recombinant protein antigen is induced by addition of IPTG solution to the culture in the fermentor.

At harvest, the culture is collected typically in 1 L centrifugation bottles and centrifuged to separate the solid pellet (cell-paste) fraction from the liquid supernatant fraction. The supernatant is discarded, and the wet cell weight (solid pellet) is recorded and the cell-paste bags stored at −20° C.

The following procedure may also be used:
*Escherichia coli* Standard Pre-Culture Each standard pre-culture were prepared using a frozen seed culture of *Escherichia coli* strains. These strains are BLR(DE3) strains transformed with a pET26b derivative containing a sequence coding for the specific construct to be evaluated.

The seed culture was thawed to room temperature and 400 µl were used to inoculate a 2 litre Erlenmeyer flask containing 400 ml of preculture medium (adapted from Zabriskie et al. (*J. Ind. Microbiol.* 2:87-95 (1987)).

The inoculated flask was then incubated at 37° C. (±1° C.) and 200 rpm. The pre-culture was stopped after 6 h of incubation. At this step the optical density at 650 nm ($OD_{650nm}$) is about 2. The pre-culture was used to inoculate medium in a fermenter as soon as the culture was stopped.

20 L Scale Fedbatch Fermentation
Method

A 20 litre fermenter (Biolafitte) was used. Nine litres of batch phase medium were aseptically transferred into the fermenter. The pH of the medium was readjusted to 6.8 with base addition. 1 ml of undiluted irradiated antifoam (SAG 471) was also added to the fermenter. The temperature (28° C.), head pressure (0.5 bar), aeration rate (20 litres sparged air per minute) and initial agitation speed (300 rpm) were then set prior to inoculation. The level of dissolved oxygen in these conditions was 100%. The head pressure and aeration rate were maintained at a constant level during the fermentation.

Inoculation was achieved by the addition of an equivalent 10 ml OD650 nm=2 of pre-culture (prepared as described above, in Example 2) following the next formula:

$$\text{Preculture Volume (ml)} = \frac{20}{\text{Preculture Final } OD650 \text{ nm}}$$

During batch phase (0-15 h), the temperature was maintained at 28° C. The level of dissolved oxygen was set at 20%. The level of dissolved oxygen (DO) was regulated by increasing stirring when the DO fell below 20%. Glucose exhaustion resulted in an increase in DO and a concomitant decrease in stirring.

When glucose is exhausted, the feeding rate is started based on a pH signal that increases above 7.0. From this point forward, the feeding rate was controlled by oxygen demand, increasing the flow rate when dissolved oxygen tends to drop below the 20% set point. At this step the agitation speed is maintained at 900 rpm.

During the fed-batch phase (before induction), the pH was maintained at 6.8 by addition of base, the temperature was regulated at 30° C.

Two strategies were applied to produce the protein:

The "High Cell Density Induction" (HCDI) is applied when culture is induced with 1 mM IPTG (isopropyl-beta-D-thiogalactopyranoside) at an optical density of 80±5, typically reached after 40 h of culture. The temperature was maintained at 28° C. and feeding rate still controlled by oxygen demand with a constant agitation speed at 900 rpm.

The "Low Cell Density Induction" (LCDI) process means an induction at an optical density of 40±5 usually reached after 24 h of culture. The temperature was decreased to 30° C. and the constant feeding rate of 0.5 ml/min is applied. Then 1 mM IPTG is added to the culture. At this step, the DO level was maintained at 20% by controlling the stirring rate.

At the end of the induction phase (72 h), cell paste was collected by centrifugation (6,500×g, 4° C. for 1 h), and stored at −20° C.

Figure 2:
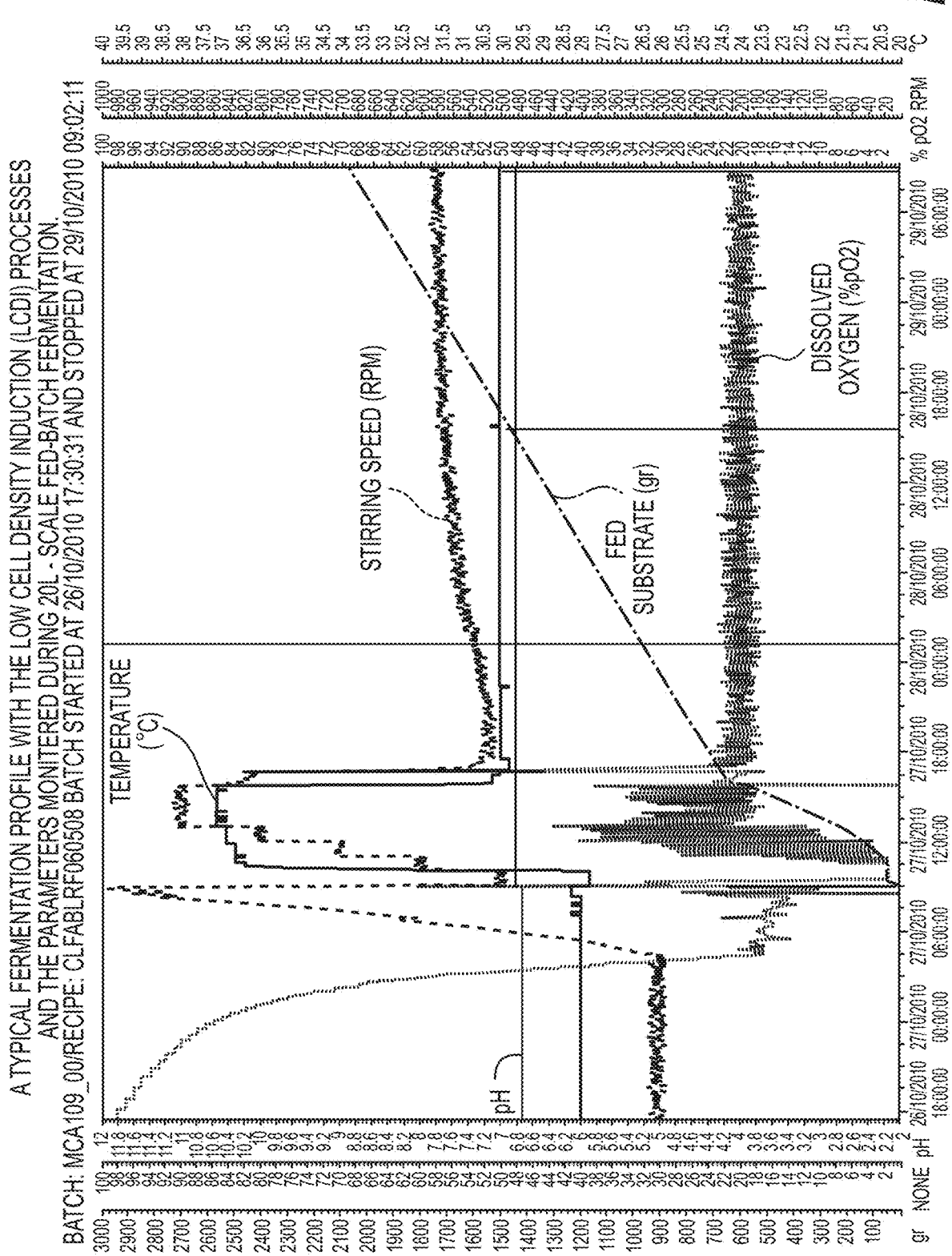
FIG. 2: A typical fermentation profile with the Low Cell Density Induction (LCDI) processes and the parameters monitored during 20 L-scale fed-batch fermentation.

FIGS. 1 and 2 illustrate a typical fermentation profile with the HCDI and the LCD processes and the parameters monitored during 20 L-scale fed-batch fermentation.

Table 4 sets forth the constructs evaluated in fermenter and UspA2 yield obtained for each one.

TABLE 4

| Construct ID | Name | Helix | His tag | Process used | UspA2 Yield (g/l) |
|---|---|---|---|---|---|
| MC-008 | UspA2 + Helix + 2 His | Full | 2 res | HCDI | 2.21 |
| MC-007 | UspA2 + Helix + 6 His | Full | 6 res | LCDI | 2.60 |

TABLE 4-continued

| Construct ID | Name | Helix | His tag | Process used | UspA2 Yield (g/l) |
|---|---|---|---|---|---|
| MC-010 | UspA2 + Helix | Full | No | HCDI | 0.22 |
| MC-005 | UspA2 ΔHelix + 6 His | No | 6 res | LCDI | 1.92 |
| MC-006 | UspA2 ΔHelix | No | No | LCDI | 1.14 |
| MC-004 | UspA2 + ½ Helix + 2 His | ½ | 2 res | LCDI | 0.92 |
| MC-001 | UspA2 + ½ Helix + 6 His | ½ | 6 res | HCDI | 3.68 |
| MC-002 | UspA2 + ½ Helix | ½ | No | HCDI | 0.49 |

His = histidine

Figure 3:
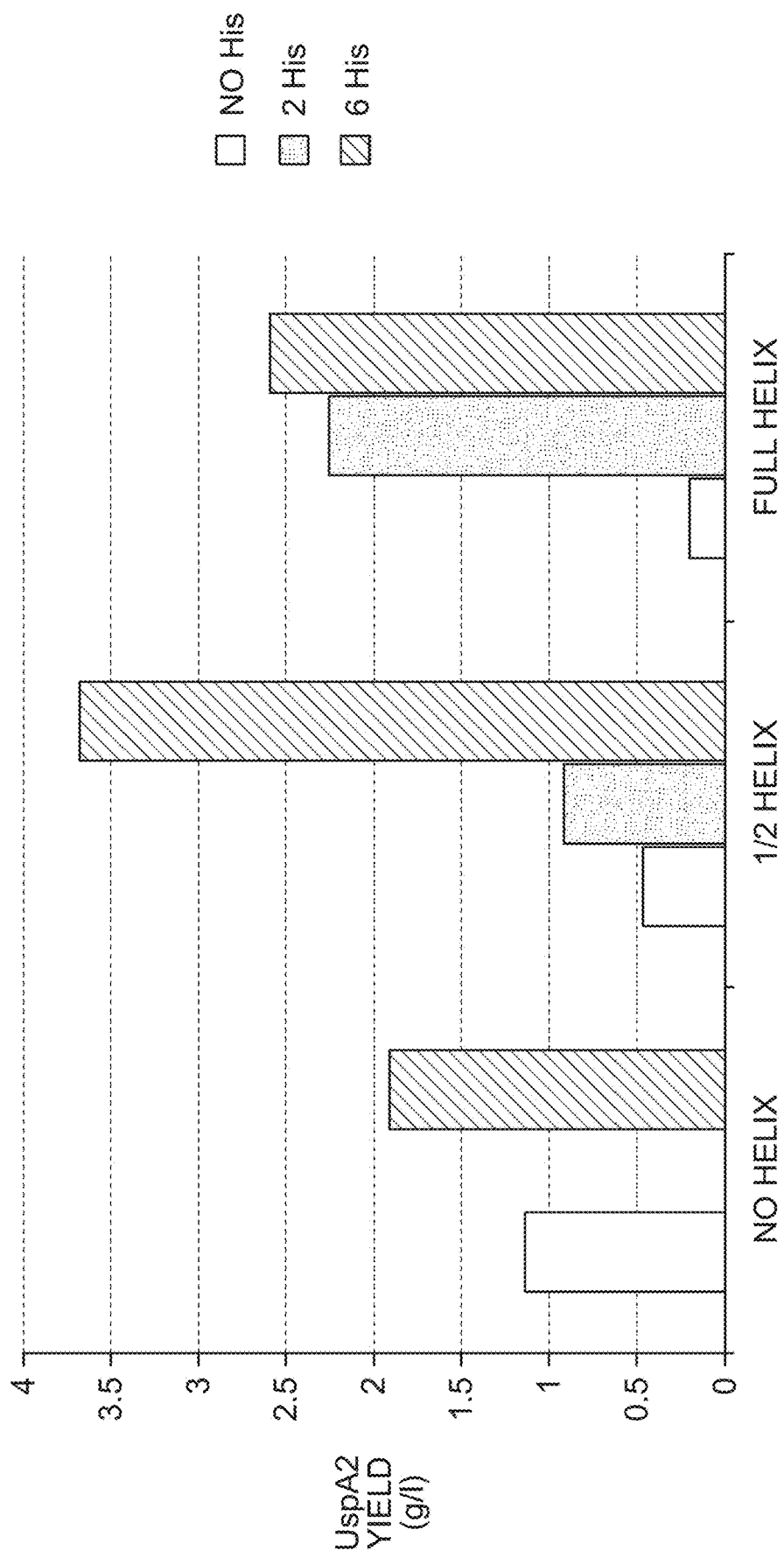
FIG. 3: UspA2 yield from protein constructs MC-001, MC-002, MC-004, MC-005, MC-006, MC-007, MC-008 and MC-010 evaluated in fermenter; data from Table 4.

FIG. 3 depicts in graphical form the UspA2 yield in Table 4 from the constructs evaluated in fermenter.

In this figure, UspA2 yield is affected by histidine residues present in the construct. ($p<0.05$, one way, three levels, Type II ANOVA). A positive correlation between the number of histidine residues and UspA2 fermentation yield was observed, with a yield increase higher than 400% between 0 and 6 residues in fed-batch fermentations.

It was also observed that one histidine residue added to half-helix pattern (MC-003 construct) produced a UspA2 yield of about 1 g/l of protein.

Example 6: Protein Characterization

Analytical Ultracentrifugation

Analytical ultracentrifugation is used to determine the homogeneity and size distribution in solution of the different species within a protein sample by measuring the rate at which molecules move in response to a centrifugal force. This is based on the calculation of the coefficients of sedimentation of the different species that are obtained by sedimentation velocity experiment, which depend on their molecular shape and mass.

The following protein samples were spun in a Beckman-Coulter ProteomeLab XL-1 analytical ultracentrifuge at 28 000RPM after the AN-60Ti rotor had been equilibrated to 15° C.
  a. MC-005 lot BMP53 675 µg/ml in 20 mM $NaPO_4$, 10 mM NaCl, pH8.0
  b. MC-001 lot BMP13 545 µg/ml in 20 mM $NaPO_4$, 10 mM NaCl, pH8.0
  c. MC-001 lot BMP14 545 µg/ml in 20 mM $NaPO_4$, 10 mM NaCl, pH8.0
  d. MC-001 lot BMP54 445 µg/ml in 20 mM $NaPO_4$, 10 mM NaCl, pH8.0
  e. MC-007 lot BMP70, 510 µg/ml in 20 mM $NaPO_4$, 10 mM NaCl, pH8.0

For data collection, from 133 to 325 scans were recorded at 280 nm every 5 minutes.

Data analysis was performed using the program SEDFIT (available through the National Institutes for Health) for determination of the C(S) distribution. The C(S) distribution is a representation of the relative intensity of the different components in a mixture of macromolecules separated by their coefficient of sedimentation, which is a function of molecule size and conformation. Determination of the partial specific volume of the proteins at 15° C. was performed with the SEDNTERP software from their amino acid sequence. SEDNTERP (SEDNTERP is distributed and supported through the Biomolecular Interaction Technologies Center at the University of New Hampshire) was also used to determine the viscosity and the density of the buffer at 15° C.

Determination of the relative abundance of all species has been performed by considering the total area under the curve of the overall distribution as 100% of the sample and by calculating the percentage of this total area represented by the contribution of every species. C(S) distribution plot (concentration vs sedimentation coefficient) has been used for that calculation, considering that it's a better representation of the raw data than the C(M) distribution (concentration vs molecular weight).

Analytical ultracentrifugation of the different purified constructs allowed observation that UspA2 4helix, UspA2½ helix and UspA2 full helix with C-terminal his tag are present mainly as trimers in solution when 500 mM L-arginine is added during cell lysis prior to purification (FIGS. 4, 5, 7 and 8).

A heterogeneous size distribution has been observed for UspA2½ helix when no L-arginine was added during cell lysis. Two major populations are observed. It was not possible to confirm the molecular weight of the species detected by AUC (analytical ultracentrifugation) with this protein preparation, since the frictional ratio which is essential for molecular weight estimation needs to be calculated from an homogeneous sample. However, based on sedimentation coefficients, none of the observed species seem to correspond to the trimer observed in other samples.

Figure 4:
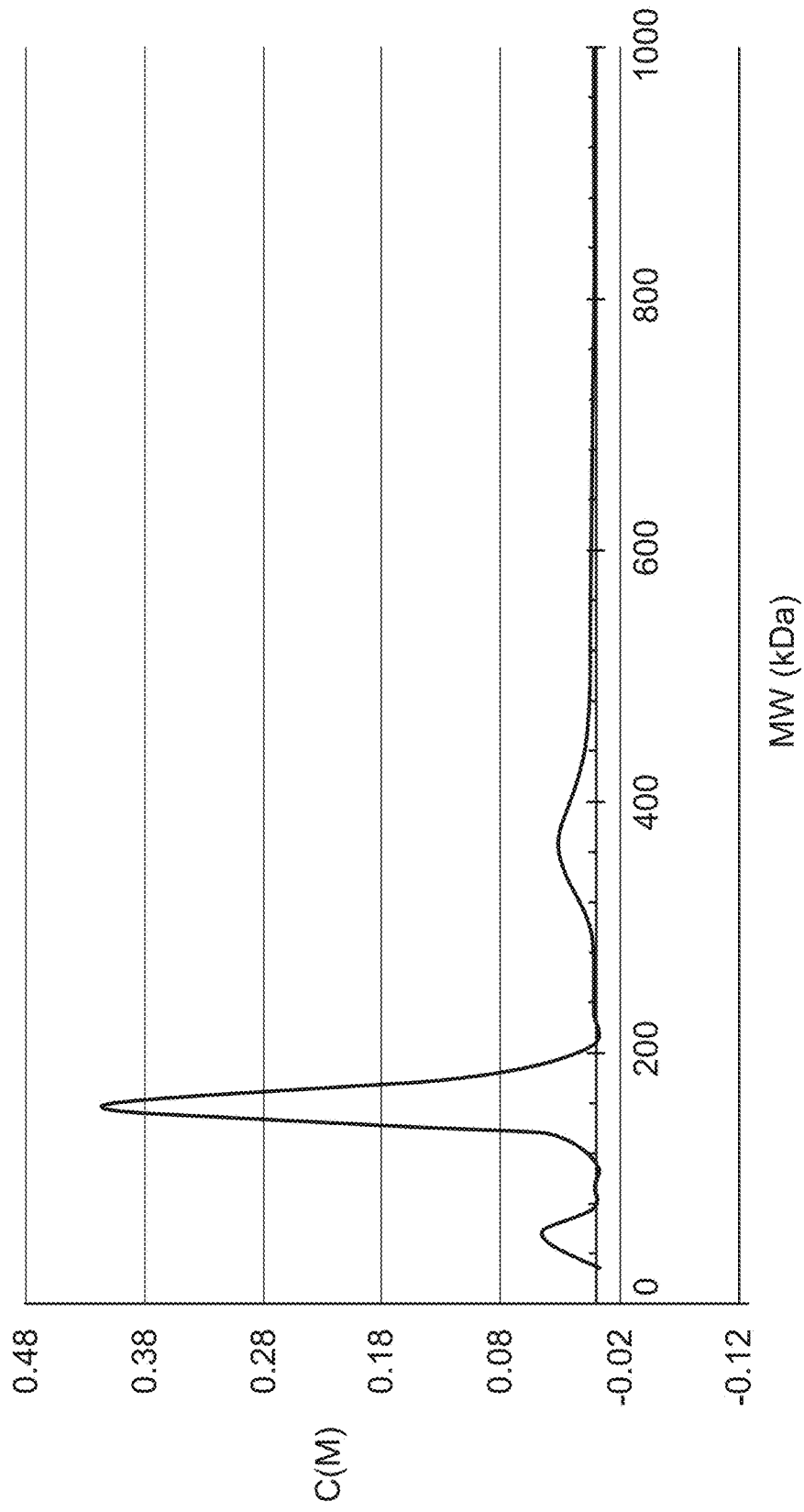
FIG. 4: Molecular weight distribution of purified MC-005 determined by sedimentation velocity analytical ultracentrifugation. The majority of protein is found as a trimer, with a small proportion of a higher molecular weight oligomer that may correspond to dimer of trimer. MW=molecular weight. kDa=kilodalton.

FIG. 4 illustrates the molecular weight distribution of purified MC-005 determined by sedimentation velocity analytical ultracentrifugation. The majority of protein is found as a trimer, with a small proportion of a higher molecular weight oligomer that may correspond to dimer of trimer.

Figure 5:
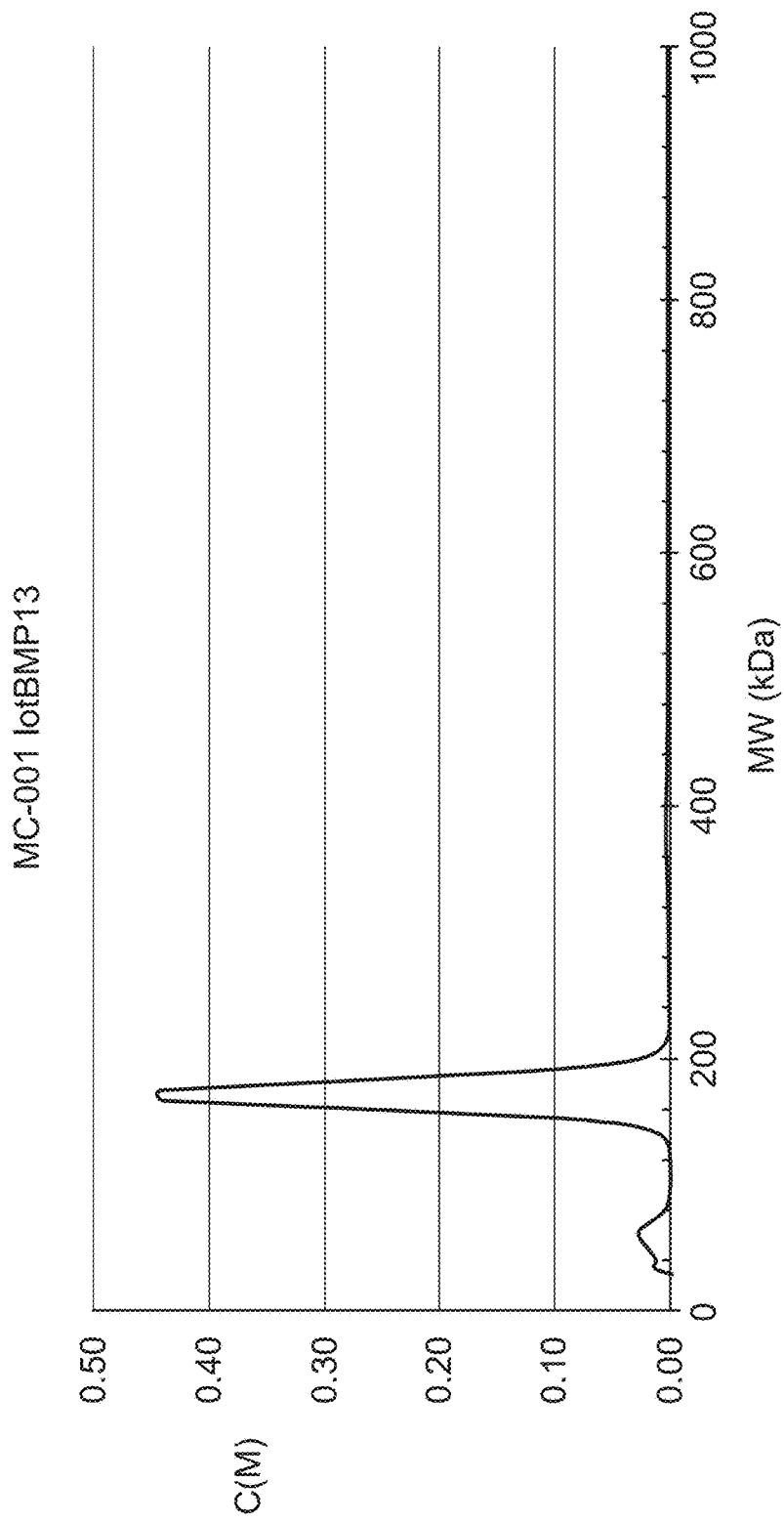
FIG. 5: Molecular weight distribution of purified MC-001 determined by sedimentation velocity analytical ultracentrifugation. Majority of protein is found as a trimer.

FIG. 5 illustrates the molecular weight distribution of purified MC-001 determined by sedimentation velocity analytical ultracentrifugation. Majority of protein is found as a trimer.

Figure 6:
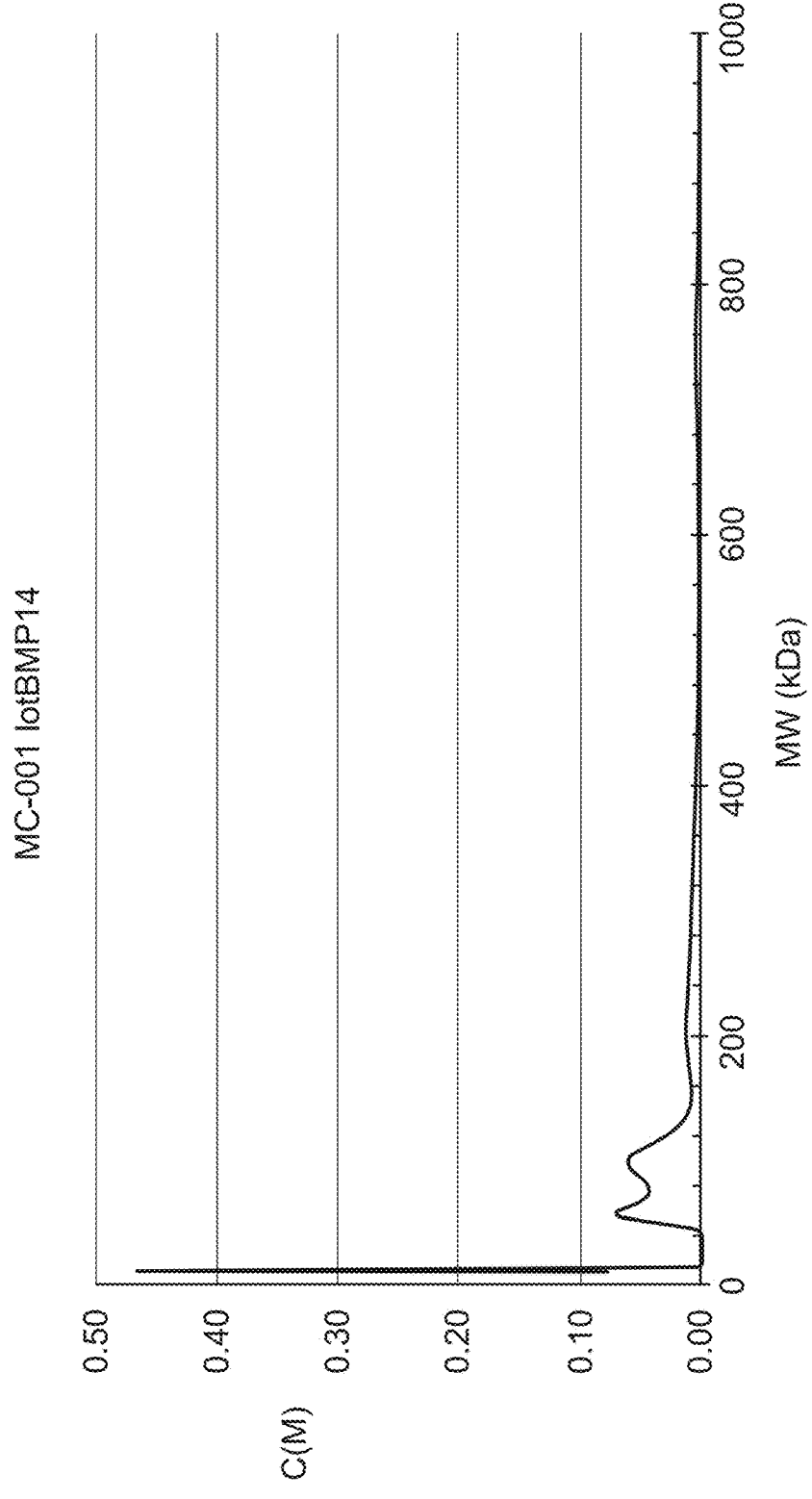
FIG. 6: Molecular weight distribution of purified MC-001 determined by sedimentation velocity analytical ultracentrifugation. The sample presents multiple species and is highly polydisperse. The sedimentation coefficient of the major species detected doesn't correspond to the one of the trimers normally detected in the other lots.

FIG. 6 illustrates the molecular weight distribution of purified MC-001 determined by sedimentation velocity analytical ultracentrifugation. The sample presents multiple species and is highly polydisperse. The sedimentation coefficient of the major species detected doesn't correspond to the one of the trimers normally detected in the other lots.

Figure 7:
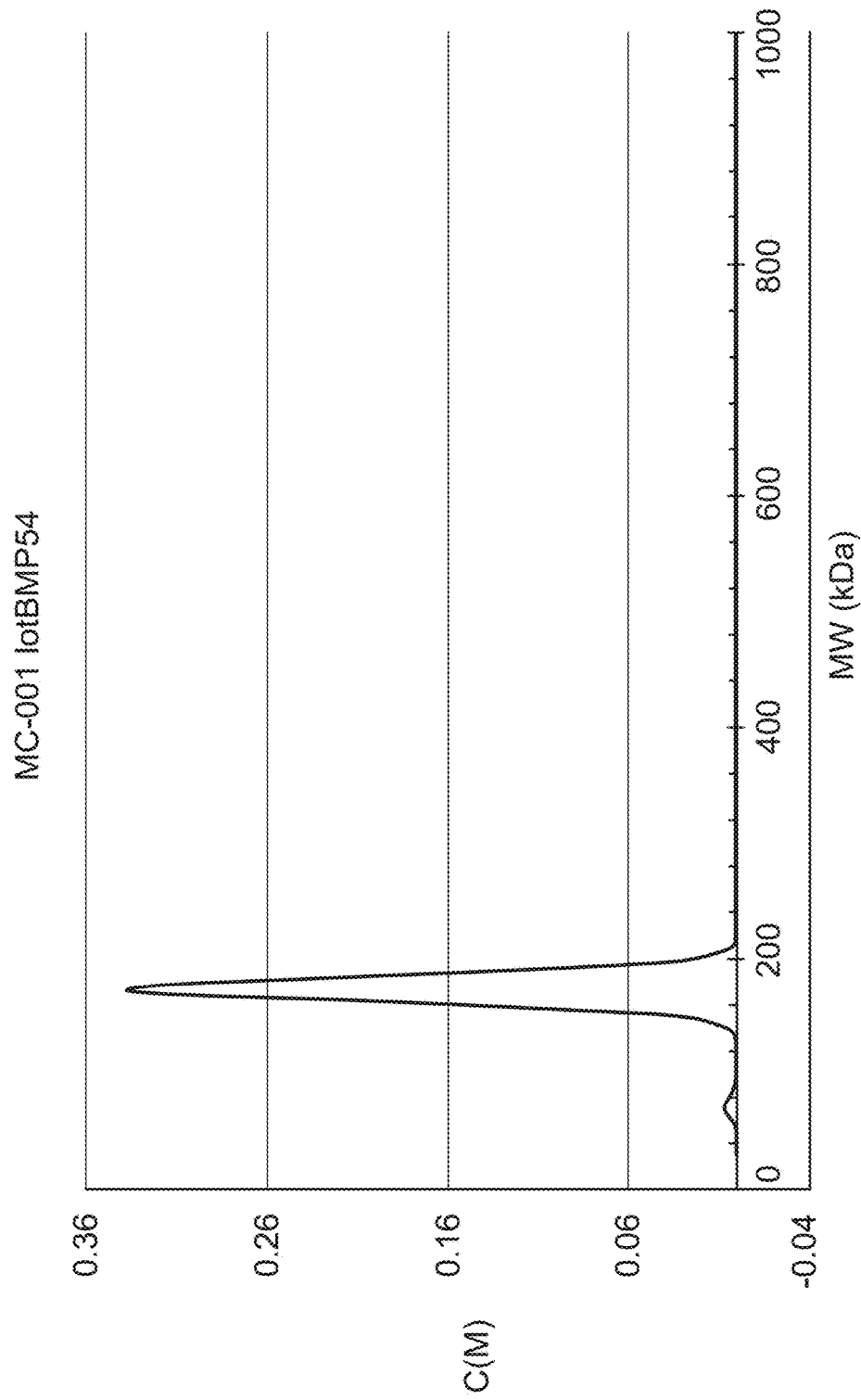
FIG. 7: Molecular weight distribution of purified MC-001 determined by sedimentation velocity analytical ultracentrifugation. Majority of protein is found as a trimer.

FIG. 7 illustrates the molecular weight distribution of purified MC-001 determined by sedimentation velocity analytical ultracentrifugation. The majority of protein is found as a trimer.

Figure 8:
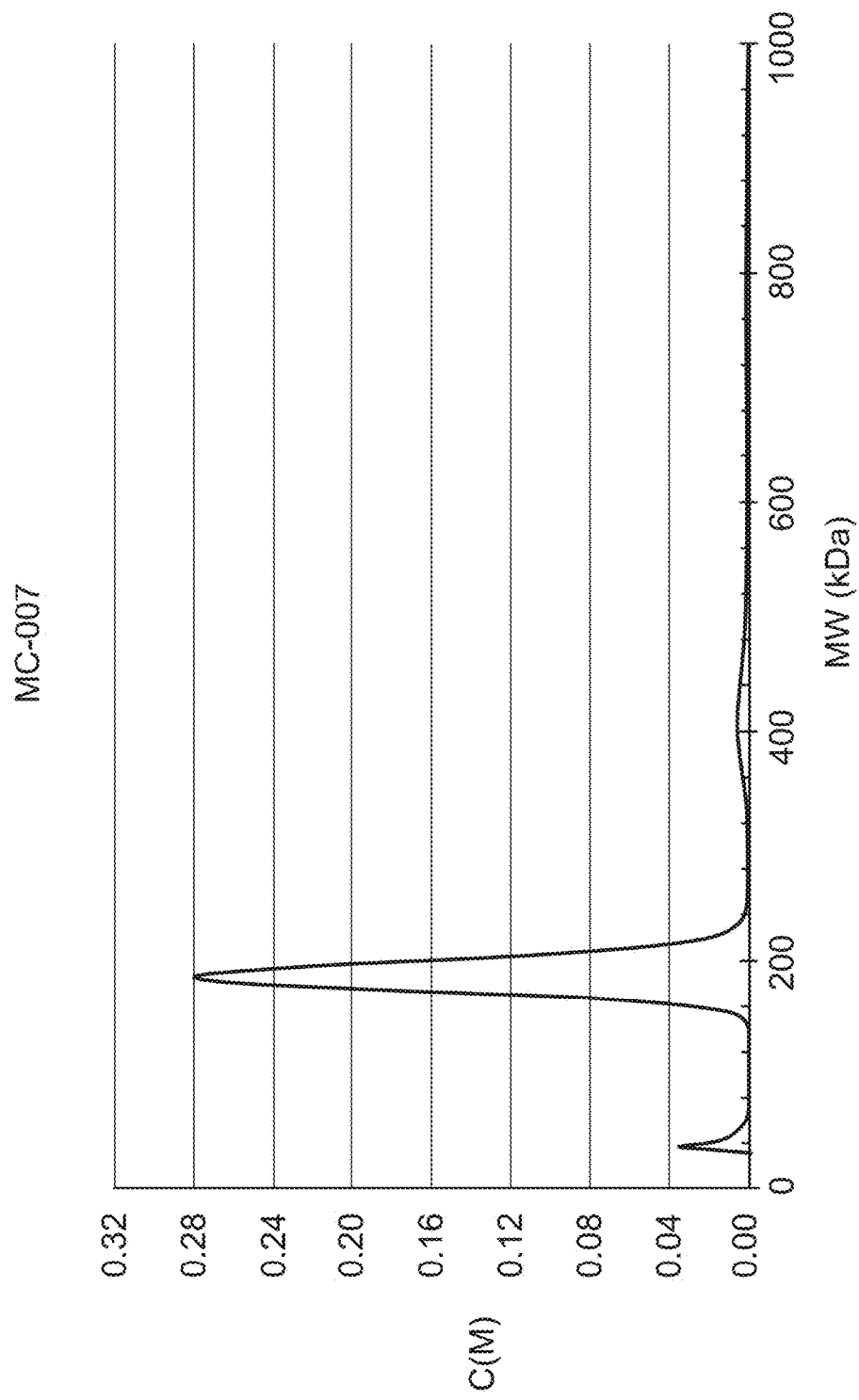
FIG. 8: Molecular weight distribution of purified MC-007 determined by sedimentation velocity analytical ultracentrifugation. Majority of protein is found as a trimer.

FIG. 8 illustrates the molecular weight distribution of purified MC-007 determined by sedimentation velocity analytical ultracentrifugation. The majority of protein is found as a trimer.

Circular dichroism/Secondary Structure

Circular dichroism (CD) is used to determine the secondary structure composition of a protein by measuring the difference in the absorption of left-handed polarized light versus right-handed polarized light which is due to structural asymmetry. The shape and the magnitude of the CD spectra in the far-UV region (190-250 nm) are different whether a protein exhibits a beta-sheet, alpha-helix or random coil structure. The relative aboundance of each secondary structure type in a given protein sample can be calculated by comparison to reference spectra.

Far UV spectra are measured using an optical path of 0.01 cm from 178 to 250 nm, with a 1 nm resolution and bandwidth on a Jasco J-720 spectropolarimeter. Temperature of the cell is maintained at different temperatures by a Peltier thermostated RTE-111 cell block. A nitrogen flow of 10 L/min is maintained during the measurements.

Concentration of the following protein constructs was adjusted to 400 µg/ml in 20 mM $NaPO_4$, 10 mM NaCl, pH8.0 buffer.

a. MC-005 lot BMP53 in 20 mM NaPO4, 10 mM NaCl, pH8.0
b. MC-001 lot BMP13 in 20 mM NaPO4, 10 mM NaCl, pH8.0
c. MC-001 Lot BMP14 in 20 mM NaPO4, 10 mM NaCl, pH8.0
d. MC-001 lot BMP54 in 20 mM NaPO4, 10 mM NaCl, pH8.0
e. MC-007 lot BMP70, in 20 mM NaPO4, 10 mM NaCl, pH8.0

Calculations of secondary structures have been done using the following algorithms:

Selcon 3 (Sreerama and Woody, Anal. Biochem. (1993), 209, 32; Sreerama and Woody, Biochemistry, 33, 10022-25 (1994); Sreerama et al. Protein Science, 8, 370-380 (1999); Johnson W. C. Jr., Proteins: Str. Func. Genet. 35, 307-312 (1999)) CDSSTR (Johnson W. C. Proteins: Struc. Func. Genet. 35, 307-312 (1999) modified by Sreerama. N.(Anal. Biochem., 287,252 (2000)).

Displayed results are an average of the percentage calculated with both algorithms and are subjected to a 5% error margin.

Results of the secondary structure calculations for fermentor expressed proteins are displayed in Table 5, considering a 5% error margin.

TABLE 5

Secondary structure calculations at 22° C.

| Protein | Helix | Beta | random |
|---|---|---|---|
| MC-005 BMP53 | 40.8 | 26.4 | 34.1 |
| MC-007 BMP70 | 58.2 | 18.2 | 24.7 |
| MC-001 BMP54 | 53.7 | 14.2 | 34.4 |

Calculations are compatible with the shape and visual analysis of the spectra, where helical content increases with the intensity of minima at 208 and 220 nm. Proteins are composed of a high proportion of helical structures, with presence of beta structures.

Figure 9:
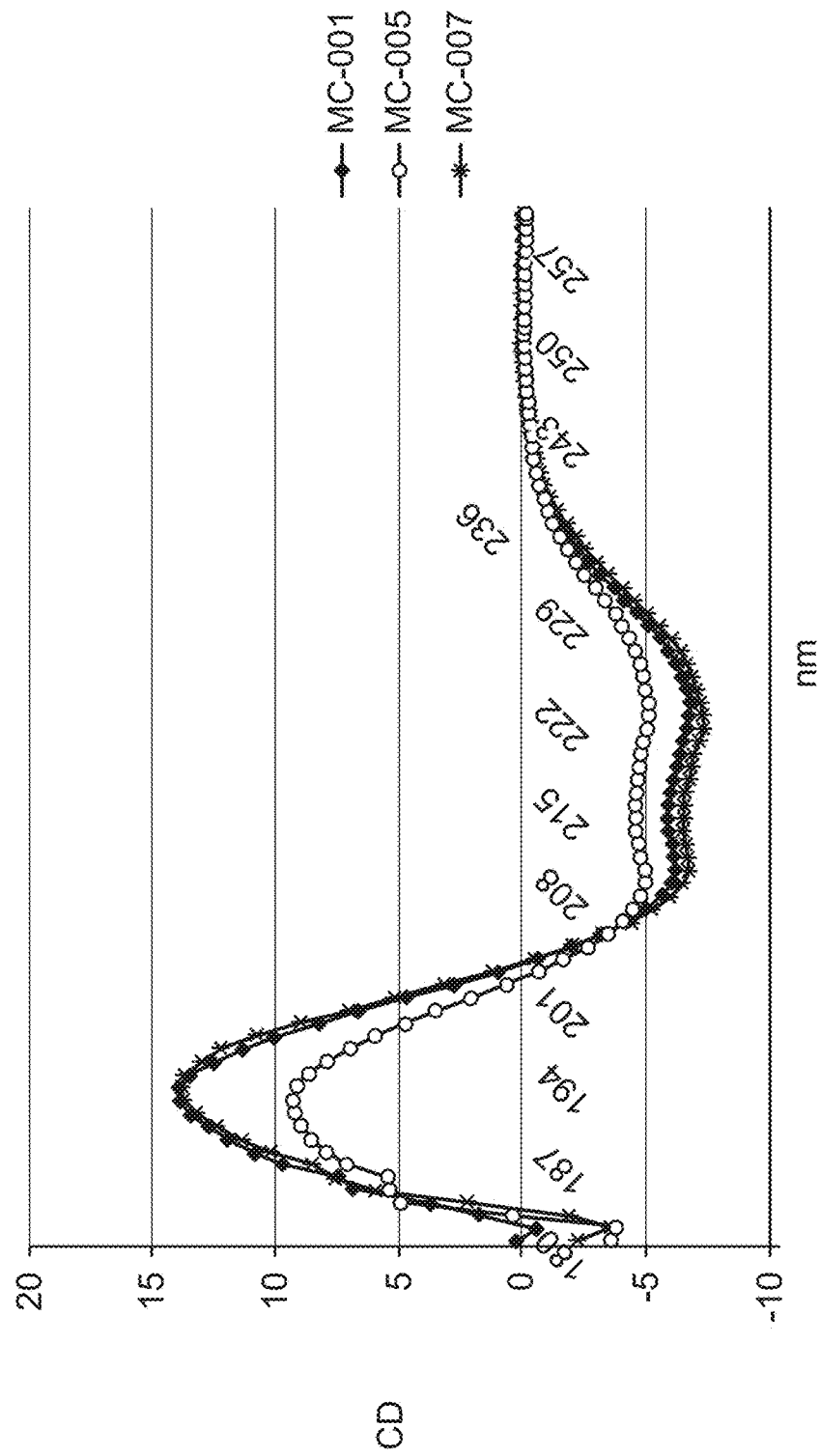
FIG. 9: Far-UV circular dichroism (CD) spectra of UspA2 constructs giving an indication of protein secondary structures.

Superposition of the spectra on FIG. 9 shows no significant difference in the shape between constructs. Spectra of MC-005 helix shows a lower intensity which could account for a lower alpha structure that is coherent with the absence of C-terminal helix.

FIG. 9 illustrates the far-UV circular dichroism spectra of UspA2 constructs MC-001, MC-005 and MC007 giving an indication of protein secondary structures. Superposition of spectra clearly shows that constructs containing half and full C-terminal helix have no detectable difference in their secondary structures, while the construct without helix generates a spectra with a difference in intensity that could account for a different secondary structure content.

Thermal Unfolding

Measurement of far-UV CD spectra at different temperatures during thermal unfolding suggested that MC-005 is less thermally stable than MC-007. The spectra observed at 33° C. for MC-005 is similar to the typical spectra of an unfolded protein. For the MC-007 construct, even if partial loss of secondary structures is observed at 33° C., the complete unfolding seems to occur between 35° C. and 37° C. This may be an indication of higher thermal stability of the full helix containing construct MC-007.

Figure 10:
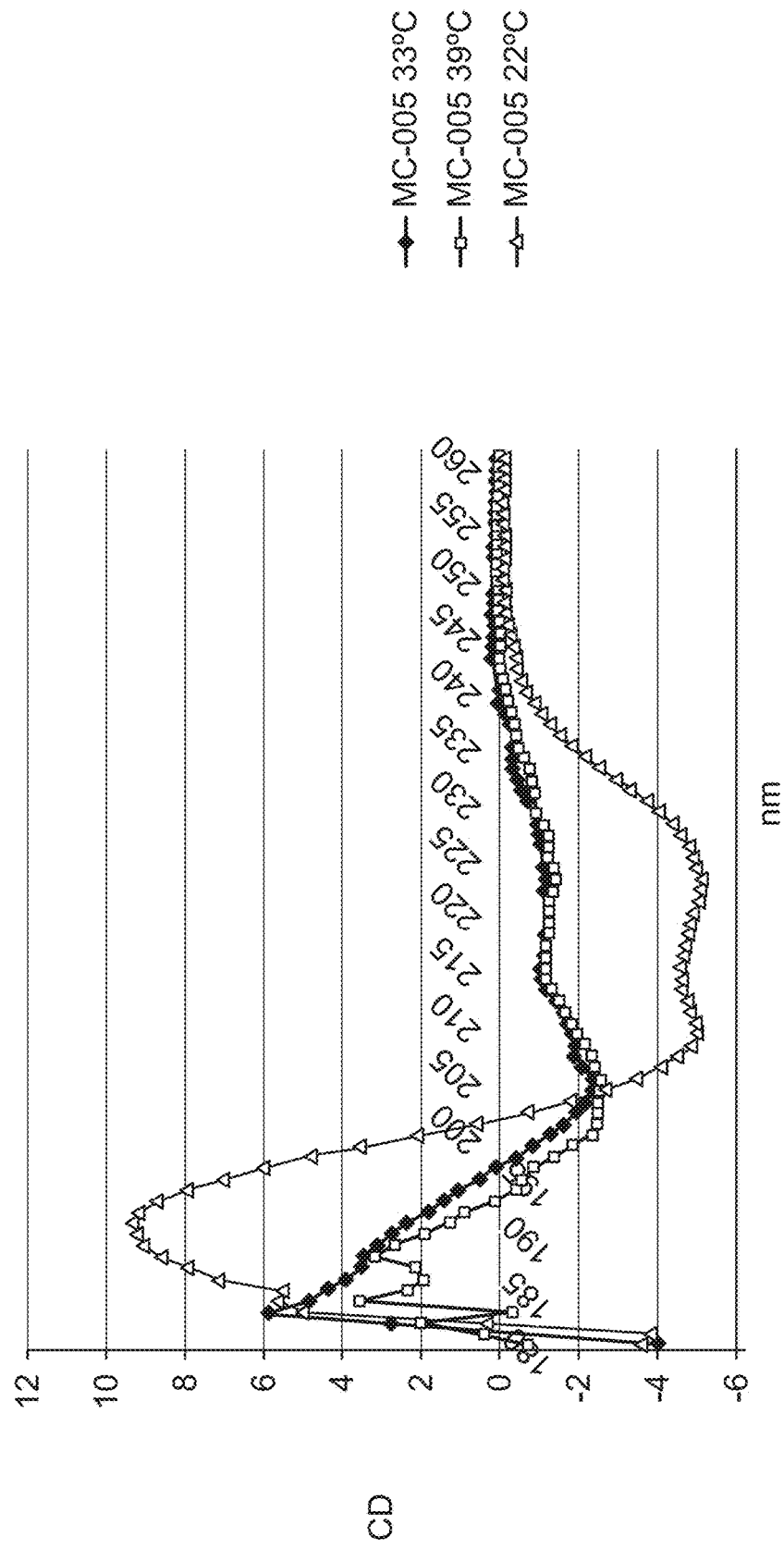
FIG. 10: Secondary structures monitoring by circular dichroism (CD) during thermal unfolding of MC-005 (UspA2Δhelix+6His). Visual analysis of the spectra clearly shows that protein loses most of its secondary structures at 33° C.

FIG. 10 illustrates secondary structures monitoring by circular dichroism during thermal unfolding of MC-005 (UspA2Δhelix+6His). Visual analysis of the spectra clearly shows that the protein loses most of its secondary structures at 33° C.

Figure 11:
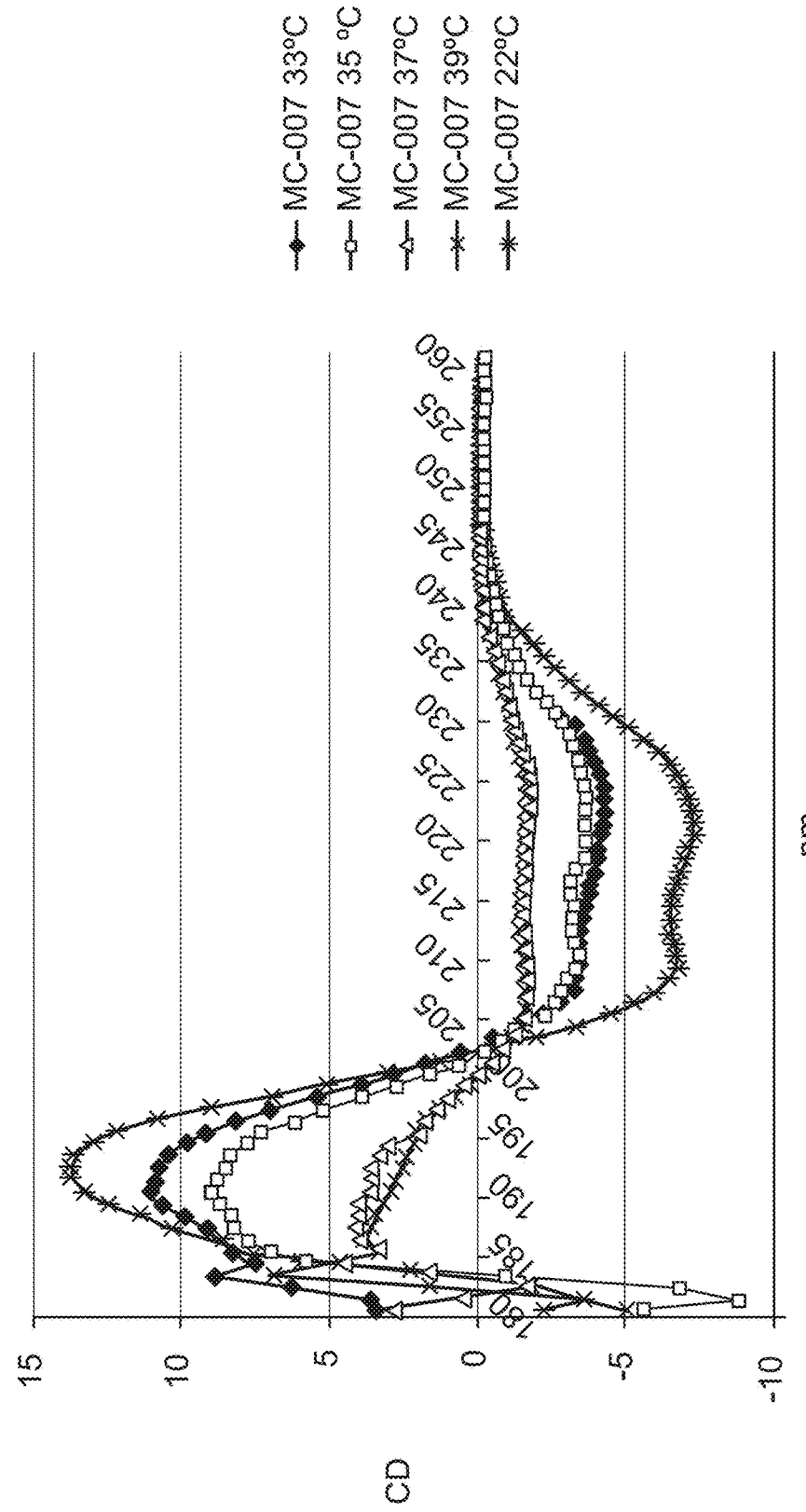
FIG. 11: Secondary structures monitoring by circular dichroism (CD) during thermal unfolding of MC-007 (UspA2 full helix+6His). Visual analysis of the spectra shows that loss of secondary structure is slower compared to the construct without helix. Structural changes are detectable upon heating to 33° C., but complete unfolding seems to occur between 35° C. and 37° C.

FIG. 11 illustrates secondary structures monitoring by circular dichroism during thermal unfolding of MC-007 (UspA2+helix+6His). Visual analysis of the spectra shows that loss of secondary structure is slower compared to the construct without helix. Structural changes are detectable upon heating to 33° C., but complete unfolding seems to occur between 35° C. and 37° C.

Differential Scanning Calorimetry (DSC) Thermal Unfolding

Thermal transitions of different UspA2 constructs were compared in order to evaluate the effect of C-terminal helix modifications on thermal stability of the proteins.

Analysis was done on VP-DSC from MicroCal (part of GE Healthcare). The buffer 20 mM NaPO4, 10 mM NaCl, 5 mM EDTA, pH8 was used as reference and subtracted from the scans. Proteins were equilibrated at initial temperature for 15 minutes before temperature ramping DSC scans were then conducted from 10° C. to 60° C. at a heating rate 90° C./hr.

Two transitions were detected in MC-001 and MC-007 constructs and only one in MC-005. Values of the transitions (or Tm) of the different constructs can be found on Table 6.

While the lower Tm of all three proteins is around 32° C., the main difference is the value of the second Tm. The construct containing a full helix (MC-007) has a higher Tm at 37.5° C. compared to 34.5° C. for the half helix (MC-001).

It has been demonstrated that for MC-001 and MC-007, the first Tm around 32° C. is reversible, while the higher Tm is irreversible. For MC-005, the only Tm detected is irreversible.

This may be an indication of a higher thermal stability of full helix containing construct MC-007.

TABLE 6

Melting points of UspA2 constructs measured by DSC

| Constructs | [mg/mL] | $Tm_1$ (° C.) | $Tm_2$ (° C.) |
|---|---|---|---|
| MC-005 lotBMP53 | 0.400 | 31.74 | — |
| MC-001 lotBMP54 | 0.400 | 32.02 | 34.51 |
| MC-007 lotBMP70 | 0.400 | 32.19 | 37.50 |

Mass Spectrometry

UspA2 protein samples were prepared by protein precipitation with $CHCl_3/MeOH/H_2O$ system. The protein pellet was centrifuged at the bottom of the eppendorf tube before being gently dried under nitrogen. The dried pellet was then dissolved in 2 μl of pure formic acid before being diluted with 3 μl of ultrapure water and 5 μl of sinapinic acid. Sinapinic acid used as matrix for MALDI-TOF (Matrix-Assisted Laser Desorption/Ionisation followed by Time-Of-Flight spectrometry analyser) analysis is prepared in 50% $CH_3CN/50\% H_2O$ supplemented by TFA 0.1% final concentration.

1 μl of the sample+matrix mixture was spotted onto a Bruker 384 ground stainless steel MALDI target and let to dry for crystallization at room temperature and atmospheric pressure (dried droplet method).

UspA2 mass spectrometry analysis was performed on a Bruker Ultraflex 2 MALDI-TOF mass spectrometer (Bruker Daltonics, Bremen, Germany) in positive ionization and linear mode. Protein samples, co-crystallized in sinapinic acid matrix, were irradiated by a smartbeam laser. Mass measurement of intact UspA2 protein were done over 10.000-100.000 Da mass range with an acceleration voltage of 25 kVolts. Laser attenuation was fine-tuned in order to get the best protein signal as possible and to avoid any fragmentation as well as background over-ionization phenomena. Calibration of the mass spectrometer was performed in close external method with homologous matrix and using the commercial Bruker Protein Calibration mixture 2, by accurate measures on the following calibrators: $[M+2H]^{2+}$ (mass measured by MS detector following addition of two $H^+$ ions to the protein dudring ionisation) species of protein A at m/z 22307 Da, $[M+H]^+$ species of trypsinogen at m/z 23982 Da, $[M+H]^+$ species of protein A at m/z 44613 Da and $[M+H]^+$ species of bovine albumin at m/z 66431 Da°. Each presented spectrum results from the sum of 500 individual shots.

The Following Samples were Analyzed:

MC-001 construct with MQAK amino acids (SEQ ID NO: 85) in N-terminal produced in shake flask, lot opt-01, MC-011 construct with MAK amino acids in N-terminal produced in shake flask, lot BM P37.

Figure 12:
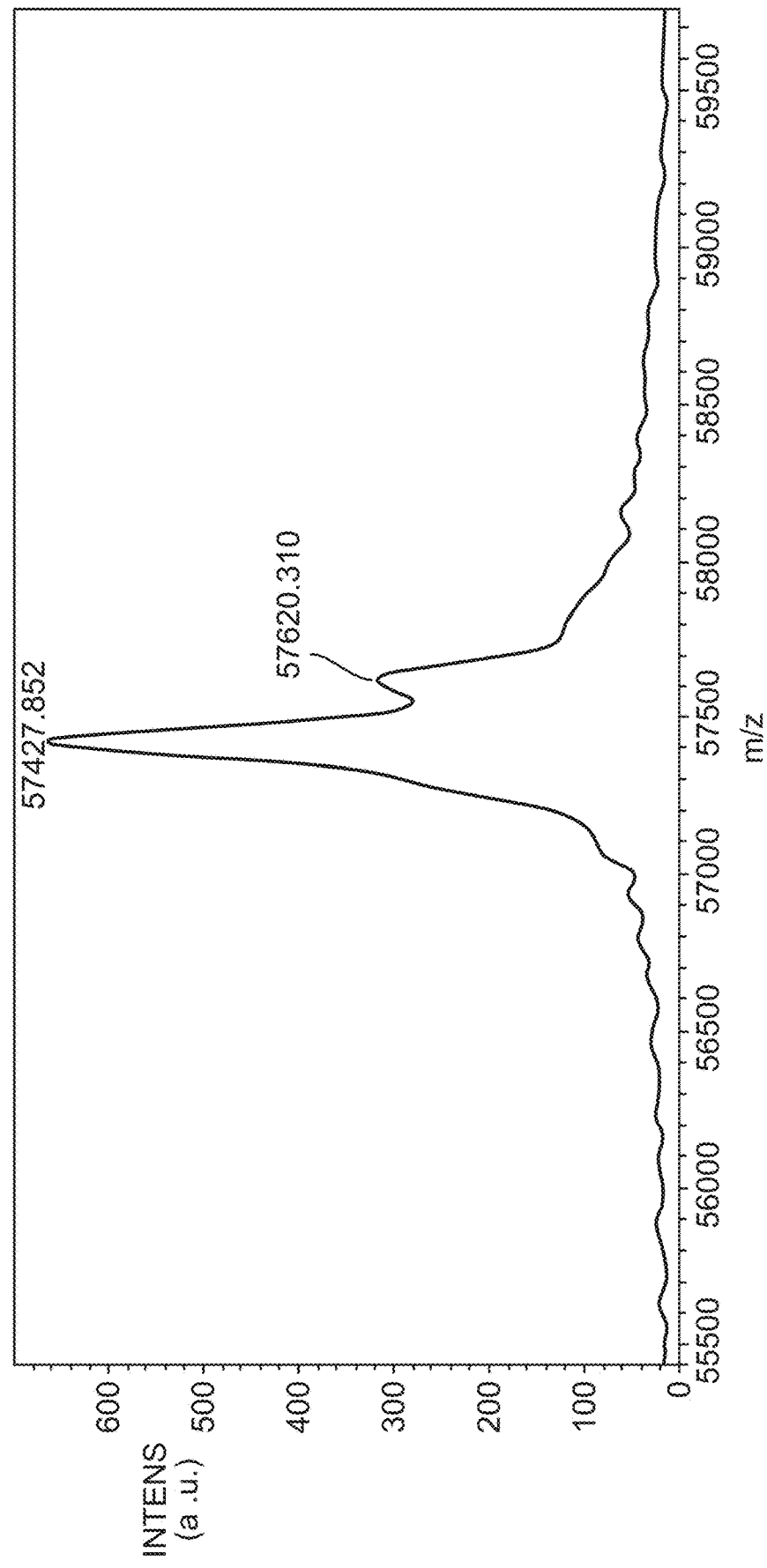
FIG. 12: MALDI spectrum of MC-001 lot opt-01. The mass observed at 57427 Da may be coherent with the demethionylated protein, while the peak at 57620 Da could correspond to the complete protein.

In Table 7 and FIG. 12, MC-001 protein with MQAK amino acids (SEQ ID NO: 85) at the N-terminal extremity has been shown to be at least partially demethionylated, as shown by the measured molecular mass of 57427 Da, compared to the expected mass of 57565 Da. The other peak of 57620 Da may represent the complete non-demethionylated protein, N-acetylated protein, or another modified protein population.

FIG. 12 illustrates the MALDI spectrum of MC-001 lot opt-01. The mass observed at 57427 Da may be coherent with the demethionylated protein, while the peak at 57620 Da could correspond to the complete protein.

Figure 13:
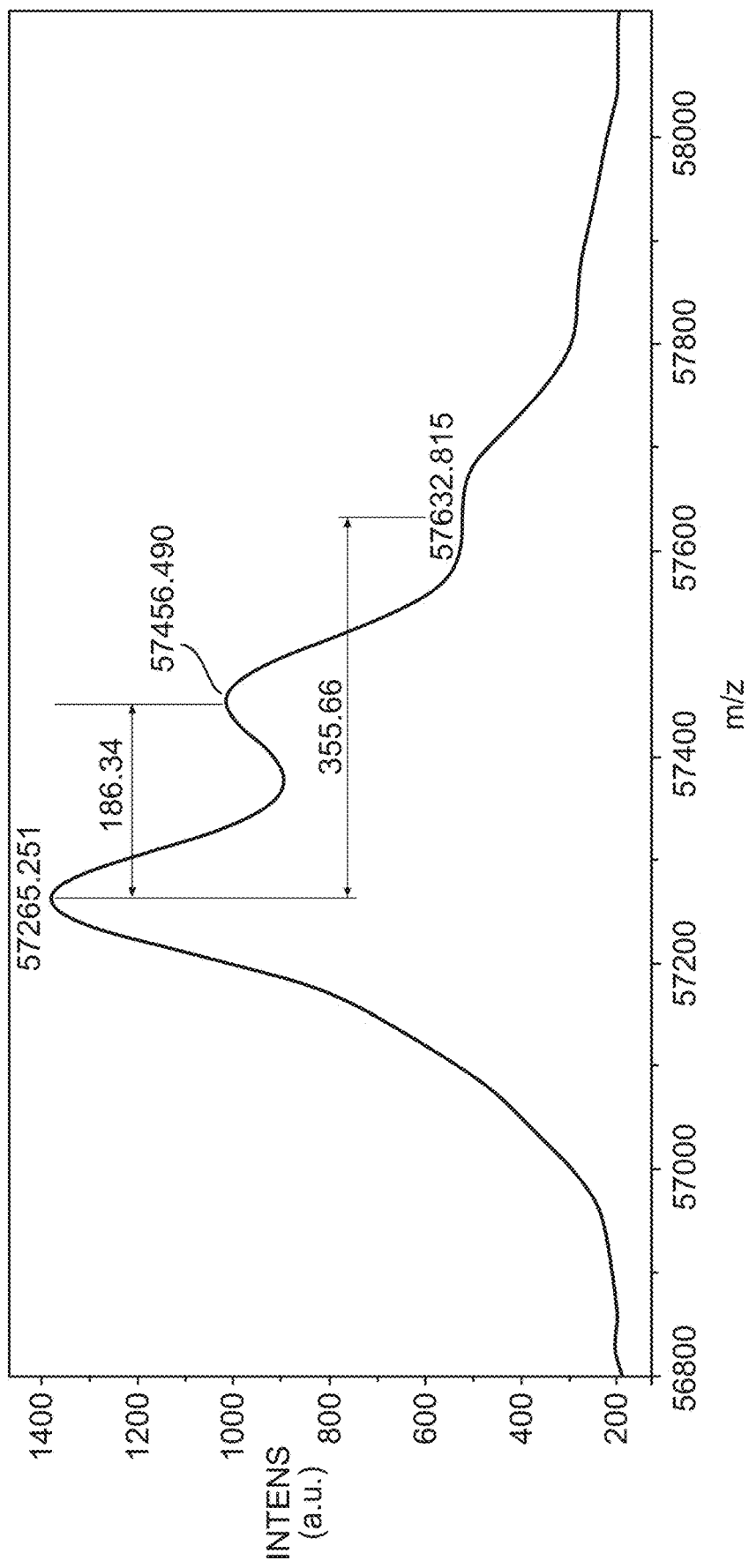
FIG. 13: MALDI spectrum of MC-011 lot BMP37. The mass observed may be coherent with the demethionylated protein. The two other peaks at +186 Da and +366 Da are unidentified.

As shown in Table 7 and FIG. 13, MC-011 protein with MAK amino acids at the N-terminal extremity gave a major population in MALDI-MS that may correspond to the demethionylated protein, with a mass of 57265 Da, compared to 57437 Da for the expected mass based on complete amino acid sequence. The two other peaks at +186 Da and +366 Da are not close to any expected post-translational modifications, so they couldn't be identified by this experiment.

TABLE 7

Molecular mass of two UspA2 constructs as measured by MALDI-MS. Both constructs have a main measured mass lower than the one expected from amino acid sequence. The mass of the major population obtained with both constructs may be coherent with a demethionylated protein.

| Protein | Theoretical mass (Da) | Measured mass (Da) | Comment |
|---|---|---|---|
| MC-001 lot opt-01 | 57565.8 | –57427.9 –57620.3 | Coherent with demethionylation (57434.6) Coherent with protein containing N-terminal methionine |
| MC-011 lot BMP37 | 57437.6 | 57265.2 | Coherent with demethionylation (57306.4) |

N-Terminal Sequencing by Edman's Degradation In order to evaluate if the optimisation of the N-terminal region (optimisation of the amino acid sequence next to the N-terminal methionine) leads to demethionylation of the protein, N-terminal sequencing has been done on the MC-011 construct carrying MAK amino acids on his N-terminal extremity.

The proteins were separated by SDS PAGE on a Novex 4%-20% polyacrylamide gel from Invitrogen, before transfer onto Problot PVDF (polyvinylidence diluoride) (Bio-Rad) membrane. The membrane was stained with amidoblack. The band of interest was then cut and analysis was carried out according to the manufacturer's protocol using an Applied Biosystems Procise sequencer system. Twelve cycles of Edman's degradation were performed.

The N-terminal amino acid sequence obtained is AKN-DITLEDLP (SEQ ID NO:86), which corresponds to the N-terminal extremity of the protein starting at the amino acid number two after the initial methionine. This indicates that the mature protein is mainly demethionylated.

Example 7: UspA2 Construct MC-001: Bactericidal Activity

Bactericidal Assay

*Moraxella catarrhalis* was cultivated overnight on Petri dish at 37° C.+5% $CO_2$. Bacteria were transferred in 12 ml HBSS-BSA (Hank's Buffered Salt Solution with Bovine Serum Album) 0.1% buffer in order to get an OD $_{620}$ of 0.650. Serum samples were heated for 45 min at 56° C. to inactivate the endogenous complement. Serial two-fold dilutions of sera in SBA buffer (HBSS-BSA 0.1%) were added on a 96-well round bottom microtitre plate (25 μl/well). Subsequently, 50 μl of SBA buffer were added in each well. Then 25 μl of *Moraxella catarrhalis* strains at $4 \times 10^4$ cfu/mL were added to the wells containing sera and incubated for 15 min at room temperature. Finally 25 μl of freshly thawed baby rabbit complement diluted ⅛ in HBSS-BSA 0.1% were added to reach a final volume of 125 μl. Plates were incubated for 1 h at 37° C. with orbital shaking (210 rpm). The reaction was stopped by laying the microplate on ice for at least 5 min.

After homogenization, various dilutions of the suspension (a mixture of bacteria, serum, complement and buffer, at a volume of 125 μl as discussed in the previous paragraph) were added onto chocolate agar plates and incubated for 24 hours at 37° C. with 5% $CO_2$ and *Moraxella catarrhalis* colonies were counted.

Eight wells without serum sample were used as bacterial controls to determine the number of *Moraxella catarrhalis* colonies per well. The mean number of CFU (colony forming unit) of the control wells was determined and used for the calculation of the killing activity for each serum sample. The bactericidal titers were expressed at the reciprocal dilution of serum inducing 50% of killing.

Anti-UspA2 antisera generated in mice, guinea pigs and rabbits against MC-001 were tested in the bactericidal assay described here above against 20 different *Moraxella catarrhalis* strains isolated from various tissues (blood, sputum, nose, middle ear fluids) in various countries (US, Finland, Netherlands, Norway, Sweden).

As shown below anti-UspA2 antibodies were able to induce a cross-bactericidal killing of *Moraxella catarrhalis*, whatever the percentage of homology of the UspA2 expressed by the tested strain. Moreover bactericidal activity was also shown against strains which only express UspA1 or the chimeric protein UspA2H. As expected, no or only weak bactericidal antibody titres were measured against UspA1 and UspA2 double knock-out mutants.

TABLE 8

Cross-bactericidal activity of anti-UspA2 MC-001 antibodies generated in mouse, guinea pig and rabbit. 1 + 2 KO is a double knockout, UspA1 & UspA2. 1KO is a UspA1 knockout only. MEF (AOM) = Middle Ear Fluid (Acute Otitis Media). "/" in the Isolate source column = not aware of the isolate source.

| Strains | | Isolate source | UspA gene present | Identity %* versus the vaccine sequence ATCC25238 | Anti-UspA2 antiserum bactericidal activity | | |
|---|---|---|---|---|---|---|---|
| | | | | | Mouse | Guinea pig | Rabbit |
| ATCC | 25238 | / | UspA1/UspA2 | 45.2/100 | +++ | ++ | +++ |
| | 43617 | Bronchitis | UspA1 | 40.1 | + | + | + |
| American | 2926 | / | UspA1 | 36.4 | − | +/− | − |
| | 2933 | / | UspA1/UspA2 | 44.6/62.4 | − | ++ | ++ |
| | 2912 | / | UspA1/UspA2 | 39.3/64.6 | ++ | ++ | +++ |
| | 2908 | / | UspA1/UspA2 | 43.3/52.8 | +++ | +++ | +++ |
| Finnish | 307 | MEF (AOM) | UspA1/UspA2 | 47.6/70.1 | − | ++ | +++ |
| | 353 | MEF (AOM) | UspA1/UspA2 | 45/61.8 | + | ++ | ++ |
| | 358 | MEF (AOM) | UspA1/UspA2 | 47/61.5 | +++ | +++ | +++ |
| | 216 | MEF (AOM) | UspA1/UspA2 | 46.6/66.9 | +++ | +++ | +++ |
| Dutch | N9 | nose | UspA1/UspA2H | 41.1/70.1 | ++ | +++ | +++ |
| | H2 | sputum | UspA1/UspA2 | 47/61.6 | +++ | +++ | +++ |
| | F10 | sputum | UspA1/UspA2 | 42.9/61.1 | ++ | +++ | +++ |
| Norvegian | 1 | Tracheotomy (Pneumonia) | UspA1/UspA2 | 44.6/60.9 | +++ | +++ | +++ |
| | 13 | Tracheotomy (Pneumonia) | UspA1/UspA2 | 47.8/55 | ++ | +++ | +++ |
| | 20 | Tracheotomy (Pneumonia) | UspA1/UspA2 | 33.7/60.6 | +++ | ++ | +++ |
| | 25 | Tracheotomy (Pneumonia) | UspA1/UspA2 | 47.8/55 | ++ | +++ | +++ |
| | 27 | Tracheotomy (Pneumonia) | UspA1/UspA2 | 46/76.1 | ++ | +++ | +++ |
| | 36 | Tracheotomy (Pneumonia) | UspA1/UspA2 | 53.6/61.6 | + | ++ | ++ |
| Swedish | BBH18 WT | sputum | UspA1/UspA2H | 42.9/57.3 | +++ | +++ | +++ |
| | BBH18 (1 + 2KO) | | − | − | + | − | − |
| | BBH18 (1KO) | | UspA2H | 57.3 | +++ | +++ | +++ |
| | RH4 WT | blood | UspA1/UspA2H | 37.4/59.9 | not done | ++ | ++ |
| | RH4 (1 + 2KO) | | − | − | − | − | + |

*determined using the software GapL/ClustalX versus the ATCC25238 UspA2 fragment AA30-540.
+++ >50000
++ >20000
+ >500
− <200

TABLE 9

UspA Expression in the *M. catarrhalis* strains in Table 8.

| Strains | | UspA1 expression | UspA2 expression | UspA2H expression |
|---|---|---|---|---|
| ATCC | 25238 | Yes | Yes | No |
| | 43617 | Yes | stop codon | No |
| American | 2926 | Yes | No | stop codon |
| | 2933 | Yes | Yes | No |
| | 2912 | Yes | Yes | No |
| | 2908 | Yes | Yes | No |
| Finnish | 307 | Yes | Yes | No |
| | 353 | Yes | Yes | No |
| | 358 | Yes | Yes | No |
| | 216 | Yes | Yes | No |
| Dutch | N9 | Yes | No | Yes |
| | H2 | Yes | Yes | No |
| | F10 | Yes | Yes | No |
| Norvegian | 1 | Yes | Yes | No |
| | 13 | Yes | Yes | No |
| | 20 | Yes | Yes | No |
| | 25 | Yes | Yes | No |
| | 27 | Yes | Yes | No |
| | 36 | Yes | Yes | No |
| Swedish | BBH18 WT | Yes | No | Yes |
| | BBH18 (1 + 2KO) | No | No | No |
| | BBH18 (1KO) | No | No | Yes |
| | RH4 WT | Yes | No | Yes |
| | RH4 (1 + 2KO) | No | No | No |

Example 8: Protection in a Mouse Model of Lung Colonization (MC-001)

Five weeks-old female Balb/c mice (n=8/5 groups) were immunized by the intramuscular route at days 0, 14 and 28 with 50 µl of vaccine containing 10 µg of UspA2 construct MC-001 formulated within AS02V. Mice were intranasally challenged at day 42 with $5 \times 10^5$ CFU of various *Moraxella catarrhalis* strains. Bacteria were counted in lungs collected 0, 3 and 6 hours post-challenge. Differences between groups were analysed using the Dunnet test.

As summarised in Table 10, UspA2 construct MC-001 induced a significant protection against both homologous and heterologous strains, including the strain 43617 which does express UspA1 but not UspA2 and the BBH18 strain which expresses the chimeric protein UspA2H (constituted of the N-terminal sequence from UspA1 and the C-terminal sequence from UspA2).

TABLE 10

Protective efficacy of UspA2. MC-001 construct.

| Strain | UspA expressed | Identity % * versus the vaccinal sequence ATCC25238 | $Log_{10}$ cfu/ml | | p value |
|---|---|---|---|---|---|
| | | | Control group | Vaccine group | |
| 25238 | UspA1 & UspA2 | 45.2/100 | 5.2 | 3.1 | 0.01 |
| 43617 | UspA1 | 40.1 | 4.9 | 3.6 | 0.01 |
| F10 | UspA1 & UspA2 | 42.9/61.1 | 4.3 | 3.9 | 0.25 |
| F10 | UspA1 & UspA2 | 42.9/61.1 | 4.4 | 3.6 | 0.01 |
| BBH18 | UspA1 & UspA2H | 42.9/57.3 | 4.3 | 3.5 | 0.01 |
| 20 | UspA1 & UspA2 | 33.7/60.6 | 4.4 | 3.9 | 0.02 |

* determined using the GapL/ClustalX software versus the ATCC25238 UspA2 fragment AA 30-540
p values in bold are significant ($p < 0.05$)

Example 9: UspA2 Construct MC-007: Antibody Bactericidal Activity

Bactericidal Assay

*Moraxella catarrhalis* 25238 was cultivated overnight on Petri dish at 37° C.+5% $CO_2$. Bacteria were transferred in 12 ml HBSS-BSA 0.1% buffer in order to get an OD 620 of 0.650. Serum samples were heated for 45 min at 56° C. to inactivate the endogenous complement.

Serial two-fold dilutions of sera in SBA buffer (HBSS-BSA 0.1%) were added on a 96-well round bottom microtitre plate (25 µl/well). Subsequently, 50 µl of SBA buffer were added in each well. Then 25 µl of *Moraxella catarrhalis* 25238 strain at 4 $10^4$ cfu/mL were added to the wells containing sera and incubated for 15 min at room temperature. Finally 25 µl of freshly thawed baby rabbit complement diluted 1/8 in HBSS-BSA 0.1% were added to reach a final volume of 125 µl. Plates were incubated for 1 h at 37° C. with orbital shaking (210 rpm). The reaction was stopped by laying the microplate on ice for at least 5 min. After homogenization, various dilutions of the suspension were added onto chocolate agar plates and incubated for 24 hours at 37° C. with 5% $CO_2$ and *Moraxella* colonies were counted. Eight wells without serum sample were used as bacterial controls to determine the number of *Moraxella catarrhalis* colonies per well. The mean number of CFU of the control wells was determined and used for the calculation of the killing activity for each serum sample. The bactericidal titers were expressed at the reciprocal dilution of serum inducing 50% of killing.

Anti-UspA2 antisera generated in mice with UspA2 construct MC-001 or MC-007 were tested in a bactericidal assay using the protocol described above against the 25238 *Moraxella catarrhalis* homologous strain.

As shown in Table 11, the MC-007 UspA2 construct elicited a high bactericidal response, similar to that induced by the MC-001.

TABLE 11

Bactericidal activity of anti-UspA2 MC-001 and MC-007 antibodies. Normal mouse sera = sera from mice immunized with AS02V only, not with UspA2.

| Samples | Bactericidal titers |
|---|---|
| Normal mouse sera (AS02V) | − |
| Mouse Anti-Killed whole cells 25238 | ++ |
| Mouse anti-UspA2 against UspA2 MC-001 | +++ |
| Mouse anti-UspA2 against UspA2 MC-007 | +++ |

Example 10: UspA2 Construct MC-007: Protective Efficacy in a Lung Challenge Model Protection in a Mouse Model of Lung Colonization Five weeks-old female Balb/c mice (8 mice per group, 5 groups max per time point) were immunized by the intramuscular route at days 0, 14 and 28 with 50 µl of vaccine containing 10 µg of UspA2 construct MC-001 formulated with AS02V or MC-007 formulated within AS02V. Mice were intranasally challenged at day 42 with 5×$10^5$ CFU of *Moraxella catarrhalis* strain ATCC (a US registered trademark) 25238™. Mice were immunized with 10 µg of killed whole cells from *Moraxella catarrhalis* strain ATCC (a US registered trademark) 25238™ (as positive control) (*M. cat.* WC 25238 in FIG. 14) or with AS02V alone (as negative control). Bacteria were counted in lungs collected 0, 3 and 6 hours post-challenge. Differences between groups were analysed using the Dunnet test.

Figure 14:
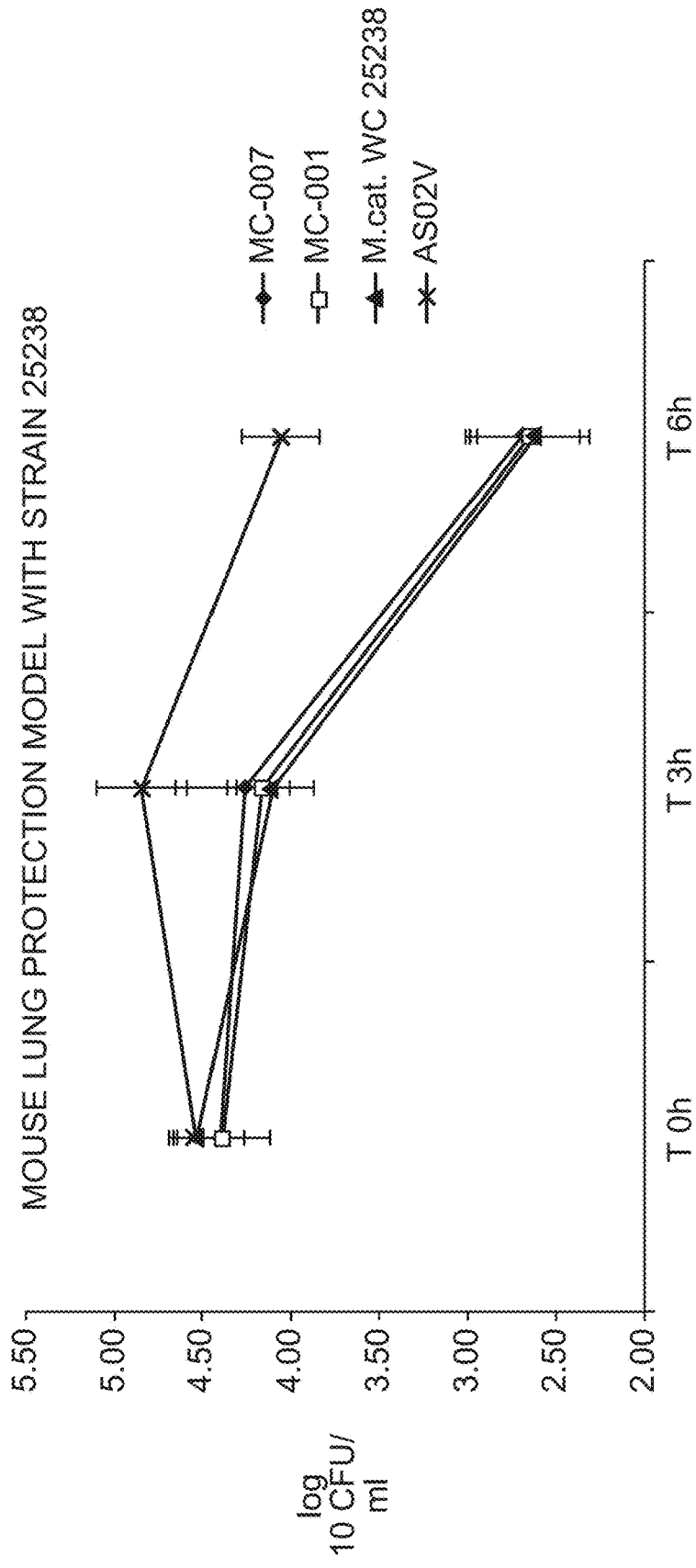
FIG. 14: Protective efficacy of MC-001 and MC-007 in a mouse model of lung colonization.

As shown in FIG. 14, both UspA2 constructs were similarly protective against ATCC (a US registered trademark) strain 25238™.

Example 11: Immunocienicity of UspA2 MC-009 Protein Formulations in Mice

Groups of 25 female Balb/c mice were immunized by the intramuscular (IM) route at days 0, 14 and 28 with 50 µl of the following formulations:
MC-009 (1 µg) $AlPO_4$ (1000 µg/ml)
MC-009 (1 µg) AS04C ($AlPO_4$/MPL 100/100 per ml)
MC-009 (1 µg) AS01E (QS21/MPL 50/50 per ml)
Anti-IgG levels were determined in individual sera collected at days 28 (PII) and 42 (PIII) using the following protocol:

ELISA to Measure Anti-UspA2 Antibodies.

Plates were coated overnight at 4° C. with 100 µl per well of UspA2 construct MC-009 at 4 µg/ml in carbonate buffer pH 9.6. The plates were washed three times with NaCl 0.09% TWEEN (a US registered trademark) 20 (polysorbate 20) 0.05%. After washing, serial two fold dilutions of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA Sigma P8787) and 5 µl of $H_2O_2$ in 10 ml of citrate 0.1M PH (pH) 4.5) was added to each well (100 µl/well) for 15 min in darkness. The reaction was stopped by addition of 50 µl of HCl 1N and the absorbance was read at 490 nm (620 nm for the reference filter).

The titers were calculated by the 4-parameters method using the SOFTMAX (a US registered trademark) Pro software.

Figure 15:
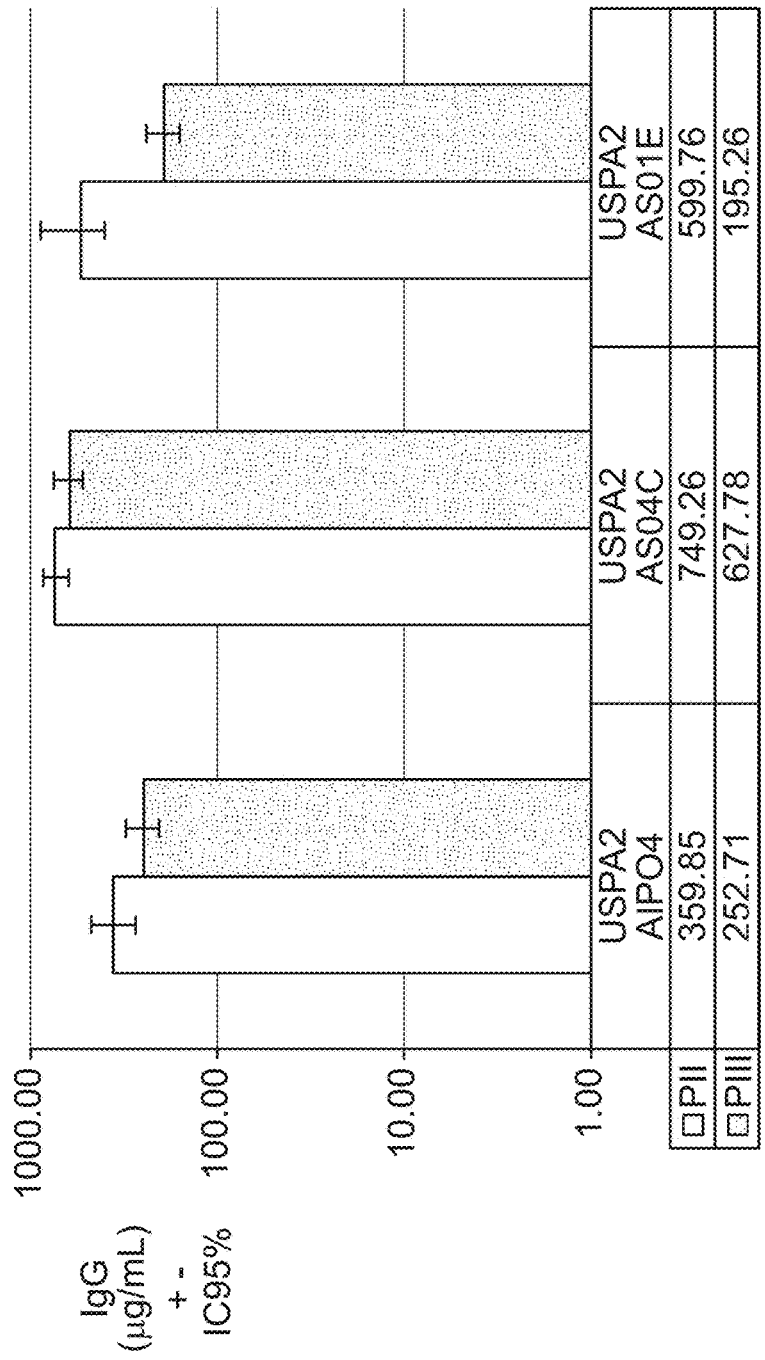
FIG. 15: Antibody response directed against UspA2 induced after intramuscular administration in mice, where PII and PIII indicate, respectively, anti-IgG levels in sera collected at day 28 (post II) and day 42 (post III).

As shown in FIG. 15, UspA2 induced high antibody levels with each adjuvant formulation.

Bactericidal Assay

The bactericidal assay was performed against *M. catarrhalis* strain (ATCC (a US registered trademark) 25238™) expressing a homologous full length UspA2 using the following protocol: *Moraxella catarrhalis* strain ATCC (a US registered trademark) 25238™ was cultivated overnight on Petri dish at 37° C.+5% $CO_2$. Bacteria were transferred in 10 ml of BHi (broth heart infusion) in order to get an OD $_{620}$ of 0.650. Serum samples were heated for 45 min at 56° C. to inactivate the endogenous complement. Serial two-fold dilutions of sera in SBA buffer (HBSS-BSA 0.1%) were added on a 96-well round bottom microtitre plate (25 µl/well). Subsequently, 50 µl of SBA buffer were added in each well. Then 25 µl of *Moraxella catarrhalis* strain 25238™ at 4×$10^3$ cfu/m L were added to the wells containing sera and incubated for 15 min at room temperature. Finally 25 µl of freshly thawed baby rabbit complement diluted 1/8 in HBSS-BSA 0.1% were added to reach a final volume of 125 µl. Plates were incubated for 1 h at 37° C. with orbital shaking (210 rpm). The reaction was stopped by laying the microplate on ice for at least 5 min. A 20 µl aliquot of each well of the plate was then transferred into the corresponding well of a 96-well flat bottom microplate and 50 µl of Mueller Hinton Broth-0.9% agar was added to each well. 50 µl of PBS 0.9% agar was added as a second layer. After 3 hours at 37° C. with 5% $CO_2$ plates were incubated overnight at 25° C., *Moraxella* colonies were counted using an automated image analysis system (KS 400, Zeiss, Oberkochen, Germany). Eight wells without serum sample were used as bacterial controls to determine the number of *Moraxella* per well. The mean number of CFU of the control wells was determined and used for the calculation of the killing activity for each serum sample. The bactericidal titers were expressed at the reciprocal dilution of serum inducing 50% of killing.

Figure 16:
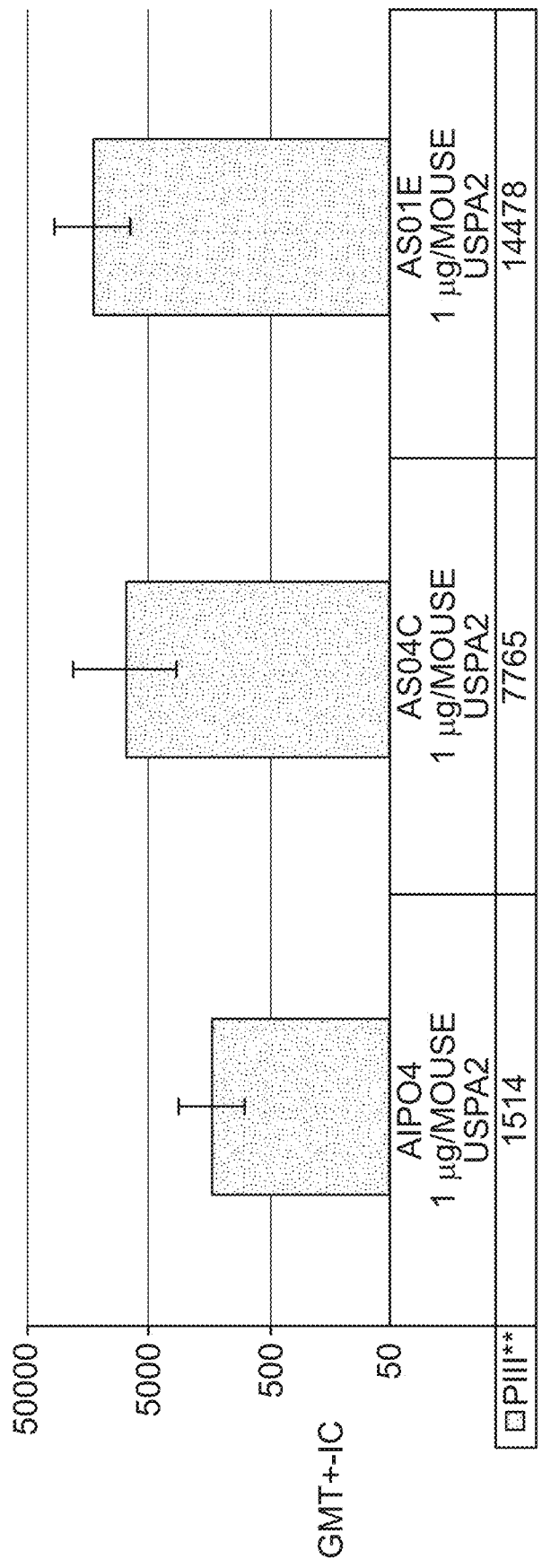
FIG. 16: Bactericidal titers induced by UspA2 against a homologous strain formulated with different adjuvants ($AS01_E$, $AS04_C$ and $AlPO_4$).

FIG. 16 illustrates the bactericidal titers induced by UspA2 against a homologous strain. In this experiment, UspA2 induced high levels of bactericidal antibodies for each adjuvant formulation. Sera were tested at PIII; five pools of five sera samples were tested.

Example 12: Immunogenicity of UspA2 in Combination with PD and PE-PilA NTHi Antigens Immunization Protocol Groups of 25 female Balb/c mice were immunized by the intramuscular (IM) route at days 0, 14 and 28 with 50 µl of the following formulations:

UspA2 construct MC-009 (1 µg) AlPO4
UspA2 construct MC-009 (1 µg) AS04C
UspA2 construct MC-009 (1 µg) AS01E
UspA2-PD-PEPilA (UspA2 construct MC-009, PEPilA construct LVL-735) AlPO4 (1 ug of each of UspA2, PD and PEPilA; 1000 mg/ml AlPO4)
UspA2-PD-PEPilA (UspA2 construct MC-009, PEPilA construct LVL-735) AS04C AlPO4 (1 ug of each of UspA2, PD and PEPilA; 100/100 per ml AlPO4/MPL)
UspA2-PD-PEPilA (UspA2 construct MC-009, PEPilA construct LVL-735) AS01E (1 ug of each of UspA2, PD and PEPilA; 50/50 per ml QS21/MPL)

ELISA to Measure Anti-UspA2 Antibodies

Anti-UspA2 IgG levels were determined in individual sera collected at days 28 and 42 using the following protocol.

Plates were coated overnight at 4° C. with 100 µl per well of UspA2 construct MC-009 at 4 µg/ml in carbonate buffer pH 9.6. The plates were washed three times with NaCl 0.09% TWEEN (a US registered trademark) 20 (polysorbate 20) 0.05%. After washing, serial two fold dilutions of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA Sigma P8787) and 5 µl of $H_2O_2$ in 10 ml of citrate 0.1M PH (pH) 4.5) was added to each well (100 µl/well) for 15 min in darkness. The reaction was stopped by addition of 50 µl of HCl 1N and the absorbance was read at 490 nm (620 nm for the reference filter). The titers were calculated by the 4-parameters method using the SOFTMAX (a US registered trademark) Pro software.

ELISA to Measure Anti-PE Antibodies

Plates were coated overnight at 4° C. with 100 µl per well of 2 µg/ml of UspA2 in carbonate buffer pH 9.6. The plates were washed three times with NaCl 0.09% TWEEN (a US registered trademark) 0.05%. After washing, serial two fold dilution of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA and 5 µl of $H_2O_2$ in 10 ml of citrate 0.1M PH 4.5) was added to each well (100 µl/well) for 15 min in darkness. The reaction was stopped by addition of 50 µl of HCl 1N and the absorbance was read at 490 nm (620 nm for the reference filter). The titers were calculated by the 4-parameters method using the SOFTMAX (a US registered trademark) Pro software.

ELISA to Measure Anti-PilA Antibodies

Plates were coated overnight at 4° C. with 100 µl per well of 4 µg/ml of PilA in carbonate buffer pH 9.6. The plates were washed three times with NaCl 0.09% TWEEN (a US registered trademark) 0.05%. After washing, serial two fold dilution of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA and 5 µl of $H_2O_2$ in 10 ml of citrate 0.1M PH 4.5) was added to each well (100 µl/well) for 15 min in darkness. The reaction was stopped by addition of 50 µl of HCl 1N and the absorbance was read at 490 nm (620 nm for the reference filter). The titers were calculated by the 4-parameters method using the SOFTMAX (a US registered trademark) Pro software.

ELISA to Measure Anti-PD Antibodies

Plates were coated overnight at 4° C. with 100 µl per well of 8 µg/ml of PD in carbonate buffer pH 9.6. The plates were washed three times with NaCl 0.09% TWEEN (a US registered trademark) 0.05%. After washing, serial two fold dilution of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA and 5 µl of $H_2O_2$ in 10 ml of citrate 0.1M PH 4.5) was added to each well (100 µl/well) for 15 min in darkness. The reaction was stopped by addition of 50 µl of HCl 1N and the absorbance was read at 490 nm (620 nm for the reference filter). The titers were calculated by the 4-parameters method using the SOFTMAX (a US registered trademark) Pro software.

Bactericidal Assay

Bactericidal titres were measured in pooled sera (5 pools/group) collected at day 42 using the following protocol:

*Moraxella catarrhalis* was cultivated overnight on Petri dish at 37° C.+5% $CO_2$. Bacteria were transferred in 10 ml BHi (broth heart infusion) medium in order to get an $OD_{620}$ of 0.650. Serum samples were heated for 45 min at 56° C. to inactivate the endogenous complement. Serial two fold dilutions of sera in SBA buffer (HBSS-BSA 0.1%) were added on a 96-well round bottom microtitre plate (25 µl/well). Subsequently, 50 µl of SBA buffer were added in each well. Then 25 µl of *Moraxella catarrhalis* strain 25238 at $4\times10^3$ cfu/mL were added to the wells containing sera and incubated for 15 min at room temperature. Finally 25 µl of freshly thawed baby rabbit complement diluted 1/8 in HBSS-BSA 0.1% were added to reach a final volume of 125 µl. Plates were incubated for 1 h at 37° C. with orbital shaking (210 rpm). The reaction was stopped by laying the microplate on ice for at least 5 min. A 20 µl aliquot of each well of the plate was then transferred into the corresponding well of a 96-well flat bottom microplate and 50 µl of Mueller Hinton Broth-0.9% agar was added to each well. 50 µl of PBS 0.9% agar was added as a second layer. After 3 hours at 37° C. with 5% $CO_2$ plates were incubated overnight at 25° C. *Moraxella* colonies were counted using an automated image analysis system (KS 400, Zeiss, Oberkochen, Germany). Eight wells without serum sample were used as bacterial controls to determine the number of *Moraxella* per well. The mean number of CFU of the control wells was determined and used for the calculation of the killing activity for each serum sample. The bactericidal titers were expressed at the reciprocal dilution of serum inducing 50% of killing.

The bactericidal assay was performed against *Moraxella catarrhalis* strain 25238™, expressing a homologous UspA2.

Figure 17:
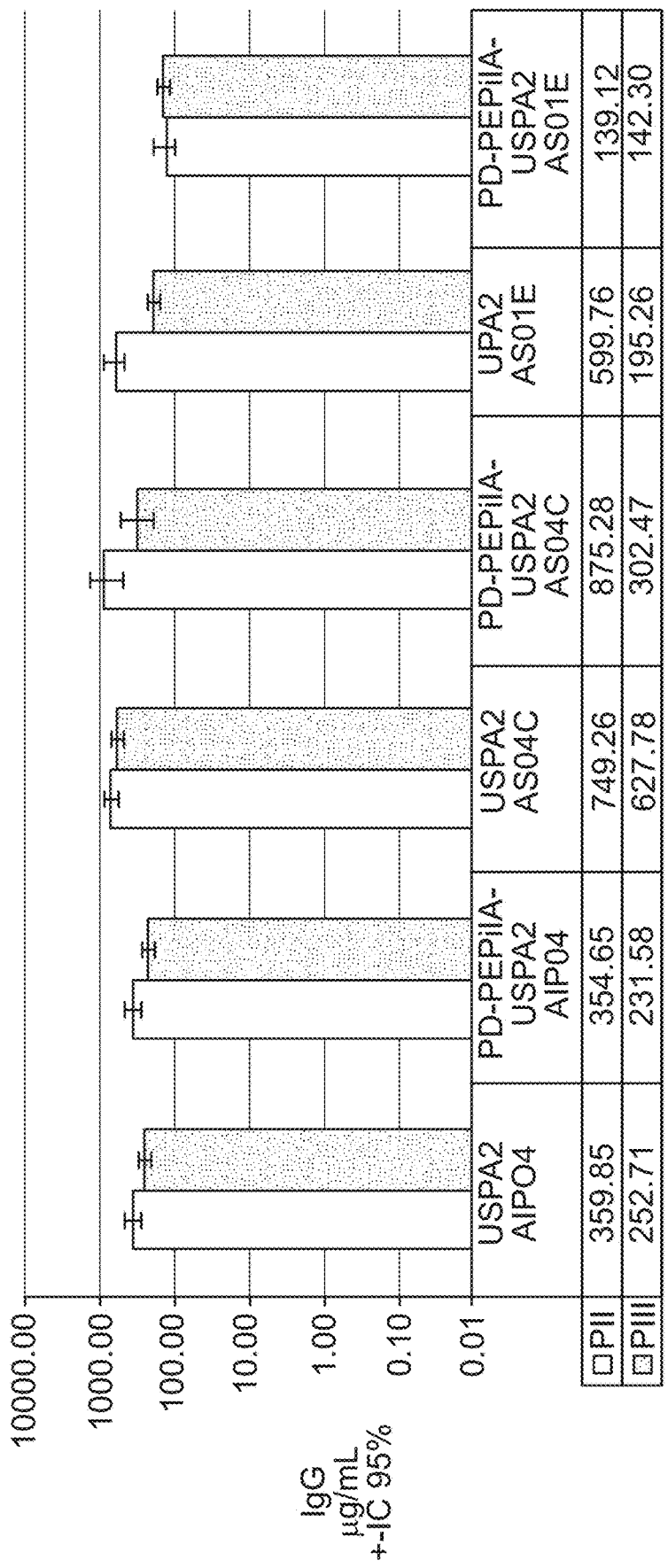
FIG. 17: Antibody response directed against UspA2 induced after intramuscular administration in mice, using different formulations of antigens and adjuvants.
Figure 18:
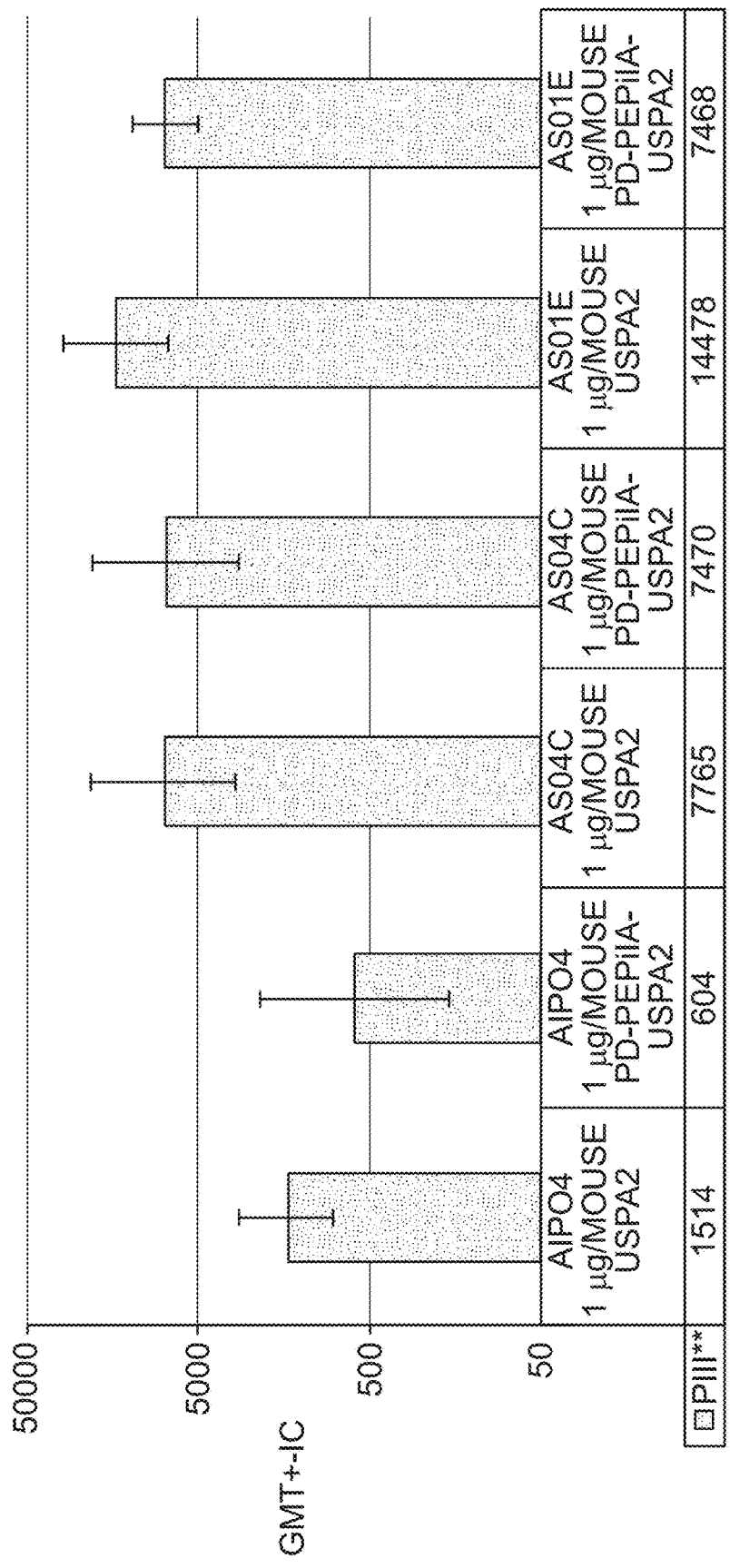
FIG. 18: Bactericidal titers induced by UspA2 against a homologous strain, using different formulations of antigens and adjuvants.
Figure 19:
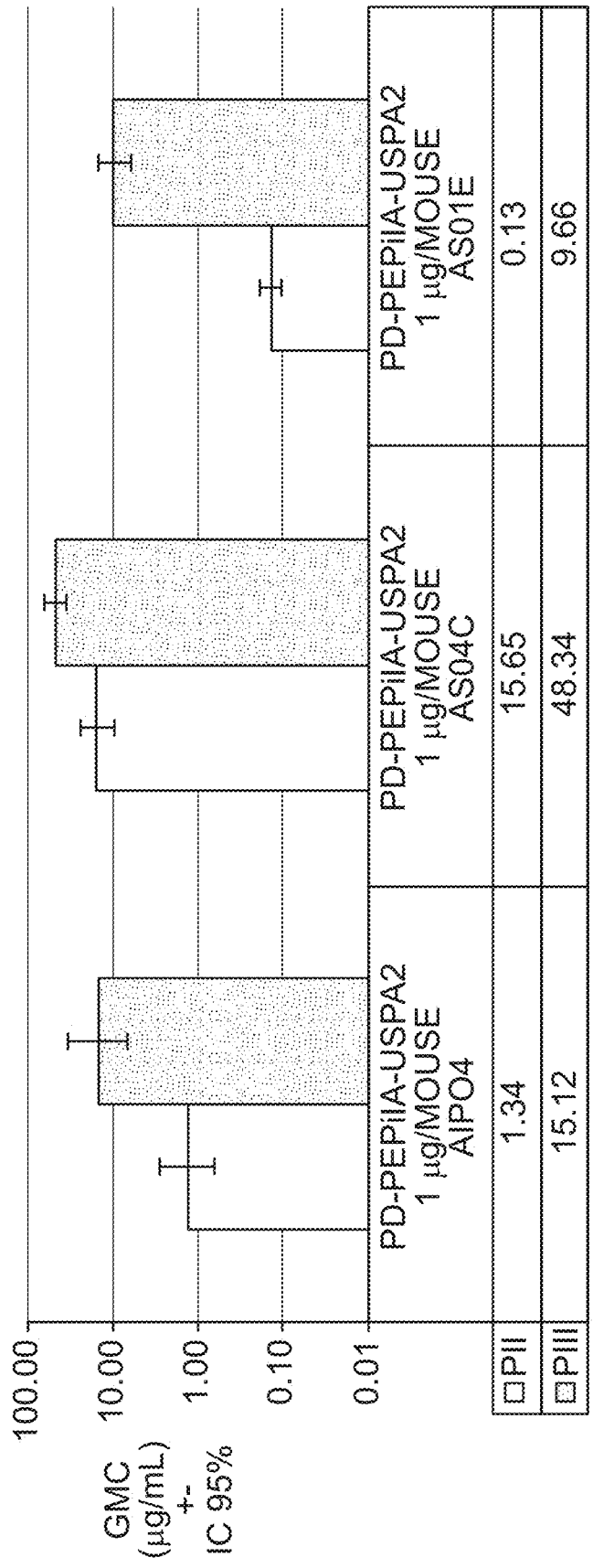
FIG. 19: IgG response induced against PD in mice by PD-PEPilA-UspA2 vaccine (a trivalent NTHi-*M. cat.* vaccine), formulated with different adjuvants.
Figure 20:
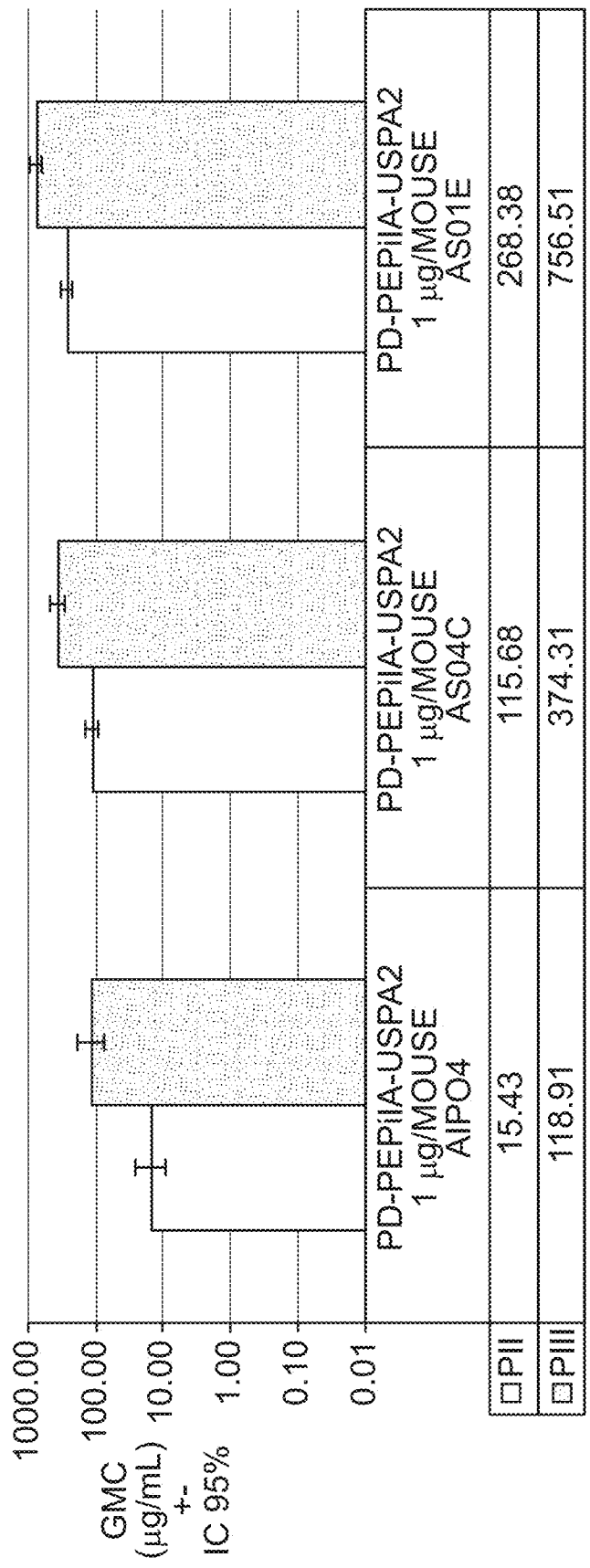
FIG. 20: IgG response induced against PE in mice by PD-PEPilA-UspA2 vaccine (a trivalent NTHi-*M. cat.* vaccine), formulated with different adjuvants.
Figure 21:
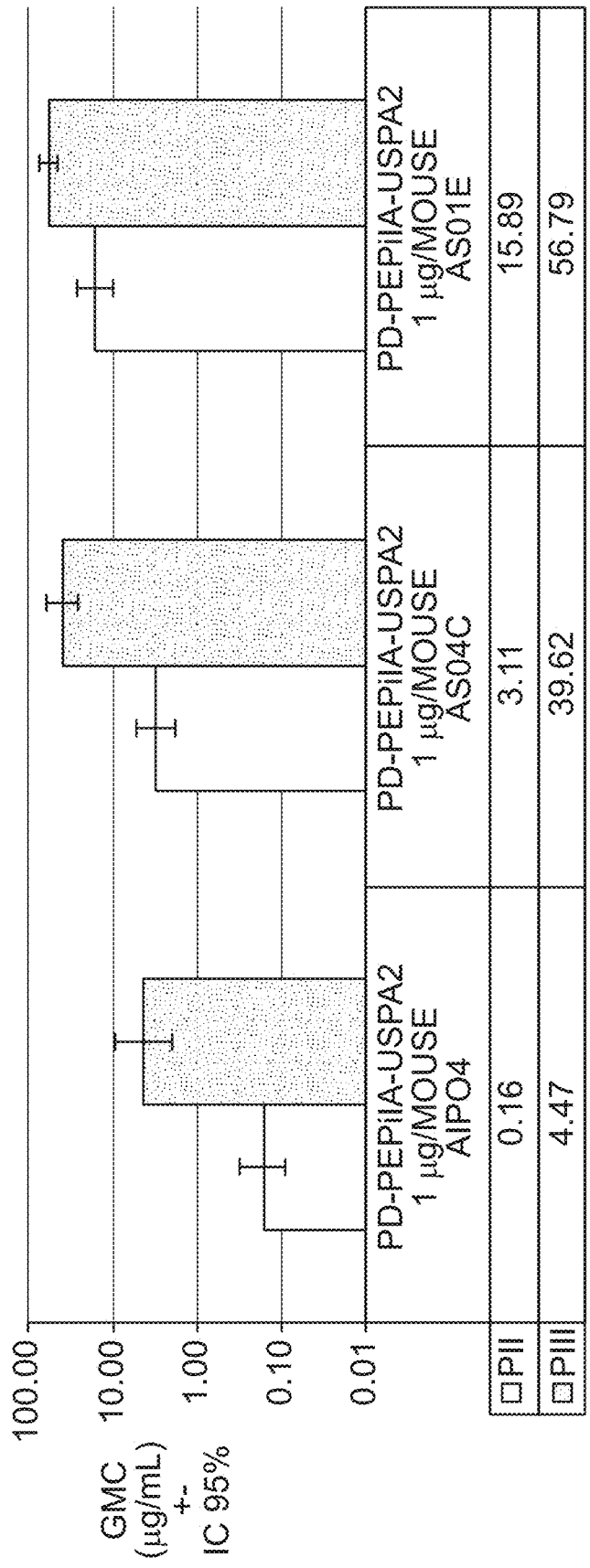
FIG. 21: IgG response induced against PilA in mice by PD-PEPilA-UspA2 vaccine (a trivalent NTHi-*M. cat.* vaccine), formulated with different adjuvants.

A negative impact of the presence of PD and PE-PilA antigens on UspA2 IgG levels was observed in AS04C (post III) and AS01E (post II) formulations (FIG. 17). However the impact remained limited 2 fold antibody decrease) and was not confirmed in the bactericidal assay (FIG. 18). The IgG responses induced against PD, PE and PilA in mice by PE-PEPilA-UspA2 vaccine are shown in FIG. 19, FIG. 20 and FIG. 21, respectively.

Therefore, UspA2 was immunogenic when combined with PD and PE-PilA.

Example 13: UspA2 Construct MC-009:
Immunodenicity of PD and PE-PilA NTHi Antigens in Combination with UspA2 in Mice Immunization Protocol Groups of 25 female Balb/c mice were immunized by the intramuscular (IM) route at days 0, 14 and 28 with 50 µl of the following formulations:

PD-PEPilA (1 µg of PD and 1 ug of PEPilA construct LVL-735) AS01E

UspA2-PD-PEPilA (1 µg of UspA2 construct MC-009, PD and PEPilA construct LVL-735) AS01E The ELISA IgG levels to PD, PE and PilA were determined in individual sera collected at days 28 (PII) and 42 (PIII).

ELISA to Measure Anti-PE Antibodies

Plates were coated overnight at 4° C. with 100 µl per well of 2 µg/ml of UspA2 in carbonate buffer pH 9.6. The plates were washed three times with NaCl 0.09% TWEEN (a US registered trademark) 0.05%. After washing, serial two fold dilution of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA and 5 µl of $H_2O_2$ in 10 ml of citrate 0.1M PH 4.5) was added to each well (100 µl/well) for 15 min in darkness. The reaction was stopped by addition of 50 µl of HCl 1N and the absorbance was read at 490 nm (620 nm for the reference filter). The titers were calculated by the 4-parameters method using the SOFT-MAX (a US registered trademark) Pro software.

ELISA to Measure Anti-PilA Antibodies

Plates were coated overnight at 4° C. with 100 µl per well of 4 µg/ml of PilA in carbonate buffer pH 9.6. The plates were washed three times with NaCl 0.09% TWEEN (a US registered trademark) 0.05%. After washing, serial two fold dilution of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA and 5 µl of $H_2O_2$ in 10 ml of citrate 0.1M PH 4.5) was added to each well (100 µl/well) for 15 min in darkness. The reaction was stopped by addition of 50 µl of HCl 1N and the absorbance was read at 490 nm (620 nm for the reference filter). The titers were calculated by the 4-parameters method using the SOFT-MAX (a US registered trademark) Pro software.

ELISA to Measure Anti-PD Antibodies

Plates were coated overnight at 4° C. with 100 µl per well of 8 µg/ml of PD in carbonate buffer pH 9.6. The plates were washed three times with NaCl 0.09% TWEEN (a US registered trademark) 0.05%. After washing, serial two fold dilution of sera were added to microwells in PBS TWEEN (a US registered trademark) 20 0.05%. The plates were placed at room temperature for 30 minutes with shaking. After washing, anti-mouse IgG antibodies (Jackson 115-035-003) conjugated to peroxydase (100 µl per well) were added, and the plates were placed at room temperature for 30 minutes with shaking. Plates were washed as above and the solution of revelation (4 mg of OPDA and 5 µl of $H_2O_2$ in 10 ml of citrate 0.1M PH 4.5) was added to each well (100 µl/well) for 15 min in darkness. The reaction was stopped by addition of 50 µl of HCl 1N and the absorbance was read at 490 nm (620 nm for the reference filter). The titers were calculated by the 4-parameters method using the SOFT-MAX (a US registered trademark) Pro software.

Figure 22:
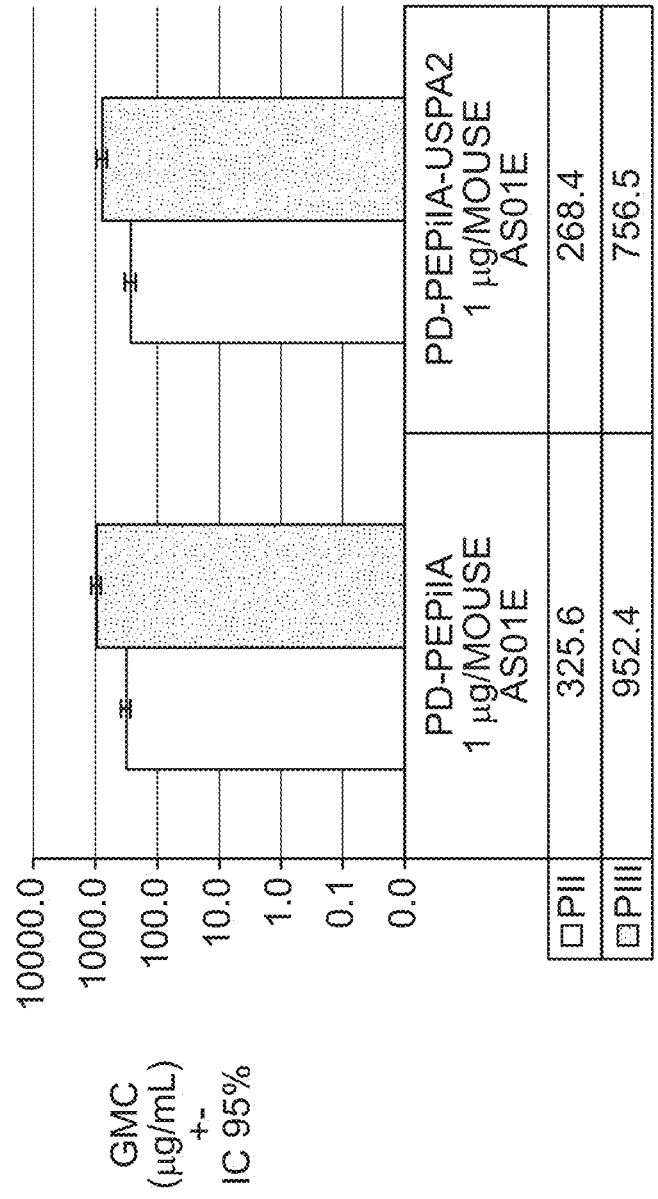
FIG. 22: Immunogenicity of PE in the bivalent PD-PEPilA and trivalent PD-PEPilA-UspA2 formulations with AS01E.
Figure 23:
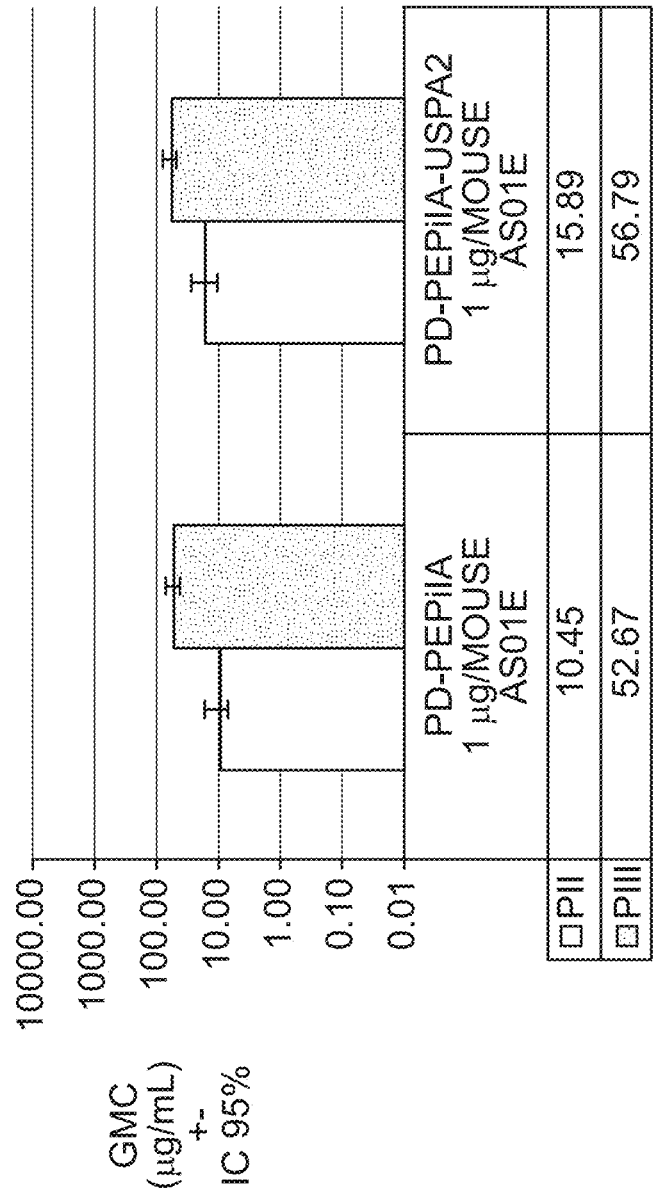
FIG. 23: Immunogenicity of PilA in the bivalent PD-PEPilA and trivalent PE-PilA-UspA2 formulations with AS01E.
Figure 24:
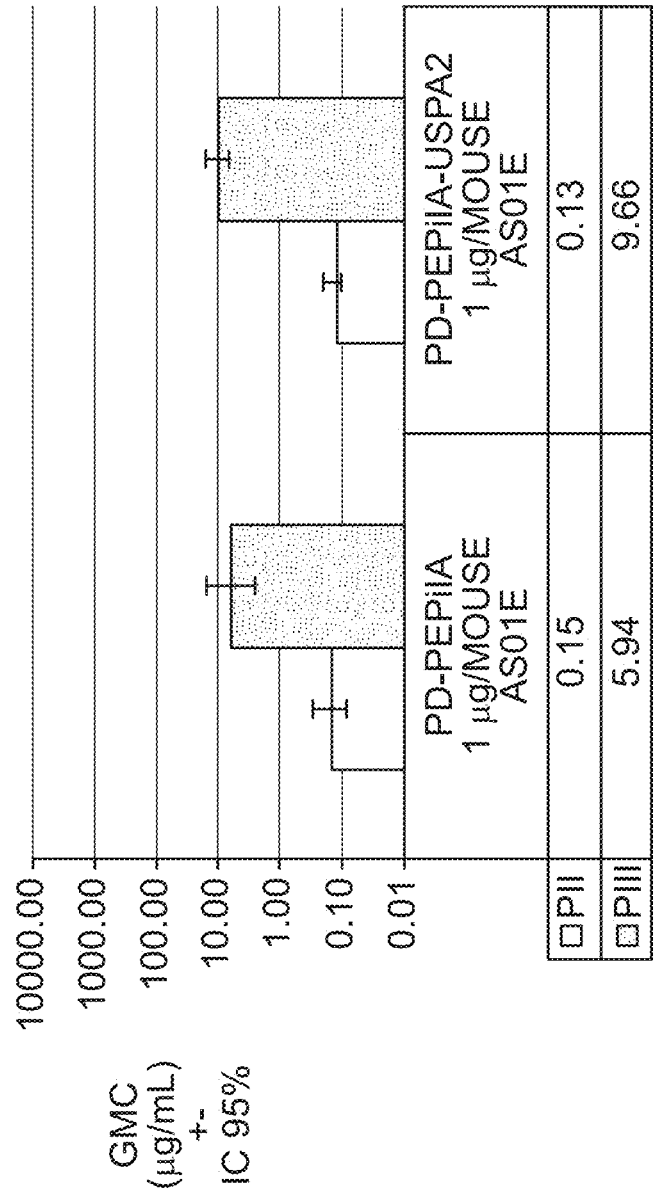
FIG. 24: Immunogenicity of PD in the bivalent PD-PEPilA and trivalent PE-PilA-UspA2 formulations with AS01E.
Figure 25:
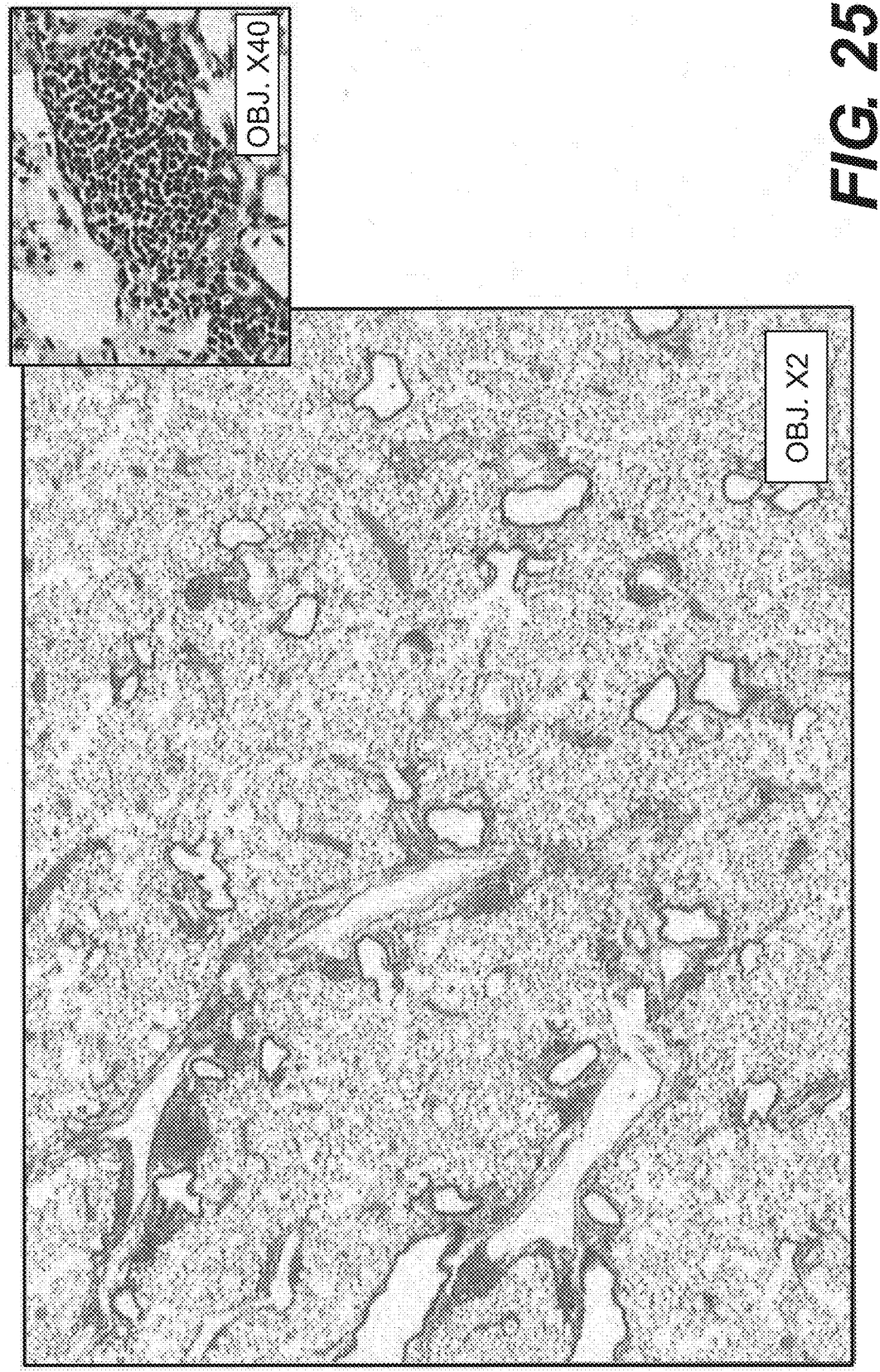
FIG. 25: Effect of the tetravalent PD/PEPilA/UspA2/$AS01_E$ vaccine formulation on mouse lungs pre-sensitized with heat inactivated *M. cat.*—Perivascularitis and peribronchiolitis in PBS immunized mice.
Figure 26:
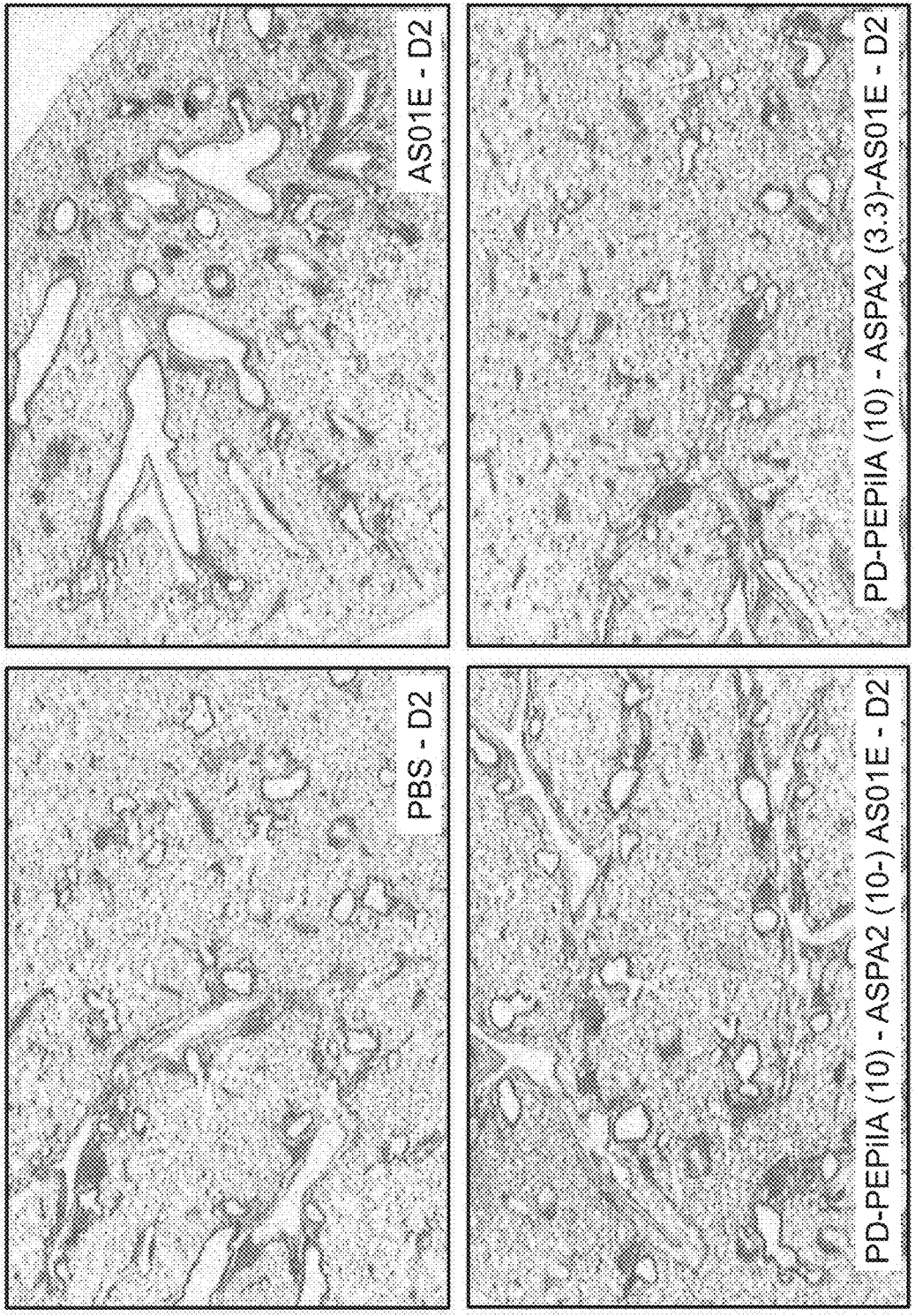
FIG. 26: Effect of the tetravalent PD/PEPilA/UspA2/$AS01_E$ vaccine formulation on mouse lungs pre-sensitized with heat inactivated *M. cat.*—Day 2 post-immunization.
Figure 30:
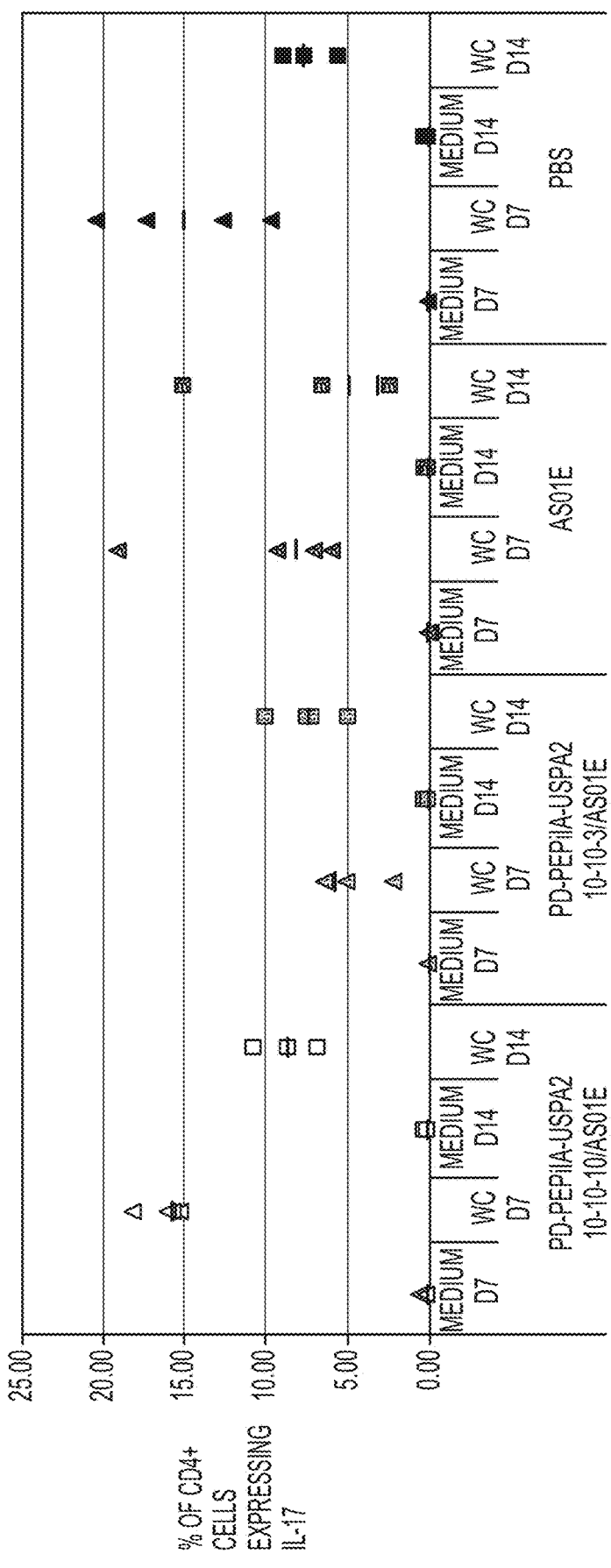
FIG. 30: Post-vaccination lung CD4 T cell responses upon *M. cat.* WC re-stimulation. Lung CD4 cells expressing IL17. Restimulated with heat-inactivated *M. cat.* whole cells (WC) or medium.
Figure 31:
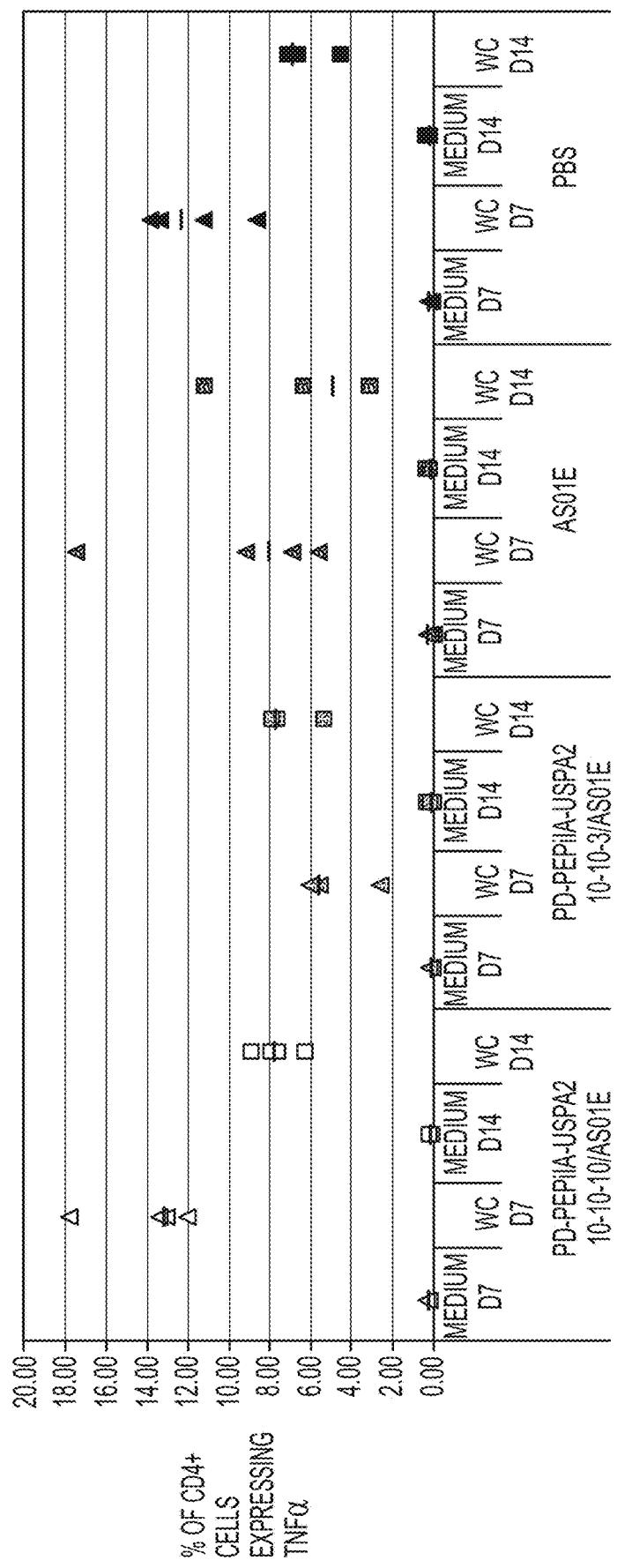
FIG. 31: Post-vaccination lung CD4 T cell responses upon *M. cat.* WC re-stimulation. Lung CD4 cells expressing TNFα. Restimulated with heat-inactivated *M. cat.* whole cells (WC) or medium.
Figure 32:
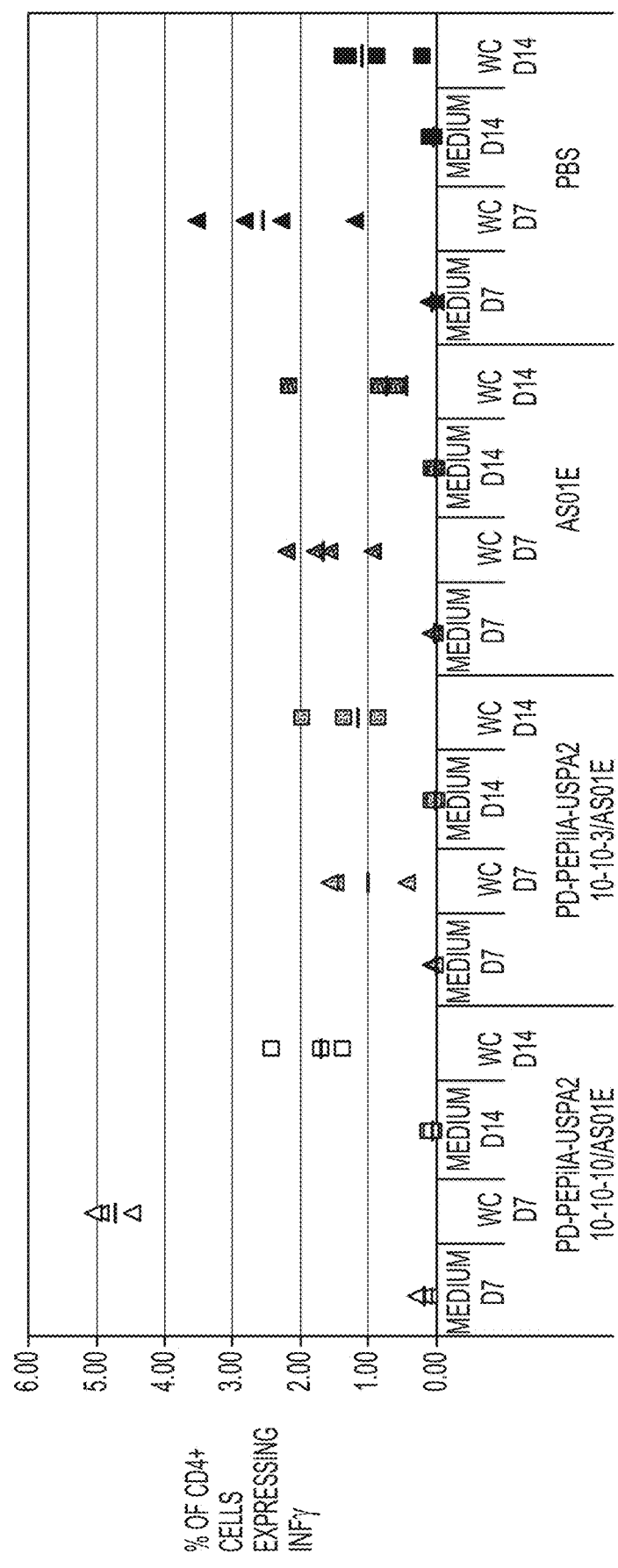
FIG. 32: Post-vaccination lung CD4 T cell responses upon *M. cat*. WC re-stimulation. Lung CD4 cells expressing IFNγ. Restimulated with heat-inactivated *M. cat*. whole cells (WC) or medium.
Figure 33:
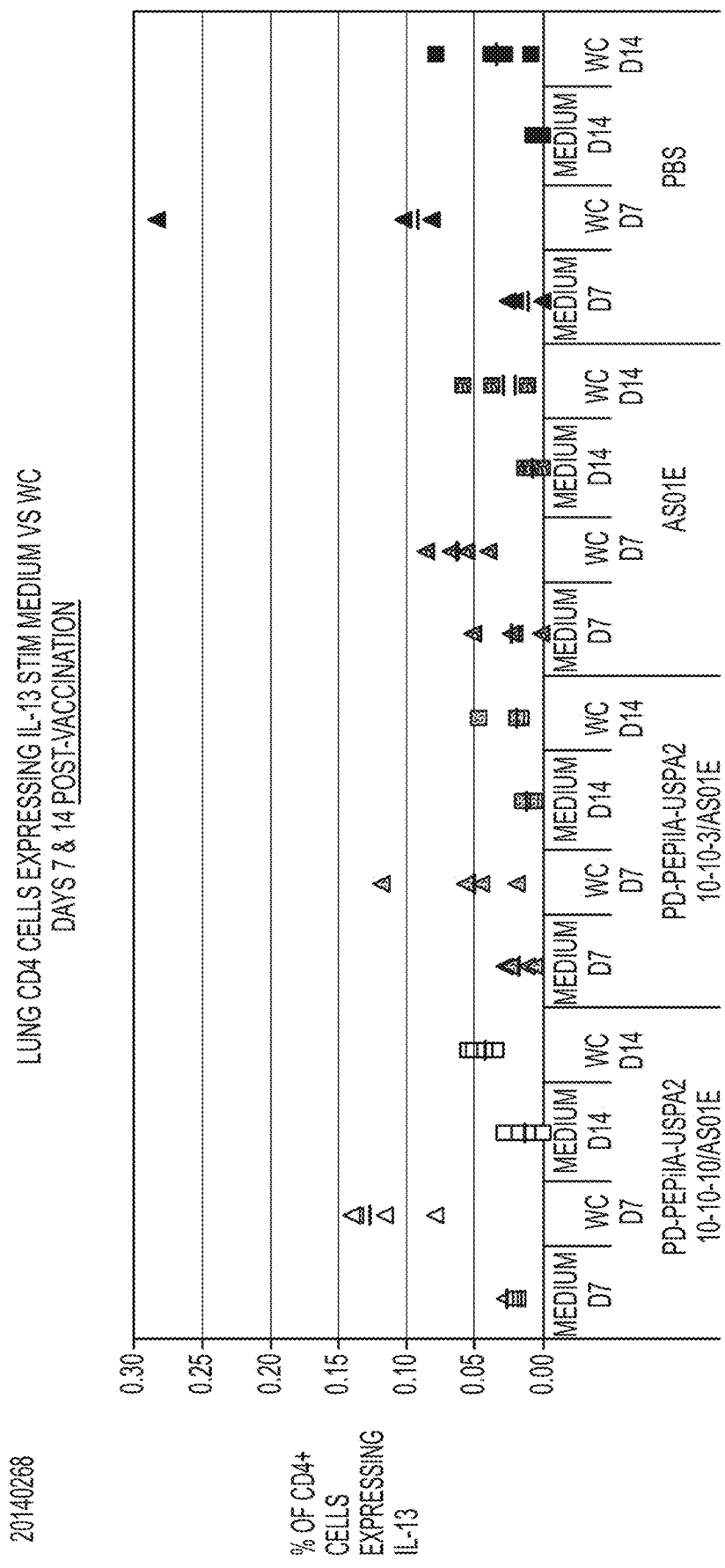
FIG. 33: Post-vaccination lung CD4 T cell responses upon *M. cat*. WC re-stimulation. Lung CD4 cells expressing IL13. Restimulated with heat-inactivated *M. cat*. whole cells (WC) or medium.
Figure 34:
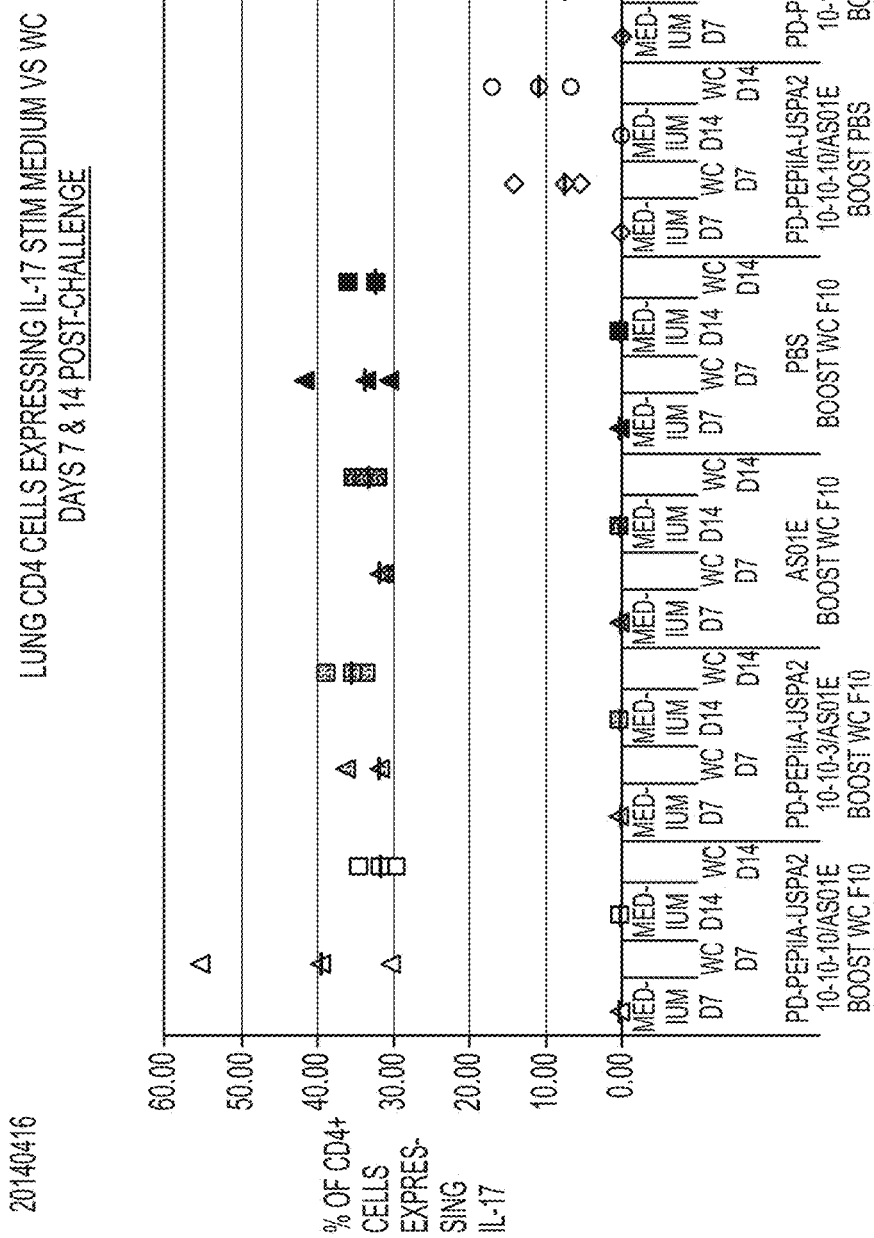
FIG. 34: Post-challenge lung CD4 T cell responses upon *M. cat*. WC re-stimulation. Lung CD4 cells expressing IL17. Restimulated with heat-inactivated *M. cat*. whole cells (WC) or medium.
Figure 35:
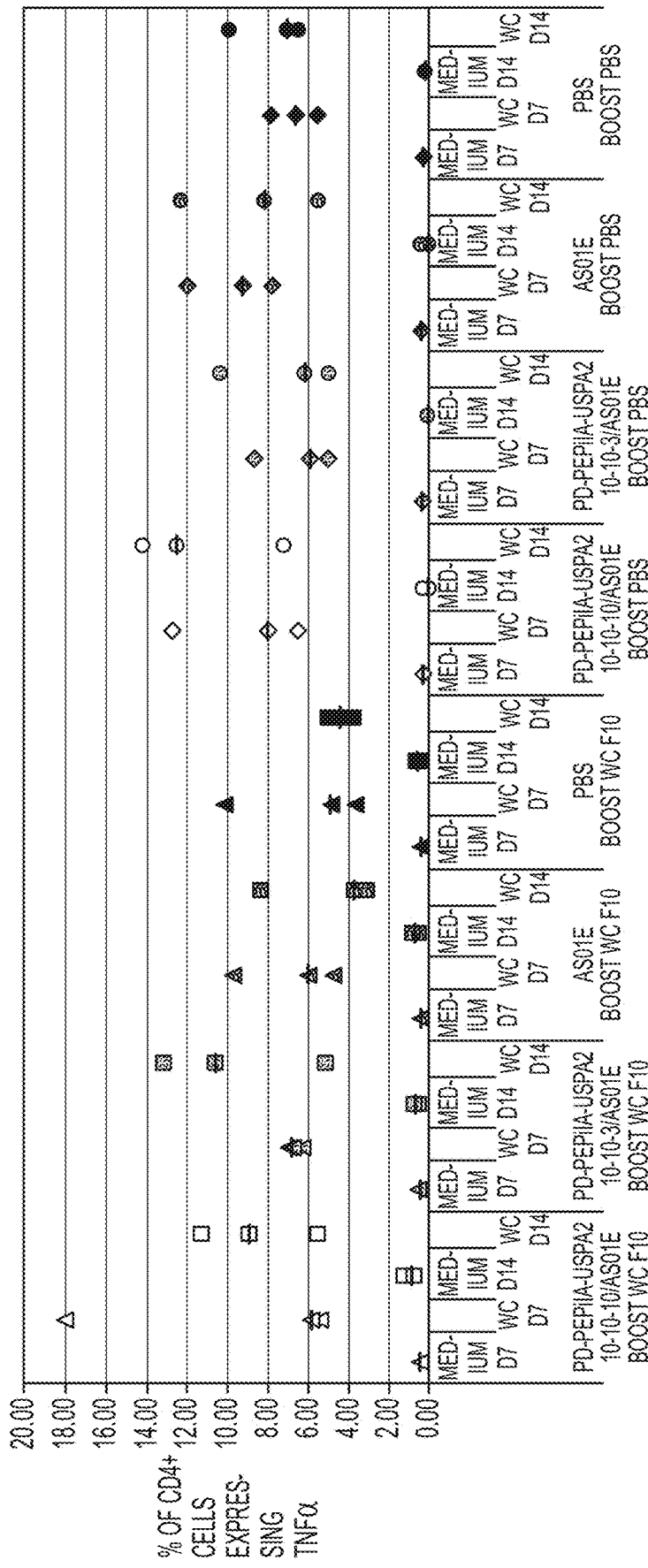
FIG. 35: Post-challenge lung CD4 T cell responses upon *M. cat*. WC re-stimulation. Lung CD4 cells expressing TNFα. Restimulated with heat-inactivated *M. cat*. whole cells (WC) or medium.
Figure 36:
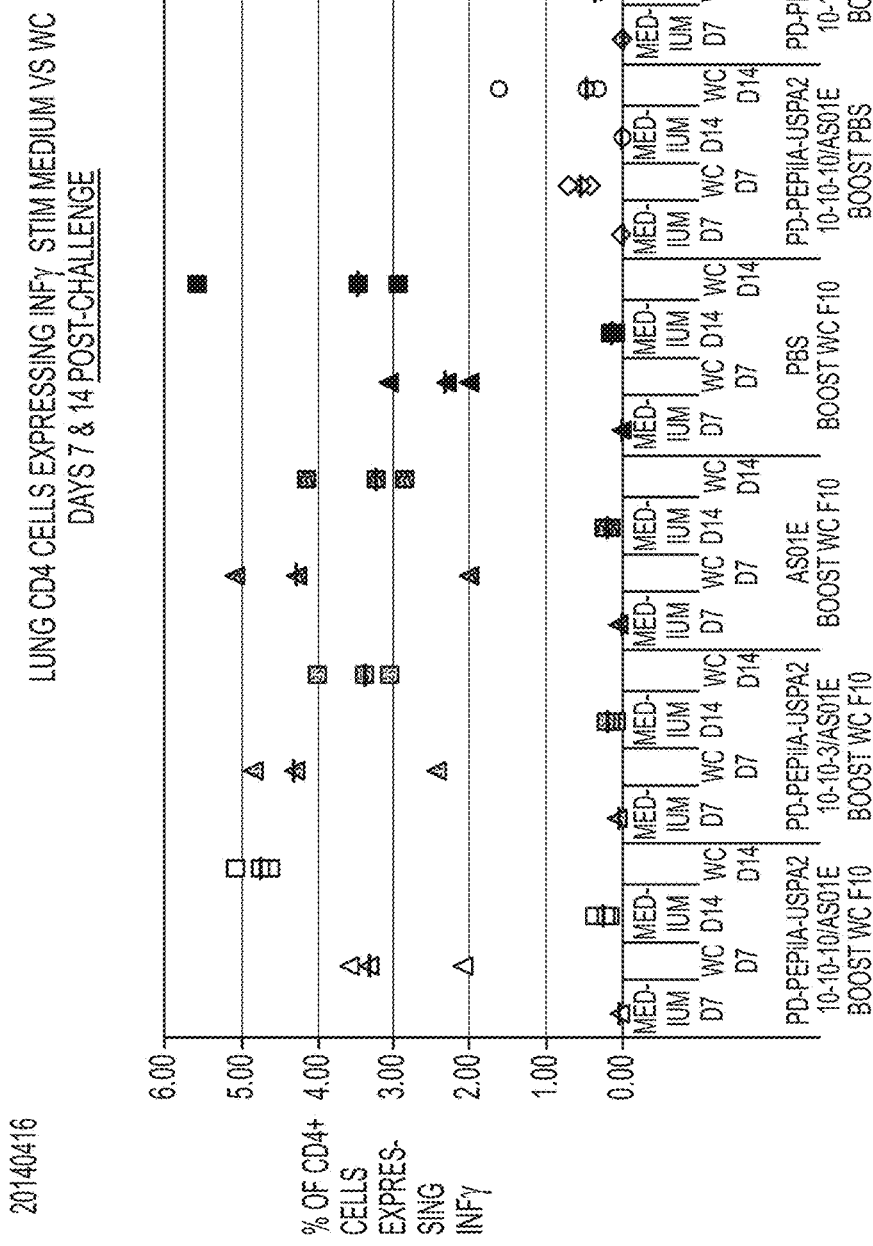
FIG. 36: Post-challenge lung CD4 T cell responses upon *M. cat*. WC re-stimulation. Lung CD4 cells expressing IFNγ. Restimulated with heat-inactivated *M. cat*. whole cells (WC) or medium.

No major impact of the addition of UspA2 on PD and PEPiIA immunogenicity in AS01E was observed as shown in FIGS. 22, 23 and 24.

Example 14: Safety of a Tetravalent Vaccine Formulation Containing UspA2 in a Mouse *Moraxella catarrhalis* Lung Inflammation Model To mitigate the risk of inducing undesirable inflammatory responses in the lungs of COPD patients upon immunization with a candidate vaccine aiming at preventing the exacerbations due to Non-typeable *Haemophilus influenzae* (NTHi) and *Moraxella catarrhalis* (*M. cat.*), various animal models were developed and used to assess the safety of this vaccine. The formulation tested contained three NTHi antigens (PD, PE and PilA, with the two last ones combined as a PEPiIA fusion protein), one *M. cat.* antigen (UspA2) and the Adjuvant System $01_E$ ($AS01_E$).

Two models were particularly dedicated to evaluate the safety of the UspA2 component of the vaccine.

Model 1:

Objective

This model aimed at assessing the possible induction of undesirable immune responses in inflamed lungs upon vaccination.

Study Design

057Bl/6 mice were sensitized by three intranasal administrations of 25 µg of heat-inactivated *M. cat.* strain ATCC (a US registered trademark) 25238™ whole cells (expressing an UspA2 which is 100% homologous to the vaccine UspA2) at days 0, 7 and 14. This treatment induced in the lungs a perivascular and peribronchiolar inflammation (with formation of lymphoid aggregates), alveolitis, pneumonitis, fibrosis and a strong *M. cat.* whole cell-specific IL-17$^+$ CD4$^+$ T cell response, which altogether mimicked the inflammatory process observed in the lungs of COPD patients (except emphysema).

The mice were then vaccinated at day 42 by the intramuscular route with ¹/₁₀th of human dose of the following formulations:

- PD 10 μg/PEPiIA (LVL735 construct, described in WO2012/139225) 10 μg/UspA2 (MC009 construct) 10 μg/AS01$_E$
- PD 10 μg/PEPiIA (LVL735 construct) 10 μg/UspA2 (MC009 construct) 3.3 μg/AS01$_E$
- AS01$_E$ (negative control)
- PBS (negative control)

To assess the impact of these formulations on the sensitization-induced lung inflammation:

Mice were daily monitored from day 43 to day 49 to look at mortality and any clinical signs indicating the induction of adverse events (prostration, piloerection, hunched position).

A histological analysis of the lungs was performed at days 2, 7 and 14 post-vaccination (with 5 mice per group and time-point) to look at a possible aggravation of the inflammation.

The induction of potentially undesirable T cell responses was evaluated on pools of lungs collected at days 7 and 14 post-vaccination (with 4 pools/group/time-point and the lungs of 3 mice per pool). The lung T cells were re-stimulated overnight either with UspA2 peptides, heat-inactivated M. cat. whole cells (WC) or medium (as a negative control) and then analyzed by flow cytometry for the expression of CD5, CD4, CD8, IL-17, IL-13, TNFα and IFNγ.

Results

No mortality or adverse event was reported.

Lung histology (FIGS. 25 to 29):

The alterations observed in the lungs were similar in severity in all groups and characterized by slight to moderate perivascular/bronchiolar mononuclear cell infiltrates.

No alveolitis and/or pneumonitis related to vaccination were observed.

T cell response:

Strong CD4$^+$ T cell responses (mainly IL-17 and TNFα producing cells) were measured in the lungs upon re-stimulation with WC, but regardless of the formulation administered (vaccines or adjuvant alone or PBS) (FIGS. 30 to 33). Low or no lung CD8$^+$ T cell responses were observed (data not shown).

No detectable T cell response was re-stimulated by UspA2 peptides, whatever the group, indicating that no UspA2-specific response was primed or boosted post-vaccination (data not shown).

Model 2:

Objective

This model aimed at assessing the possible induction of undesirable immune responses in inflamed lungs upon vaccination and M. cat. challenge.

Study Design

C57Bl/6 mice were successively:

Sensitized by three intranasal administrations of 25 μg of heat-inactivated M. cat. strain 25238 WC (expressing an UspA2 which is 100% homologous to the vaccine UspA2) at days 0, 7 and 14 (as in Model 1).

Vaccinated at day 42 by the intramuscular route with ¹/₁₀th of human dose of the following formulations (as in Model 1):

- PD (10 μg/PEPiIA (LVL735 construct) 10 μg/UspA2 (MC009 construct) 10 μg/AS01$_E$
- PD 10 μg/PEPiIA (LVL735 construct) 10 μg/UspA2 (MC009 construct) 3.3 μg/AS01$_E$
- AS01$_E$ (negative control)
- PBS (negative control)

Challenged by one intranasal administration of 25 μg of heat-inactivated M. cat. strain F10 WC (expressing an UspA2 which shares 53% homology with the vaccine UspA2) or by one intranasal administration of PBS as a control, both at day 56. The challenge strain was different from the sensitization strain to mimic the situation observed in COPD patients who experience new exacerbations due to newly acquired M. cat. strains.

To assess the impact of vaccination and challenge on the sensitization-induced lung inflammation:

Mice were daily monitored from day 43 to day 63 to look at mortality and any clinical signs indicating the induction of adverse events (prostration, piloerection, hunched position).

The induction of potentially undesirable T cell responses was evaluated on pools of lungs collected at days 7 and 14 post-challenge (with 4 pools/group/time-point and the lungs of 3 mice per pool). The lung T cells were re-stimulated overnight either with UspA2 peptides, heat-inactivated M. cat. F10 WC or medium (as a negative control) and then analyzed by flow cytometry for the expression of CD5, CD4, CD8, IL-17, IL-13, TNFα and IFNγ.

Results

No mortality or adverse event was reported.

T cell response:

Strong post-challenge CD4$^+$ T cell responses (mainly IL-17 and TNFα producing cells) were measured in the lungs upon re-stimulation with F10 WC, regardless of the formulation administered (vaccines or adjuvant alone or PBS) (FIGS. 34 to 37). Not surprisingly, these responses were higher in mice challenged with inactivated bacteria than in mice challenged with PBS. Whatever the challenge, low or no lung CD8$^+$ T cell responses were observed (data not shown).

No detectable T cell response was re-stimulated by UspA2 peptides, whatever the group, indicating that no UspA2-specific response was primed or boosted post-challenge (data not shown).

CONCLUSION

The PD/PEPilA/UspA2/AS01$_E$ formulations tested and more specifically the UspA2 component of these vaccines were shown safe in a mouse M. cat. lung inflammation model.

The invention claimed is:

1. An immunogenic composition comprising SEQ ID NO. 69.

2. An immunogenic composition of claim 1 further comprising a pharmaceutically acceptable adjuvant.

3. An immunogenic composition of claim 2 wherein the pharmaceutically acceptable adjuvant comprises 3-O-desacyl-4'-monophosphoryl lipid A), (MPL), *Quillaja saponaria* Molina fraction 21 (QS21) and liposomes.

4. An immunogenic composition of claim 2 wherein the pharmaceutically acceptable adjuvant is AS01E.

5. An immunogenic composition of claim 4 further comprising at least one antigen from *Haemophilus influenzae*.

6. The immunogenic composition of claim 5 wherein the at least one antigen from *Haemophilus influenzae* is Protein D from *Haemophilus influenzae*.

7. The immunogenic composition of claim 6 further comprising Protein E (PE).

8. The immunogenic composition of claim 7 further comprising Pilin A (PilA).

9. The immunogenic composition of claim 8 comprising PE and PilA present as a fusion protein.

10. The immunogenic composition of claim 9 wherein the PE and PilA fusion protein is LVL-735.

11. A method for the treatment of acute exacerbations of chronic obstructive pulmonary disease (AECOPD) in a subject in need thereof comprising administering to said subject a therapeutically effective amount of an immunogenic composition comprising 10 µg of protein D from *Haemophilus influenzae*, 10 µg of PEPiIA fusion protein LVL735, 3.3 µg of UspA2 MC009, and adjuvant AS01E.

12. A method for the treatment of a *M. catarrhalis* infection or disease in a subject in need thereof, said method comprising administering to said subject a therapeutically effective amount of an immunogenic composition according to claim 1.

* * * * *

SEQUENCE LISTING

<160> NUMBER OF SEQ ID NOS: 88

<210> SEQ ID NO 1
<211> LENGTH: 630
<212> TYPE: PRT
<213> ORGANISM: Moraxalla catarrhalis

<400> SEQUENCE: 1

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ala Lys
            20                  25                  30

Asn Asp Ile Thr Leu Glu Asp Leu Pro Tyr Leu Ile Lys Lys Ile Asp
        35                  40                  45

Gln Asn Glu Leu Glu Ala Asp Ile Gly Asp Ile Thr Ala Leu Glu Lys
    50                  55                  60

Tyr Leu Ala Leu Ser Gln Tyr Gly Asn Ile Leu Ala Leu Glu Glu Leu
65                  70                  75                  80

Asn Lys Ala Leu Glu Glu Leu Asp Glu Asp Val Gly Trp Asn Gln Asn
                85                  90                  95

Asp Ile Ala Asn Leu Glu Asp Asp Val Glu Thr Leu Thr Lys Asn Gln
            100                 105                 110

Asn Ala Leu Ala Glu Gln Gly Glu Ala Ile Lys Glu Asp Leu Gln Gly
        115                 120                 125

Leu Ala Asp Phe Val Glu Gly Gln Glu Gly Lys Ile Leu Gln Asn Glu
    130                 135                 140

Thr Ser Ile Lys Lys Asn Thr Gln Arg Asn Leu Val Asn Gly Phe Glu
145                 150                 155                 160

Ile Glu Lys Asn Lys Asp Ala Ile Ala Lys Asn Asn Glu Ser Ile Glu
                165                 170                 175

Asp Leu Tyr Asp Phe Gly His Glu Val Ala Glu Ser Ile Gly Glu Ile
            180                 185                 190

His Ala His Asn Glu Ala Gln Asn Glu Thr Leu Lys Gly Leu Ile Thr
        195                 200                 205

Asn Ser Ile Glu Asn Thr Asn Asn Ile Thr Lys Asn Lys Ala Asp Ile
    210                 215                 220

Gln Ala Leu Glu Asn Asn Val Val Glu Glu Leu Phe Asn Leu Ser Gly
225                 230                 235                 240

Arg Leu Ile Asp Gln Lys Ala Asp Ile Asp Asn Asn Ile Asn Asn Ile
                245                 250                 255

Tyr Glu Leu Ala Gln Gln Gln Asp Gln His Ser Ser Asp Ile Lys Thr
            260                 265                 270

Leu Lys Lys Asn Val Glu Glu Gly Leu Leu Glu Leu Ser Gly His Leu
        275                 280                 285

Ile Asp Gln Lys Thr Asp Ile Ala Gln Asn Ala Asn Ile Gln Asp
    290                 295                 300

Leu Ala Thr Tyr Asn Glu Leu Gln Asp Gln Tyr Ala Gln Lys Gln Thr
305                 310                 315                 320

Glu Ala Ile Asp Ala Leu Asn Lys Ala Ser Ser Glu Asn Thr Gln Asn
                325                 330                 335

Ile Glu Asp Leu Ala Ala Tyr Asn Glu Leu Gln Asp Ala Tyr Ala Lys
            340                 345                 350

Gln Gln Thr Glu Ala Ile Asp Ala Leu Asn Lys Ala Ser Ser Glu Asn
        355                 360                 365

```
Thr Gln Asn Ile Glu Asp Leu Ala Ala Tyr Asn Glu Leu Gln Asp Ala
    370                 375                 380

Tyr Ala Lys Gln Gln Thr Glu Ala Ile Asp Ala Leu Asn Lys Ala Ser
385                 390                 395                 400

Ser Glu Asn Thr Gln Asn Ile Ala Lys Asn Gln Ala Asp Ile Ala Asn
                405                 410                 415

Asn Ile Asn Asn Ile Tyr Glu Leu Ala Gln Gln Gln Asp Gln His Ser
            420                 425                 430

Ser Asp Ile Lys Thr Leu Ala Lys Ala Ser Ala Ala Asn Thr Asp Arg
                435                 440                 445

Ile Ala Lys Asn Lys Ala Asp Ala Asp Ala Ser Phe Glu Thr Leu Thr
450                 455                 460

Lys Asn Gln Asn Thr Leu Ile Glu Lys Asp Lys Glu His Asp Lys Leu
465                 470                 475                 480

Ile Thr Ala Asn Lys Thr Ala Ile Asp Ala Asn Lys Ala Ser Ala Asp
                485                 490                 495

Thr Lys Phe Ala Ala Thr Ala Asp Ala Ile Thr Lys Asn Gly Asn Ala
                500                 505                 510

Ile Thr Lys Asn Ala Lys Ser Ile Thr Asp Leu Gly Thr Lys Val Asp
            515                 520                 525

Gly Phe Asp Ser Arg Val Thr Ala Leu Asp Thr Lys Val Asn Ala Phe
530                 535                 540

Asp Gly Arg Ile Thr Ala Leu Asp Ser Lys Val Glu Asn Gly Met Ala
545                 550                 555                 560

Ala Gln Ala Ala Leu Ser Gly Leu Phe Gln Pro Tyr Ser Val Gly Lys
                565                 570                 575

Phe Asn Ala Thr Ala Ala Leu Gly Gly Tyr Gly Ser Lys Ser Ala Val
                580                 585                 590

Ala Ile Gly Ala Gly Tyr Arg Val Asn Pro Asn Leu Ala Phe Lys Ala
            595                 600                 605

Gly Ala Ala Ile Asn Thr Ser Gly Asn Lys Lys Gly Ser Tyr Asn Ile
    610                 615                 620

Gly Val Asn Tyr Glu Phe
625                 630

<210> SEQ ID NO 2
<211> LENGTH: 613
<212> TYPE: PRT
<213> ORGANISM: Moraxella catarrhalis

<400> SEQUENCE: 2

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ser Arg
            20                  25                  30

Asp Arg Ser Leu Glu Asp Ile Gln Asp Ser Ile Ser Lys Leu Val Gln
        35                  40                  45

Asp Asp Ile Asn Thr Leu Lys Gln Asp Gln Lys Met Asn Lys Tyr
    50                  55                  60

Leu Leu Leu Asn Gln Leu Ala Asn Thr Leu Ile Thr Asp Glu Leu Asn
65                  70                  75                  80

Asn Asn Val Ile Lys Asn Thr Asn Ser Ile Glu Ala Leu Gly Asp Glu
                85                  90                  95

Ile Gly Trp Leu Glu Asn Asp Ile Ala Asp Leu Glu Glu Gly Val Glu
                100                 105                 110
```

```
Glu Leu Thr Lys Asn Gln Asn Thr Leu Ile Glu Lys Asp Glu Glu His
            115                 120                 125

Asp Arg Leu Ile Ala Gln Asn Gln Ala Asp Ile Gln Thr Leu Glu Asn
        130                 135                 140

Asn Val Glu Glu Leu Phe Asn Leu Ser Gly Arg Leu Ile Asp Gln
145                 150                 155                 160

Glu Ala Asp Ile Ala Lys Asn Asn Ala Ser Ile Glu Glu Leu Tyr Asp
                165                 170                 175

Phe Asp Asn Glu Val Ala Glu Arg Ile Gly Glu Ile His Ala Tyr Thr
            180                 185                 190

Glu Glu Val Asn Lys Thr Leu Glu Asn Leu Ile Thr Asn Ser Val Lys
        195                 200                 205

Asn Thr Asp Asn Ile Asp Lys Asn Lys Ala Asp Ile Asp Asn Asn Ile
210                 215                 220

Asn His Ile Tyr Glu Leu Ala Gln Gln Asp Gln His Ser Ser Asp
225                 230                 235                 240

Ile Lys Thr Leu Lys Asn Asn Val Glu Glu Gly Leu Leu Glu Leu Ser
                245                 250                 255

Gly His Leu Ile Asp Gln Lys Ala Asp Leu Thr Lys Asp Ile Lys Ala
            260                 265                 270

Leu Glu Ser Asn Val Glu Glu Gly Leu Leu Asp Leu Ser Gly Arg Leu
        275                 280                 285

Leu Asp Gln Lys Ala Asp Leu Thr Lys Asp Ile Lys Ala Leu Glu Ser
290                 295                 300

Asn Val Glu Glu Gly Leu Leu Asp Leu Ser Gly Arg Leu Leu Asp Gln
305                 310                 315                 320

Lys Ala Asp Ile Ala Gln Asn Gln Thr Asp Ile Gln Asp Leu Ala Ala
                325                 330                 335

Tyr Asn Glu Leu Gln Asp Gln Tyr Ala Gln Lys Gln Thr Glu Ala Ile
            340                 345                 350

Asp Ala Leu Asn Lys Ala Ser Ser Glu Asn Thr Gln Asn Ile Glu Asp
        355                 360                 365

Leu Ala Ala Tyr Asn Glu Leu Gln Asp Ala Tyr Ala Lys Gln Gln Thr
370                 375                 380

Glu Ala Ile Asp Ala Leu Asn Lys Ala Ser Ser Glu Asn Thr Gln Asn
385                 390                 395                 400

Ile Ala Lys Asn Gln Ala Asp Ile Ala Asn Asn Ile Asn Asn Ile Tyr
                405                 410                 415

Glu Leu Ala Gln Gln Asp Gln His Ser Ser Asp Ile Lys Thr Leu
            420                 425                 430

Ala Lys Ala Ser Ala Ala Asn Thr Asn Arg Ile Ala Thr Ala Glu Leu
        435                 440                 445

Gly Ile Ala Glu Asn Lys Lys Asp Ala Gln Ile Ala Lys Ala Gln Ala
450                 455                 460

Asn Ala Asn Lys Thr Ala Ile Asp Glu Asn Lys Ala Ser Ala Asp Thr
465                 470                 475                 480

Lys Phe Ala Ala Thr Ala Asp Ala Ile Thr Lys Asn Gly Asn Ala Ile
                485                 490                 495

Thr Lys Asn Ala Lys Ser Ile Thr Asp Leu Gly Thr Lys Val Asp Gly
            500                 505                 510

Phe Asp Gly Arg Val Thr Ala Leu Asp Thr Lys Val Asn Ala Phe Asp
        515                 520                 525
```

```
Gly Arg Ile Thr Ala Leu Asp Ser Lys Val Glu Asn Gly Met Ala Ala
            530                 535                 540

Gln Ala Ala Leu Ser Gly Leu Phe Gln Pro Tyr Ser Val Gly Lys Phe
545                 550                 555                 560

Asn Ala Thr Ala Ala Leu Gly Gly Tyr Gly Ser Lys Ser Ala Val Ala
                565                 570                 575

Ile Gly Ala Gly Tyr Arg Val Asn Pro Asn Leu Ala Phe Lys Ala Gly
                580                 585                 590

Ala Ala Ile Asn Thr Ser Gly Asn Lys Lys Gly Ser Tyr Asn Ile Gly
                595                 600                 605

Val Asn Tyr Glu Phe
    610

<210> SEQ ID NO 3
<211> LENGTH: 644
<212> TYPE: PRT
<213> ORGANISM: Moraxella catarrhalis

<400> SEQUENCE: 3

Met Lys Thr Met Lys Leu Leu Pro Leu Lys Ile Ala Val Thr Ser Ala
1               5                   10                  15

Leu Ile Ile Gly Leu Gly Ala Ala Ser Thr Ala Asn Ala Gln Gln Gln
                20                  25                  30

Leu Gln Thr Glu Thr Phe Leu Pro Asn Phe Leu Ser Asn Asp Asn Tyr
            35                  40                  45

Asp Leu Thr Asp Pro Phe Tyr His Asn Met Ile Leu Gly Asp Thr Ala
    50                  55                  60

Leu Leu Asp Lys Gln Asp Gly Ser Gln Pro Gln Leu Lys Phe Tyr Ser
65                  70                  75                  80

Asn Asp Lys Asp Ser Val Pro Asp Ser Leu Leu Phe Ser Lys Leu Leu
                85                  90                  95

His Glu Gln Gln Leu Asn Gly Phe Lys Lys Gly Asp Thr Ile Ile Pro
            100                 105                 110

Leu Asp Lys Asp Gly Lys Pro Val Tyr Gln Val Asp Tyr Lys Leu Asp
    115                 120                 125

Gly Lys Gly Lys Lys Gln Lys Arg Arg Gln Val Tyr Ser Val Thr Thr
    130                 135                 140

Lys Thr Ala Thr Asp Asp Asp Val Asn Ser Ala Tyr Ser Arg Gly Ile
145                 150                 155                 160

Leu Gly Lys Val Asp Asp Leu Asp Asp Glu Met Asn Phe Leu Asn His
                165                 170                 175

Asp Ile Thr Ser Leu Tyr Asp Val Thr Ala Asn Gln Gln Asp Ala Ile
            180                 185                 190

Lys Asp Leu Lys Lys Gly Val Lys Gly Leu Asn Lys Glu Leu Lys Glu
    195                 200                 205

Leu Asp Lys Glu Val Gly Val Leu Ser Arg Asp Ile Gly Ser Leu Asn
    210                 215                 220

Asp Asp Val Ala Gln Asn Asn Glu Ser Ile Glu Asp Leu Tyr Asp Phe
225                 230                 235                 240

Ser Gln Glu Val Ala Asp Ser Ile Gly Glu Ile His Ala His Asn Lys
                245                 250                 255

Ala Gln Asn Glu Thr Leu Gln Asp Leu Ile Thr Asn Ser Val Glu Asn
            260                 265                 270

Thr Asn Asn Ile Thr Lys Asn Lys Ala Asp Ile Gln Ala Leu Glu Asn
    275                 280                 285
```

Asn Val Val Glu Glu Leu Phe Asn Leu Ser Gly Arg Leu Ile Asp Gln
            290                 295                 300

Lys Ala Asp Leu Thr Lys Asp Ile Lys Thr Leu Glu Ser Asn Val Glu
305                 310                 315                 320

Glu Gly Leu Leu Glu Leu Ser Gly His Leu Ile Asp Gln Lys Ala Asp
                325                 330                 335

Ile Ala Lys Asn Gln Ala Asp Ile Ala Gln Asn Gln Ala Asn Ile Gln
            340                 345                 350

Asp Leu Ala Ala Tyr Asn Glu Leu Gln Asp Ala Tyr Ala Lys Gln Gln
                355                 360                 365

Thr Glu Ala Ile Asp Ala Leu Asn Lys Ala Ser Ser Glu Asn Thr Gln
370                 375                 380

Asn Ile Glu Asp Leu Ala Ala Tyr Asn Glu Leu Gln Asp Ala Tyr Ala
385                 390                 395                 400

Lys Gln Gln Thr Glu Ala Ile Asp Ala Leu Asn Lys Ala Ser Ser Glu
                405                 410                 415

Asn Thr Gln Asn Ile Ala Lys Asn Gln Ala Asp Ile Ala Asn Asn Ile
            420                 425                 430

Asn Asn Ile Tyr Glu Leu Ala Gln Gln Gln Asp Gln His Ser Ser Asp
            435                 440                 445

Ile Lys Thr Leu Ala Lys Ala Ser Ala Ala Asn Thr Asp Arg Ile Ala
450                 455                 460

Lys Asn Lys Ala Asp Ala Asp Ala Ser Phe Glu Thr Leu Thr Lys Asn
465                 470                 475                 480

Gln Asn Thr Leu Ile Glu Lys Asp Lys Glu His Asp Lys Leu Ile Thr
                485                 490                 495

Ala Asn Lys Thr Ala Ile Asp Glu Asn Lys Ala Ser Ala Asp Thr Lys
            500                 505                 510

Phe Ala Ala Thr Ala Asp Ala Ile Thr Lys Asn Gly Asn Ala Ile Thr
                515                 520                 525

Lys Asn Ala Lys Ser Ile Thr Asp Leu Gly Thr Lys Val Asp Gly Phe
530                 535                 540

Asp Ser Arg Val Thr Ala Leu Asp Thr Lys Val Asn Ala Phe Asp Gly
545                 550                 555                 560

Arg Ile Thr Ala Leu Asp Ser Lys Val Glu Asn Gly Met Ala Ala Gln
                565                 570                 575

Ala Ala Leu Ser Gly Leu Phe Gln Pro Tyr Ser Val Gly Lys Phe Asn
            580                 585                 590

Ala Thr Ala Ala Leu Gly Gly Tyr Gly Ser Lys Ser Ala Val Ala Ile
                595                 600                 605

Gly Ala Gly Tyr Arg Val Asn Pro Asn Leu Ala Phe Lys Ala Gly Ala
            610                 615                 620

Ala Ile Asn Thr Ser Gly Asn Lys Lys Gly Ser Tyr Asn Ile Gly Val
625                 630                 635                 640

Asn Tyr Glu Phe

<210> SEQ ID NO 4
<211> LENGTH: 591
<212> TYPE: PRT
<213> ORGANISM: Moraxella catarrhalis

<400> SEQUENCE: 4

Met Lys Thr Met Lys Leu Leu Pro Leu Lys Ile Ala Val Thr Ser Ala
1               5                   10                  15

```
Leu Ile Val Gly Leu Gly Ala Ala Ser Thr Ala Asn Ala Gln Leu Val
         20                  25                  30

Glu Arg Phe Phe Pro Asn Ile Phe Leu Asp Lys Pro Leu Ala Lys Gln
             35                  40                  45

His Tyr His Asn Val Val Gly Asp Thr Ser Ile Val Ser Asp Leu
 50                  55                  60

Gln Ser Asn Ser Asp Gln Leu Lys Phe Tyr Ser Asp Glu Gly Leu
 65                  70                  75                  80

Val Pro Asp Ser Leu Leu Phe Asn Lys Met Leu His Glu Gln Leu Leu
             85                  90                  95

Asn Gly Phe Lys Glu Gly Asp Thr Ile Ile Pro Leu Asp Glu Asn Gly
             100                 105                 110

Lys Pro Val Tyr Lys Val Asp Tyr Lys Leu Asp Gly Lys Glu Pro Arg
             115                 120                 125

Lys Val Tyr Ser Val Thr Thr Lys Ile Ala Thr Ala Glu Asp Val Ala
             130                 135                 140

Thr Ser Ser Tyr Ala Asn Gly Ile Gln Lys Asp Ile Asp Asp Leu Tyr
145                 150                 155                 160

Asp Phe Asp His Gln Val Thr Glu Arg Leu Thr Gln His Gly Lys Thr
             165                 170                 175

Ile Tyr Arg Asn Gly Glu Arg Ile Leu Ala Asn Glu Ser Val Gln
             180                 185                 190

Tyr Leu Asn Lys Glu Val Gln Asn Asn Ile Glu His Ile Tyr Glu Leu
             195                 200                 205

Ala Gln Gln Asp Gln His Ser Ser Asp Ile Lys Thr Leu Glu Ser
     210                 215                 220

Asn Val Glu Lys Gly Leu Leu Glu Leu Ser Gly His Leu Ile Asp Gln
225                 230                 235                 240

Lys Ala Asp Leu Thr Lys Asp Ile Lys Thr Leu Glu Ser Asn Val Glu
             245                 250                 255

Glu Gly Leu Leu Asp Leu Ser Gly Arg Leu Ile Asp Gln Lys Ala Asp
             260                 265                 270

Leu Thr Lys Asp Ile Lys Thr Leu Glu Ser Asn Val Glu Glu Gly Leu
             275                 280                 285

Leu Asp Leu Ser Gly Arg Leu Ile Asp Gln Lys Ala Asp Ile Ala Gln
             290                 295                 300

Asn Gln Ala Asn Ile Gln Asp Leu Ala Ala Tyr Asn Glu Leu Gln Asp
305                 310                 315                 320

Gln Tyr Ala Gln Lys Gln Thr Glu Ala Ile Asp Ala Leu Asn Lys Ala
             325                 330                 335

Ser Ser Glu Asn Thr Gln Asn Ile Glu Asp Leu Ala Ala Tyr Asn Glu
             340                 345                 350

Leu Gln Asp Ala Tyr Ala Lys Gln Gln Thr Glu Ala Ile Asp Ala Leu
             355                 360                 365

Asn Lys Ala Ser Ser Glu Asn Thr Gln Asn Ile Ala Lys Asn Gln Ala
             370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
             405                 410                 415

Asn Thr Asn Arg Ile Ala Thr Ala Glu Leu Gly Ile Ala Glu Asn Lys
             420                 425                 430
```

-continued

```
Lys Asp Ala Gln Ile Ala Lys Ala Gln Ala Asn Ala Asn Lys Thr Ala
            435                 440                 445

Ile Asp Glu Asn Lys Ala Ser Ala Asp Thr Lys Phe Ala Ala Thr Ala
450                 455                 460

Asp Ala Ile Thr Lys Asn Gly Asn Ala Ile Thr Lys Asn Ala Lys Ser
465                 470                 475                 480

Ile Thr Asp Leu Gly Thr Lys Val Asp Gly Phe Asp Ser Arg Val Thr
                485                 490                 495

Ala Leu Asp Thr Lys Val Asn Ala Phe Asp Gly Arg Ile Thr Ala Leu
            500                 505                 510

Asp Ser Lys Val Glu Asn Gly Met Ala Gln Ala Ala Leu Ser Gly
            515                 520                 525

Leu Phe Gln Pro Tyr Ser Val Gly Lys Phe Asn Ala Thr Ala Ala Leu
530                 535                 540

Gly Gly Tyr Gly Ser Lys Ser Ala Val Ala Ile Gly Ala Gly Tyr Arg
545                 550                 555                 560

Val Asn Pro Asn Leu Ala Phe Lys Ala Gly Ala Ala Ile Asn Thr Ser
                565                 570                 575

Gly Asn Lys Lys Gly Ser Tyr Asn Ile Gly Val Asn Tyr Glu Phe
            580                 585                 590
```

<210> SEQ ID NO 5
<211> LENGTH: 687
<212> TYPE: PRT
<213> ORGANISM: Moraxella catarrhalis

<400> SEQUENCE: 5

```
Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Gln Gln
                20                  25                  30

Gln Gln Gln Gln Gln Gln Gln Ser Arg Thr Glu Ile Phe Phe Pro
            35                  40                  45

Asn Ile Phe Phe Asn Glu Asn His Asp Glu Leu Asp Asp Ala Tyr His
50                  55                  60

Asn Ile Ile Leu Gly Asp Thr Ala Leu Leu Asp Lys Gln Asp Gly Ser
65                  70                  75                  80

Gln Pro Gln Leu Lys Phe Tyr Ser Asn Asp Lys Asp Ser Val Pro Asp
                85                  90                  95

Ser Leu Leu Phe Ser Lys Leu Leu His Glu Gln Gln Leu Asn Gly Phe
            100                 105                 110

Lys Lys Gly Asp Thr Ile Ile Pro Leu Asp Lys Asp Gly Lys Pro Val
            115                 120                 125

Tyr Gln Val Asp Tyr Lys Leu Asp Gly Lys Gly Lys Gln Lys Arg
130                 135                 140

Arg Gln Val Tyr Ser Val Thr Thr Lys Thr Ala Thr Asp Asp Val
145                 150                 155                 160

Asn Ser Ala Tyr Ser Arg Gly Ile Leu Gly Lys Val Asp Leu Asp
                165                 170                 175

Asp Glu Met Asn Phe Leu Asn His Asp Ile Thr Ser Leu Tyr Asp Val
            180                 185                 190

Thr Ala Asn Gln Gln Asp Ala Ile Lys Gly Leu Lys Lys Gly Val Lys
            195                 200                 205

Gly Leu Asn Lys Glu Leu Lys Glu Leu Asp Lys Glu Val Gly Val Leu
210                 215                 220
```

```
Ser Arg Asp Ile Gly Ser Leu Asn Asp Asp Val Ala Gln Asn Asn Glu
225                 230                 235                 240

Ser Ile Glu Asp Leu Tyr Asp Phe Ser Gln Glu Val Ala Asp Ser Ile
                245                 250                 255

Gly Glu Ile His Ala His Asn Lys Ala Gln Asn Glu Thr Leu Gln Asp
            260                 265                 270

Leu Ile Thr Asn Ser Val Glu Asn Thr Asn Ile Thr Lys Asn Lys
        275                 280                 285

Ala Asp Ile Gln Ala Leu Glu Asn Asn Val Val Glu Glu Leu Phe Asn
290                 295                 300

Leu Ser Gly Arg Leu Ile Asp Gln Lys Ala Asp Leu Thr Lys Asp Ile
305                 310                 315                 320

Lys Thr Leu Glu Ser Asn Val Glu Glu Gly Leu Leu Glu Leu Ser Gly
                325                 330                 335

His Leu Ile Asp Gln Lys Ala Asp Ile Ala Lys Asn Gln Ala Asp Ile
            340                 345                 350

Ala Gln Asn Gln Ala Asn Ile Gln Asp Leu Ala Ala Tyr Asn Glu Leu
            355                 360                 365

Gln Asp Ala Tyr Ala Lys Gln Gln Thr Glu Ala Ile Asp Ala Leu Asn
370                 375                 380

Lys Ala Ser Ser Glu Asn Thr Gln Asn Ile Glu Asp Leu Ala Ala Tyr
385                 390                 395                 400

Asn Glu Leu Gln Asp Ala Tyr Ala Lys Gln Gln Thr Glu Ala Ile Asp
                405                 410                 415

Ala Leu Asn Lys Ala Ser Ser Glu Asn Thr Gln Asn Ile Glu Asp Leu
            420                 425                 430

Ala Ala Tyr Asn Glu Leu Gln Asp Ala Tyr Ala Lys Gln Gln Thr Glu
            435                 440                 445

Ala Ile Asp Ala Leu Asn Lys Ala Ser Ser Glu Asn Thr Gln Asn Ile
450                 455                 460

Ala Lys Asn Gln Ala Asp Ile Ala Asn Asn Ile Asn Asn Ile Tyr Glu
465                 470                 475                 480

Leu Ala Gln Gln Gln Asp Gln His Ser Ser Asp Ile Lys Thr Leu Ala
                485                 490                 495

Lys Ala Ser Ala Ala Asn Thr Asp Arg Ile Ala Lys Asn Lys Ala Asp
            500                 505                 510

Ala Asp Ala Ser Phe Glu Thr Leu Thr Lys Asn Gln Asn Thr Leu Ile
            515                 520                 525

Glu Lys Asp Lys Glu His Asp Lys Leu Ile Thr Ala Asn Lys Thr Ala
530                 535                 540

Ile Asp Glu Asn Lys Ala Ser Ala Asp Thr Lys Phe Ala Ala Thr Ala
545                 550                 555                 560

Asp Ala Ile Thr Lys Asn Gly Asn Ala Ile Thr Lys Asn Ala Lys Ser
                565                 570                 575

Ile Thr Asp Leu Gly Thr Lys Val Asp Ala Phe Asp Gly Arg Val Thr
            580                 585                 590

Ala Leu Asp Thr Lys Val Asn Ala Phe Asp Gly Arg Ile Thr Ala Leu
            595                 600                 605

Asp Ser Lys Val Glu Asn Gly Met Ala Ala Gln Ala Ala Leu Ser Gly
610                 615                 620

Leu Phe Gln Pro Tyr Ser Val Gly Lys Phe Asn Ala Thr Ala Ala Leu
625                 630                 635                 640
```

```
Gly Gly Tyr Gly Ser Lys Ser Ala Val Ala Ile Gly Ala Gly Tyr Arg
            645                 650                 655

Val Asn Pro Asn Leu Ala Phe Lys Ala Gly Ala Ala Ile Asn Thr Ser
            660                 665                 670

Gly Asn Lys Lys Gly Ser Tyr Asn Ile Gly Val Asn Tyr Glu Phe
            675                 680                 685

<210> SEQ ID NO 6
<211> LENGTH: 683
<212> TYPE: PRT
<213> ORGANISM: Moraxella catarrhalis

<400> SEQUENCE: 6

Met Lys Thr Met Lys Leu Leu Pro Leu Lys Ile Ala Val Thr Ser Ala
1               5                   10                  15

Met Ile Val Gly Leu Gly Met Ala Ser Thr Ala Asn Ala Gln Gln Gln
            20                  25                  30

Lys Ser Pro Lys Thr Glu Thr Phe Leu Pro Asn Ile Phe Phe Asn Glu
            35                  40                  45

Tyr Ala Asp Asp Leu Asp Thr Leu Tyr His Asn Met Ile Leu Gly Asp
50                  55                  60

Thr Ala Ile Thr His Asp Asp Gln Tyr Lys Phe Tyr Ala Asp Asp Ala
65                  70                  75                  80

Thr Glu Val Pro Asp Ser Leu Phe Phe Asn Lys Ile Leu His Asp Gln
                85                  90                  95

Leu Leu Tyr Gly Phe Lys Glu Gly Asp Lys Ile Ile Pro Leu Asp Glu
            100                 105                 110

Asn Gly Lys Pro Val Tyr Lys Leu Asp Lys Arg Leu Glu Asn Gly Val
            115                 120                 125

Gln Lys Thr Val Tyr Ser Val Thr Thr Lys Thr Ala Thr Ala Asp Asp
            130                 135                 140

Val Asn Ser Ala Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Arg Glu Val
            180                 185                 190

Gln Asn Asn Ile Glu Asn Ile His Glu Leu Ala Gln Gln Gln Asp Gln
            195                 200                 205

His Ser Ser Asp Ile Lys Thr Leu Lys Lys Asn Val Glu Lys Asp Leu
        210                 215                 220

Leu Asp Leu Ser Gly Arg Leu Ile Ala Gln Lys Glu Asp Ile Ala Gln
225                 230                 235                 240

Asn Gln Thr Asp Ile Gln Asp Leu Ala Thr Tyr Asn Glu Leu Gln Asp
                245                 250                 255

Gln Tyr Ala Gln Lys Gln Thr Glu Ala Ile Asp Ala Leu Asn Lys Ala
            260                 265                 270

Ser Ser Glu Asn Thr Gln Asn Ile Ala Lys Asn Ser Asn His Ile Lys
        275                 280                 285

Thr Leu Glu Asn Asn Ile Glu Glu Gly Leu Leu Glu Leu Ser Gly His
        290                 295                 300

Leu Ile Asp Gln Lys Ala Asp Leu Thr Lys Asp Ile Lys Ala Leu Glu
305                 310                 315                 320

Ser Asn Val Glu Glu Gly Leu Leu Asp Leu Ser Gly Arg Leu Ile Asp
                325                 330                 335
```

Gln Lys Ala Asp Ile Ala Gln Asn Gln Ala Asn Ile Gln Asp Leu Ala
                340                 345                 350

Ala Tyr Asn Glu Leu Gln Asp Ala Tyr Ala Lys Gln Gln Thr Glu Ala
                355                 360                 365

Ile Asp Ala Leu Asn Lys Ala Ser Ser Glu Asn Thr Gln Asn Ile Glu
370                 375                 380

Asp Leu Ala Ala Tyr Asn Glu Leu Gln Asp Ala Tyr Ala Lys Gln Gln
385                 390                 395                 400

Thr Glu Ala Ile Asp Ala Leu Asn Lys Ala Ser Ser Glu Asn Thr Gln
                405                 410                 415

Asn Ile Glu Asp Leu Ala Ala Tyr Asn Glu Leu Gln Asp Ala Tyr Ala
                420                 425                 430

Lys Gln Gln Thr Glu Ala Ile Asp Ala Leu Asn Lys Ala Ser Ser Glu
                435                 440                 445

Asn Thr Gln Asn Ile Ala Lys Asn Gln Ala Asp Ile Ala Asn Asn Ile
            450                 455                 460

Asn Asn Ile Tyr Glu Leu Ala Gln Gln Gln Asp Gln His Ser Ser Asp
465                 470                 475                 480

Ile Lys Thr Leu Ala Lys Ala Ser Ala Ala Asn Thr Asp Arg Ile Ala
                485                 490                 495

Lys Asn Lys Ala Asp Ala Asp Ala Ser Phe Glu Thr Leu Thr Lys Asn
            500                 505                 510

Gln Asn Thr Leu Ile Glu Lys Asp Lys Glu His Asp Lys Leu Ile Thr
            515                 520                 525

Ala Asn Lys Thr Ala Ile Asp Ala Asn Lys Ala Ser Ala Asp Thr Lys
            530                 535                 540

Phe Ala Ala Thr Ala Asp Ala Ile Thr Lys Asn Gly Asn Ala Ile Thr
545                 550                 555                 560

Lys Asn Ala Lys Ser Ile Thr Asp Leu Gly Thr Lys Val Asp Gly Phe
                565                 570                 575

Asp Gly Arg Val Thr Ala Leu Asp Thr Lys Val Asn Ala Leu Asp Thr
                580                 585                 590

Lys Val Asn Ala Phe Asp Gly Arg Ile Thr Ala Leu Asp Ser Lys Val
                595                 600                 605

Glu Asn Gly Met Ala Ala Gln Ala Ala Leu Ser Gly Leu Phe Gln Pro
            610                 615                 620

Tyr Ser Val Gly Lys Phe Asn Ala Thr Ala Ala Leu Gly Gly Tyr Gly
625                 630                 635                 640

Ser Lys Ser Ala Val Ala Ile Gly Ala Gly Tyr Arg Val Asn Pro Asn
                645                 650                 655

Leu Ala Phe Lys Ala Gly Ala Ala Ile Asn Thr Ser Gly Asn Lys Lys
                660                 665                 670

Gly Ser Tyr Asn Ile Gly Val Asn Tyr Glu Phe
            675                 680

<210> SEQ ID NO 7
<211> LENGTH: 684
<212> TYPE: PRT
<213> ORGANISM: Moraxella catarrhalis

<400> SEQUENCE: 7

Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln

```
            20                  25                  30
Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
    50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
                85                  90                  95

Gln Leu Leu His Gly Phe Lys Glu Gly Gly Thr Ile Ile Pro Leu Asp
            100                 105                 110

Glu Asn Gly Lys Pro Val Tyr Lys Leu Asp Ser Ile Val Glu Gln Gly
        115                 120                 125

Lys Thr Lys Thr Val Tyr Ser Val Thr Thr Lys Thr Ala Thr Ala Asp
        130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
        195                 200                 205

Gln His Ser Ser Asp Ile Lys Thr Leu Lys Lys Asn Val Glu Lys Asp
    210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
        275                 280                 285

Lys Thr Leu Glu Asn Asn Ile Glu Glu Gly Leu Leu Glu Leu Ser Gly
    290                 295                 300

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
                325                 330                 335

Asp Gln Lys Ala Asp Ile Ala Gln Asn Gln Ala Asn Ile Gln Asp Leu
            340                 345                 350

Ala Ala Tyr Asn Glu Leu Gln Asp Ala Tyr Ala Lys Gln Gln Thr Glu
        355                 360                 365

Ala Ile Asp Ala Leu Asn Lys Ala Ser Ser Glu Asn Thr Gln Asn Ile
        370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
                405                 410                 415

Gln Asn Ile Glu Asp Leu Ala Ala Tyr Asn Glu Leu Gln Asp Ala Tyr
            420                 425                 430

Ala Lys Gln Gln Thr Glu Ala Ile Asp Ala Leu Asn Lys Ala Ser Ser
        435                 440                 445
```

```
Glu Asn Thr Gln Asn Ile Ala Lys Asn Gln Ala Asp Ile Ala Asn Asn
    450                 455                 460

Ile Asn Asn Ile Tyr Glu Leu Ala Gln Gln Gln Asp Gln His Ser Ser
465                 470                 475                 480

Asp Ile Lys Thr Leu Ala Lys Ala Ser Ala Ala Asn Thr Asp Arg Ile
                485                 490                 495

Ala Lys Asn Lys Ala Asp Ala Asp Ala Ser Phe Glu Thr Leu Thr Lys
                500                 505                 510

Asn Gln Asn Thr Leu Ile Glu Lys Asp Lys Glu His Asp Lys Leu Ile
                515                 520                 525

Thr Ala Asn Lys Thr Ala Ile Asp Ala Asn Lys Ala Ser Ala Asp Thr
                530                 535                 540

Lys Phe Ala Ala Thr Ala Asp Ala Ile Thr Lys Asn Gly Asn Ala Ile
545                 550                 555                 560

Thr Lys Asn Ala Lys Ser Ile Thr Asp Leu Gly Thr Lys Val Asp Gly
                565                 570                 575

Phe Asp Gly Arg Val Thr Ala Leu Asp Thr Lys Val Asn Ala Leu Asp
                580                 585                 590

Thr Lys Val Asn Ala Phe Asp Gly Arg Ile Thr Ala Leu Asp Ser Lys
                595                 600                 605

Val Glu Asn Gly Met Ala Ala Gln Ala Ala Leu Ser Gly Leu Phe Gln
610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
                645                 650                 655

Asn Leu Ala Phe Lys Ala Gly Ala Ala Ile Asn Thr Ser Gly Asn Lys
                660                 665                 670

Lys Gly Ser Tyr Asn Ile Gly Val Asn Tyr Glu Phe
                675                 680

<210> SEQ ID NO 8
<211> LENGTH: 684
<212> TYPE: PRT
<213> ORGANISM: Moraxella catarrhalis

<400> SEQUENCE: 8

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Gln Gln
                20                  25                  30

Gln Lys Thr Lys Thr Glu Val Phe Leu Pro Asn Leu Phe Asp Asn Asp
            35                  40                  45

Tyr Tyr Asp Leu Thr Asp Pro Leu Tyr His Ser Met Ile Leu Gly Asp
    50                  55                  60

Thr Ala Thr Leu Phe Asp Gln Gln Asp Asn Ser Lys Ser Gln Leu Lys
65                  70                  75                  80

Phe Tyr Ser Asn Asp Lys Asp Ser Val Pro Asp Ser Leu Leu Phe Ser
                85                  90                  95

Lys Leu Leu His Glu Gln Gln Leu Asn Gly Phe Lys Ala Gly Asp Thr
                100                 105                 110

Ile Ile Pro Leu Asp Lys Asp Gly Lys Pro Val Tyr Thr Gln Asp Thr
            115                 120                 125

Arg Thr Lys Asp Gly Lys Val Glu Thr Val Tyr Ser Val Thr Thr Lys
```

-continued

```
                130                 135                 140
Ile Ala Thr Gln Asp Asp Val Glu Gln Ser Ala Tyr Ser Arg Gly Ile
145                 150                 155                 160

Gln Gly Asp Ile Asp Asp Leu Tyr Asp Ile Asn Arg Glu Val Asn Glu
                165                 170                 175

Tyr Leu Lys Ala Thr His Asp Tyr Asn Glu Arg Gln Thr Glu Ala Ile
            180                 185                 190

Asp Ala Leu Asn Lys Ala Ser Ser Ala Asn Thr Asp Arg Ile Asp Thr
                195                 200                 205

Ala Glu Glu Arg Ile Asp Lys Asn Glu Tyr Asp Ile Lys Ala Leu Glu
            210                 215                 220

Ser Asn Val Gly Lys Asp Leu Leu Asp Leu Ser Gly Arg Leu Ile Ala
225                 230                 235                 240

Gln Lys Glu Asp Ile Asp Asn Asn Ile Asn His Ile Tyr Glu Leu Ala
                245                 250                 255

Gln Gln Gln Asp Gln His Ser Ser Asp Ile Lys Thr Leu Lys Asn Asn
            260                 265                 270

Val Glu Glu Gly Leu Leu Glu Leu Ser Gly His Leu Ile Asp Gln Lys
        275                 280                 285

Ala Asp Leu Thr Lys Asp Ile Lys Thr Leu Glu Asn Asn Ile Glu Glu
        290                 295                 300

Gly Leu Leu Glu Leu Ser Gly His Leu Ile Asp Gln Lys Ala Asp Leu
305                 310                 315                 320

Thr Lys Asp Ile Lys Thr Leu Glu Asn Asn Ile Glu Glu Gly Leu Leu
                325                 330                 335

Glu Leu Ser Gly His Leu Ile Asp Gln Lys Ala Asp Ile Ala Gln Asn
            340                 345                 350

Gln Ala Asn Ile Gln Asp Leu Ala Ala Tyr Asn Glu Leu Gln Asp Gln
            355                 360                 365

Tyr Ala Gln Lys Gln Thr Glu Ala Ile Asp Ala Leu Asn Lys Ala Ser
        370                 375                 380

Ser Glu Asn Thr Gln Asn Ile Glu Asp Leu Ala Ala Tyr Asn Glu Leu
385                 390                 395                 400

Gln Asp Ala Tyr Ala Lys Gln Gln Thr Glu Ala Ile Asp Ala Leu Asn
                405                 410                 415

Lys Ala Ser Ser Glu Asn Thr Gln Asn Ile Glu Asp Leu Ala Ala Tyr
            420                 425                 430

Asn Glu Leu Gln Asp Ala Tyr Ala Lys Gln Gln Thr Glu Ala Ile Asp
        435                 440                 445

Ala Leu Asn Lys Ala Ser Ser Glu Asn Thr Gln Asn Ile Ala Lys Asn
        450                 455                 460

Gln Ala Asp Ile Ala Asn Asn Ile Asn Asn Ile Tyr Glu Leu Ala Gln
465                 470                 475                 480

Gln Gln Asp Gln His Ser Ser Asp Ile Lys Thr Leu Ala Lys Val Ser
                485                 490                 495

Ala Ala Asn Thr Asp Arg Ile Ala Lys Asn Lys Ala Asp Ala Asp Ala
            500                 505                 510

Ser Phe Glu Thr Leu Thr Lys Asn Gln Asn Thr Leu Ile Glu Lys Asp
        515                 520                 525

Lys Glu His Asp Lys Leu Ile Thr Ala Asn Lys Thr Ala Ile Asp Ala
        530                 535                 540

Asn Lys Ala Ser Ala Asp Thr Lys Phe Ala Ala Thr Ala Asp Ala Ile
545                 550                 555                 560
```

```
Thr Lys Asn Gly Asn Ala Ile Thr Lys Asn Ala Lys Ser Ile Thr Asp
            565                 570                 575

Leu Gly Thr Lys Val Asp Gly Phe Asp Gly Arg Val Thr Ala Leu Asp
            580                 585                 590

Thr Lys Val Asn Ala Phe Asp Gly Arg Ile Thr Ala Leu Asp Ser Lys
            595                 600                 605

Val Glu Asn Gly Met Ala Ala Gln Ala Ala Leu Ser Gly Leu Phe Gln
            610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
            645                 650                 655

Asn Leu Ala Phe Lys Ala Gly Ala Ala Ile Asn Thr Ser Gly Asn Lys
            660                 665                 670

Lys Gly Ser Tyr Asn Ile Gly Val Asn Tyr Glu Phe
            675                 680

<210> SEQ ID NO 9
<211> LENGTH: 684
<212> TYPE: PRT
<213> ORGANISM: Moraxella catarrhalis

<400> SEQUENCE: 9

Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
            35                  40                  45

Asn Thr Glu Leu Thr Asp Pro Leu Tyr His Asn Met Ile Leu Gly Asn
        50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
            85                  90                  95

Gln Leu Leu His Gly Phe Lys Lys Gly Asp Thr Ile Ile Pro Leu Asp
            100                 105                 110

Glu Asn Gly Lys Pro Val Tyr Lys Leu Asp Ser Ile Val Glu Gln Gly
            115                 120                 125

Lys Thr Lys Thr Val Tyr Ser Val Thr Thr Lys Thr Ala Thr Ala Asp
        130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
            165                 170                 175

Asp Lys Ile Phe Ala Asn Glu Glu Ser Val Gln Tyr Leu Asn Arg Glu
            180                 185                 190

Val Gln Asn Asn Ile Glu Asn Ile Tyr Glu Leu Val Gln Gln Gln Asp
            195                 200                 205

Gln His Ser Ser Asp Ile Lys Thr Leu Lys Lys Asn Val Glu Lys Asp
        210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
```

-continued

```
                245                 250                 255
Asp Gln Tyr Ala Gln Lys Gln Thr Glu Ala Ile Asp Ala Leu Asn Lys
            260                 265                 270
Ala Ser Ser Glu Asn Thr Gln Asn Ile Ala Lys Asn Ser Asn His Ile
        275                 280                 285
Lys Thr Leu Glu Asn Asn Ile Glu Glu Gly Leu Leu Glu Leu Ser Gly
    290                 295                 300
His Leu Ile Asp Gln Lys Ala Asp Leu Thr Lys Asp Ile Lys Ala Leu
305                 310                 315                 320
Glu Ser Asn Val Glu Glu Gly Leu Leu Asp Leu Ser Gly Arg Leu Ile
                325                 330                 335
Asp Gln Lys Ala Asp Ile Ala Gln Asn Gln Ala Asn Ile Gln Asp Leu
            340                 345                 350
Ala Ala Tyr Asn Glu Leu Gln Asp Ala Tyr Ala Lys Gln Gln Thr Glu
        355                 360                 365
Ala Ile Asp Ala Leu Asn Lys Ala Ser Ser Glu Asn Thr Gln Asn Ile
    370                 375                 380
Glu Asp Leu Ala Ala Tyr Asn Glu Leu Gln Asp Ala Tyr Ala Lys Gln
385                 390                 395                 400
Gln Thr Glu Ala Ile Asp Ala Leu Asn Lys Ala Ser Ser Glu Asn Thr
                405                 410                 415
Gln Asn Ile Glu Asp Leu Ala Ala Tyr Asn Glu Leu Gln Asp Ala Tyr
            420                 425                 430
Ala Lys Gln Gln Thr Glu Ala Ile Asp Ala Leu Asn Lys Ala Ser Ser
        435                 440                 445
Glu Asn Thr Gln Asn Ile Ala Lys Asn Gln Ala Asp Ile Ala Asn Asn
    450                 455                 460
Ile Asn Asn Ile Tyr Glu Leu Ala Gln Gln Gln Asp Gln His Ser Ser
465                 470                 475                 480
Asp Ile Lys Thr Leu Ala Lys Ala Ser Ala Ala Asn Thr Asp Arg Ile
                485                 490                 495
Ala Lys Asn Lys Ala Asp Ala Asp Ala Ser Phe Glu Thr Leu Thr Lys
            500                 505                 510
Asn Gln Asn Thr Leu Ile Glu Lys Asp Lys Glu His Asp Lys Leu Ile
        515                 520                 525
Thr Ala Asn Lys Thr Ala Ile Asp Ala Asn Lys Ala Ser Ala Asp Thr
    530                 535                 540
Lys Phe Ala Ala Thr Ala Asp Ala Ile Thr Lys Asn Gly Asn Ala Ile
545                 550                 555                 560
Thr Lys Asn Ala Lys Ser Ile Thr Asp Leu Gly Thr Lys Val Asp Gly
                565                 570                 575
Phe Asp Gly Arg Val Thr Ala Leu Asp Thr Lys Val Asn Ala Leu Asp
            580                 585                 590
Thr Lys Val Asn Ala Phe Asp Gly Arg Ile Thr Ala Leu Asp Ser Lys
        595                 600                 605
Val Glu Asn Gly Met Ala Ala Gln Ala Ala Leu Ser Gly Leu Phe Gln
    610                 615                 620
Pro Tyr Ser Val Gly Lys Phe Asn Ala Thr Ala Ala Leu Gly Gly Tyr
625                 630                 635                 640
Gly Ser Lys Ser Ala Val Ala Ile Gly Ala Gly Tyr Arg Val Asn Pro
                645                 650                 655
Asn Leu Ala Phe Lys Ala Gly Ala Ala Ile Asn Thr Ser Gly Asn Lys
            660                 665                 670
```

```
Lys Gly Ser Tyr Asn Ile Gly Val Asn Tyr Glu Phe
        675                 680

<210> SEQ ID NO 10
<211> LENGTH: 574
<212> TYPE: PRT
<213> ORGANISM: Moraxella catarrhalis

<400> SEQUENCE: 10

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Leu Ala
            20                  25                  30

Glu Gln Phe Phe Pro Asn Ile Phe Ser Asn His Ala Pro Val Lys Gln
        35                  40                  45

His Tyr His Asn Val Val Gly Asp Thr Ser Ile Val Glu Asn Leu
    50                  55                  60

Gln Asp Ser Asp Asp Thr Gln Leu Lys Phe Tyr Ser Asn Asp Glu Tyr
65                  70                  75                  80

Ser Val Pro Asp Ser Leu Leu Phe Asn Lys Met Leu His Glu Gln Gln
                85                  90                  95

Leu Asn Gly Phe Lys Lys Gly Asp Thr Ile Ile Pro Leu Asp Glu Asn
            100                 105                 110

Gly Lys Pro Val Tyr Lys Val Asp Tyr Lys Leu Asp Gly Gln Glu Pro
        115                 120                 125

Arg Arg Val Tyr Ser Val Thr Thr Lys Ile Ala Thr Gln Asp Asp Val
130                 135                 140

Asp Asn Ser Pro Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Lys Glu Val
            180                 185                 190

Gln Asn Asn Ile Glu Asn Ile Tyr Glu Leu Ala Gln Gln Gln Asp Gln
        195                 200                 205

His Ser Ser Asp Ile Lys Thr Leu Lys Lys Asn Val Glu Glu Gly Leu
    210                 215                 220

Leu Glu Leu Ser Gly His Leu Ile Asp Gln Lys Ala Asp Leu Thr Lys
225                 230                 235                 240

Asp Ile Lys Thr Leu Glu Ser Asn Val Glu Glu Gly Leu Leu Glu Leu
                245                 250                 255

Ser Gly His Leu Ile Asp Gln Lys Ala Asp Ile Ala Lys Asn Gln Ala
            260                 265                 270

Asp Ile Ala Gln Asn Gln Ala Asn Ile Gln Asp Leu Ala Ala Tyr Asn
        275                 280                 285

Glu Leu Gln Asp Ala Tyr Ala Lys Gln Gln Thr Glu Ala Ile Asp Ala
    290                 295                 300

Leu Asn Lys Ala Ser Ser Glu Asn Thr Gln Asn Ile Glu Asp Leu Ala
305                 310                 315                 320

Ala Tyr Asn Glu Leu Gln Asp Ala Tyr Ala Lys Gln Gln Thr Glu Ala
                325                 330                 335

Ile Asp Ala Leu Asn Lys Ala Ser Ser Glu Asn Thr Gln Asn Ile Ala
            340                 345                 350

Lys Asn Gln Ala Asp Ile Ala Asn Asn Ile Asn Asn Ile Tyr Glu Leu
```

```
              355                 360                 365
Ala Gln Gln Gln Asp Gln His Ser Ser Asp Ile Lys Thr Leu Ala Lys
370                 375                 380

Ala Ser Ala Ala Asn Thr Asp Arg Ile Ala Lys Asn Lys Ala Asp Ala
385                 390                 395                 400

Asp Ala Ser Phe Glu Thr Leu Thr Lys Asn Gln Asn Thr Leu Ile Glu
                405                 410                 415

Lys Asp Lys Glu His Asp Lys Leu Ile Thr Ala Asn Lys Thr Ala Ile
            420                 425                 430

Asp Ala Asn Lys Ala Ser Ala Asp Thr Lys Phe Ala Ala Thr Ala Asp
        435                 440                 445

Ala Ile Thr Lys Asn Gly Asn Ala Ile Thr Lys Asn Ala Lys Ser Ile
450                 455                 460

Thr Asp Leu Gly Thr Lys Val Asp Ala Phe Asp Gly Arg Val Thr Ala
465                 470                 475                 480

Leu Asp Thr Lys Val Asn Ala Phe Asp Gly Arg Ile Thr Ala Leu Asp
                485                 490                 495

Ser Lys Val Glu Asn Gly Met Ala Ala Gln Ala Ala Leu Ser Gly Leu
            500                 505                 510

Phe Gln Pro Tyr Ser Val Gly Lys Phe Asn Ala Thr Ala Ala Leu Gly
        515                 520                 525

Gly Tyr Gly Ser Lys Ser Ala Val Ala Ile Gly Ala Gly Tyr Arg Val
530                 535                 540

Asn Pro Asn Leu Ala Phe Lys Ala Gly Ala Ala Ile Asn Thr Ser Gly
545                 550                 555                 560

Asn Lys Lys Gly Ser Tyr Asn Ile Gly Val Asn Tyr Glu Phe
                565                 570

<210> SEQ ID NO 11
<211> LENGTH: 678
<212> TYPE: PRT
<213> ORGANISM: Moraxella catarrhalis

<400> SEQUENCE: 11

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Gln Gln
            20                  25                  30

Pro Gln Thr Glu Thr Phe Phe Pro Asn Ile Phe Phe Asn Glu Asn His
        35                  40                  45

Asp Ala Leu Asp Asp Val Tyr His Asn Met Ile Leu Gly Asp Thr Ala
    50                  55                  60

Ile Thr Gln Asp Asn Gln Tyr Lys Phe Tyr Ala Asp Ala Ile Ser Glu
65                  70                  75                  80

Val Pro Asp Ser Leu Leu Phe Asn Lys Ile Leu His Asp Gln Gln Leu
                85                  90                  95

Asn Gly Phe Lys Glu Gly Asp Thr Ile Ile Pro Leu Asp Glu Asn Gly
            100                 105                 110

Lys Pro Val Tyr Lys Leu Asp Glu Lys Val Glu Asn Gly Val Lys Lys
        115                 120                 125

Ser Val Tyr Ser Val Thr Thr Lys Thr Ala Thr Arg Ala Asp Val Glu
    130                 135                 140

Gln Ser Ala Tyr Ser Arg Gly Ile Gln Gly Asp Ile Asp Asp Leu Tyr
145                 150                 155                 160
```

```
Glu Ala Asn Lys Glu Asn Val Asn Arg Leu Ile Glu His Gly Asp Lys
                165                 170                 175
Ile Phe Ala Asn Glu Glu Ser Val Gln Tyr Leu Asn Lys Glu Val Gln
            180                 185                 190
Asn Asn Ile Glu Asn Ile His Glu Leu Ala Gln Gln Gln Asp Gln His
        195                 200                 205
Ser Ser Asp Ile Lys Thr Leu Lys Lys Asn Val Glu Glu Gly Leu Leu
    210                 215                 220
Glu Leu Ser Gly His Leu Ile Asp Gln Lys Ala Asp Leu Thr Lys Asp
225                 230                 235                 240
Ile Lys Thr Leu Glu Ser Asn Val Glu Glu Gly Leu Leu Asp Leu Ser
                245                 250                 255
Gly Arg Leu Leu Asp Gln Lys Ala Asp Ile Ala Gln Asn Gln Ala Asn
            260                 265                 270
Ile Gln Asp Leu Ala Ala Tyr Asn Glu Leu Gln Asp Ala Tyr Ala Lys
        275                 280                 285
Gln Gln Thr Glu Ala Ile Asp Ala Leu Asn Lys Ala Ser Ser Glu Asn
    290                 295                 300
Thr Gln Asn Ile Glu Asp Leu Ala Ala Tyr Asn Glu Leu Gln Asp Ala
305                 310                 315                 320
Tyr Ala Lys Gln Gln Thr Glu Ala Ile Asp Ala Leu Asn Lys Ala Ser
                325                 330                 335
Ser Glu Asn Thr Gln Asn Ile Glu Asp Leu Ala Ala Tyr Asn Glu Leu
            340                 345                 350
Gln Asp Ala Tyr Ala Lys Gln Gln Thr Glu Ala Ile Asp Ala Leu Asn
        355                 360                 365
Lys Ala Ser Ser Glu Asn Thr Gln Asn Ile Glu Asp Leu Ala Ala Tyr
    370                 375                 380
Asn Glu Leu Gln Asp Ala Tyr Ala Lys Gln Gln Thr Glu Ala Ile Asp
385                 390                 395                 400
Ala Leu Asn Lys Ala Ser Ser Glu Asn Thr Gln Asn Ile Glu Asp Leu
                405                 410                 415
Ala Ala Tyr Asn Glu Leu Gln Asp Ala Tyr Ala Lys Gln Gln Thr Glu
            420                 425                 430
Ala Ile Asp Ala Leu Asn Lys Ala Ser Ser Glu Asn Thr Gln Asn Ile
        435                 440                 445
Ala Lys Asn Gln Ala Asp Ile Ala Asn Asn Ile Asn Asn Ile Tyr Glu
    450                 455                 460
Leu Ala Gln Gln Gln Asp Gln His Ser Ser Asp Ile Lys Thr Leu Ala
465                 470                 475                 480
Lys Ala Ser Ala Ala Asn Thr Asp Arg Ile Ala Lys Asn Lys Ala Asp
                485                 490                 495
Ala Asp Ala Ser Phe Glu Thr Leu Thr Lys Asn Gln Asn Thr Leu Ile
            500                 505                 510
Glu Lys Asp Lys Glu His Asp Lys Leu Ile Thr Ala Asn Lys Thr Ala
        515                 520                 525
Ile Asp Ala Asn Lys Ala Ser Ala Asp Thr Lys Phe Ala Ala Thr Ala
    530                 535                 540
Asp Ala Ile Thr Lys Asn Gly Asn Ala Ile Thr Lys Asn Ala Lys Ser
545                 550                 555                 560
Ile Thr Asp Leu Gly Thr Lys Val Asp Ala Phe Asp Gly Arg Val Thr
                565                 570                 575
Ala Leu Asp Thr Lys Val Asn Ala Leu Asp Thr Lys Val Asn Ala Phe
```

```
                    580                 585                 590
Asp Gly Arg Ile Thr Ala Leu Asp Ser Lys Val Glu Asn Gly Met Ala
                595                 600                 605

Ala Gln Ala Ala Leu Ser Gly Leu Phe Gln Pro Tyr Ser Val Gly Lys
    610                 615                 620

Phe Asn Ala Thr Ala Ala Leu Gly Gly Tyr Gly Ser Lys Ser Ala Val
625                 630                 635                 640

Ala Ile Gly Ala Gly Tyr Arg Val Asn Pro Asn Leu Ala Phe Lys Ala
                645                 650                 655

Gly Ala Ala Ile Asn Thr Ser Gly Asn Lys Lys Gly Ser Tyr Asn Ile
                660                 665                 670

Gly Val Asn Tyr Glu Phe
                675

<210> SEQ ID NO 12
<211> LENGTH: 678
<212> TYPE: PRT
<213> ORGANISM: Moraxella catarrhalis

<400> SEQUENCE: 12

Met Lys Thr Met Lys Leu Leu Pro Leu Lys Ile Ala Val Thr Ser Ala
1               5                  10                  15

Met Ile Val Gly Leu Gly Ala Ala Ser Thr Ala Asn Ala Gln Gln Gln
                20                  25                  30

Gln Gln Pro Arg Thr Glu Thr Phe Phe Pro Asn Ile Phe Phe Asn Glu
                35                  40                  45

Asn His Asp Ala Leu Asp Asp Val Tyr His Asn Met Ile Leu Gly Asp
            50                  55                  60

Thr Ala Ile Thr Gln Asp Asn Gln Tyr Lys Phe Tyr Ala Asp Ala Ile
65                  70                  75                  80

Ser Glu Val Pro Asp Ser Leu Leu Phe Asn Lys Ile Leu His Asp Gln
                85                  90                  95

Gln Leu Asn Gly Phe Lys Glu Gly Asp Thr Ile Ile Pro Leu Asp Glu
                100                 105                 110

Asn Gly Lys Pro Val Tyr Lys Leu Asp Glu Lys Val Glu Asn Gly Val
                115                 120                 125

Lys Lys Ser Val Tyr Ser Val Thr Thr Lys Thr Ala Thr Arg Ala Asp
    130                 135                 140

Val Glu Gln Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
                180                 185                 190

Val Gln Asn Asn Ile Glu Asn Ile His Glu Leu Ala Gln Gln Gln Asp
            195                 200                 205

Gln His Ser Ser Asp Ile Lys Thr Leu Lys Lys Asn Val Glu Lys Asp
    210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
                260                 265                 270
```

```
Ala Ser Ser Glu Asn Thr Gln Asn Ile Ala Lys Asn Ser Asn His Ile
            275                 280                 285
Lys Thr Leu Glu Asn Asn Ile Glu Glu Gly Leu Leu Glu Leu Ser Gly
        290                 295                 300
His Leu Ile Asp Gln Lys Ala Asp Leu Thr Lys Asp Ile Lys Thr Leu
305                 310                 315                 320
Glu Asn Asn Ile Glu Glu Gly Leu Leu Glu Leu Ser Gly His Leu Ile
                325                 330                 335
Asp Gln Lys Ala Asp Leu Thr Lys Asp Ile Lys Ala Leu Glu Ser Asn
            340                 345                 350
Val Glu Glu Gly Leu Leu Asp Leu Ser Gly Arg Leu Leu Asp Gln Lys
        355                 360                 365
Ala Asp Ile Ala Gln Asn Gln Ala Asn Ile Gln Asp Leu Ala Ala Tyr
    370                 375                 380
Asn Glu Leu Gln Asp Gln Tyr Ala Gln Lys Gln Thr Glu Ala Ile Asp
385                 390                 395                 400
Ala Leu Asn Lys Ala Ser Ser Glu Asn Thr Gln Asn Ile Glu Asp Leu
                405                 410                 415
Ala Ala Tyr Asn Glu Leu Gln Asp Ala Tyr Ala Lys Gln Gln Thr Glu
            420                 425                 430
Ala Ile Asp Ala Leu Asn Lys Ala Ser Ser Glu Asn Thr Gln Asn Ile
        435                 440                 445
Ala Lys Asn Gln Ala Asp Ile Ala Asn Asn Ile Asn Asn Ile Tyr Glu
    450                 455                 460
Leu Ala Gln Gln Gln Asp Gln His Ser Ser Asp Ile Lys Thr Leu Ala
465                 470                 475                 480
Lys Ala Ser Ala Ala Asn Thr Asp Arg Ile Ala Lys Asn Lys Ala Asp
                485                 490                 495
Ala Asp Ala Ser Phe Glu Thr Leu Thr Lys Asn Gln Asn Thr Leu Ile
            500                 505                 510
Glu Lys Asp Lys Glu His Asp Lys Leu Ile Thr Ala Asn Lys Thr Ala
        515                 520                 525
Ile Asp Thr Asn Lys Ala Ser Ala Asp Thr Lys Phe Ala Ala Thr Ala
    530                 535                 540
Asp Ala Ile Thr Lys Asn Gly Asn Ala Ile Thr Lys Asn Ala Lys Ser
545                 550                 555                 560
Ile Thr Asp Leu Gly Thr Lys Val Asp Gly Phe Asp Gly Arg Val Thr
                565                 570                 575
Ala Leu Asp Thr Lys Val Asn Ala Leu Asp Thr Lys Val Asn Ala Phe
            580                 585                 590
Asp Gly Arg Ile Thr Ala Leu Asp Ser Lys Val Glu Asn Gly Met Ala
        595                 600                 605
Ala Gln Ala Ala Leu Ser Gly Leu Phe Gln Pro Tyr Ser Val Gly Lys
    610                 615                 620
Phe Asn Ala Thr Ala Ala Leu Gly Gly Tyr Gly Ser Lys Ser Ala Val
625                 630                 635                 640
Ala Ile Gly Ala Gly Tyr Arg Val Asn Pro Asn Leu Ala Phe Lys Ala
                645                 650                 655
Gly Ala Ala Ile Asn Thr Ser Gly Asn Lys Lys Gly Ser Tyr Asn Ile
            660                 665                 670
Gly Val Asn Tyr Glu Phe
        675
```

```
<210> SEQ ID NO 13
<211> LENGTH: 587
<212> TYPE: PRT
<213> ORGANISM: Moraxella catarrhalis

<400> SEQUENCE: 13
```

| | | | | | | | | | | | | | | |
|---|---|---|---|---|---|---|---|---|---|---|---|---|---|---|
|Met|Lys|Thr|Met|Lys|Leu|Leu|Pro|Leu|Lys|Ile|Ala|Val|Thr|Ser|Ala|
|1| | | |5| | | | |10| | | | |15| |

| | | | | | | | | | | | | | | |
|---|---|---|---|---|---|---|---|---|---|---|---|---|---|---|
|Leu|Ile|Val|Gly|Leu|Gly|Ala|Ala|Ser|Thr|Ala|Asn|Ala|Gln|Leu|Val|
| | | | |20| | | | |25| | | | |30| |

| | | | | | | | | | | | | | | |
|---|---|---|---|---|---|---|---|---|---|---|---|---|---|---|
|Glu|Arg|Phe|Phe|Pro|Asn|Ile|Phe|Leu|Asp|Lys|Pro|Leu|Ala|Lys|Gln|
| | | | |35| | | | |40| | | | |45| |

| | | | | | | | | | | | | | | |
|---|---|---|---|---|---|---|---|---|---|---|---|---|---|---|
|His|Tyr|His|Asn|Val|Val|Gly|Asp|Thr|Ser|Ile|Val|Ser|Asp|Leu|
| | | | |50| | | | |55| | | | |60|

| | | | | | | | | | | | | | | |
|---|---|---|---|---|---|---|---|---|---|---|---|---|---|---|
|Gln|Ser|Asn|Ser|Asp|Gln|Leu|Lys|Phe|Tyr|Ser|Asp|Glu|Gly|Leu|
|65| | | | |70| | | | |75| | | | |80|

| | | | | | | | | | | | | | | |
|---|---|---|---|---|---|---|---|---|---|---|---|---|---|---|
|Val|Pro|Asp|Ser|Leu|Leu|Phe|Asn|Lys|Met|Leu|His|Glu|Gln|Leu|Leu|
| | | | |85| | | | |90| | | | |95| |

| | | | | | | | | | | | | | | |
|---|---|---|---|---|---|---|---|---|---|---|---|---|---|---|
|Asn|Gly|Phe|Lys|Glu|Gly|Asp|Thr|Ile|Ile|Pro|Leu|Asp|Glu|Asn|Gly|
| | | | |100| | | | |105| | | | |110| |

| | | | | | | | | | | | | | | |
|---|---|---|---|---|---|---|---|---|---|---|---|---|---|---|
|Lys|Pro|Val|Tyr|Lys|Val|Asp|Tyr|Lys|Leu|Asp|Gly|Lys|Glu|Pro|Arg|
| | | | |115| | | | |120| | | | |125| |

| | | | | | | | | | | | | | | |
|---|---|---|---|---|---|---|---|---|---|---|---|---|---|---|
|Lys|Val|Tyr|Ser|Val|Thr|Thr|Lys|Ile|Ala|Thr|Ala|Glu|Asp|Val|Ala|
| | | | |130| | | | |135| | | | |140| |

| | | | | | | | | | | | | | | |
|---|---|---|---|---|---|---|---|---|---|---|---|---|---|---|
|Thr|Ser|Ser|Tyr|Ala|Asn|Gly|Ile|Gln|Lys|Asp|Ile|Asp|Asp|Leu|Tyr|
|145| | | | |150| | | | |155| | | | |160|

| | | | | | | | | | | | | | | |
|---|---|---|---|---|---|---|---|---|---|---|---|---|---|---|
|Asp|Phe|Asp|His|Gln|Val|Thr|Glu|Arg|Leu|Thr|Gln|His|Gly|Lys|Thr|
| | | | |165| | | | |170| | | | |175| |

| | | | | | | | | | | | | | | |
|---|---|---|---|---|---|---|---|---|---|---|---|---|---|---|
|Ile|Tyr|Arg|Asn|Gly|Glu|Arg|Ile|Leu|Ala|Asn|Glu|Glu|Ser|Val|Gln|
| | | | |180| | | | |185| | | | |190| |

| | | | | | | | | | | | | | | |
|---|---|---|---|---|---|---|---|---|---|---|---|---|---|---|
|Tyr|Leu|Asn|Lys|Glu|Val|Gln|Asn|Asn|Ile|Glu|His|Ile|Tyr|Glu|Leu|
| | | | |195| | | | |200| | | | |205| |

| | | | | | | | | | | | | | | |
|---|---|---|---|---|---|---|---|---|---|---|---|---|---|---|
|Ala|Gln|Gln|Gln|Asp|Gln|His|Ser|Ser|Asp|Ile|Lys|Thr|Leu|Glu|Ser|
| | | | |210| | | | |215| | | | |220| |

| | | | | | | | | | | | | | | |
|---|---|---|---|---|---|---|---|---|---|---|---|---|---|---|
|Asn|Val|Glu|Lys|Gly|Leu|Leu|Glu|Leu|Ser|Gly|His|Leu|Ile|Asp|Gln|
|225| | | | |230| | | | |235| | | | |240|

| | | | | | | | | | | | | | | |
|---|---|---|---|---|---|---|---|---|---|---|---|---|---|---|
|Lys|Ala|Asp|Leu|Thr|Lys|Asp|Ile|Lys|Thr|Leu|Glu|Asn|Asn|Val|Glu|
| | | | |245| | | | |250| | | | |255| |

| | | | | | | | | | | | | | | |
|---|---|---|---|---|---|---|---|---|---|---|---|---|---|---|
|Glu|Gly|Leu|Leu|Asp|Leu|Ser|Gly|Arg|Leu|Ile|Asp|Gln|Lys|Ala|Asp|
| | | | |260| | | | |265| | | | |270| |

| | | | | | | | | | | | | | | |
|---|---|---|---|---|---|---|---|---|---|---|---|---|---|---|
|Ile|Ala|Gln|Asn|Gln|Ala|Asn|Ile|Gln|Asp|Leu|Ala|Ala|Tyr|Asn|Glu|
| | | | |275| | | | |280| | | | |285| |

| | | | | | | | | | | | | | | |
|---|---|---|---|---|---|---|---|---|---|---|---|---|---|---|
|Leu|Gln|Asp|Gln|Tyr|Ala|Gln|Lys|Gln|Thr|Glu|Ala|Ile|Asp|Ala|Leu|
| | | | |290| | | | |295| | | | |300| |

| | | | | | | | | | | | | | | |
|---|---|---|---|---|---|---|---|---|---|---|---|---|---|---|
|Asn|Lys|Ala|Ser|Ser|Glu|Asn|Thr|Gln|Asn|Ile|Glu|Asp|Leu|Ala|Ala|
|305| | | | |310| | | | |315| | | | |320|

| | | | | | | | | | | | | | | |
|---|---|---|---|---|---|---|---|---|---|---|---|---|---|---|
|Tyr|Asn|Glu|Leu|Gln|Asp|Ala|Tyr|Ala|Lys|Gln|Gln|Thr|Glu|Ala|Ile|
| | | | |325| | | | |330| | | | |335| |

| | | | | | | | | | | | | | | |
|---|---|---|---|---|---|---|---|---|---|---|---|---|---|---|
|Asp|Ala|Leu|Asn|Lys|Ala|Ser|Ser|Glu|Asn|Thr|Gln|Asn|Ile|Ala|Lys|
| | | | |340| | | | |345| | | | |350| |

| | | | | | | | | | | | | | | |
|---|---|---|---|---|---|---|---|---|---|---|---|---|---|---|
|Asn|Gln|Ala|Asp|Ile|Ala|Asn|Asn|Ile|Asn|Asn|Ile|Tyr|Glu|Leu|Ala|
| | | | |355| | | | |360| | | | |365| |

| | | | | | | | | | | | | | | |
|---|---|---|---|---|---|---|---|---|---|---|---|---|---|---|
|Gln|Gln|Gln|Asp|Gln|His|Ser|Ser|Asp|Ile|Lys|Thr|Leu|Ala|Lys|Ala|
| | | | |370| | | | |375| | | | |380| |

```
Ser Ala Ala Asn Thr Asp Arg Ile Ala Lys Asn Lys Ala Asp Ala Asp
385                 390                 395                 400

Ala Ser Phe Glu Thr Leu Thr Lys Asn Gln Asn Thr Leu Ile Glu Lys
            405                 410                 415

Asp Lys Glu His Asp Lys Leu Ile Thr Ala Asn Lys Thr Ala Ile Asp
            420                 425                 430

Thr Asn Lys Ala Ser Ala Asp Thr Lys Phe Ala Ala Thr Ala Asp Ala
        435                 440                 445

Ile Thr Lys Asn Gly Asn Ala Ile Thr Lys Asn Ala Lys Ser Ile Thr
        450                 455                 460

Asp Leu Gly Thr Lys Val Asp Gly Phe Asp Ser Arg Val Thr Ala Leu
465                 470                 475                 480

Asp Thr Lys Val Asn Ala Leu Asp Thr Lys Val Asn Ala Leu Asp Thr
            485                 490                 495

Lys Val Asn Ala Phe Asp Gly Arg Ile Thr Ala Leu Asp Ser Lys Val
            500                 505                 510

Glu Asn Gly Met Ala Ala Gln Ala Ala Leu Ser Gly Leu Phe Gln Pro
        515                 520                 525

Tyr Ser Val Gly Lys Phe Asn Ala Thr Ala Leu Gly Gly Tyr Gly
        530                 535                 540

Ser Lys Ser Ala Val Ala Ile Gly Ala Gly Tyr Arg Val Asn Pro Asn
545                 550                 555                 560

Leu Ala Phe Lys Ala Gly Ala Ile Asn Thr Ser Gly Asn Lys Lys
            565                 570                 575

Gly Ser Tyr Asn Ile Gly Val Asn Tyr Glu Phe
        580                 585

<210> SEQ ID NO 14
<211> LENGTH: 678
<212> TYPE: PRT
<213> ORGANISM: Moraxella catarrhalis

<400> SEQUENCE: 14

Met Lys Thr Met Lys Leu Leu Pro Leu Lys Ile Ala Val Thr Ser Ala
1               5                   10                  15

Met Ile Val Gly Leu Gly Ala Ala Ser Thr Ala Asn Ala Gln Gln Gln
            20                  25                  30

Gln Gln Pro Arg Thr Glu Thr Phe Phe Pro Asn Ile Phe Phe Asn Glu
        35                  40                  45

Asn His Asp Ala Leu Asp Asp Val Tyr His Asn Met Ile Leu Gly Asp
    50                  55                  60

Thr Ala Ile Thr Gln Asp Asn Gln Tyr Lys Phe Tyr Ala Asp Ala Ile
65                  70                  75                  80

Ser Glu Val Pro Asp Ser Leu Leu Phe Asn Lys Ile Leu His Asp Gln
            85                  90                  95

Gln Leu Asn Gly Phe Lys Glu Gly Asp Thr Ile Ile Pro Leu Asp Glu
        100                 105                 110

Asn Gly Lys Pro Val Tyr Lys Leu Asp Glu Lys Val Glu Asn Gly Val
    115                 120                 125

Lys Lys Ser Val Tyr Ser Val Thr Thr Lys Thr Ala Thr Arg Ala Asp
    130                 135                 140

Val Glu Gln Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
            165                 170                 175
```

```
Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
        195                 200                 205

Gln His Ser Ser Asp Ile Lys Thr Leu Lys Lys Asn Val Glu Lys Asp
    210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
        275                 280                 285

Lys Thr Leu Glu Asn Asn Ile Glu Glu Gly Leu Leu Glu Leu Ser Gly
    290                 295                 300

His Leu Ile Asp Gln Lys Ala Asp Leu Thr Lys Asp Ile Lys Thr Leu
305                 310                 315                 320

Glu Asn Asn Ile Glu Glu Gly Leu Leu Glu Leu Ser Gly His Leu Ile
                325                 330                 335

Asp Gln Lys Ala Asp Leu Thr Lys Asp Ile Lys Ala Leu Glu Ser Asn
            340                 345                 350

Val Glu Glu Gly Leu Leu Asp Leu Ser Gly Arg Leu Leu Asp Gln Lys
        355                 360                 365

Ala Asp Ile Ala Gln Asn Gln Ala Asn Ile Gln Asp Leu Ala Ala Tyr
    370                 375                 380

Asn Glu Leu Gln Asp Gln Tyr Ala Gln Lys Gln Thr Glu Ala Ile Asp
385                 390                 395                 400

Ala Leu Asn Lys Ala Ser Ser Glu Asn Thr Gln Asn Ile Glu Asp Leu
                405                 410                 415

Ala Ala Tyr Asn Glu Leu Gln Asp Ala Tyr Ala Lys Gln Gln Thr Glu
            420                 425                 430

Ala Ile Asp Ala Leu Asn Lys Ala Ser Ser Glu Asn Thr Gln Asn Ile
        435                 440                 445

Ala Lys Asn Gln Ala Asp Ile Ala Asn Ile Asn Asn Ile Tyr Glu
    450                 455                 460

Leu Ala Gln Gln Gln Asp Gln His Ser Ser Asp Ile Lys Thr Leu Ala
465                 470                 475                 480

Lys Ala Ser Ala Ala Asn Thr Asp Arg Ile Ala Lys Asn Lys Ala Asp
                485                 490                 495

Ala Asp Ala Ser Phe Glu Thr Leu Thr Lys Asn Gln Asn Thr Leu Ile
            500                 505                 510

Glu Lys Asp Lys Glu His Asp Lys Leu Ile Thr Ala Asn Lys Thr Ala
        515                 520                 525

Ile Asp Thr Asn Lys Ala Ser Ala Asp Thr Lys Phe Ala Ala Thr Ala
    530                 535                 540

Asp Ala Ile Thr Lys Asn Gly Asn Ala Ile Thr Lys Asn Ala Lys Ser
545                 550                 555                 560

Ile Thr Asp Leu Gly Thr Lys Val Asp Gly Phe Asp Gly Arg Val Thr
                565                 570                 575

Ala Leu Asp Thr Lys Val Asn Ala Leu Asp Thr Lys Val Asn Ala Phe
            580                 585                 590
```

```
Asp Gly Arg Ile Thr Ala Leu Asp Ser Lys Val Glu Asn Gly Met Ala
            595                 600                 605

Ala Gln Ala Ala Leu Ser Gly Leu Phe Gln Pro Tyr Ser Val Gly Lys
610                 615                 620

Phe Asn Ala Thr Ala Ala Leu Gly Gly Tyr Gly Ser Lys Ser Ala Val
625                 630                 635                 640

Ala Ile Gly Ala Gly Tyr Arg Val Asn Pro Asn Leu Ala Phe Lys Ala
            645                 650                 655

Gly Ala Ala Ile Asn Thr Ser Gly Asn Lys Lys Gly Ser Tyr Asn Ile
            660                 665                 670

Gly Val Asn Tyr Glu Phe
            675

<210> SEQ ID NO 15
<211> LENGTH: 616
<212> TYPE: PRT
<213> ORGANISM: Moraxella catarrhalis

<400> SEQUENCE: 15

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Val Arg
            20                  25                  30

Asp Lys Ser Leu Glu Asp Ile Glu Ala Leu Leu Gly Lys Ile Asp Ile
        35                  40                  45

Ser Lys Leu Glu Lys Glu Lys Lys Gln Gln Thr Glu Leu Gln Lys Tyr
    50                  55                  60

Leu Leu Leu Ser Gln Tyr Ala Asn Val Leu Thr Met Glu Glu Leu Asn
65                  70                  75                  80

Lys Asn Val Glu Lys Asn Thr Asn Ser Ile Glu Ala Leu Gly Tyr Glu
                85                  90                  95

Ile Gly Trp Leu Glu Asn Asp Ile Ala Asp Leu Glu Glu Gly Val Glu
            100                 105                 110

Glu Leu Thr Lys Asn Gln Asn Thr Leu Ile Glu Lys Asp Glu Glu His
        115                 120                 125

Asp Arg Leu Ile Ala Gln Asn Gln Ala Asp Ile Lys Thr Leu Glu Asn
    130                 135                 140

Asn Val Val Glu Glu Leu Phe Asn Leu Ser Asp Arg Leu Ile Asp Gln
145                 150                 155                 160

Glu Ala Asp Ile Ala Lys Asn Asn Ala Ser Ile Glu Glu Leu Tyr Asp
                165                 170                 175

Phe Asp Asn Glu Val Ala Glu Arg Ile Gly Glu Ile His Ala Tyr Thr
            180                 185                 190

Glu Glu Val Asn Lys Thr Leu Glu Lys Leu Ile Thr Asn Ser Val Lys
        195                 200                 205

Asn Thr Asp Asn Ile Asp Lys Asn Lys Ala Asp Ile Gln Ala Leu Glu
    210                 215                 220

Asn Asn Val Glu Glu Gly Leu Leu Glu Leu Ser Gly His Leu Ile Asp
225                 230                 235                 240

Gln Lys Ala Asp Leu Thr Lys Asp Ile Lys Ala Leu Glu Ser Asn Val
                245                 250                 255

Glu Glu Gly Leu Leu Asp Leu Ser Gly Arg Leu Leu Asp Gln Lys Ala
            260                 265                 270

Asp Ile Ala Lys Asn Gln Ala Asp Ile Ala Gln Asn Gln Thr Asp Ile
        275                 280                 285
```

```
Gln Asp Leu Ala Ala Tyr Asn Glu Leu Gln Asp Gln Tyr Ala Gln Lys
        290                 295                 300

Gln Thr Glu Ala Ile Asp Ala Leu Asn Lys Ala Ser Ser Glu Asn Thr
305                 310                 315                 320

Gln Asn Ile Glu Asp Leu Ala Ala Tyr Asn Glu Leu Gln Asp Ala Tyr
                325                 330                 335

Ala Lys Gln Gln Thr Glu Ala Ile Asp Ala Leu Asn Lys Ala Ser Ser
        340                 345                 350

Glu Asn Thr Gln Asn Ile Glu Asp Leu Ala Ala Tyr Asn Glu Leu Gln
            355                 360                 365

Asp Ala Tyr Ala Lys Gln Gln Thr Glu Ala Ile Asp Ala Leu Asn Lys
370                 375                 380

Ala Ser Ser Glu Asn Thr Gln Asn Ile Ala Lys Asn Gln Ala Asp Ile
385                 390                 395                 400

Ala Asn Asn Ile Asn Asn Ile Tyr Glu Leu Ala Gln Gln Gln Asp Gln
                405                 410                 415

His Ser Ser Asp Ile Lys Thr Leu Ala Lys Val Ser Ala Ala Asn Thr
                420                 425                 430

Asp Arg Ile Ala Lys Asn Lys Ala Asp Ala Asp Ala Ser Phe Glu Thr
                435                 440                 445

Leu Thr Lys Asn Gln Asn Thr Leu Ile Glu Lys Asp Lys Glu His Asp
450                 455                 460

Lys Leu Ile Thr Ala Asn Lys Thr Ala Ile Asp Ala Asn Lys Ala Ser
465                 470                 475                 480

Ala Asp Thr Lys Phe Ala Ala Thr Ala Asp Ala Ile Thr Lys Asn Gly
                485                 490                 495

Asn Ala Ile Thr Lys Asn Ala Lys Ser Ile Thr Asp Leu Gly Thr Lys
                500                 505                 510

Val Asp Gly Phe Asp Ser Arg Val Thr Ala Leu Asp Thr Lys Val Asn
                515                 520                 525

Ala Phe Asp Gly Arg Ile Thr Ala Leu Asp Ser Lys Val Glu Asn Gly
            530                 535                 540

Met Ala Ala Gln Ala Ala Leu Ser Gly Leu Phe Gln Pro Tyr Ser Val
545                 550                 555                 560

Gly Lys Phe Asn Ala Thr Ala Ala Leu Gly Gly Tyr Gly Ser Lys Ser
                565                 570                 575

Ala Val Ala Ile Gly Ala Gly Tyr Arg Val Asn Pro Asn Leu Ala Phe
            580                 585                 590

Lys Ala Gly Ala Ala Ile Asn Thr Ser Gly Asn Lys Lys Gly Ser Tyr
        595                 600                 605

Asn Ile Gly Val Asn Tyr Glu Phe
610                 615

<210> SEQ ID NO 16
<211> LENGTH: 676
<212> TYPE: PRT
<213> ORGANISM: Moraxella catarrhalis

<400> SEQUENCE: 16

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Thr
            20                  25                  30

Glu Thr Phe Leu Pro Asn Leu Phe Asp Asn Asp Tyr Thr Glu Thr Thr
```

-continued

```
                35                  40                  45
Asp Pro Leu Tyr His Gly Met Ile Leu Gly Asn Thr Ala Ile Thr Gln
 50                  55                  60
Asp Thr Gln Tyr Lys Phe Tyr Ala Glu Asn Gly Asn Glu Val Pro Asp
 65                  70                  75                  80
Ser Leu Phe Phe Asn Lys Ile Leu His Asp Gln Gln Leu Asn Gly Phe
                 85                  90                  95
Lys Glu Gly Asp Thr Ile Ile Pro Leu Asp Glu Asn Gly Lys Pro Val
                100                 105                 110
Tyr Lys Leu Asp Glu Ile Thr Glu Asn Gly Val Lys Arg Lys Val Tyr
            115                 120                 125
Ser Val Thr Thr Lys Thr Ala Thr Arg Glu Asp Val Glu Gln Ser Ala
            130                 135                 140
Tyr Ser Arg Gly Ile Gln Gly Asp Ile Asp Asp Leu Tyr Glu Ala Asn
145                 150                 155                 160
Lys Glu Asn Val Asn Arg Leu Ile Glu His Gly Asp Lys Ile Phe Ala
                165                 170                 175
Asn Glu Glu Ser Val Gln Tyr Leu Asn Lys Glu Val Gln Asn Asn Ile
            180                 185                 190
Glu Asn Ile His Glu Leu Ala Gln Gln Gln Asp Gln His Ser Ser Asp
            195                 200                 205
Ile Lys Thr Leu Lys Lys Asn Val Glu Glu Gly Leu Leu Glu Leu Ser
210                 215                 220
Gly His Leu Ile Asp Gln Lys Ala Asp Leu Thr Lys Asp Ile Lys Ala
225                 230                 235                 240
Leu Glu Ser Asn Val Glu Glu Gly Leu Leu Asp Leu Ser Gly His Leu
                245                 250                 255
Ile Asp Gln Lys Ala Asp Leu Thr Lys Asp Ile Lys Ala Leu Glu Ser
            260                 265                 270
Asn Val Glu Glu Gly Leu Leu Asp Leu Ser Gly Arg Leu Leu Asp Gln
            275                 280                 285
Lys Ala Asp Ile Ala Lys Asn Gln Ala Asp Ile Ala Gln Asn Gln Thr
290                 295                 300
Asp Ile Gln Asp Leu Ala Ala Tyr Asn Glu Leu Gln Asp Gln Tyr Ala
305                 310                 315                 320
Gln Lys Gln Thr Glu Ala Ile Asp Ala Leu Asn Lys Ala Ser Ser Glu
                325                 330                 335
Asn Thr Gln Asn Ile Glu Asp Leu Ala Ala Tyr Asn Glu Leu Gln Asp
            340                 345                 350
Gln Tyr Ala Gln Lys Gln Thr Glu Ala Ile Asp Ala Leu Asn Lys Ala
            355                 360                 365
Ser Ser Glu Asn Thr Gln Asn Ile Glu Asp Leu Ala Ala Tyr Asn Glu
370                 375                 380
Leu Gln Asp Gln Tyr Ala Gln Lys Gln Thr Glu Ala Ile Asp Ala Leu
385                 390                 395                 400
Asn Lys Ala Ser Ser Glu Asn Thr Gln Asn Ile Glu Asp Leu Ala Ala
                405                 410                 415
Tyr Asn Glu Leu Gln Asp Gln Tyr Ala Gln Lys Gln Thr Glu Ala Ile
            420                 425                 430
Asp Ala Leu Asn Lys Ala Ser Ser Glu Asn Thr Gln Asn Ile Ala Lys
            435                 440                 445
Asn Gln Ala Asp Ile Ala Asn Asn Ile Asn Asn Ile Tyr Glu Leu Ala
450                 455                 460
```

Gln Gln Gln Asp Gln His Ser Ser Asp Ile Lys Thr Leu Ala Lys Ala
465                 470                 475                 480

Ser Ala Ala Asn Thr Asp Arg Ile Ala Lys Asn Lys Ala Asp Ala Asp
            485                 490                 495

Ala Ser Phe Glu Thr Leu Thr Lys Asn Gln Asn Thr Leu Ile Glu Lys
            500                 505                 510

Asp Lys Glu His Asp Lys Leu Ile Thr Ala Asn Lys Thr Ala Ile Asp
            515                 520                 525

Ala Asn Lys Ala Ser Ala Asp Thr Lys Phe Ala Ala Thr Ala Asp Ala
530                 535                 540

Ile Thr Lys Asn Gly Asn Ala Ile Thr Lys Asn Ala Lys Ser Ile Thr
545                 550                 555                 560

Asp Leu Gly Thr Lys Val Asp Gly Phe Asp Gly Arg Val Thr Ala Leu
            565                 570                 575

Asp Thr Lys Val Asn Ala Leu Asp Thr Lys Val Asn Ala Phe Asp Gly
            580                 585                 590

Arg Ile Thr Ala Leu Asp Ser Lys Val Glu Asn Gly Met Ala Ala Gln
            595                 600                 605

Ala Ala Leu Ser Gly Leu Phe Gln Pro Tyr Ser Val Gly Lys Phe Asn
610                 615                 620

Ala Thr Ala Ala Leu Gly Gly Tyr Gly Ser Lys Ser Ala Val Ala Ile
625                 630                 635                 640

Gly Ala Gly Tyr Arg Val Asn Pro Asn Leu Ala Phe Lys Ala Gly Ala
            645                 650                 655

Ala Ile Asn Thr Ser Gly Asn Lys Lys Gly Ser Tyr Asn Ile Gly Val
            660                 665                 670

Asn Tyr Glu Phe
            675

<210> SEQ ID NO 17
<211> LENGTH: 629
<212> TYPE: PRT
<213> ORGANISM: Moraxella catarrhalis

<400> SEQUENCE: 17

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Asn Gly
            20                  25                  30

Thr Ser Thr Lys Leu Lys Asn Leu Lys Glu Tyr Ala Gln Tyr Leu Asp
        35                  40                  45

Asn Tyr Ala Gln Tyr Leu Asp Asp Ile Asp Asp Leu Asp Lys Glu
    50                  55                  60

Val Gly Glu Leu Ser Gln Asn Ile Ala Lys Asn Gln Ala Asn Ile Lys
65                  70                  75                  80

Asp Leu Asn Lys Lys Leu Ser Arg Asp Ile Asp Ser Leu Arg Glu Asp
            85                  90                  95

Val Tyr Asp Asn Gln Tyr Glu Ile Val Asn Asn Gln Ala Asp Ile Glu
            100                 105                 110

Lys Asn Gln Asp Asp Ile Lys Glu Leu Glu Asn Val Gly Lys Glu
            115                 120                 125

Leu Leu Asn Leu Ser Gly Arg Leu Leu Asp Gln Lys Ala Asp Ile Asp
130                 135                 140

Asn Asn Ile Asn Asn Ile Tyr Glu Leu Ala Gln Gln Gln Asp Gln His

-continued

```
            145                 150                 155                 160
        Ser Ser Asp Ile Lys Thr Leu Lys Lys Asn Val Glu Glu Gly Leu Leu
                        165                 170                 175
        Glu Leu Ser Gly His Leu Ile Asp Gln Lys Ser Asp Ile Ala Gln Asn
                    180                 185                 190
        Gln Thr Asp Ile Gln Asp Leu Ala Thr Tyr Asn Glu Leu Gln Asp Gln
                195                 200                 205
        Tyr Ala Gln Lys Gln Thr Glu Ala Ile Asp Ala Leu Asn Lys Ala Ser
            210                 215                 220
        Ser Glu Asn Thr Gln Asn Ile Glu Asp Leu Ala Ala Tyr Asn Glu Leu
        225                 230                 235                 240
        Gln Asp Ala Tyr Ala Lys Gln Thr Glu Ala Ile Asp Ala Leu Asn
                        245                 250                 255
        Lys Ala Ser Ser Glu Asn Thr Gln Asn Ile Gln Asp Leu Ala Ala Tyr
                    260                 265                 270
        Asn Glu Leu Gln Asp Ala Tyr Ala Lys Gln Thr Glu Ala Ile Asp
                275                 280                 285
        Ala Leu Asn Lys Ala Ser Ser Glu Asn Thr Gln Asn Ile Glu Asp Leu
            290                 295                 300
        Ala Ala Tyr Asn Glu Leu Gln Asp Ala Tyr Ala Lys Gln Thr Glu
        305                 310                 315                 320
        Ala Ile Asp Ala Leu Asn Lys Ala Ser Ser Glu Asn Thr Gln Asn Ile
                        325                 330                 335
        Glu Asp Leu Ala Ala Tyr Asn Glu Leu Gln Asp Ala Tyr Ala Lys Gln
                    340                 345                 350
        Gln Thr Glu Ala Ile Asp Ala Leu Asn Lys Ala Ser Ser Glu Asn Thr
                355                 360                 365
        Gln Asn Ile Glu Asp Leu Ala Ala Tyr Asn Glu Leu Gln Asp Ala Tyr
            370                 375                 380
        Ala Lys Gln Gln Thr Glu Ala Ile Asp Ala Leu Asn Lys Ala Ser Ser
        385                 390                 395                 400
        Glu Asn Thr Gln Asn Ile Ala Lys Asn Gln Ala Asp Ile Ala Asn Asn
                        405                 410                 415
        Ile Asn Asn Ile Tyr Glu Leu Ala Gln Gln Asp Gln His Ser Ser
                    420                 425                 430
        Asp Ile Lys Thr Leu Ala Lys Ala Ser Ala Ala Asn Thr Asp Arg Ile
                435                 440                 445
        Ala Lys Asn Lys Ala Asp Ala Asp Ala Ser Phe Glu Thr Leu Thr Lys
        450                 455                 460
        Asn Gln Asn Thr Leu Ile Glu Lys Asp Lys Glu His Asp Lys Leu Ile
        465                 470                 475                 480
        Thr Ala Asn Lys Thr Ala Ile Asp Ala Asn Lys Ala Ser Ala Asp Thr
                        485                 490                 495
        Lys Phe Ala Ala Thr Ala Asp Ile Thr Lys Asn Gly Asn Ala Ile
                    500                 505                 510
        Thr Lys Asn Ala Lys Ser Ile Thr Asp Leu Gly Thr Lys Val Asp Ala
                515                 520                 525
        Phe Asp Gly Arg Val Thr Ala Leu Asp Thr Lys Val Asn Ala Phe Asp
                530                 535                 540
        Gly Arg Ile Thr Ala Leu Asp Ser Lys Val Glu Asn Gly Met Ala Ala
        545                 550                 555                 560
        Gln Ala Ala Leu Ser Gly Leu Phe Gln Pro Tyr Ser Val Gly Lys Phe
                        565                 570                 575
```

```
Asn Ala Thr Ala Ala Leu Gly Gly Tyr Gly Ser Lys Ser Ala Val Ala
            580                 585                 590

Ile Gly Ala Gly Tyr Arg Val Asn Pro Asn Leu Ala Phe Lys Ala Gly
        595                 600                 605

Ala Ala Ile Asn Thr Ser Gly Asn Lys Gly Ser Tyr Asn Ile Gly
    610                 615                 620

Val Asn Tyr Glu Phe
625

<210> SEQ ID NO 18
<211> LENGTH: 683
<212> TYPE: PRT
<213> ORGANISM: Moraxella catarrhalis

<400> SEQUENCE: 18

Met Lys Thr Met Lys Leu Leu Pro Leu Lys Ile Ala Val Thr Ser Ala
1               5                   10                  15

Met Ile Val Gly Leu Gly Met Ala Ser Thr Ala Asn Ala Gln Gln Gln
            20                  25                  30

Arg Ser Pro Lys Thr Glu Thr Phe Leu Pro Asn Ile Phe Phe Asn Glu
        35                  40                  45

Tyr Ala Asp Asp Leu Asp Thr Leu Tyr His Asn Met Ile Leu Gly Asp
    50                  55                  60

Thr Ala Ile Thr His Asp Asp Gln Tyr Lys Phe Tyr Ala Asp Asp Ala
65                  70                  75                  80

Thr Glu Val Pro Asp Ser Leu Phe Phe Asn Lys Ile Leu His Asp Gln
                85                  90                  95

Leu Leu Tyr Gly Phe Lys Glu Gly Asp Lys Ile Ile Pro Leu Asp Glu
            100                 105                 110

Asn Gly Lys Pro Val Tyr Lys Leu Asp Lys Arg Leu Asp Asn Gly Val
        115                 120                 125

Gln Lys Thr Val Tyr Ser Val Thr Thr Lys Thr Ala Thr Ala Asp Asp
    130                 135                 140

Val Asn Ser Ala Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Lys Glu Val
            180                 185                 190

Gln Asn Asn Ile Glu Asn Ile His Glu Leu Ala Gln Gln Gln Asp Gln
        195                 200                 205

His Ser Ser Asp Ile Lys Thr Leu Lys Lys Asn Val Glu Glu Gly Leu
    210                 215                 220

Leu Glu Leu Ser Gly His Leu Ile Asp Gln Lys Thr Asp Ile Ala Gln
225                 230                 235                 240

Asn Gln Thr Asp Ile Gln Asp Leu Ala Thr Tyr Asn Glu Leu Gln Asp
                245                 250                 255

Gln Tyr Ala Gln Lys Gln Thr Glu Ala Ile Asp Ala Leu Asn Lys Ala
            260                 265                 270

Ser Ser Glu Asn Thr Gln Asn Ile Ala Lys Asn Ser Asn Arg Ile Lys
        275                 280                 285

Ala Leu Glu Asn Asn Ile Glu Glu Gly Leu Leu Glu Leu Ser Gly His
    290                 295                 300

Leu Ile Asp Gln Lys Ala Asp Leu Thr Lys Asp Ile Lys Ala Leu Glu
```

```
            305                 310                 315                 320
Ser Asn Val Glu Glu Gly Leu Leu Asp Leu Ser Gly Arg Leu Ile Asp
                    325                 330                 335

Gln Lys Ala Asp Ile Ala Gln Asn Gln Ala Asn Ile Gln Asp Leu Ala
                340                 345                 350

Ala Tyr Asn Glu Leu Gln Asp Ala Tyr Ala Lys Gln Thr Glu Ala
            355                 360                 365

Ile Asp Ala Leu Asn Lys Ala Ser Ser Glu Asn Thr Gln Asn Ile Glu
370                 375                 380

Asp Leu Ala Ala Tyr Asn Glu Leu Gln Asp Ala Tyr Ala Lys Gln Gln
385                 390                 395                 400

Thr Glu Ala Ile Asp Ala Leu Asn Lys Ala Ser Ser Glu Asn Thr Gln
                    405                 410                 415

Asn Ile Glu Asp Leu Ala Ala Tyr Asn Glu Leu Gln Asp Ala Tyr Ala
                420                 425                 430

Lys Gln Gln Thr Glu Ala Ile Asp Ala Leu Asn Lys Ala Ser Ser Glu
            435                 440                 445

Asn Thr Gln Asn Ile Ala Lys Asn Gln Ala Asp Ile Ala Asn Asn Ile
450                 455                 460

Asn Asn Ile Tyr Glu Leu Ala Gln Gln Gln Asp Gln His Ser Ser Asp
465                 470                 475                 480

Ile Lys Thr Leu Ala Lys Ala Ser Ala Ala Asn Thr Asp Arg Ile Ala
                    485                 490                 495

Lys Asn Lys Ala Asp Ala Asp Ala Ser Phe Glu Thr Leu Thr Lys Asn
                500                 505                 510

Gln Asn Thr Leu Ile Glu Lys Asp Lys Glu His Asp Lys Leu Ile Thr
            515                 520                 525

Ala Asn Lys Thr Ala Ile Asp Ala Asn Lys Ala Ser Ala Asp Thr Lys
            530                 535                 540

Phe Ala Ala Thr Ala Asp Ala Ile Thr Lys Asn Gly Asn Ala Ile Thr
545                 550                 555                 560

Lys Asn Ala Lys Ser Ile Thr Asp Leu Gly Thr Lys Val Asp Gly Phe
                    565                 570                 575

Asp Gly Arg Val Thr Ala Leu Asp Thr Lys Val Asn Ala Leu Asp Thr
                580                 585                 590

Lys Val Asn Ala Phe Asp Gly Arg Ile Thr Ala Leu Asp Ser Lys Val
            595                 600                 605

Glu Asn Gly Met Ala Ala Gln Ala Ala Leu Ser Gly Leu Phe Gln Pro
610                 615                 620

Tyr Ser Val Gly Lys Phe Asn Ala Thr Ala Leu Gly Gly Tyr Gly
625                 630                 635                 640

Ser Lys Ser Ala Val Ala Ile Gly Ala Gly Tyr Arg Val Asn Pro Asn
                    645                 650                 655

Leu Ala Phe Lys Ala Gly Ala Ala Ile Asn Thr Ser Gly Asn Lys Lys
                660                 665                 670

Gly Ser Tyr Asn Ile Gly Val Asn Tyr Glu Phe
            675                 680

<210> SEQ ID NO 19
<211> LENGTH: 700
<212> TYPE: PRT
<213> ORGANISM: Moraxella catarrhalis

<400> SEQUENCE: 19
```

```
Met Lys Thr Met Lys Leu Leu Pro Leu Lys Ile Ala Val Thr Ser Ala
 1               5                  10                  15
Met Ile Val Gly Leu Gly Ala Ala Ser Thr Ala Asn Ala Gln Ala Gln
             20                  25                  30
Ser Asn Arg Ser Leu Asp Gln Val Gln Ala Leu Leu Arg Gly Ile Asp
             35                  40                  45
Glu Thr Lys Ile Lys Lys Glu Ile Gln Gln Ser Gln Gln Pro Glu Leu
 50                  55                  60
Asn Lys Tyr Leu Thr Phe Asn Gln Leu Ala Asn Ala Leu Asn Ile Glu
 65                  70                  75                  80
Glu Leu Asn Asn Val Gln Lys Asn Thr Gln Arg Leu Asp Ser Ala
             85                  90                  95
Ala Thr Leu Tyr Gly Asp Leu Ser Lys Thr Val Pro Lys Ser Ile Lys
             100                 105                 110
Glu Asn Lys Glu Ser Ile Lys Glu Asn Lys Glu Ser Ile Lys Glu Asn
             115                 120                 125
Lys Glu Ser Ile Lys Glu Asn Lys Glu Ser Ile Lys Glu Asn Lys Glu
 130                 135                 140
Ser Ile Lys Glu Asn Lys Glu Ser Ile Thr Thr Leu Thr Arg Lys Ser
 145                 150                 155                 160
Phe Gln Asn Gln Val Asp Ile Val Arg Asn Asn Ala Ser Ile Glu Asp
             165                 170                 175
Leu Tyr Ala Tyr Gly Gln Glu Val Ala Lys Ser Ile Gly Glu Ile His
             180                 185                 190
Ala Tyr Thr Glu Glu Val Asn Lys Thr Leu Glu Asn Leu Ile Thr Asn
             195                 200                 205
Ser Val Glu Asn Thr Asn Asn Ile Thr Lys Asn Lys Ala Asp Ile Gln
 210                 215                 220
Ala Leu Glu Asn Asn Val Val Glu Glu Leu Phe Asn Leu Ser Gly Arg
 225                 230                 235                 240
Leu Ile Asp Gln Lys Ala Asp Ile Asp Asn Asn Ile Asn Asn Ile Tyr
             245                 250                 255
Glu Leu Ala Gln Gln Gln Asp Gln His Ser Ser Asp Ile Lys Thr Leu
             260                 265                 270
Lys Lys Asn Val Glu Glu Gly Leu Leu Glu Leu Ser Gly His Leu Ile
 275                 280                 285
Asp Gln Lys Ala Asp Leu Thr Lys Asp Ile Lys Thr Leu Glu Ser Asn
             290                 295                 300
Val Glu Glu Gly Leu Leu Asp Leu Ser Gly Arg Leu Leu Asp Gln Lys
 305                 310                 315                 320
Ala Asp Ile Ala Gln Asn Gln Ala Asn Ile Gln Asp Leu Ala Ala Tyr
             325                 330                 335
Asn Glu Leu Gln Asp Ala Tyr Ala Lys Gln Gln Thr Glu Ala Ile Asp
             340                 345                 350
Ala Leu Asn Lys Ala Ser Ser Glu Asn Thr Gln Asn Ile Glu Asp Leu
             355                 360                 365
Ala Ala Tyr Asn Glu Leu Gln Asp Ala Tyr Ala Lys Gln Gln Thr Glu
             370                 375                 380
Ala Ile Asp Ala Leu Asn Lys Ala Ser Ser Glu Asn Thr Gln Asn Ile
 385                 390                 395                 400
Glu Asp Leu Ala Ala Tyr Asn Glu Leu Gln Asp Ala Tyr Ala Lys Gln
             405                 410                 415
Gln Thr Glu Ala Ile Asp Ala Leu Asn Lys Ala Ser Ser Glu Asn Thr
```

```
                420                 425                 430
Gln Asn Ile Glu Asp Leu Ala Ala Tyr Asn Glu Leu Gln Asp Ala Tyr
        435                 440                 445

Ala Lys Gln Gln Thr Glu Ala Ile Asp Ala Leu Asn Lys Ala Ser Ser
450                 455                 460

Glu Asn Thr Gln Asn Ile Ala Lys Asn Gln Ala Asp Ile Ala Asn Asn
465                 470                 475                 480

Ile Asn Asn Ile Tyr Glu Leu Ala Gln Gln Asp Gln His Ser Ser
                485                 490                 495

Asp Ile Lys Thr Leu Ala Lys Ala Ser Ala Ala Asn Thr Asp Arg Ile
            500                 505                 510

Ala Lys Asn Lys Ala Asp Ala Asp Ala Ser Phe Glu Thr Leu Thr Lys
        515                 520                 525

Asn Gln Asn Thr Leu Ile Glu Lys Asp Lys Glu His Asp Lys Leu Ile
    530                 535                 540

Thr Ala Asn Lys Thr Val Ile Asp Ala Asn Lys Ala Ser Ala Asp Thr
545                 550                 555                 560

Lys Phe Ala Ala Thr Ala Asp Ala Ile Thr Lys Asn Gly Asn Ala Ile
                565                 570                 575

Thr Lys Asn Ala Lys Ser Ile Thr Asp Leu Gly Thr Lys Val Asp Gly
            580                 585                 590

Phe Asp Gly Arg Val Thr Ala Leu Asp Thr Lys Val Asn Ala Leu Asp
        595                 600                 605

Thr Lys Val Asn Ala Phe Asp Gly Arg Ile Thr Ala Leu Asp Ser Lys
    610                 615                 620

Val Glu Asn Gly Met Ala Ala Gln Ala Ala Leu Ser Gly Leu Phe Gln
625                 630                 635                 640

Pro Tyr Ser Val Gly Lys Phe Asn Ala Thr Ala Ala Leu Gly Gly Tyr
                645                 650                 655

Gly Ser Lys Ser Ala Val Ala Ile Gly Ala Gly Tyr Arg Val Asn Pro
            660                 665                 670

Asn Leu Ala Phe Lys Ala Gly Ala Ala Ile Asn Thr Ser Gly Asn Lys
        675                 680                 685

Lys Gly Ser Tyr Asn Ile Gly Val Asn Tyr Glu Phe
    690                 695                 700

<210> SEQ ID NO 20
<211> LENGTH: 676
<212> TYPE: PRT
<213> ORGANISM: Moraxella catarrhalis

<400> SEQUENCE: 20

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Thr
            20                  25                  30

Glu Thr Phe Leu Pro Asn Leu Phe Asp Asn Asp Tyr Ile Glu Thr Thr
        35                  40                  45

Asp Pro Leu Tyr His Gly Met Ile Leu Gly Asn Thr Ala Ile Thr Gln
    50                  55                  60

Asp Thr Gln Tyr Lys Phe Tyr Ala Glu Asn Gly Asn Glu Val Pro Asp
65                  70                  75                  80

Ser Leu Phe Phe Asn Lys Ile Leu His Asp Gln Gln Leu Asn Gly Phe
                85                  90                  95
```

Lys Glu Gly Asp Thr Ile Ile Pro Leu Asp Glu Asn Gly Lys Pro Val
                100                 105                 110

Tyr Lys Leu Asp Glu Ile Thr Glu Asn Gly Val Lys Arg Lys Val Tyr
            115                 120                 125

Ser Val Thr Thr Lys Thr Ala Thr Arg Glu Asp Val Glu Gln Ser Ala
        130                 135                 140

Tyr Ser Arg Gly Ile Gln Gly Asp Ile Asp Asp Leu Tyr Glu Ala Asn
145                 150                 155                 160

Lys Glu Asn Val Asn Arg Leu Ile Glu His Gly Asp Lys Ile Phe Ala
                165                 170                 175

Asn Glu Glu Ser Val Gln Tyr Leu Asn Lys Glu Val Gln Asn Asn Ile
            180                 185                 190

Glu Asn Ile His Glu Leu Ala Gln Gln Asp Gln His Ser Ser Asp
        195                 200                 205

Ile Lys Thr Leu Lys Lys Asn Val Glu Glu Gly Leu Leu Glu Leu Ser
    210                 215                 220

Gly His Leu Ile Asp Gln Lys Ala Asp Leu Thr Lys Asp Ile Lys Thr
225                 230                 235                 240

Leu Glu Asn Asn Val Glu Glu Gly Leu Leu Glu Leu Ser Gly His Leu
                245                 250                 255

Ile Asp Gln Lys Ala Asp Leu Thr Lys Asp Ile Lys Ala Leu Glu Ser
            260                 265                 270

Asn Val Glu Glu Gly Leu Leu Asp Leu Ser Gly Arg Leu Leu Asp Gln
        275                 280                 285

Lys Ala Asp Ile Ala Lys Asn Gln Ala Asp Ile Ala Gln Asn Gln Thr
290                 295                 300

Asp Ile Gln Asp Leu Ala Ala Tyr Asn Glu Leu Gln Asp Gln Tyr Ala
305                 310                 315                 320

Gln Lys Gln Thr Glu Ala Ile Asp Ala Leu Asn Lys Ala Ser Ser Glu
                325                 330                 335

Asn Thr Gln Asn Ile Glu Asp Leu Ala Ala Tyr Asn Glu Leu Gln Asp
            340                 345                 350

Gln Tyr Ala Gln Lys Gln Thr Glu Ala Ile Asp Ala Leu Asn Lys Ala
        355                 360                 365

Ser Ser Glu Asn Thr Gln Asn Ile Glu Asp Leu Ala Ala Tyr Asn Glu
    370                 375                 380

Leu Gln Asp Gln Tyr Ala Gln Lys Gln Thr Glu Ala Ile Asp Ala Leu
385                 390                 395                 400

Asn Lys Ala Ser Ser Glu Asn Thr Gln Asn Ile Glu Asp Leu Ala Ala
                405                 410                 415

Tyr Asn Glu Leu Gln Asp Gln Tyr Ala Gln Lys Gln Thr Glu Ala Ile
            420                 425                 430

Asp Ala Leu Asn Lys Ala Ser Ser Glu Asn Thr Gln Asn Ile Ala Lys
        435                 440                 445

Asn Gln Ala Asp Ile Ala Asn Asn Ile Asn Asn Ile Tyr Glu Leu Ala
    450                 455                 460

Gln Gln Gln Asp Gln His Ser Ser Asp Ile Lys Thr Leu Ala Lys Ala
465                 470                 475                 480

Ser Ala Ala Asn Thr Asp Arg Ile Ala Lys Asn Lys Ala Asp Ala Asp
                485                 490                 495

Ala Ser Phe Glu Thr Leu Thr Lys Asn Gln Asn Thr Leu Ile Glu Lys
            500                 505                 510

Asp Lys Glu His Asp Lys Leu Ile Thr Ala Asn Lys Thr Ala Ile Asp

```
            515                 520                 525
Ala Asn Lys Ala Ser Ala Asp Thr Lys Phe Ala Ala Thr Ala Asp Ala
        530                 535                 540

Ile Thr Lys Asn Gly Asn Ala Ile Thr Lys Asn Ala Lys Ser Ile Thr
545                 550                 555                 560

Asp Leu Gly Thr Lys Val Asp Gly Phe Asp Gly Arg Val Thr Ala Leu
                565                 570                 575

Asp Thr Lys Val Asn Ala Leu Asp Thr Lys Val Asn Ala Phe Asp Gly
            580                 585                 590

Arg Ile Thr Ala Leu Asp Ser Lys Val Glu Asn Gly Met Ala Ala Gln
        595                 600                 605

Ala Ala Leu Ser Gly Leu Phe Gln Pro Tyr Ser Val Gly Lys Phe Asn
        610                 615                 620

Ala Thr Ala Ala Leu Gly Gly Tyr Gly Ser Lys Ser Ala Val Ala Ile
625                 630                 635                 640

Gly Ala Gly Tyr Arg Val Asn Pro Asn Leu Ala Phe Lys Ala Gly Ala
                645                 650                 655

Ala Ile Asn Thr Ser Gly Asn Lys Lys Gly Ser Tyr Asn Ile Gly Val
            660                 665                 670

Asn Tyr Glu Phe
        675

<210> SEQ ID NO 21
<211> LENGTH: 678
<212> TYPE: PRT
<213> ORGANISM: Moraxella catarrhalis

<400> SEQUENCE: 21

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Leu Ala
            20                  25                  30

Glu Gln Phe Phe Pro Asn Ile Phe Ser Asn His Ala Pro Val Lys Gln
        35                  40                  45

His Tyr His Asn Val Val Gly Asp Thr Ser Ile Val Glu Asn Leu
    50                  55                  60

Gln Asp Ser Asp Asp Thr Gln Leu Lys Phe Tyr Ser Asn Asp Glu Tyr
65                  70                  75                  80

Ser Val Pro Asp Ser Leu Leu Phe Asn Lys Met Leu His Glu Gln Gln
                85                  90                  95

Leu Asn Gly Phe Lys Lys Gly Asp Thr Ile Ile Pro Leu Asp Glu Asn
            100                 105                 110

Gly Lys Pro Val Tyr Lys Val Asp Tyr Lys Leu Asp Gly Gln Glu Pro
        115                 120                 125

Arg Arg Val Tyr Ser Val Thr Thr Lys Ile Ala Thr Gln Asp Asp Val
    130                 135                 140

Asp Asn Ser Pro Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Lys Glu Val
            180                 185                 190

Gln Asn Asn Ile Glu Asn Ile Tyr Glu Leu Ala Gln Gln Gln Asp Gln
        195                 200                 205
```

```
His Ser Ser Asp Ile Lys Thr Leu Lys Lys Asn Val Glu Glu Gly Leu
    210                 215                 220

Leu Glu Leu Ser Gly Arg Leu Ile Asp Gln Lys Ala Asp Ile Ala Gln
225                 230                 235                 240

Asn Gln Ala Asn Ile Gln Asp Leu Ala Ala Tyr Asn Glu Leu Gln Asp
                245                 250                 255

Gln Tyr Ala Gln Lys Gln Thr Glu Ala Ile Asp Ala Leu Asn Lys Ala
                260                 265                 270

Ser Ser Glu Asn Thr Gln Asn Ile Glu Asp Leu Ala Ala Tyr Asn Glu
                275                 280                 285

Leu Gln Asp Ala Tyr Ala Lys Gln Gln Thr Glu Ala Ile Asp Ala Leu
    290                 295                 300

Asn Lys Ala Ser Ser Glu Asn Thr Gln Asn Ile Glu Asp Leu Ala Ala
305                 310                 315                 320

Tyr Asn Glu Leu Gln Asp Ala Tyr Ala Lys Gln Gln Thr Glu Ala Ile
                325                 330                 335

Asp Ala Leu Asn Lys Ala Ser Ser Glu Asn Thr Gln Asn Ile Glu Asp
                340                 345                 350

Leu Ala Ala Tyr Asn Glu Leu Gln Asp Ala Tyr Ala Lys Gln Gln Thr
                355                 360                 365

Glu Ala Ile Asp Ala Leu Asn Lys Ala Ser Ser Glu Asn Thr Gln Asn
    370                 375                 380

Ile Glu Asp Leu Ala Ala Tyr Asn Glu Leu Gln Asp Ala Tyr Ala Lys
385                 390                 395                 400

Gln Gln Thr Glu Ala Ile Asp Ala Leu Asn Lys Ala Ser Ser Glu Asn
                405                 410                 415

Thr Gln Asn Ile Glu Asp Leu Ala Ala Tyr Asn Glu Leu Gln Asp Ala
                420                 425                 430

Tyr Ala Lys Gln Gln Thr Glu Ala Ile Asp Ala Leu Asn Lys Ala Ser
                435                 440                 445

Ser Glu Asn Thr Gln Asn Ile Ala Lys Asn Gln Ala Asp Ile Ala Asn
    450                 455                 460

Asn Ile Asn Asn Ile Tyr Glu Leu Ala Gln Gln Gln Asp Gln His Ser
465                 470                 475                 480

Ser Asp Ile Lys Thr Leu Ala Lys Val Ser Ala Ala Asn Thr Asp Arg
                485                 490                 495

Ile Ala Lys Asn Lys Ala Asp Ala Asp Ala Ser Phe Glu Thr Leu Thr
                500                 505                 510

Lys Asn Gln Asn Thr Leu Ile Glu Lys Asp Lys Glu His Asp Lys Leu
                515                 520                 525

Ile Thr Ala Asn Lys Thr Ala Ile Asp Ala Asn Lys Ala Ser Ala Asp
    530                 535                 540

Thr Lys Phe Ala Ala Thr Ala Asp Ala Ile Thr Lys Asn Gly Asn Ala
545                 550                 555                 560

Ile Thr Lys Asn Ala Lys Ser Ile Thr Asp Leu Gly Thr Lys Val Asp
                565                 570                 575

Gly Phe Asp Gly Arg Val Thr Ala Leu Asp Thr Lys Val Asn Ala Phe
                580                 585                 590

Asp Gly Arg Ile Thr Ala Leu Asp Ser Lys Val Glu Asn Gly Met Ala
                595                 600                 605

Ala Gln Ala Ala Leu Ser Gly Leu Phe Gln Pro Tyr Ser Val Gly Lys
    610                 615                 620

Phe Asn Ala Thr Ala Ala Leu Gly Gly Tyr Gly Ser Lys Ser Ala Val
```

```
                        625                 630                 635                 640

Ala Ile Gly Ala Gly Tyr Arg Val Asn Pro Asn Leu Ala Phe Lys Ala
                            645                 650                 655

Gly Ala Ala Ile Asn Thr Ser Gly Asn Lys Lys Gly Ser Tyr Asn Ile
                            660                 665                 670

Gly Val Asn Tyr Glu Phe
                    675

<210> SEQ ID NO 22
<211> LENGTH: 613
<212> TYPE: PRT
<213> ORGANISM: Moraxella catarrhalis

<400> SEQUENCE: 22

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ser Arg
                20                  25                  30

Asp Arg Ser Leu Glu Asp Ile Gln Asp Ser Ile Ser Lys Leu Val Gln
            35                  40                  45

Asp Asp Ile Asn Thr Leu Lys Gln Asp Gln Gln Lys Met Asn Lys Tyr
        50                  55                  60

Leu Leu Leu Asn Gln Leu Ala Asn Thr Leu Ile Thr Asp Glu Leu Asn
65                  70                  75                  80

Asn Asn Val Ile Lys Asn Thr Asn Ser Ile Glu Ala Leu Gly Asp Glu
                85                  90                  95

Ile Gly Trp Leu Glu Asn Asp Ile Ala Asp Leu Glu Glu Gly Val Glu
                100                 105                 110

Glu Leu Thr Lys Asn Gln Asn Thr Leu Ile Glu Lys Asp Glu Glu His
            115                 120                 125

Asp Arg Leu Ile Ala Gln Asn Gln Ala Asp Ile Gln Thr Leu Glu Asn
        130                 135                 140

Asn Val Val Glu Glu Leu Phe Asn Leu Ser Gly Arg Leu Ile Asp Gln
145                 150                 155                 160

Glu Ala Asp Ile Ala Lys Asn Asn Ala Ser Ile Glu Glu Leu Tyr Asp
                165                 170                 175

Phe Asp Asn Glu Val Ala Glu Arg Ile Gly Glu Ile His Ala Tyr Thr
            180                 185                 190

Glu Glu Val Asn Lys Thr Leu Glu Asn Leu Ile Thr Asn Ser Val Lys
        195                 200                 205

Asn Thr Asp Asn Ile Asp Lys Asn Lys Ala Asp Ile Asp Asn Asn Ile
    210                 215                 220

Asn His Ile Tyr Glu Leu Ala Gln Gln Gln Asp Gln His Ser Ser Asp
225                 230                 235                 240

Ile Lys Thr Leu Lys Asn Asn Val Glu Glu Gly Leu Leu Glu Leu Ser
                245                 250                 255

Gly His Leu Ile Asp Gln Lys Ala Asp Leu Thr Lys Asp Ile Lys Ala
            260                 265                 270

Leu Glu Ser Asn Val Glu Glu Gly Leu Leu Asp Leu Ser Gly Arg Leu
        275                 280                 285

Leu Asp Gln Lys Ala Asp Leu Thr Lys Asp Ile Lys Ala Leu Glu Ser
    290                 295                 300

Asn Val Glu Glu Gly Leu Leu Asp Leu Ser Gly Arg Leu Leu Asp Gln
305                 310                 315                 320
```

```
Lys Ala Asp Ile Ala Gln Asn Gln Thr Asp Ile Gln Asp Leu Ala Ala
                325                 330                 335

Tyr Asn Glu Leu Gln Asp Gln Tyr Ala Gln Lys Gln Thr Glu Ala Ile
            340                 345                 350

Asp Ala Leu Asn Lys Ala Ser Ser Glu Asn Thr Gln Asn Ile Glu Asp
        355                 360                 365

Leu Ala Ala Tyr Asn Glu Leu Gln Asp Ala Tyr Ala Lys Gln Gln Thr
    370                 375                 380

Glu Ala Ile Asp Ala Leu Asn Lys Ala Ser Glu Asn Thr Gln Asn
385                 390                 395                 400

Ile Ala Lys Asn Gln Ala Asp Ile Ala Asn Asn Ile Asn Asn Ile Tyr
                405                 410                 415

Glu Leu Ala Gln Gln Gln Asp Gln His Ser Ser Asp Ile Lys Thr Leu
            420                 425                 430

Ala Lys Ala Ser Ala Ala Asn Thr Asn Arg Ile Ala Thr Ala Glu Leu
        435                 440                 445

Gly Ile Ala Glu Asn Lys Lys Asp Ala Gln Ile Ala Lys Ala Gln Ala
    450                 455                 460

Asn Ala Asn Lys Thr Ala Ile Asp Glu Asn Lys Ala Ser Ala Asp Thr
465                 470                 475                 480

Lys Phe Ala Ala Thr Ala Asp Ala Ile Thr Lys Asn Gly Asn Ala Ile
                485                 490                 495

Thr Lys Asn Ala Lys Ser Ile Thr Asp Leu Gly Thr Lys Val Asp Gly
            500                 505                 510

Phe Asp Gly Arg Val Thr Ala Leu Asp Thr Lys Val Asn Ala Phe Asp
        515                 520                 525

Gly Arg Ile Thr Ala Leu Asp Ser Lys Val Glu Asn Gly Met Ala Ala
    530                 535                 540

Gln Ala Ala Leu Ser Gly Leu Phe Gln Pro Tyr Ser Val Gly Lys Phe
545                 550                 555                 560

Asn Ala Thr Ala Ala Leu Gly Gly Tyr Gly Ser Lys Ser Ala Val Ala
                565                 570                 575

Ile Gly Ala Gly Tyr Arg Val Asn Pro Asn Leu Ala Phe Lys Ala Gly
            580                 585                 590

Ala Ala Ile Asn Thr Ser Gly Asn Lys Lys Gly Ser Tyr Asn Ile Gly
        595                 600                 605

Val Asn Tyr Glu Phe
    610

<210> SEQ ID NO 23
<211> LENGTH: 589
<212> TYPE: PRT
<213> ORGANISM: Moraxella catarrhalis

<400> SEQUENCE: 23

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Thr
            20                  25                  30

Asn Lys Asp Ile Thr Leu Glu Asp Val Leu Lys Ser Ile Glu Glu Ile
        35                  40                  45

Asp Pro Tyr Glu Leu Arg Asp Tyr Ile Glu Tyr Pro Thr Ala Ile Glu
    50                  55                  60

Arg Phe Leu Leu Leu Ser Gln Tyr Gly Asn Thr Leu Thr Leu Glu Glu
65                  70                  75                  80
```

```
Phe Asp Asn Asp Ile Glu Leu Leu Asp Gln Asp Val Glu Asp Leu Glu
            85                  90                  95
Glu Ser Val Thr Glu Leu Ala Lys Asn Gln Asn Ser Leu Ile Glu Gln
                100                 105                 110
Gly Glu Ala Ile Lys Glu Asp Leu Gln Gly Leu Ala Asp Phe Val Glu
            115                 120                 125
Arg Gln Glu Asp Lys Ile Leu Gln Asn Glu Thr Ser Ile Lys Lys Asn
130                 135                 140
Thr Gln Arg Asn Leu Val Asn Gly Phe Glu Ile Glu Lys Asn Lys Asp
145                 150                 155                 160
Ala Ile Ala Lys Asn Asn Glu Ser Ile Glu Asp Leu Tyr Asp Phe Gly
                165                 170                 175
His Glu Val Ala Lys Ser Ile Gly Glu Ile His Ala His Asn Glu Ala
            180                 185                 190
Gln Asn Glu Thr Leu Lys Asp Leu Ile Thr Asn Ser Val Lys Asn Thr
            195                 200                 205
Asp Asn Ile Thr Lys Asn Lys Ala Asp Ile Gln Ala Leu Glu Ser Asn
            210                 215                 220
Val Glu Lys Gly Leu Leu Glu Leu Ser Gly His Leu Ile Asp Gln Lys
225                 230                 235                 240
Ala Asp Ile Asp Asn Asn Ile Asn Asn Ile His Glu Leu Ala Gln Gln
                245                 250                 255
Gln Asp Gln His Ser Ser Asp Ile Lys Thr Leu Lys Lys Asn Val Glu
            260                 265                 270
Glu Gly Leu Leu Glu Leu Ser Gly His Leu Ile Asp Gln Lys Ser Asp
            275                 280                 285
Ile Ala Gln Asn Gln Ala Asn Ile Gln Asp Leu Ala Thr Tyr Asn Glu
290                 295                 300
Leu Gln Asp Gln Tyr Ala Gln Lys Gln Thr Glu Ala Ile Asp Ala Leu
305                 310                 315                 320
Asn Lys Ala Ser Ser Glu Asn Thr Gln Asn Ile Glu Asp Leu Ala Ala
                325                 330                 335
Tyr Asn Glu Leu Gln Asp Ala Tyr Ala Lys Gln Gln Thr Glu Ala Ile
            340                 345                 350
Asp Ala Leu Asn Lys Ala Ser Ser Glu Asn Thr Gln Asn Ile Ala Lys
            355                 360                 365
Asn Gln Ala Asp Ile Ala Asn Asn Ile Asn Asn Ile Tyr Glu Leu Ala
            370                 375                 380
Gln Gln Gln Asp Gln His Ser Ser Asp Ile Lys Thr Leu Ala Lys Ala
385                 390                 395                 400
Ser Ala Ala Asn Thr Asp Arg Ile Ala Lys Asn Lys Ala Asp Ala Asp
                405                 410                 415
Ala Ser Phe Glu Thr Leu Thr Lys Asn Gln Asn Thr Leu Ile Glu Lys
            420                 425                 430
Asp Lys Glu His Asp Lys Leu Ile Thr Ala Asn Lys Thr Ala Ile Asp
            435                 440                 445
Ala Asn Lys Ala Ser Ala Asp Thr Lys Phe Ala Ala Thr Ala Asp Ala
            450                 455                 460
Ile Thr Lys Asn Gly Asn Ala Ile Thr Lys Asn Ala Lys Ser Ile Thr
465                 470                 475                 480
Asp Leu Gly Thr Lys Val Asp Gly Phe Asp Ser Arg Val Thr Ala Leu
                485                 490                 495
```

-continued

```
Asp Thr Lys Val Asn Ala Phe Asp Gly Arg Ile Thr Ala Leu Asp Ser
            500                 505                 510

Lys Val Glu Asn Gly Met Ala Ala Gln Ala Ala Leu Ser Gly Leu Phe
        515                 520                 525

Gln Pro Tyr Ser Val Gly Lys Phe Asn Ala Thr Ala Ala Leu Gly Gly
    530                 535                 540

Tyr Gly Ser Lys Ser Ala Val Ala Ile Gly Ala Gly Tyr Arg Val Asn
545                 550                 555                 560

Pro Asn Leu Ala Phe Lys Ala Gly Ala Ala Ile Asn Thr Ser Gly Asn
                565                 570                 575

Lys Lys Gly Ser Tyr Asn Ile Gly Val Asn Tyr Glu Phe
            580                 585
```

<210> SEQ ID NO 24
<211> LENGTH: 684
<212> TYPE: PRT
<213> ORGANISM: Moraxella catarrhalis

<400> SEQUENCE: 24

```
Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
    50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
                85                  90                  95

Gln Leu Leu His Gly Phe Lys Glu Gly Asp Thr Ile Ile Pro Leu Asp
            100                 105                 110

Glu Asn Gly Lys Pro Val Tyr Lys Leu Asp Ser Ile Val Glu Gln Gly
        115                 120                 125

Lys Thr Lys Thr Val Tyr Ser Val Thr Thr Lys Thr Ala Thr Ala Asp
    130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
        195                 200                 205

Gln His Ser Ser Asp Ile Lys Thr Leu Lys Lys Asn Val Glu Lys Asp
    210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
        275                 280                 285
```

Lys Thr Leu Glu Asn Asn Ile Glu Glu Gly Leu Leu Glu Leu Ser Gly
        290                 295                 300

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
                325                 330                 335

Asp Gln Lys Ala Asp Ile Ala Gln Asn Ala Asn Ile Gln Asp Leu
                340                 345                 350

Ala Ala Tyr Asn Glu Leu Gln Asp Ala Tyr Ala Lys Gln Gln Thr Glu
            355                 360                 365

Ala Ile Asp Ala Leu Asn Lys Ala Ser Ser Glu Asn Thr Gln Asn Ile
370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
                405                 410                 415

Gln Asn Ile Glu Asp Leu Ala Ala Tyr Asn Glu Leu Gln Asp Ala Tyr
                420                 425                 430

Ala Lys Gln Gln Thr Glu Ala Ile Asp Ala Leu Asn Lys Ala Ser Ser
            435                 440                 445

Glu Asn Thr Gln Asn Ile Ala Lys Asn Gln Ala Asp Ile Ala Asn Asn
450                 455                 460

Ile Asn Asn Ile Tyr Glu Leu Ala Gln Gln Asp Gln His Ser Ser
465                 470                 475                 480

Asp Ile Lys Thr Leu Ala Lys Ala Ser Ala Asn Thr Asp Arg Ile
                485                 490                 495

Ala Lys Asn Lys Ala Asp Ala Asp Ala Ser Phe Glu Thr Leu Thr Lys
            500                 505                 510

Asn Gln Asn Thr Leu Ile Glu Lys Asp Lys Glu His Asp Lys Leu Ile
            515                 520                 525

Thr Ala Asn Lys Thr Ala Ile Asp Ala Asn Lys Ala Ser Ala Asp Thr
530                 535                 540

Lys Phe Ala Ala Thr Ala Asp Ala Ile Thr Lys Asn Gly Asn Ala Ile
545                 550                 555                 560

Thr Lys Asn Ala Lys Ser Ile Thr Asp Leu Gly Thr Lys Val Asp Gly
                565                 570                 575

Phe Asp Gly Arg Val Thr Ala Leu Asp Thr Lys Val Asn Ala Leu Asp
                580                 585                 590

Thr Lys Val Asn Ala Phe Asp Gly Arg Ile Thr Ala Leu Asp Ser Lys
            595                 600                 605

Val Glu Asn Gly Met Ala Ala Gln Ala Ala Leu Ser Gly Leu Phe Gln
610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
                645                 650                 655

Asn Leu Ala Phe Lys Ala Gly Ala Ala Ile Asn Thr Ser Gly Asn Lys
                660                 665                 670

Lys Gly Ser Tyr Asn Ile Gly Val Asn Tyr Glu Phe
            675                 680

<210> SEQ ID NO 25
<211> LENGTH: 650

<212> TYPE: PRT
<213> ORGANISM: Moraxella catarrhalis

<400> SEQUENCE: 25

```
Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Gln Gln
            20                  25                  30

Gln Lys Thr Lys Thr Glu Val Phe Leu Pro Asn Leu Phe Tyr Asn Asp
        35                  40                  45

Tyr Ile Glu Glu Thr Asp Leu Leu Tyr His Asn Met Ile Leu Gly Asp
50                  55                  60

Thr Ala Ala Leu Val Asp Arg Gln Asn Tyr Ser Asn Ser Gln Leu Lys
65                  70                  75                  80

Phe Tyr Ser Asn Asp Glu Glu Ser Val Pro Asp Ser Leu Leu Phe Ser
                85                  90                  95

Lys Met Leu Asn Asn Gln Gln Leu Asn Gly Phe Lys Ala Gly Asp Ile
            100                 105                 110

Ile Ile Pro Val Asp Ala Asn Gly Gln Val Ile Tyr Gln Lys Asp Thr
        115                 120                 125

Arg Val Glu Gly Gly Lys Thr Arg Thr Val Leu Ser Val Thr Thr Lys
130                 135                 140

Ile Ala Thr Gln Gln Asp Val Asp Ser Ala Tyr Ser Arg Gly Ile Gln
145                 150                 155                 160

Gly Lys Val Asn Asp Leu Asp Asp Glu Met Asn Phe Leu Asn His Asp
                165                 170                 175

Ile Thr Ser Leu Tyr Asp Val Thr Ala Asn Gln Gln Asp Asp Ile Lys
            180                 185                 190

Gly Leu Lys Lys Gly Val Lys Asp Leu Lys Lys Gly Val Lys Gly Leu
        195                 200                 205

Asn Lys Glu Leu Lys Glu Leu Asp Lys Glu Val Gly Val Leu Ser Arg
210                 215                 220

Asp Ile Gly Ser Leu Asn Asp Asp Val Ala Gln Asn Asn Glu Ser Ile
225                 230                 235                 240

Glu Asp Leu Tyr Asp Phe Ser Gln Glu Val Ala Asp Ser Ile Gly Glu
                245                 250                 255

Ile His Ala His Asn Lys Ala Gln Asn Glu Thr Leu Gln Asp Leu Ile
            260                 265                 270

Thr Asn Ser Val Glu Asn Thr Asn Ile Thr Lys Asn Lys Ala Asp
        275                 280                 285

Ile Gln Ala Leu Glu Asn Asn Val Val Glu Glu Leu Phe Asn Leu Ser
290                 295                 300

Gly Arg Leu Ile Asp Gln Lys Ala Asp Leu Thr Lys Asp Ile Lys Thr
305                 310                 315                 320

Leu Glu Ser Asn Val Glu Glu Gly Leu Leu Glu Leu Ser Gly His Leu
                325                 330                 335

Ile Asp Gln Lys Ala Asp Ile Ala Lys Asn Gln Ala Asp Ile Ala Gln
            340                 345                 350

Asn Gln Ala Asn Ile Gln Asp Leu Ala Ala Tyr Asn Glu Leu Gln Asp
        355                 360                 365

Ala Tyr Ala Lys Gln Gln Thr Glu Ala Ile Asp Ala Leu Asn Lys Ala
370                 375                 380

Ser Ser Glu Asn Thr Gln Asn Ile Glu Asp Leu Ala Ala Tyr Asn Glu
385                 390                 395                 400
```

```
Leu Gln Asp Ala Tyr Ala Lys Gln Gln Thr Glu Ala Ile Asp Ala Leu
                405                 410                 415

Asn Lys Ala Ser Ser Glu Asn Thr Gln Asn Ile Ala Lys Asn Gln Ala
            420                 425                 430

Asp Ile Ala Asn Asn Ile Asn Asn Ile Tyr Glu Leu Ala Gln Gln Gln
            435                 440                 445

Asp Gln His Ser Ser Asp Ile Lys Thr Leu Ala Lys Ala Ser Ala Ala
        450                 455                 460

Asn Thr Asp Arg Ile Ala Lys Asn Lys Ala Asp Ala Asp Ala Ser Phe
465                 470                 475                 480

Glu Thr Leu Thr Lys Asn Gln Asn Thr Leu Ile Glu Lys Asp Lys Glu
                485                 490                 495

His Asp Lys Leu Ile Thr Ala Asn Lys Thr Ala Ile Asp Glu Asn Lys
            500                 505                 510

Ala Ser Ala Asp Thr Lys Phe Ala Ala Thr Ala Asp Ala Ile Thr Lys
        515                 520                 525

Asn Gly Asn Ala Ile Thr Lys Asn Ala Lys Ser Ile Thr Asp Leu Gly
530                 535                 540

Thr Lys Val Asp Gly Phe Asp Gly Arg Val Thr Ala Leu Asp Thr Lys
545                 550                 555                 560

Val Asn Ala Phe Asp Gly Arg Ile Thr Ala Leu Asp Ser Lys Val Glu
                565                 570                 575

Asn Gly Met Ala Ala Gln Ala Ala Leu Ser Gly Leu Phe Gln Pro Tyr
            580                 585                 590

Ser Val Gly Lys Phe Asn Ala Thr Ala Ala Leu Gly Gly Tyr Gly Ser
        595                 600                 605

Lys Ser Ala Val Ala Ile Gly Ala Gly Tyr Arg Val Asn Pro Asn Leu
    610                 615                 620

Ala Phe Lys Ala Gly Ala Ala Ile Asn Thr Ser Gly Asn Lys Lys Gly
625                 630                 635                 640

Ser Tyr Asn Ile Gly Val Asn Tyr Glu Phe
                645                 650

<210> SEQ ID NO 26
<211> LENGTH: 616
<212> TYPE: PRT
<213> ORGANISM: Moraxella catarrhalis

<400> SEQUENCE: 26

Met Lys Thr Met Lys Leu Leu Pro Leu Lys Ile Ala Val Thr Ser Ala
1               5                   10                  15

Leu Ile Val Gly Leu Gly Ala Val Ser Thr Thr Asn Ala Gln Ala Gln
            20                  25                  30

Ser Arg Ser Leu Asp Gln Ile Gln Thr Lys Leu Ala Asp Leu Ala Gly
        35                  40                  45

Lys Ile Ala Ala Gly Lys Asn Gly Gly Gln Asn Asn Gln Asn Asn
    50                  55                  60

Gln Asn Asp Ile Asn Lys Tyr Leu Phe Leu Ser Gln Tyr Ala Asn Ile
65                  70                  75                  80

Leu Thr Met Glu Glu Leu Asn Asn Asn Val Val Lys Asn Ser Ser Ser
                85                  90                  95

Ile Glu Thr Leu Glu Thr Asp Phe Gly Trp Leu Glu Asn Asp Val Ala
            100                 105                 110

Asp Leu Glu Asp Gly Val Glu Glu Leu Thr Lys Asn Gln Asn Thr Leu
```

-continued

```
            115                 120                 125
Ile Glu Lys Asp Glu His Asp Arg Leu Ile Ala Gln Asn Gln Ala
            130                 135                 140
Asp Ile Gln Thr Leu Glu Asn Asn Val Val Glu Glu Leu Phe Asn Leu
145                 150                 155                 160
Ser Asp Arg Leu Ile Asp Gln Lys Ala Asp Ile Ala Lys Asn Gln Ala
                165                 170                 175
Asp Ile Ala Gln Asn Asn Glu Ser Ile Glu Glu Leu Tyr Asp Phe Asp
            180                 185                 190
Asn Glu Val Ala Glu Lys Ile Gly Glu Ile His Ala Tyr Thr Glu Glu
            195                 200                 205
Val Asn Lys Thr Leu Gln Asp Leu Ile Thr Asn Ser Val Lys Asn Thr
210                 215                 220
Asp Asn Ile Asp Lys Asn Lys Ala Asp Ile Asp Asn Asn Ile Asn His
225                 230                 235                 240
Ile Tyr Glu Leu Ala Gln Gln Gln Asp Gln His Ser Ser Asp Ile Lys
                245                 250                 255
Thr Leu Lys Asn Asn Val Glu Glu Gly Leu Leu Glu Leu Ser Gly His
            260                 265                 270
Leu Ile Asp Gln Lys Ala Asp Leu Thr Lys Asp Ile Lys Thr Leu Glu
            275                 280                 285
Asn Asn Val Glu Glu Gly Leu Leu Asp Leu Ser Gly Arg Leu Ile Asp
290                 295                 300
Gln Lys Ala Asp Ile Ala Lys Asn Gln Ala Asp Ile Ala Gln Asn Gln
305                 310                 315                 320
Thr Asp Ile Gln Asp Leu Ala Ala Tyr Asn Glu Leu Gln Asp Gln Tyr
                325                 330                 335
Ala Gln Lys Gln Thr Glu Ala Ile Asp Ala Leu Asn Lys Ala Ser Ser
            340                 345                 350
Glu Asn Thr Gln Asn Ile Glu Asp Leu Ala Ala Tyr Asn Glu Leu Gln
            355                 360                 365
Asp Ala Tyr Ala Lys Gln Gln Thr Glu Ala Ile Asp Ala Leu Asn Lys
370                 375                 380
Ala Ser Ser Glu Asn Thr Gln Asn Ile Ala Lys Asn Gln Ala Asp Ile
385                 390                 395                 400
Ala Asn Asn Ile Asn Asn Ile Tyr Glu Leu Ala Gln Gln Gln Asp Gln
                405                 410                 415
His Ser Ser Asp Ile Lys Thr Leu Ala Lys Ala Ser Ala Ala Asn Thr
            420                 425                 430
Asp Arg Ile Ala Lys Asn Lys Ala Asp Ala Asp Ala Ser Phe Glu Thr
            435                 440                 445
Leu Thr Lys Asn Gln Asn Thr Leu Ile Glu Lys Asp Lys Glu His Asp
450                 455                 460
Lys Leu Ile Thr Ala Asn Lys Thr Ala Ile Asp Glu Asn Lys Ala Ser
465                 470                 475                 480
Ala Asp Thr Lys Phe Ala Ala Thr Ala Asp Ala Ile Thr Lys Asn Gly
                485                 490                 495
Asn Ala Ile Thr Lys Asn Ala Lys Ser Ile Thr Asp Leu Gly Thr Lys
            500                 505                 510
Val Asp Gly Phe Asp Gly Arg Val Thr Ala Leu Asp Thr Lys Val Asn
            515                 520                 525
Ala Phe Asp Gly Arg Ile Thr Ala Leu Asp Ser Lys Val Glu Asn Gly
            530                 535                 540
```

```
Met Ala Ala Gln Ala Ala Leu Ser Gly Leu Phe Gln Pro Tyr Ser Val
545                 550                 555                 560

Gly Lys Phe Asn Ala Thr Ala Leu Gly Tyr Gly Ser Lys Ser
                565                 570                 575

Ala Val Ala Ile Gly Ala Gly Tyr Arg Val Asn Pro Asn Leu Ala Phe
                580                 585                 590

Lys Ala Gly Ala Ala Ile Asn Thr Ser Gly Asn Lys Lys Gly Ser Tyr
                595                 600                 605

Asn Ile Gly Val Asn Tyr Glu Phe
                610             615

<210> SEQ ID NO 27
<211> LENGTH: 668
<212> TYPE: PRT
<213> ORGANISM: Moraxella catarrhalis

<400> SEQUENCE: 27

Met Lys Thr Met Lys Leu Leu Pro Leu Lys Ile Ala Val Thr Ser Ala
1               5                   10                  15

Leu Ile Val Gly Leu Gly Thr Ala Ser Thr Ala Asn Ala Gln Val Ala
                20                  25                  30

Ser Pro Ala Asn Gln Lys Ile Gln Gln Lys Ile Lys Lys Val Arg Lys
                35                  40                  45

Glu Leu Arg Gln Asp Ile Lys Ser Leu Arg Asn Asp Ile Asp Ser Asn
            50                  55                  60

Thr Ala Asp Ile Gly Ser Leu Asn Asp Asp Val Ala Asp Asn Gln Asp
65                  70                  75                  80

Asp Ile Leu Asp Asn Gln Ala Asp Ile Ala Lys Asn Gln Asp Asp Ile
                85                  90                  95

Glu Lys Asn Gln Ala Asp Ile Lys Glu Leu Asp Lys Glu Val Gly Val
                100                 105                 110

Leu Ser Arg Glu Ile Gly Ser Leu Asn Asp Asp Ile Ala Asp Asn Tyr
                115                 120                 125

Thr Asp Ile Ile Asp Asn Tyr Thr Asp Ile Ile Asp Asn Gln Ala Asn
            130                 135                 140

Ile Ala Lys Asn Gln Asp Asp Ile Glu Lys Asn Gln Ala Asp Ile Lys
145                 150                 155                 160

Glu Leu Asp Lys Glu Val Gly Val Leu Ser Arg Glu Ile Gly Ser Leu
                165                 170                 175

Asn Asp Asp Val Ala Asp Asn Gln Asp Asp Ile Ala Lys Asn Gln Ala
                180                 185                 190

Asp Ile Gln Thr Leu Glu Asn Asn Val Glu Glu Gly Leu Leu Glu Leu
                195                 200                 205

Ser Gly His Leu Leu Asp Gln Lys Ala Asp Ile Asp Asn Asn Ile Asn
            210                 215                 220

Asn Ile Tyr Glu Leu Ala Gln Gln Gln Asp Gln His Ser Ser Asp Ile
225                 230                 235                 240

Lys Thr Leu Lys Lys Asn Val Glu Glu Gly Leu Leu Glu Leu Ser Gly
                245                 250                 255

His Leu Ile Asp Gln Lys Thr Asp Ile Ala Gln Asn Gln Ala Asn Ile
                260                 265                 270

Gln Asp Leu Ala Thr Tyr Asn Glu Leu Gln Asp Gln Tyr Ala Gln Glu
                275                 280                 285

Gln Thr Glu Ala Ile Asp Ala Leu Asn Lys Ala Ser Ser Glu Asn Thr
```

```
            290             295             300
Gln Asn Ile Ala Lys Asn Ser Asn Arg Ile Lys Ala Leu Glu Ser Asn
305                 310                 315                 320
Val Glu Glu Gly Leu Leu Glu Leu Ser Gly His Leu Ile Asp Gln Lys
                325                 330                 335
Ala Asp Leu Thr Lys Asp Ile Lys Ala Leu Glu Ser Asn Val Glu Glu
                340                 345                 350
Gly Leu Leu Glu Leu Ser Gly His Leu Ile Asp Gln Lys Ala Asp Ile
                355                 360                 365
Ala Gln Asn Gln Ala Asn Ile Gln Asp Leu Ala Ala Tyr Asn Glu Leu
                370                 375                 380
Gln Asp Gln Tyr Ala Gln Lys Gln Thr Glu Ala Ile Asp Ala Leu Asn
385                 390                 395                 400
Lys Ala Ser Ser Glu Asn Thr Gln Asn Ile Glu Asp Leu Ala Ala Tyr
                405                 410                 415
Asn Glu Leu Gln Asp Ala Tyr Ala Lys Gln Gln Thr Glu Ala Ile Asp
                420                 425                 430
Ala Leu Asn Lys Ala Ser Ser Glu Asn Thr Gln Asn Ile Ala Lys Asn
                435                 440                 445
Gln Ala Asp Ile Ala Asn Asn Ile Asn Asn Ile Tyr Glu Leu Ala Gln
                450                 455                 460
Gln Gln Asp Gln His Ser Ser Asp Ile Lys Thr Leu Ala Lys Ala Ser
465                 470                 475                 480
Ala Ala Asn Thr Asp Arg Ile Ala Lys Asn Lys Ala Asp Ala Asp Ala
                485                 490                 495
Ser Phe Glu Thr Leu Thr Lys Asn Gln Asn Thr Leu Ile Glu Lys Asp
                500                 505                 510
Lys Glu His Asp Lys Leu Ile Thr Ala Asn Lys Thr Ala Ile Asp Ala
                515                 520                 525
Asn Lys Val Ser Ala Asp Thr Lys Phe Ala Ala Thr Ala Asp Ala Ile
                530                 535                 540
Thr Lys Asn Gly Asn Ala Ile Thr Lys Asn Ala Lys Ser Ile Thr Asp
545                 550                 555                 560
Leu Gly Thr Lys Val Asp Ala Phe Asp Ser Arg Val Thr Ala Leu Asp
                565                 570                 575
Thr Lys Val Asn Ala Phe Asp Gly Arg Ile Thr Ala Leu Asp Ser Lys
                580                 585                 590
Val Glu Asn Gly Met Ala Ala Gln Ala Ala Leu Ser Gly Leu Phe Gln
                595                 600                 605
Pro Tyr Ser Val Gly Lys Phe Asn Ala Thr Ala Ala Leu Gly Gly Tyr
                610                 615                 620
Gly Ser Lys Ser Ala Val Ala Ile Gly Ala Gly Tyr Arg Val Asn Pro
625                 630                 635                 640
Asn Leu Ala Phe Lys Ala Gly Ala Ala Ile Asn Thr Ser Gly Asn Lys
                645                 650                 655
Lys Gly Ser Tyr Asn Ile Gly Val Asn Tyr Glu Phe
                660                 665
```

<210> SEQ ID NO 28
<211> LENGTH: 674
<212> TYPE: PRT
<213> ORGANISM: Moraxella catarrhalis

<400> SEQUENCE: 28

```
Met Lys Thr Met Lys Leu Leu Pro Leu Lys Ile Ala Val Thr Ser Ala
1               5                   10                  15
Met Ile Val Gly Leu Gly Ala Thr Ser Thr Val Asn Ala Gln Val Val
                20                  25                  30
Glu Gln Phe Phe Pro Asn Ile Phe Phe Asn Glu Asn His Asp Glu Leu
            35                  40                  45
Asp Asp Ala Tyr His Asn Met Ile Leu Gly Asp Thr Ala Ile Val Ser
        50                  55                  60
Asn Ser Gln Asp Asn Ser Thr Gln Leu Lys Phe Tyr Ser Asn Asp Glu
65                  70                  75                  80
Asp Ser Val Pro Asp Ser Leu Leu Phe Ser Lys Leu Leu His Glu Gln
                85                  90                  95
Gln Leu Asn Gly Phe Lys Ala Gly Asp Thr Ile Ile Pro Leu Asp Lys
            100                 105                 110
Asp Gly Lys Pro Val Tyr Thr Lys Asp Thr Arg Thr Lys Asp Gly Lys
        115                 120                 125
Val Glu Thr Val Tyr Ser Val Thr Thr Lys Ile Ala Thr Gln Asp Asp
    130                 135                 140
Val Glu Gln Ser Ala Tyr Ser Arg Gly Ile Gln Gly Asp Ile Asp Asp
145                 150                 155                 160
Leu Tyr Asp Ile Asn Arg Glu Val Asn Glu Tyr Leu Lys Ala Thr His
                165                 170                 175
Asp Tyr Asn Glu Arg Gln Thr Glu Ala Ile Asp Ala Leu Asn Lys Ala
            180                 185                 190
Ser Ser Ala Asn Thr Asp Arg Ile Asp Thr Ala Glu Glu Arg Ile Asp
        195                 200                 205
Lys Asn Glu Tyr Asp Ile Lys Ala Leu Glu Ser Asn Val Glu Glu Gly
    210                 215                 220
Leu Leu Glu Leu Ser Gly His Leu Ile Asp Gln Lys Ala Asp Leu Thr
225                 230                 235                 240
Lys Asp Ile Lys Ala Leu Glu Ser Asn Val Glu Glu Gly Leu Leu Glu
                245                 250                 255
Leu Ser Gly His Leu Ile Asp Gln Lys Ala Asp Leu Thr Lys Asp Ile
            260                 265                 270
Lys Ala Leu Glu Ser Asn Val Glu Glu Gly Leu Leu Asp Leu Ser Gly
        275                 280                 285
Arg Leu Ile Asp Gln Lys Ala Asp Ile Ala Gln Asn Gln Ala Asn Ile
    290                 295                 300
Gln Asp Leu Ala Ala Tyr Asn Glu Leu Gln Asp Ala Tyr Ala Lys Gln
305                 310                 315                 320
Gln Thr Glu Ala Ile Asp Ala Leu Asn Lys Ala Ser Ser Glu Asn Thr
                325                 330                 335
Gln Asn Ile Glu Asp Leu Ala Ala Tyr Asn Glu Leu Gln Asp Ala Tyr
            340                 345                 350
Ala Lys Gln Gln Thr Glu Ala Ile Asp Ala Leu Asn Lys Ala Ser Ser
        355                 360                 365
Glu Asn Thr Gln Asn Ile Glu Asp Leu Ala Ala Tyr Asn Glu Leu Gln
    370                 375                 380
Asp Ala Tyr Ala Lys Gln Gln Thr Glu Ala Ile Asp Ala Leu Asn Lys
385                 390                 395                 400
Ala Ser Ser Glu Asn Thr Gln Asn Ile Glu Asp Leu Ala Ala Tyr Asn
                405                 410                 415
Glu Leu Gln Asp Ala Tyr Ala Lys Gln Gln Thr Glu Ala Ile Asp Ala
```

```
            420                 425                 430
Leu Asn Lys Ala Ser Ser Glu Asn Thr Gln Asn Ile Ala Lys Asn Gln
        435                 440                 445

Ala Asp Ile Ala Asn Asn Ile Asn Asn Ile Tyr Glu Leu Ala Gln Gln
    450                 455                 460

Gln Asp Gln His Ser Ser Asp Ile Lys Thr Leu Ala Lys Ala Ser Ala
465                 470                 475                 480

Ala Asn Thr Asp Arg Ile Ala Lys Asn Lys Ala Asp Ala Asp Ala Ser
                485                 490                 495

Phe Glu Thr Leu Thr Lys Asn Gln Asn Thr Leu Ile Glu Lys Asp Lys
            500                 505                 510

Glu His Asp Lys Leu Ile Thr Ala Asn Lys Thr Ala Ile Asp Ala Asn
        515                 520                 525

Lys Ala Ser Ala Asp Thr Lys Phe Ala Ala Thr Ala Asp Ala Ile Thr
    530                 535                 540

Lys Asn Gly Asn Ala Ile Thr Lys Asn Ala Lys Ser Ile Thr Asp Leu
545                 550                 555                 560

Gly Thr Lys Val Asp Gly Phe Asp Gly Arg Val Thr Ala Leu Asp Thr
                565                 570                 575

Lys Val Asn Ala Leu Asp Thr Lys Val Asn Ala Phe Asp Gly Arg Ile
            580                 585                 590

Thr Ala Leu Asp Ser Lys Val Glu Asn Gly Met Ala Ala Gln Ala Ala
        595                 600                 605

Leu Ser Gly Leu Phe Gln Pro Tyr Ser Val Gly Lys Phe Asn Ala Thr
    610                 615                 620

Ala Ala Leu Gly Gly Tyr Gly Ser Lys Ser Ala Val Ala Ile Gly Ala
625                 630                 635                 640

Gly Tyr Arg Val Asn Pro Asn Leu Ala Phe Lys Ala Gly Ala Ala Ile
                645                 650                 655

Asn Thr Ser Gly Asn Lys Lys Gly Ser Tyr Asn Ile Gly Val Asn Tyr
            660                 665                 670

Glu Phe

<210> SEQ ID NO 29
<211> LENGTH: 613
<212> TYPE: PRT
<213> ORGANISM: Moraxella catarrhalis

<400> SEQUENCE: 29

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ser Arg
            20                  25                  30

Asp Arg Ser Leu Glu Asp Ile Gln Asp Ser Ile Ser Lys Leu Val Gln
        35                  40                  45

Asp Asp Ile Asp Thr Leu Lys Gln Asp Gln Gln Lys Met Asn Lys Tyr
    50                  55                  60

Leu Leu Leu Asn Gln Leu Ala Asn Thr Leu Ile Thr Asp Glu Leu Asn
65                  70                  75                  80

Asn Asn Val Ile Lys Asn Thr Asn Ser Ile Glu Ala Leu Gly Asp Glu
                85                  90                  95

Ile Gly Trp Leu Glu Asn Asp Ile Ala Asp Leu Glu Glu Gly Val Glu
            100                 105                 110

Glu Leu Thr Lys Asn Gln Asn Thr Leu Ile Glu Lys Asp Glu Glu His
```

```
            115                 120                 125
Asp Arg Leu Ile Ala Gln Asn Gln Ala Asp Ile Gln Thr Leu Glu Asn
            130                 135                 140
Asn Val Val Glu Glu Leu Phe Asn Leu Ser Gly Arg Leu Ile Asp Gln
145                 150                 155                 160
Glu Ala Asp Ile Ala Lys Asn Asn Ala Ser Ile Glu Glu Leu Tyr Asp
                165                 170                 175
Phe Asp Asn Glu Val Ala Glu Arg Ile Gly Glu Ile His Ala Tyr Thr
            180                 185                 190
Glu Glu Val Asn Lys Thr Leu Glu Asn Leu Ile Thr Asn Ser Val Lys
            195                 200                 205
Asn Thr Asp Asn Ile Asp Lys Asn Lys Ala Asp Ile Asp Asn Asn Ile
210                 215                 220
Asn His Ile Tyr Glu Leu Ala Gln Gln Gln Asp Gln His Ser Ser Asp
225                 230                 235                 240
Ile Lys Thr Leu Lys Asn Asn Val Glu Glu Gly Leu Leu Glu Leu Ser
                245                 250                 255
Gly His Leu Ile Asp Gln Lys Ala Asp Leu Thr Lys Asp Ile Lys Ala
            260                 265                 270
Leu Glu Ser Asn Val Glu Glu Gly Leu Leu Asp Leu Ser Gly Arg Leu
            275                 280                 285
Leu Asp Gln Lys Ala Asp Leu Thr Lys Asp Ile Lys Ala Leu Glu Ser
290                 295                 300
Asn Val Glu Glu Gly Leu Leu Asp Leu Ser Gly Arg Leu Leu Asp Gln
305                 310                 315                 320
Lys Ala Asp Ile Ala Gln Asn Gln Thr Asp Ile Gln Asp Leu Ala Ala
                325                 330                 335
Tyr Asn Glu Leu Gln Asp Gln Tyr Ala Gln Lys Gln Thr Glu Ala Ile
            340                 345                 350
Asp Ala Leu Asn Lys Ala Ser Ser Glu Asn Thr Gln Asn Ile Glu Asp
            355                 360                 365
Leu Ala Ala Tyr Asn Glu Leu Gln Asp Ala Tyr Ala Lys Gln Gln Thr
370                 375                 380
Glu Ala Ile Asp Ala Leu Asn Lys Ala Ser Ser Glu Asn Thr Gln Asn
385                 390                 395                 400
Ile Ala Lys Asn Gln Ala Asp Ile Ala Asn Asn Ile Asn Asn Ile Tyr
                405                 410                 415
Glu Leu Ala Gln Gln Gln Asp Gln His Ser Ser Asp Ile Lys Thr Leu
            420                 425                 430
Ala Lys Ala Ser Ala Ala Asn Thr Asn Arg Ile Ala Thr Ala Glu Leu
            435                 440                 445
Gly Ile Ala Glu Asn Lys Lys Asp Ala Gln Ile Ala Lys Ala Gln Ala
            450                 455                 460
Asn Ala Asn Lys Thr Ala Ile Asp Glu Asn Lys Ala Ser Ala Asp Thr
465                 470                 475                 480
Lys Phe Ala Ala Thr Ala Asp Ala Ile Thr Lys Asn Gly Asn Ala Ile
                485                 490                 495
Thr Lys Asn Ala Lys Ser Ile Thr Asp Leu Gly Thr Lys Val Asp Gly
            500                 505                 510
Phe Asp Gly Arg Val Thr Ala Leu Asp Thr Lys Val Asn Ala Phe Asp
            515                 520                 525
Gly Arg Ile Thr Ala Leu Asp Ser Lys Val Glu Asn Gly Met Ala Ala
            530                 535                 540
```

-continued

Gln Ala Ala Leu Ser Gly Leu Phe Gln Pro Tyr Ser Val Gly Lys Phe
545                 550                 555                 560

Asn Ala Thr Ala Ala Leu Gly Gly Tyr Gly Ser Lys Ser Ala Val Ala
                565                 570                 575

Ile Gly Ala Gly Tyr Arg Val Asn Pro Asn Leu Ala Phe Lys Ala Gly
            580                 585                 590

Ala Ala Ile Asn Thr Ser Gly Asn Lys Lys Gly Ser Tyr Asn Ile Gly
            595                 600                 605

Val Asn Tyr Glu Phe
        610

<210> SEQ ID NO 30
<211> LENGTH: 576
<212> TYPE: PRT
<213> ORGANISM: Moraxella catarrhalis

<400> SEQUENCE: 30

Met Lys Thr Met Lys Leu Leu Pro Leu Lys Ile Ala Val Thr Ser Ala
1               5                   10                  15

Met Ile Val Gly Leu Gly Ala Thr Ser Thr Val Asn Ala Gln Val Val
            20                  25                  30

Glu Gln Phe Phe Pro Asn Ile Phe Asn Glu Asn His Asp Glu Leu
        35                  40                  45

Asp Asp Ala Tyr His Asn Met Ile Leu Gly Asp Thr Ala Ile Val Ser
    50                  55                  60

Asn Ser Gln Asp Asn Ser Thr Gln Leu Lys Phe Tyr Ser Asn Asp Glu
65                  70                  75                  80

Asp Ser Val Pro Asp Ser Leu Leu Phe Ser Lys Leu Leu His Glu Gln
                85                  90                  95

Gln Leu Asn Gly Phe Lys Ala Gly Asp Thr Ile Ile Pro Leu Asp Lys
            100                 105                 110

Asp Gly Lys Pro Val Tyr Thr Lys Asp Thr Arg Thr Lys Asp Gly Lys
        115                 120                 125

Val Glu Thr Val Tyr Ser Val Thr Thr Lys Ile Ala Thr Gln Asp Asp
130                 135                 140

Val Glu Gln Ser Ala Tyr Ser Arg Gly Ile Gln Gly Asp Ile Asp Asp
145                 150                 155                 160

Leu Tyr Asp Ile Asn Arg Glu Val Asn Glu Tyr Leu Lys Ala Thr His
                165                 170                 175

Asp Tyr Asn Glu Arg Gln Thr Glu Ala Ile Asp Ala Leu Asn Lys Ala
            180                 185                 190

Ser Ser Ala Asn Thr Asp Arg Ile Asp Thr Ala Glu Glu Arg Ile Asp
        195                 200                 205

Lys Asn Glu Tyr Asp Ile Lys Ala Leu Glu Ser Asn Val Glu Glu Gly
    210                 215                 220

Leu Leu Glu Leu Ser Gly His Leu Ile Asp Gln Lys Ala Asp Leu Thr
225                 230                 235                 240

Lys Asp Ile Lys Ala Leu Glu Ser Asn Val Glu Glu Gly Leu Leu Glu
                245                 250                 255

Leu Ser Gly His Leu Ile Asp Gln Lys Ala Asp Leu Thr Lys Asp Ile
            260                 265                 270

Lys Ala Leu Glu Ser Asn Val Glu Glu Gly Leu Leu Asp Leu Ser Gly
        275                 280                 285

Arg Leu Leu Asp Gln Lys Ala Asp Ile Ala Lys Asn Gln Ala Asp Ile

|   |   |   |   |   | 290 |   |   |   |   | 295 |   |   |   |   | 300 |
|---|---|---|---|---|---|---|---|---|---|---|---|---|---|---|---|

Ala Gln Asn Gln Thr Asp Ile Gln Asp Leu Ala Ala Tyr Asn Glu Leu
305                 310                 315                 320

Gln Asp Ala Tyr Ala Lys Gln Thr Glu Ala Ile Asp Ala Leu Asn
            325                 330                 335

Lys Ala Ser Ser Glu Asn Thr Gln Asn Ile Ala Lys Asn Gln Ala Asp
                340                 345                 350

Ile Ala Asn Asn Ile Asn Asn Ile Tyr Glu Leu Ala Gln Gln Gln Asp
            355                 360                 365

Gln His Ser Ser Asp Ile Lys Thr Leu Ala Lys Ala Ser Ala Ala Asn
    370                 375                 380

Thr Asp Arg Ile Ala Lys Asn Lys Ala Asp Ala Asp Ala Ser Phe Glu
385                 390                 395                 400

Thr Leu Thr Lys Asn Gln Asn Thr Leu Ile Glu Lys Asp Lys Glu His
                405                 410                 415

Asp Lys Leu Ile Thr Ala Asn Lys Thr Ala Ile Asp Ala Asn Lys Ala
            420                 425                 430

Ser Ala Asp Thr Lys Phe Ala Ala Thr Ala Asp Ala Ile Thr Lys Asn
    435                 440                 445

Gly Asn Ala Ile Thr Lys Asn Ala Lys Ser Ile Thr Asp Leu Gly Thr
450                 455                 460

Lys Val Asp Gly Phe Asp Gly Arg Val Thr Ala Leu Asp Thr Lys Val
465                 470                 475                 480

Asn Ala Leu Asp Thr Lys Val Asn Ala Phe Asp Gly Arg Ile Thr Ala
                485                 490                 495

Leu Asp Ser Lys Val Glu Asn Gly Met Ala Ala Gln Ala Ala Leu Ser
            500                 505                 510

Gly Leu Phe Gln Pro Tyr Ser Val Gly Lys Phe Asn Ala Thr Ala Ala
    515                 520                 525

Leu Gly Gly Tyr Gly Ser Lys Ser Ala Val Ala Ile Gly Ala Gly Tyr
    530                 535                 540

Arg Val Asn Pro Asn Leu Ala Phe Lys Ala Gly Ala Ala Ile Asn Thr
545                 550                 555                 560

Ser Gly Asn Lys Lys Gly Ser Tyr Asn Ile Gly Val Asn Tyr Glu Phe
                565                 570                 575

<210> SEQ ID NO 31
<211> LENGTH: 684
<212> TYPE: PRT
<213> ORGANISM: Moraxella catarrhalis

<400> SEQUENCE: 31

Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
    50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
            85                  90                  95

-continued

Gln Leu Leu His Gly Phe Lys Glu Gly Asp Thr Ile Ile Pro Leu Asp
            100                 105                 110

Glu Asn Gly Lys Pro Val Tyr Lys Leu Asp Ser Ile Val Glu Gln Gly
            115                 120                 125

Lys Thr Lys Thr Val Tyr Ser Val Thr Thr Lys Thr Ala Thr Ala Asp
130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
            195                 200                 205

Gln His Ser Ser Asp Ile Lys Thr Leu Lys Lys Asn Val Glu Lys Asp
            210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
            245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
            275                 280                 285

Lys Thr Leu Glu Asn Asn Ile Glu Glu Gly Leu Leu Glu Leu Ser Gly
            290                 295                 300

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
            325                 330                 335

Asp Gln Lys Ala Asp Ile Ala Gln Asn Gln Ala Asn Ile Gln Asp Leu
            340                 345                 350

Ala Ala Tyr Asn Glu Leu Gln Asp Ala Tyr Ala Lys Gln Gln Thr Glu
            355                 360                 365

Ala Ile Asp Ala Leu Asn Lys Ala Ser Ser Glu Asn Thr Gln Asn Ile
370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
            405                 410                 415

Gln Asn Ile Glu Asp Leu Ala Ala Tyr Asn Glu Leu Gln Asp Ala Tyr
            420                 425                 430

Ala Lys Gln Gln Thr Glu Ala Ile Asp Ala Leu Asn Lys Ala Ser Ser
            435                 440                 445

Glu Asn Thr Gln Asn Ile Ala Lys Asn Gln Ala Asp Ile Ala Asn Asn
            450                 455                 460

Ile Asn Asn Ile Tyr Glu Leu Ala Gln Gln Asp Gln His Ser Ser
465                 470                 475                 480

Asp Ile Lys Thr Leu Ala Lys Ala Ser Ala Ala Asn Thr Asp Arg Ile
                485                 490                 495

Ala Lys Asn Lys Ala Asp Ala Asp Ala Ser Phe Glu Thr Leu Thr Lys
            500                 505                 510

Asn Gln Asn Thr Leu Ile Glu Lys Asp Lys Glu His Asp Lys Leu Ile

```
                515                 520                 525
Thr Ala Asn Lys Thr Ala Ile Asp Ala Asn Lys Ala Ser Ala Asp Thr
            530                 535                 540
Lys Phe Ala Ala Thr Ala Asp Ala Ile Thr Lys Asn Gly Asn Ala Ile
545                 550                 555                 560
Thr Lys Asn Ala Lys Ser Ile Thr Asp Leu Gly Thr Lys Val Asp Gly
                565                 570                 575
Phe Asp Gly Arg Val Thr Ala Leu Asp Thr Lys Val Asn Ala Leu Asp
            580                 585                 590
Thr Lys Val Asn Ala Phe Asp Gly Arg Ile Thr Ala Leu Asp Ser Lys
                595                 600                 605
Val Glu Asn Gly Met Ala Ala Gln Ala Ala Leu Ser Gly Leu Phe Gln
610                 615                 620
Pro Tyr Ser Val Gly Lys Phe Asn Ala Thr Ala Ala Leu Gly Gly Tyr
625                 630                 635                 640
Gly Ser Lys Ser Ala Val Ala Ile Gly Ala Gly Tyr Arg Val Asn Pro
                645                 650                 655
Asn Leu Ala Phe Lys Ala Gly Ala Ala Ile Asn Thr Ser Gly Asn Lys
                660                 665                 670
Lys Gly Ser Tyr Asn Ile Gly Val Asn Tyr Glu Phe
                675                 680

<210> SEQ ID NO 32
<211> LENGTH: 686
<212> TYPE: PRT
<213> ORGANISM: Moraxella catarrhalis

<400> SEQUENCE: 32

Met Lys Thr Met Lys Leu Leu Pro Leu Lys Ile Ala Val Thr Ser Ala
1               5                   10                  15
Met Ile Ile Gly Leu Gly Ala Ala Ser Thr Ala Asn Ala Gln Ala Thr
                20                  25                  30
Glu Thr Phe Leu Pro Asn Leu Phe Asp Asn Asp Tyr Thr Glu Thr Thr
            35                  40                  45
Asp Pro Leu Tyr His Gly Met Ile Leu Gly Asn Thr Ala Ile Thr Gln
        50                  55                  60
Asp Thr Gln Tyr Lys Phe Tyr Ala Glu Asn Gly Asn Glu Val Pro Asp
65                  70                  75                  80
Ser Leu Phe Phe Asn Lys Ile Leu His Asp Gln Leu Asn Gly Phe
                85                  90                  95
Lys Glu Gly Asp Thr Ile Ile Pro Leu Asp Glu Asn Gly Lys Pro Val
                100                 105                 110
Tyr Lys Leu Asp Glu Ile Thr Glu Asn Gly Val Lys Arg Lys Val Tyr
            115                 120                 125
Ser Val Thr Thr Lys Thr Ala Thr Arg Glu Asp Val Glu Gln Ser Ala
        130                 135                 140
Tyr Ser Arg Gly Ile Gln Gly Asp Ile Asp Asp Leu Tyr Glu Ala Asn
145                 150                 155                 160
Lys Glu Asn Val Asn Arg Leu Ile Glu His Gly Asp Lys Ile Phe Ala
                165                 170                 175
Asn Glu Glu Ser Val Gln Tyr Leu Asn Lys Glu Val Gln Asn Asn Ile
                180                 185                 190
Glu Asn Ile His Glu Leu Ala Gln Gln Gln Asp Gln His Ser Ser Asp
            195                 200                 205
```

```
Ile Lys Thr Leu Lys Lys Asn Val Glu Glu Gly Leu Leu Glu Leu Ser
    210                 215                 220
Gly Arg Leu Ile Ala Gln Lys Glu Asp Ile Ala Gln Asn Gln Thr Asp
225                 230                 235                 240
Ile Gln Asp Leu Ala Thr Tyr Asn Glu Leu Gln Asp Gln Tyr Ala Gln
                245                 250                 255
Lys Gln Thr Glu Ala Ile Asp Ala Leu Asn Lys Ala Ser Ser Glu Asn
                260                 265                 270
Thr Gln Asn Ile Ala Lys Asn Ser Asn His Ile Lys Thr Leu Glu Asn
                275                 280                 285
Asn Ile Glu Glu Gly Leu Leu Glu Leu Ser Gly His Leu Ile Asp Gln
290                 295                 300
Lys Ala Asp Leu Thr Lys Asp Ile Lys Ala Leu Glu Ser Asn Val Glu
305                 310                 315                 320
Glu Gly Leu Leu Asp Leu Ser Gly Arg Leu Leu Asp Gln Lys Ala Asp
                325                 330                 335
Ile Ala Lys Asn Gln Ala Asp Ile Ala Gln Asn Gln Thr Asp Ile Gln
                340                 345                 350
Asp Leu Ala Ala Tyr Asn Glu Leu Gln Asp Gln Tyr Ala Gln Lys Gln
                355                 360                 365
Thr Glu Ala Ile Asp Ala Leu Asn Lys Ala Ser Ser Glu Asn Thr Gln
370                 375                 380
Asn Ile Glu Asp Leu Ala Ala Tyr Asn Glu Leu Gln Asp Ala Tyr Ala
385                 390                 395                 400
Lys Gln Gln Thr Glu Ala Ile Asp Ala Leu Asn Lys Ala Ser Ser Glu
                405                 410                 415
Asn Thr Gln Asn Ile Glu Asp Leu Ala Ala Tyr Asn Glu Leu Gln Asp
                420                 425                 430
Ala Tyr Ala Lys Gln Gln Thr Glu Ala Ile Asp Ala Leu Asn Lys Ala
                435                 440                 445
Ser Ser Glu Asn Thr Gln Asn Ile Ala Lys Asn Gln Ala Asp Ile Ala
    450                 455                 460
Asn Asn Ile Asn Asn Ile Tyr Glu Leu Ala Gln Gln Gln Asp Gln His
465                 470                 475                 480
Ser Ser Asp Ile Lys Thr Leu Ala Lys Ala Ser Ala Ala Asn Thr Asp
                485                 490                 495
Arg Ile Ala Lys Asn Lys Ala Asp Ala Asp Ala Ser Phe Glu Thr Leu
                500                 505                 510
Thr Lys Asn Gln Asn Thr Leu Ile Glu Lys Asp Lys Glu His Asp Lys
    515                 520                 525
Leu Ile Thr Ala Asn Lys Thr Ala Ile Asp Ala Asn Lys Ala Ser Ala
    530                 535                 540
Asp Thr Lys Phe Ala Ala Thr Ala Asp Ala Ile Thr Lys Asn Gly Asn
545                 550                 555                 560
Ala Ile Thr Lys Asn Ala Lys Ser Ile Thr Asp Leu Gly Thr Lys Val
                565                 570                 575
Asp Gly Phe Asp Gly Arg Val Thr Ala Leu Asp Thr Lys Val Asn Ala
                580                 585                 590
Leu Asp Thr Lys Val Asn Ala Phe Asp Gly Arg Ile Thr Ala Leu Asp
                595                 600                 605
Ser Lys Val Glu Asn Gly Met Ala Ala Gln Ala Leu Ser Gly Leu
    610                 615                 620
Phe Gln Pro Tyr Ser Val Gly Lys Phe Asn Ala Thr Ala Ala Leu Gly
```

```
                625                 630                 635                 640
        Gly Tyr Gly Ser Lys Ser Ala Val Ala Ile Gly Ala Gly Tyr Arg Val
                            645                 650                 655

Asn Pro Asn Leu Ala Phe Lys Ala Gly Ala Ala Ile Asn Thr Ser Gly
                            660                 665                 670

Asn Lys Lys Gly Ser Tyr Asn Ile Gly Val Asn Tyr Glu Phe
                            675                 680                 685

<210> SEQ ID NO 33
<211> LENGTH: 630
<212> TYPE: PRT
<213> ORGANISM: Moraxella catarrhalis

<400> SEQUENCE: 33

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ala Lys
            20                  25                  30

Asn Asp Ile Thr Leu Glu Asp Leu Pro Tyr Leu Ile Lys Lys Ile Asp
        35                  40                  45

Gln Asn Glu Leu Glu Ala Asp Ile Gly Asp Ile Thr Ala Leu Glu Lys
    50                  55                  60

Tyr Leu Ala Leu Ser Gln Tyr Gly Asn Ile Leu Ala Leu Glu Leu
65                  70                  75                  80

Asn Lys Ala Leu Glu Glu Leu Asp Glu Asp Val Gly Trp Asn Gln Asn
            85                  90                  95

Asp Ile Ala Asn Leu Glu Asp Val Glu Thr Leu Thr Lys Asn Gln
        100                 105                 110

Asn Ala Leu Ala Glu Gln Gly Glu Ala Ile Lys Glu Asp Leu Gln Gly
    115                 120                 125

Leu Ala Asp Phe Val Glu Gly Gln Gly Lys Ile Leu Gln Asn Glu
130                 135                 140

Thr Ser Ile Lys Lys Asn Thr Gln Arg Asn Leu Val Asn Gly Phe Glu
145                 150                 155                 160

Ile Glu Lys Asn Lys Asp Ala Ile Ala Lys Asn Asn Glu Ser Ile Glu
            165                 170                 175

Asp Leu Tyr Asp Phe Gly His Glu Val Ala Glu Ser Ile Gly Glu Ile
        180                 185                 190

His Ala His Asn Glu Ala Gln Asn Glu Thr Leu Lys Gly Leu Ile Thr
    195                 200                 205

Asn Ser Ile Glu Asn Thr Asn Ile Thr Lys Asn Lys Ala Asp Ile
210                 215                 220

Gln Ala Leu Glu Asn Asn Val Val Glu Glu Leu Phe Asn Leu Ser Gly
225                 230                 235                 240

Arg Leu Ile Asp Gln Lys Ala Asp Ile Asp Asn Asn Ile Asn Asn Ile
            245                 250                 255

Tyr Glu Leu Ala Gln Gln Asp Gln His Ser Ser Asp Ile Lys Thr
        260                 265                 270

Leu Lys Lys Asn Val Glu Glu Gly Leu Leu Glu Leu Ser Gly His Leu
    275                 280                 285

Ile Asp Gln Lys Thr Asp Ile Ala Gln Asn Gln Ala Asn Ile Gln Asp
        290                 295                 300

Leu Ala Thr Tyr Asn Glu Leu Gln Asp Gln Tyr Ala Gln Lys Gln Thr
305                 310                 315                 320
```

-continued

Glu Ala Ile Asp Ala Leu Asn Lys Ala Ser Ser Glu Asn Thr Gln Asn
                325                 330                 335

Ile Glu Asp Leu Ala Ala Tyr Asn Glu Leu Gln Asp Ala Tyr Ala Lys
            340                 345                 350

Gln Gln Thr Glu Ala Ile Asp Ala Leu Asn Lys Ala Ser Ser Glu Asn
        355                 360                 365

Thr Gln Asn Ile Glu Asp Leu Ala Ala Tyr Asn Glu Leu Gln Asp Ala
    370                 375                 380

Tyr Ala Lys Gln Gln Thr Glu Ala Ile Asp Ala Leu Asn Lys Ala Ser
385                 390                 395                 400

Ser Glu Asn Thr Gln Asn Ile Ala Lys Asn Gln Ala Asp Ile Ala Asn
                405                 410                 415

Asn Ile Asn Asn Ile Tyr Glu Leu Ala Gln Gln Gln Asp Gln His Ser
            420                 425                 430

Ser Asp Ile Lys Thr Leu Ala Lys Ala Ser Ala Ala Asn Thr Asp Arg
        435                 440                 445

Ile Ala Lys Asn Lys Ala Asp Asp Ala Ser Phe Glu Thr Leu Thr
    450                 455                 460

Lys Asn Gln Asn Thr Leu Ile Glu Lys Asp Lys Glu His Asp Lys Leu
465                 470                 475                 480

Ile Thr Ala Asn Lys Thr Ala Ile Asp Ala Asn Lys Ala Ser Ala Asp
                485                 490                 495

Thr Lys Phe Ala Ala Thr Ala Asp Ala Ile Thr Lys Asn Gly Asn Ala
            500                 505                 510

Ile Thr Lys Asn Ala Lys Ser Ile Thr Asp Leu Gly Thr Lys Val Asp
        515                 520                 525

Gly Phe Asp Ser Arg Val Thr Ala Leu Asp Thr Lys Val Asn Ala Phe
    530                 535                 540

Asp Gly Arg Ile Thr Ala Leu Asp Ser Lys Val Glu Asn Gly Met Ala
545                 550                 555                 560

Ala Gln Ala Ala Leu Ser Gly Leu Phe Gln Pro Tyr Ser Val Gly Lys
                565                 570                 575

Phe Asn Ala Thr Ala Ala Leu Gly Gly Tyr Gly Ser Lys Ser Ala Val
            580                 585                 590

Ala Ile Gly Ala Gly Tyr Arg Val Asn Pro Asn Leu Ala Phe Lys Ala
        595                 600                 605

Gly Ala Ala Ile Asn Thr Ser Gly Asn Lys Lys Gly Ser Tyr Asn Ile
    610                 615                 620

Gly Val Asn Tyr Glu Phe
625                 630

<210> SEQ ID NO 34
<211> LENGTH: 616
<212> TYPE: PRT
<213> ORGANISM: Moraxella catarrhalis

<400> SEQUENCE: 34

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Gln
            20                  25                  30

Asp Arg Ser Leu Glu Gln Ile Gln Asp Lys Leu Ala Asn Leu Val Glu
        35                  40                  45

Lys Ile Glu Gln Ala Lys Ser Gln Asn Gly Gln Ser Gln Lys Asp Ile
    50                  55                  60

-continued

```
Asn Gln Tyr Leu Leu Leu Ser Gln Tyr Ala Asn Val Leu Thr Met Glu
65                  70                  75                  80

Glu Leu Asn Asn Asn Val Val Lys Asn Ser Ser Ile Glu Thr Leu
                85                  90                  95

Asp Asn Asp Ile Ala Trp Leu Asn Asp Asp Leu Ile Asp Leu Asp Lys
            100                 105                 110

Glu Val Gly Val Leu Ser Arg Asp Ile Gly Ser Leu His Asp Asp Val
            115                 120                 125

Ala Gln Asn Gln Ala Asp Ile Lys Thr Leu Lys Asn Asn Val Val Glu
130                 135                 140

Glu Leu Phe Asn Leu Ser Asp Arg Leu Ile Asp Gln Glu Ala Asp Ile
145                 150                 155                 160

Ala Gln Asn Asn Glu Ser Ile Glu Asp Leu Tyr Asp Phe Gly Arg Glu
            165                 170                 175

Val Ala Glu Ser Ile Gly Glu Ile His Ala His Asn Glu Ala Gln Asn
            180                 185                 190

Glu Thr Leu Lys Asp Leu Ile Thr Asn Ser Val Lys Asn Thr Asp Asn
            195                 200                 205

Ile Thr Lys Asn Lys Ala Asp Ile Gln Ala Leu Glu Asn Asp Val Gly
            210                 215                 220

Lys Glu Leu Leu Asn Leu Ser Gly Arg Leu Ile Asp Gln Lys Ala Asp
225                 230                 235                 240

Ile Asp Asn Asn Ile Asn His Ile Tyr Glu Leu Ala Gln Gln Gln Asp
            245                 250                 255

Gln His Ser Ser Asp Ile Lys Thr Leu Lys Asn Asn Val Glu Glu Gly
            260                 265                 270

Leu Leu Glu Leu Ser Gly His Leu Ile Asp Gln Lys Ala Asp Leu Thr
            275                 280                 285

Lys Asp Ile Lys Ala Leu Glu Ser Asn Val Glu Glu Gly Leu Leu Asp
            290                 295                 300

Leu Ser Gly Arg Leu Leu Asp Gln Lys Ala Asp Ile Ala Gln Asn Gln
305                 310                 315                 320

Ala Asn Ile Gln Asp Leu Ala Ala Tyr Asn Glu Leu Gln Asp Ala Tyr
            325                 330                 335

Ala Lys Gln Gln Thr Glu Ala Ile Asp Ala Leu Asn Lys Ala Ser Ser
            340                 345                 350

Glu Asn Thr Gln Asn Ile Glu Asp Leu Ala Ala Tyr Asn Glu Leu Gln
            355                 360                 365

Asp Ala Tyr Ala Lys Gln Gln Thr Glu Ala Ile Asp Ala Leu Asn Lys
            370                 375                 380

Ala Ser Ser Glu Asn Thr Gln Asn Ile Ala Lys Asn Gln Ala Asp Ile
385                 390                 395                 400

Ala Asn Asn Ile Asn Asn Ile Tyr Glu Leu Ala Gln Gln Gln Asp Gln
            405                 410                 415

His Ser Ser Asp Ile Lys Thr Leu Ala Lys Ala Ser Ala Ala Asn Thr
            420                 425                 430

Asp Arg Ile Ala Lys Asn Lys Ala Asp Ala Asp Ala Ser Phe Glu Thr
            435                 440                 445

Leu Thr Lys Asn Gln Asn Thr Leu Ile Glu Lys Asp Lys Glu His Asp
            450                 455                 460

Lys Leu Ile Thr Ala Asn Lys Thr Ala Ile Asp Ala Asn Lys Ala Ser
465                 470                 475                 480
```

```
Ala Asp Thr Lys Phe Ala Thr Ala Asp Ala Ile Thr Lys Asn Gly
            485                 490                 495

Asn Ala Ile Thr Lys Asn Ala Lys Ser Ile Thr Asp Leu Gly Thr Lys
            500                 505                 510

Val Asp Gly Phe Asp Ser Arg Val Thr Ala Leu Asp Thr Lys Val Asn
            515                 520                 525

Ala Phe Asp Gly Arg Ile Thr Ala Leu Asp Ser Lys Val Glu Asn Gly
            530                 535                 540

Met Ala Ala Gln Ala Ala Leu Ser Gly Leu Phe Gln Pro Tyr Ser Val
545                 550                 555                 560

Gly Lys Phe Asn Ala Thr Ala Ala Leu Gly Gly Tyr Gly Ser Lys Ser
            565                 570                 575

Ala Val Ala Ile Gly Ala Gly Tyr Arg Val Asn Pro Asn Leu Ala Phe
            580                 585                 590

Lys Ala Gly Ala Ala Ile Asn Thr Ser Gly Asn Lys Lys Gly Ser Tyr
            595                 600                 605

Asn Ile Gly Val Asn Tyr Glu Phe
            610                 615

<210> SEQ ID NO 35
<211> LENGTH: 614
<212> TYPE: PRT
<213> ORGANISM: Moraxella catarrhalis

<400> SEQUENCE: 35

Met Lys Thr Met Lys Leu Leu Pro Leu Lys Ile Ala Val Thr Ser Ala
1               5                   10                  15

Met Ile Ile Gly Leu Gly Ala Thr Ser Thr Val Asn Ala Gln Val Val
            20                  25                  30

Glu Gln Phe Phe Pro Asn Ile Phe Asn Glu Asn His Asp Glu Leu
            35                  40                  45

Asp Asp Ala Tyr His Asn Met Ile Leu Gly Asp Thr Ala Ile Val Ser
        50                  55                  60

Asn Ser Gln Asp Asn Ser Thr Gln Leu Lys Phe Tyr Ser Asn Asp Glu
65                  70                  75                  80

Asp Ser Val Pro Asp Ser Leu Leu Phe Ser Lys Leu Leu His Glu Gln
                85                  90                  95

Gln Leu Asn Gly Phe Lys Ala Gly Asp Thr Ile Ile Pro Leu Asp Lys
            100                 105                 110

Asp Gly Lys Pro Val Tyr Thr Lys Asp Thr Arg Thr Lys Asp Gly Lys
            115                 120                 125

Val Glu Thr Val Tyr Ser Val Thr Thr Lys Ile Ala Thr Gln Asp Asp
            130                 135                 140

Val Glu Gln Ser Ala Tyr Ser Arg Gly Ile Gln Gly Asp Ile Asp Asp
145                 150                 155                 160

Leu Tyr Asp Ile Asn Arg Glu Val Asn Glu Tyr Leu Lys Ala Thr His
                165                 170                 175

Asp Tyr Asn Glu Arg Gln Thr Glu Ala Ile Asp Ala Leu Asn Lys Ala
            180                 185                 190

Ser Ser Ala Asn Thr Asp Arg Ile Asp Thr Ala Glu Glu Arg Ile Asp
            195                 200                 205

Lys Asn Glu Tyr Asp Ile Lys Ala Leu Glu Ser Asn Val Gly Lys Asp
            210                 215                 220

Leu Leu Asp Leu Ser Gly Arg Leu Ile Ala Gln Lys Glu Asp Ile Asp
225                 230                 235                 240
```

Asn Asn Ile Asn His Ile Tyr Glu Leu Ala Gln Gln Asp Gln His
                245                 250                 255

Ser Ser Asp Ile Lys Thr Leu Lys Asn Asn Val Glu Glu Gly Leu Leu
            260                 265                 270

Glu Leu Ser Gly His Leu Ile Asp Gln Lys Ala Asp Leu Thr Lys Asp
        275                 280                 285

Ile Lys Thr Leu Glu Ser Asn Val Glu Glu Gly Leu Leu Asp Leu Ser
    290                 295                 300

Gly Arg Leu Ile Asp Gln Lys Ala Asp Ile Ala Gln Asn Gln Ala Asn
305                 310                 315                 320

Ile Gln Asp Leu Ala Ala Tyr Asn Glu Leu Gln Asp Gln Tyr Ala Gln
                325                 330                 335

Lys Gln Thr Glu Ala Ile Asp Ala Leu Asn Lys Ala Ser Ser Glu Asn
            340                 345                 350

Thr Gln Asn Ile Glu Asp Leu Ala Ala Tyr Asn Glu Leu Gln Asp Ala
        355                 360                 365

Tyr Ala Lys Gln Gln Thr Glu Ala Ile Asp Ala Leu Asn Lys Ala Ser
    370                 375                 380

Ser Glu Asn Thr Gln Asn Ile Ala Lys Asn Gln Ala Asp Ile Ala Asn
385                 390                 395                 400

Asn Ile Asn Asn Ile Tyr Glu Leu Ala Gln Gln Asp Gln His Ser
                405                 410                 415

Ser Asp Ile Lys Thr Leu Ala Lys Val Ser Ala Ala Asn Thr Asp Arg
            420                 425                 430

Ile Ala Lys Asn Lys Ala Asp Ala Asp Ala Ser Phe Glu Thr Leu Thr
        435                 440                 445

Lys Asn Gln Asn Thr Leu Ile Glu Lys Asp Lys Glu His Asp Lys Leu
    450                 455                 460

Ile Thr Ala Asn Lys Thr Ala Ile Asp Ala Asn Lys Ala Ser Ala Asp
465                 470                 475                 480

Thr Lys Phe Ala Ala Thr Ala Asp Ala Ile Thr Lys Asn Gly Asn Ala
                485                 490                 495

Ile Thr Lys Asn Ala Lys Ser Ile Thr Asp Leu Gly Thr Lys Val Asp
            500                 505                 510

Gly Phe Asp Gly Arg Val Thr Ala Leu Asp Thr Lys Val Asn Ala Phe
        515                 520                 525

Asp Gly Arg Ile Thr Ala Leu Asp Ser Lys Val Glu Asn Gly Met Ala
    530                 535                 540

Ala Gln Ala Ala Leu Ser Gly Leu Phe Gln Pro Tyr Ser Val Gly Lys
545                 550                 555                 560

Phe Asn Ala Thr Ala Ala Leu Gly Gly Tyr Gly Ser Lys Ser Ala Val
                565                 570                 575

Ala Ile Gly Ala Gly Tyr Arg Val Asn Pro Asn Leu Ala Phe Lys Ala
            580                 585                 590

Gly Ala Ala Ile Asn Thr Ser Gly Asn Lys Lys Gly Ser Tyr Asn Ile
        595                 600                 605

Gly Val Asn Tyr Glu Phe
    610

<210> SEQ ID NO 36
<211> LENGTH: 679
<212> TYPE: PRT
<213> ORGANISM: Moraxella catarrhalis

<400> SEQUENCE: 36

Met Lys Thr Met Lys Leu Pro Pro Leu Lys Ile Ala Val Thr Ser Ala
1               5                   10                  15

Met Ile Ile Gly Leu Gly Ala Ala Ser Thr Ala Asn Ala Gln Thr Thr
            20                  25                  30

Glu Thr Phe Leu Pro Asn Leu Phe Asp Asn Asp Tyr Thr Glu Thr Thr
        35                  40                  45

Asp Pro Leu Tyr His Gly Met Ile Leu Gly Asp Thr Ala Ile Thr Gln
    50                  55                  60

Asp Thr Gln Tyr Lys Phe Tyr Ala Glu Asn Gly Asn Glu Val Pro Asp
65                  70                  75                  80

Ser Leu Phe Phe Asn Lys Ile Leu His Asp Gln Leu Leu Asn Gly Phe
                85                  90                  95

Lys Ala Gly Asp Thr Ile Ile Pro Leu Asp Glu Asn Gly Lys Pro Val
            100                 105                 110

Tyr Lys Leu Asp Glu Arg Thr Glu Asn Gly Val Lys Arg Lys Val Tyr
        115                 120                 125

Ser Val Thr Thr Lys Thr Ala Thr Gln Ala Asp Val Glu Gln Ser Ala
    130                 135                 140

Tyr Ser Arg Gly Ile Gln Gly Asp Ile Asp Asp Leu Tyr Glu Ala Asn
145                 150                 155                 160

Lys Glu Asn Val Asn Arg Leu Ile Glu His Gly Asp Lys Ile Phe Ala
                165                 170                 175

Asn Glu Glu Ser Val Gln Tyr Leu Asn Arg Glu Val Gln Asn Asn Ile
            180                 185                 190

Glu Asn Ile His Glu Leu Ala Gln Gln Gln Asp Gln His Ser Ser Asp
        195                 200                 205

Ile Lys Thr Leu Lys Lys Asn Val Glu Lys Asp Leu Leu Asp Leu Ser
    210                 215                 220

Gly Arg Leu Ile Ala Gln Lys Glu Asp Ile Ala Gln Asn Gln Thr Asp
225                 230                 235                 240

Ile Gln Asp Leu Ala Thr Tyr Asn Glu Leu Gln Asp Gln Tyr Ala Gln
                245                 250                 255

Lys Gln Thr Glu Ala Ile Asp Ala Leu Asn Lys Ala Ser Ser Glu Asn
            260                 265                 270

Thr Gln Asn Ile Ala Lys Asn Ser Asn His Ile Lys Thr Leu Glu Asn
        275                 280                 285

Asn Ile Glu Glu Cys Leu Leu Glu Leu Ser Gly His Leu Ile Asp Gln
    290                 295                 300

Lys Ala Asp Leu Thr Lys Asp Ile Lys Ala Leu Glu Ser Asn Val Glu
305                 310                 315                 320

Glu Gly Leu Leu Asp Leu Ser Gly Arg Leu Ile Asp Gln Lys Ala Asp
                325                 330                 335

Ile Ala Gln Asn Gln Ala Asn Ile Gln Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Glu Asp Leu Ala Ala
    370                 375                 380

Tyr Asn Glu Leu Gln Asp Ala Tyr Ala Lys Gln Gln Thr Glu Ala Ile
385                 390                 395                 400

Asp Ala Leu Asn Lys Ala Ser Ser Glu Asn Thr Gln Asn Ile Glu Asp
                405                 410                 415

```
Leu Ala Ala Tyr Asn Glu Leu Gln Asp Ala Tyr Ala Lys Gln Gln Thr
            420                 425                 430

Glu Ala Ile Asp Ala Leu Asn Lys Ala Ser Ser Glu Asn Thr Gln Asn
            435                 440                 445

Ile Ala Lys Asn Gln Ala Asp Ile Ala Asn Asn Ile Asn Asn Ile Tyr
450                 455                 460

Glu Leu Ala Gln Gln Gln Asp Gln His Ser Ser Asp Ile Lys Thr Leu
465                 470                 475                 480

Ala Lys Ala Ser Ala Ala Asn Thr Asp Arg Ile Ala Lys Asn Lys Ala
            485                 490                 495

Asp Ala Asp Ala Ser Phe Glu Thr Leu Thr Lys Asn Gln Asn Thr Leu
            500                 505                 510

Ile Glu Lys Asp Lys Glu His Asp Lys Leu Ile Thr Ala Asn Lys Thr
            515                 520                 525

Ala Ile Asp Ala Asn Lys Ala Ser Ala Asp Thr Lys Phe Ala Ala Thr
            530                 535                 540

Ala Asp Ala Ile Thr Lys Asn Gly Asn Ala Ile Thr Lys Asn Ala Lys
545                 550                 555                 560

Ser Ile Thr Asp Leu Gly Thr Lys Val Asp Gly Phe Asp Gly Arg Val
            565                 570                 575

Thr Ala Leu Asp Thr Lys Val Asn Ala Leu Asp Thr Lys Val Asn Ala
            580                 585                 590

Phe Asp Gly Arg Ile Thr Ala Leu Asp Ser Lys Val Glu Asn Gly Met
            595                 600                 605

Ala Ala Gln Ala Ala Leu Ser Gly Leu Phe Gln Pro Tyr Ser Val Gly
            610                 615                 620

Lys Phe Asn Ala Thr Ala Ala Leu Gly Gly Tyr Gly Ser Lys Ser Ala
625                 630                 635                 640

Val Ala Ile Gly Ala Gly Tyr Arg Val Asn Pro Asn Leu Ala Phe Lys
            645                 650                 655

Ala Gly Ala Ala Ile Asn Thr Ser Gly Asn Lys Lys Gly Ser Tyr Asn
            660                 665                 670

Ile Gly Val Asn Tyr Glu Phe
            675

<210> SEQ ID NO 37
<211> LENGTH: 724
<212> TYPE: PRT
<213> ORGANISM: Moraxella catarrhalis

<400> SEQUENCE: 37

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Glu Thr
            20                  25                  30

Leu Glu Glu Val Leu Glu Ser Ile Lys Gln Ile Asn Glu Gln Asp Leu
            35                  40                  45

Gln Asp Asp Ile Gly Tyr Asn Ser Ala Leu Asp Arg Tyr Leu Val Leu
        50                  55                  60

Ser Gln Tyr Gly Asn Leu Leu Ile Ala Lys Glu Leu Asn Glu Asn Val
65                  70                  75                  80

Glu Lys Asn Ser Asn Ser Ile Ala Lys Asn Ser Asn Ser Ile Ala Asp
            85                  90                  95

Leu Glu Ala Asp Val Gly Tyr Leu Ala Glu Asn Gln Asn Thr Leu Ile
```

```
            100             105                 110
Glu Gln Asn Glu Thr Ile Asn Gln Glu Leu Glu Gly Ile Thr His Glu
            115             120                 125

Leu Glu Ser Phe Ile Ala Tyr Ala His Ala Gln Asp Gln Lys Asn Leu
            130             135                 140

Val Asn Glu Phe Glu Ile Glu Lys Asn Lys Asp Ala Ile Ala Lys Asn
145             150                 155                     160

Asn Glu Ser Ile Glu Asp Leu Tyr Asp Phe Gly His Glu Val Ala Glu
            165                 170                 175

Ser Ile Gly Glu Ile His Ala Tyr Thr Glu Val Asn Lys Thr Leu
            180             185                 190

Glu Asn Leu Ile Thr Asn Ser Val Lys Asn Thr Asp Asn Ile Thr Lys
            195             200                 205

Asn Lys Ala Asp Ile Gln Ala Leu Glu Ser Asn Val Glu Lys Glu Leu
            210             215                 220

Leu Asn Leu Ser Gly Arg Leu Ile Asp Gln Lys Ala Asp Ile Asp Asn
225             230                 235                     240

Asn Ile Asn His Ile Tyr Glu Leu Ala Gln Gln Gln Asp Gln His Ser
            245             250                 255

Ser Asp Ile Lys Thr Leu Lys Lys Asn Val Glu Glu Gly Leu Leu Glu
            260             265                 270

Leu Ser Gly His Leu Ile Asp Gln Lys Ser Asp Ile Ala Gln Asn Gln
            275             280                 285

Thr Asp Ile Gln Asp Leu Ala Thr Tyr Asn Glu Leu Gln Asp Gln Tyr
            290             295                 300

Ala Gln Lys Gln Thr Glu Ala Ile Asp Ala Leu Asn Lys Ala Ser Ser
305             310                 315                     320

Glu Asn Thr Gln Asn Ile Glu Asp Leu Ala Ala Tyr Asn Glu Leu Gln
            325             330                 335

Asp Ala Tyr Ala Lys Gln Gln Thr Glu Ala Ile Asp Ala Leu Asn Lys
            340             345                 350

Ala Ser Ser Glu Asn Thr Gln Asn Ile Glu Asp Leu Ala Ala Tyr Asn
            355             360                 365

Glu Leu Gln Asp Ala Tyr Ala Lys Gln Gln Thr Glu Ala Ile Asp Ala
            370             375                 380

Leu Asn Lys Ala Ser Ser Glu Asn Thr Gln Asn Ile Glu Asp Leu Ala
385             390                 395                     400

Ala Tyr Asn Glu Leu Gln Asp Ala Tyr Ala Lys Gln Gln Thr Glu Ala
            405             410                 415

Ile Asp Ala Leu Asn Lys Ala Ser Ser Glu Asn Thr Gln Asn Ile Glu
            420             425                 430

Asp Leu Ala Ala Tyr Asn Glu Leu Gln Asp Ala Tyr Ala Lys Gln Gln
            435             440                 445

Thr Glu Ala Ile Asp Ala Leu Asn Lys Ala Ser Ser Glu Asn Thr Gln
            450             455                 460

Asn Ile Glu Asp Leu Ala Ala Tyr Asn Glu Leu Gln Asp Ala Tyr Ala
465             470                 475                     480

Lys Gln Gln Thr Glu Ala Ile Asp Ala Leu Asn Lys Ala Ser Ser Glu
            485             490                 495

Asn Thr Gln Asn Ile Ala Lys Asn Gln Ala Asp Ile Ala Asn Asn Ile
            500             505                 510

Asn Asn Ile Tyr Glu Leu Ala Gln Gln Gln Asp Gln His Ser Ser Asp
            515             520                 525
```

```
Ile Lys Thr Leu Ala Lys Ala Ser Ala Ala Asn Thr Asp Arg Ile Ala
    530                 535                 540

Lys Asn Lys Ala Asp Ala Asp Ala Ser Phe Glu Thr Leu Thr Lys Asn
545                 550                 555                 560

Gln Asn Thr Leu Ile Glu Lys Asp Lys Glu His Asp Lys Leu Ile Thr
            565                 570                 575

Ala Asn Lys Thr Ala Ile Asp Ala Asn Lys Ala Ser Ala Asp Thr Lys
                580                 585                 590

Phe Ala Ala Thr Ala Asp Ala Ile Thr Lys Asn Gly Asn Ala Ile Thr
            595                 600                 605

Lys Asn Ala Lys Ser Ile Thr Asp Leu Gly Thr Lys Val Asp Gly Phe
610                 615                 620

Asp Ser Arg Val Thr Ala Leu Asp Thr Lys Val Asn Ala Phe Asp Gly
625                 630                 635                 640

Arg Ile Thr Ala Leu Asp Ser Lys Val Glu Asn Gly Met Ala Ala Gln
            645                 650                 655

Ala Ala Leu Ser Gly Leu Phe Gln Pro Tyr Ser Val Gly Lys Phe Asn
                660                 665                 670

Ala Thr Ala Ala Leu Gly Gly Tyr Gly Ser Lys Ser Ala Val Ala Ile
            675                 680                 685

Gly Ala Gly Tyr Arg Val Asn Pro Asn Leu Ala Phe Lys Ala Gly Ala
690                 695                 700

Ala Ile Asn Thr Ser Gly Asn Lys Lys Gly Ser Tyr Asn Ile Gly Val
705                 710                 715                 720

Asn Tyr Glu Phe

<210> SEQ ID NO 38
<211> LENGTH: 611
<212> TYPE: PRT
<213> ORGANISM: Moraxella catarrhalis

<400> SEQUENCE: 38

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Gln
                20                  25                  30

Ala Arg Asp Arg Ser Leu Glu Asp Ile Gln Ala Leu Ile Gly Asn Ile
            35                  40                  45

Asp Val Asp Lys Ile Arg Ser Gln Lys Gln Lys Asn Pro Glu Ile Phe
        50                  55                  60

Gln Tyr Leu Leu Leu Asn Gln Leu Ser Asn Thr Leu Ile Thr Asp Glu
65                  70                  75                  80

Leu Asn Asn Asn Val Ile Lys Asn Thr Asn Ser Ile Glu Thr Leu Asp
                85                  90                  95

Asn Asp Ile Ala Trp Leu Asn Asp Leu Ile Asp Leu Asp Lys Glu
            100                 105                 110

Val Gly Val Leu Ser Arg Asp Ile Gly Ser Leu His Asp Asp Val Ala
        115                 120                 125

Gln Asn Gln Ala Asp Ile Lys Thr Leu Glu Asn Val Val Glu Glu
    130                 135                 140

Leu Phe Asn Leu Ser Asp Arg Leu Ile Asp Gln Glu Ala Glu Ile Ala
145                 150                 155                 160

Gln Asn Asn Glu Ser Ile Glu Asp Leu Tyr Asp Phe Gly Arg Glu Val
                165                 170                 175
```

```
Ala Glu Ser Ile Gly Glu Ile His Ala His Asn Glu Ala Gln Asn Glu
            180                 185                 190

Thr Leu Lys Asp Leu Ile Thr Asn Ser Val Lys Asn Thr Asp Asn Ile
            195                 200                 205

Asp Lys Asn Lys Ala Asp Ile Gln Ala Leu Glu Asn Asn Val Glu Glu
210                 215                 220

Gly Leu Leu Glu Leu Ser Gly His Leu Ile Asp Gln Lys Ala Asp Leu
225                 230                 235                 240

Thr Lys Asp Ile Lys Ala Leu Glu Ser Asn Val Glu Glu Gly Leu Leu
                245                 250                 255

Asp Leu Ser Gly Arg Leu Leu Asp Gln Lys Ala Asp Ile Ala Lys Asn
            260                 265                 270

Gln Ala Asp Ile Ala Gln Asn Gln Thr Asp Ile Gln Asp Leu Ala Ala
            275                 280                 285

Tyr Asn Glu Leu Gln Asp Gln Tyr Ala Gln Lys Gln Thr Glu Ala Ile
            290                 295                 300

Asp Ala Leu Asn Lys Ala Ser Ser Glu Asn Thr Gln Asn Ile Glu Asp
305                 310                 315                 320

Leu Ala Ala Tyr Asn Glu Leu Gln Asp Ala Tyr Ala Lys Gln Gln Thr
                325                 330                 335

Glu Ala Ile Asp Ala Leu Asn Lys Ala Ser Ser Glu Asn Thr Gln Asn
            340                 345                 350

Ile Glu Asp Leu Ala Ala Tyr Asn Glu Leu Gln Asp Ala Tyr Ala Lys
            355                 360                 365

Gln Gln Thr Glu Ala Ile Asp Ala Leu Asn Lys Ala Ser Ser Glu Asn
            370                 375                 380

Thr Gln Asn Ile Ala Lys Asn Gln Ala Asp Ile Ala Asn Asn Ile Asn
385                 390                 395                 400

Asn Ile Tyr Glu Leu Ala Gln Gln Gln Asp Gln His Ser Ser Asp Ile
                405                 410                 415

Lys Thr Leu Ala Lys Val Ser Ala Ala Asn Thr Asp Arg Ile Ala Lys
            420                 425                 430

Asn Lys Ala Asp Ala Asp Ala Ser Phe Glu Thr Leu Thr Lys Asn Gln
            435                 440                 445

Asn Thr Leu Ile Glu Lys Asp Lys Glu His Asp Lys Leu Ile Thr Ala
            450                 455                 460

Asn Lys Thr Ala Ile Asp Ala Asn Lys Ala Ser Ala Asp Thr Lys Phe
465                 470                 475                 480

Ala Ala Thr Ala Asp Ala Ile Thr Lys Asn Gly Asn Ala Ile Thr Lys
                485                 490                 495

Asn Ala Lys Ser Ile Thr Asp Leu Gly Thr Lys Val Asp Gly Phe Asp
            500                 505                 510

Ser Arg Val Thr Ala Leu Asp Thr Lys Val Asn Ala Phe Asp Gly Arg
            515                 520                 525

Ile Thr Ala Leu Asp Ser Lys Val Glu Asn Gly Met Ala Ala Gln Ala
            530                 535                 540

Ala Leu Ser Gly Leu Phe Gln Pro Tyr Ser Val Gly Lys Phe Asn Ala
545                 550                 555                 560

Thr Ala Ala Leu Gly Gly Tyr Gly Ser Lys Ser Ala Val Ala Ile Gly
                565                 570                 575

Ala Gly Tyr Arg Val Asn Pro Asn Leu Ala Phe Lys Ala Gly Ala Ala
            580                 585                 590
```

Ile Asn Thr Ser Gly Asn Lys Lys Gly Ser Tyr Asn Ile Gly Val Asn
            595                 600                 605

Tyr Glu Phe
    610

<210> SEQ ID NO 39
<211> LENGTH: 511
<212> TYPE: PRT
<213> ORGANISM: Moraxella catarrhalis

<400> SEQUENCE: 39

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp
    50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Gln Glu Gly Lys Ile Leu
            100                 105                 110

Gln Asn Glu Thr Ser Ile Lys Lys Asn Thr Gln Arg Asn Leu Val Asn
        115                 120                 125

Gly Phe Glu Ile Glu Lys Asn Lys Asp Ala Ile Ala Lys Asn Asn Glu
130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Asn Ile Thr Lys Asn Lys
            180                 185                 190

Ala Asp Ile Gln Ala Leu Glu Asn Asn Val Val Glu Glu Leu Phe Asn
        195                 200                 205

Leu Ser Gly Arg Leu Ile Asp Gln Lys Ala Asp Ile Asp Asn Asn Ile
    210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
            260                 265                 270

Ile Gln Asp Leu Ala Thr Tyr Asn Glu Leu Gln Asp Gln Tyr Ala Gln
        275                 280                 285

Lys Gln Thr Glu Ala Ile Asp Ala Leu Asn Lys Ala Ser Ser Glu Asn
    290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
            340                 345                 350

```
Gln Asp Ala Tyr Ala Lys Gln Gln Thr Glu Ala Ile Asp Ala Leu Asn
            355                 360                 365

Lys Ala Ser Ser Glu Asn Thr Gln Asn Ile Ala Lys Asn Gln Ala Asp
    370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
                405                 410                 415

Thr Asp Arg Ile Ala Lys Asn Lys Ala Asp Ala Asp Ala Ser Phe Glu
            420                 425                 430

Thr Leu Thr Lys Asn Gln Asn Thr Leu Ile Glu Lys Asp Lys Glu His
            435                 440                 445

Asp Lys Leu Ile Thr Ala Asn Lys Thr Ala Ile Asp Ala Asn Lys Ala
        450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser Ile Thr Asp Leu Gly Thr
                485                 490                 495

Lys Val Asp Gly Phe Asp Ser Arg Val Thr Ala Leu Asp Thr Lys
            500                 505                 510

<210> SEQ ID NO 40
<211> LENGTH: 510
<212> TYPE: PRT
<213> ORGANISM: Moraxella catarrhalis

<400> SEQUENCE: 40

Ala Lys Asn Asp Ile Thr Leu Glu Asp Leu Pro Tyr Leu Ile Lys Lys
1               5                   10                  15

Ile Asp Gln Asn Glu Leu Glu Ala Asp Ile Gly Asp Ile Thr Ala Leu
            20                  25                  30

Glu Lys Tyr Leu Ala Leu Ser Gln Tyr Gly Asn Ile Leu Ala Leu Glu
        35                  40                  45

Glu Leu Asn Lys Ala Leu Glu Glu Leu Asp Glu Asp Val Gly Trp Asn
    50                  55                  60

Gln Asn Asp Ile Ala Asn Leu Glu Asp Val Glu Thr Leu Thr Lys
65                  70                  75                  80

Asn Gln Asn Ala Leu Ala Glu Gln Gly Glu Ala Ile Lys Glu Asp Leu
                85                  90                  95

Gln Gly Leu Ala Asp Phe Val Glu Gly Gln Gly Lys Ile Leu Gln
            100                 105                 110

Asn Glu Thr Ser Ile Lys Lys Asn Thr Gln Arg Asn Leu Val Asn Gly
        115                 120                 125

Phe Glu Ile Glu Lys Asn Lys Asp Ala Ile Ala Lys Asn Asn Glu Ser
    130                 135                 140

Ile Glu Asp Leu Tyr Asp Phe Gly His Glu Val Ala Glu Ser Ile Gly
145                 150                 155                 160

Glu Ile His Ala His Asn Glu Ala Gln Asn Glu Thr Leu Lys Gly Leu
                165                 170                 175

Ile Thr Asn Ser Ile Glu Asn Thr Asn Ile Thr Lys Asn Lys Ala
            180                 185                 190

Asp Ile Gln Ala Leu Glu Asn Asn Val Val Glu Glu Leu Phe Asn Leu
        195                 200                 205

Ser Gly Arg Leu Ile Asp Gln Lys Ala Asp Ile Asp Asn Asn Ile Asn
```

Asn Ile Tyr Glu Leu Ala Gln Gln Asp Gln His Ser Ser Asp Ile
225                 230                 235                 240

Lys Thr Leu Lys Lys Asn Val Glu Glu Gly Leu Leu Glu Leu Ser Gly
            245                 250                 255

His Leu Ile Asp Gln Lys Thr Asp Ile Ala Gln Asn Gln Ala Asn Ile
        260                 265                 270

Gln Asp Leu Ala Thr Tyr Asn Glu Leu Gln Asp Gln Tyr Ala Gln Lys
    275                 280                 285

Gln Thr Glu Ala Ile Asp Ala Leu Asn Lys Ala Ser Ser Glu Asn Thr
290                 295                 300

Gln Asn Ile Glu Asp Leu Ala Ala Tyr Asn Glu Leu Gln Asp Ala Tyr
305                 310                 315                 320

Ala Lys Gln Gln Thr Glu Ala Ile Asp Ala Leu Asn Lys Ala Ser Ser
            325                 330                 335

Glu Asn Thr Gln Asn Ile Glu Asp Leu Ala Ala Tyr Asn Glu Leu Gln
        340                 345                 350

Asp Ala Tyr Ala Lys Gln Gln Thr Glu Ala Ile Asp Ala Leu Asn Lys
    355                 360                 365

Ala Ser Ser Glu Asn Thr Gln Asn Ile Ala Lys Asn Gln Ala Asp Ile
370                 375                 380

Ala Asn Asn Ile Asn Asn Ile Tyr Glu Leu Ala Gln Gln Asp Gln
385                 390                 395                 400

His Ser Ser Asp Ile Lys Thr Leu Ala Lys Ala Ser Ala Ala Asn Thr
            405                 410                 415

Asp Arg Ile Ala Lys Asn Lys Ala Asp Ala Asp Ala Ser Phe Glu Thr
        420                 425                 430

Leu Thr Lys Asn Gln Asn Thr Leu Ile Glu Lys Asp Lys Glu His Asp
    435                 440                 445

Lys Leu Ile Thr Ala Asn Lys Thr Ala Ile Asp Ala Asn Lys Ala Ser
450                 455                 460

Ala Asp Thr Lys Phe Ala Ala Thr Ala Asp Ala Ile Thr Lys Asn Gly
465                 470                 475                 480

Asn Ala Ile Thr Lys Asn Ala Lys Ser Ile Thr Asp Leu Gly Thr Lys
            485                 490                 495

Val Asp Gly Phe Asp Ser Arg Val Thr Ala Leu Asp Thr Lys
        500                 505                 510

<210> SEQ ID NO 41
<211> LENGTH: 490
<212> TYPE: PRT
<213> ORGANISM: Moraxella catarrhalis

<400> SEQUENCE: 41

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp
    50                  55                  60

Asn Gln Asn Asp Ile Ala Asn Leu Glu Asp Asp Val Glu Thr Leu Thr
65                  70                  75                  80

```
Lys Asn Gln Asn Ala Leu Ala Glu Gln Gly Glu Ala Ile Lys Glu Asp
                85                  90                  95

Leu Gln Gly Leu Ala Asp Phe Val Glu Gly Glu Gly Lys Ile Leu
        100                 105                 110

Gln Asn Glu Thr Ser Ile Lys Lys Asn Thr Gln Arg Asn Leu Val Asn
        115                 120                 125

Gly Phe Glu Ile Glu Lys Asn Lys Asp Ala Ile Ala Lys Asn Asn Glu
    130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Asn Ile Thr Lys Asn Lys
                180                 185                 190

Ala Asp Ile Gln Ala Leu Glu Asn Asn Val Val Glu Leu Phe Asn
        195                 200                 205

Leu Ser Gly Arg Leu Ile Asp Gln Lys Ala Asp Ile Asp Asn Asn Ile
210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
                260                 265                 270

Ile Gln Asp Leu Ala Thr Tyr Asn Glu Leu Gln Asp Gln Tyr Ala Gln
        275                 280                 285

Lys Gln Thr Glu Ala Ile Asp Ala Leu Asn Lys Ala Ser Ser Glu Asn
    290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
                340                 345                 350

Gln Asp Ala Tyr Ala Lys Gln Gln Thr Glu Ala Ile Asp Ala Leu Asn
        355                 360                 365

Lys Ala Ser Ser Glu Asn Thr Gln Asn Ile Ala Lys Asn Gln Ala Asp
    370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
                405                 410                 415

Thr Asp Arg Ile Ala Lys Asn Lys Ala Asp Ala Asp Ala Ser Phe Glu
                420                 425                 430

Thr Leu Thr Lys Asn Gln Asn Thr Leu Ile Glu Lys Asp Lys Glu His
                435                 440                 445

Asp Lys Leu Ile Thr Ala Asn Lys Thr Ala Ile Asp Ala Asn Lys Ala
    450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser
                485                 490
```

```
<210> SEQ ID NO 42
<211> LENGTH: 535
<212> TYPE: PRT
<213> ORGANISM: Moraxella catarrhalis

<400> SEQUENCE: 42
```

| | | | | | | | | | | | | | | | |
|---|---|---|---|---|---|---|---|---|---|---|---|---|---|---|---|
| Gln | Ala | Lys | Asn | Asp | Ile | Thr | Leu | Glu | Asp | Leu | Pro | Tyr | Leu | Ile | Lys |
| 1 | | | | 5 | | | | | 10 | | | | | 15 | |
| Lys | Ile | Asp | Gln | Asn | Glu | Leu | Glu | Ala | Asp | Ile | Gly | Asp | Ile | Thr | Ala |
| | | | 20 | | | | | 25 | | | | | 30 | | |
| Leu | Glu | Lys | Tyr | Leu | Ala | Leu | Ser | Gln | Tyr | Gly | Asn | Ile | Leu | Ala | Leu |
| | | 35 | | | | | 40 | | | | | 45 | | | |
| Glu | Glu | Leu | Asn | Lys | Ala | Leu | Glu | Glu | Leu | Asp | Glu | Asp | Val | Gly | Trp |
| | 50 | | | | | 55 | | | | | 60 | | | | |
| Asn | Gln | Asn | Asp | Ile | Ala | Asn | Leu | Glu | Asp | Asp | Val | Glu | Thr | Leu | Thr |
| 65 | | | | | 70 | | | | | 75 | | | | | 80 |
| Lys | Asn | Gln | Asn | Ala | Leu | Ala | Glu | Gln | Gly | Glu | Ala | Ile | Lys | Glu | Asp |
| | | | | 85 | | | | | 90 | | | | | 95 | |
| Leu | Gln | Gly | Leu | Ala | Asp | Phe | Val | Glu | Gly | Gln | Glu | Gly | Lys | Ile | Leu |
| | | | 100 | | | | | 105 | | | | | 110 | | |
| Gln | Asn | Glu | Thr | Ser | Ile | Lys | Lys | Asn | Thr | Gln | Arg | Asn | Leu | Val | Asn |
| | | | 115 | | | | | 120 | | | | | 125 | | |
| Gly | Phe | Glu | Ile | Glu | Lys | Asn | Lys | Asp | Ala | Ile | Ala | Lys | Asn | Asn | Glu |
| | | 130 | | | | | 135 | | | | | 140 | | | |
| Ser | Ile | Glu | Asp | Leu | Tyr | Asp | Phe | Gly | His | Glu | Val | Ala | Glu | Ser | Ile |
| 145 | | | | | 150 | | | | | 155 | | | | | 160 |
| Gly | Glu | Ile | His | Ala | His | Asn | Glu | Ala | Gln | Asn | Glu | Thr | Leu | Lys | Gly |
| | | | | 165 | | | | | 170 | | | | | 175 | |
| Leu | Ile | Thr | Asn | Ser | Ile | Glu | Asn | Thr | Asn | Asn | Ile | Thr | Lys | Asn | Lys |
| | | | 180 | | | | | 185 | | | | | 190 | | |
| Ala | Asp | Ile | Gln | Ala | Leu | Glu | Asn | Asn | Val | Val | Glu | Glu | Leu | Phe | Asn |
| | | 195 | | | | | 200 | | | | | 205 | | | |
| Leu | Ser | Gly | Arg | Leu | Ile | Asp | Gln | Lys | Ala | Asp | Ile | Asp | Asn | Asn | Ile |
| 210 | | | | | 215 | | | | | 220 | | | | | |
| Asn | Asn | Ile | Tyr | Glu | Leu | Ala | Gln | Gln | Gln | Asp | Gln | His | Ser | Ser | Asp |
| 225 | | | | | 230 | | | | | 235 | | | | | 240 |
| Ile | Lys | Thr | Leu | Lys | Lys | Asn | Val | Glu | Glu | Gly | Leu | Leu | Glu | Leu | Ser |
| | | | | 245 | | | | | 250 | | | | | 255 | |
| Gly | His | Leu | Ile | Asp | Gln | Lys | Thr | Asp | Ile | Ala | Gln | Asn | Gln | Ala | Asn |
| | | | 260 | | | | | 265 | | | | | 270 | | |
| Ile | Gln | Asp | Leu | Ala | Thr | Tyr | Asn | Glu | Leu | Gln | Asp | Gln | Tyr | Ala | Gln |
| | | 275 | | | | | 280 | | | | | 285 | | | |
| Lys | Gln | Thr | Glu | Ala | Ile | Asp | Ala | Leu | Asn | Lys | Ala | Ser | Ser | Glu | Asn |
| 290 | | | | | 295 | | | | | 300 | | | | | |
| Thr | Gln | Asn | Ile | Glu | Asp | Leu | Ala | Ala | Tyr | Asn | Glu | Leu | Gln | Asp | Ala |
| 305 | | | | | 310 | | | | | 315 | | | | | 320 |
| Tyr | Ala | Lys | Gln | Gln | Thr | Glu | Ala | Ile | Asp | Ala | Leu | Asn | Lys | Ala | Ser |
| | | | | 325 | | | | | 330 | | | | | 335 | |
| Ser | Glu | Asn | Thr | Gln | Asn | Ile | Glu | Asp | Leu | Ala | Ala | Tyr | Asn | Glu | Leu |
| | | | 340 | | | | | 345 | | | | | 350 | | |
| Gln | Asp | Ala | Tyr | Ala | Lys | Gln | Gln | Thr | Glu | Ala | Ile | Asp | Ala | Leu | Asn |
| | | 355 | | | | | 360 | | | | | 365 | | | |
| Lys | Ala | Ser | Ser | Glu | Asn | Thr | Gln | Asn | Ile | Ala | Lys | Asn | Gln | Ala | Asp |
| 370 | | | | | 375 | | | | | 380 | | | | | |

```
Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
            405                 410                 415

Thr Asp Arg Ile Ala Lys Asn Lys Ala Asp Ala Asp Ala Ser Phe Glu
        420                 425                 430

Thr Leu Thr Lys Asn Gln Asn Thr Leu Ile Glu Lys Asp Lys Glu His
            435                 440                 445

Asp Lys Leu Ile Thr Ala Asn Lys Thr Ala Ile Asp Ala Asn Lys Ala
        450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser Ile Thr Asp Leu Gly Thr
            485                 490                 495

Lys Val Asp Gly Phe Asp Ser Arg Val Thr Ala Leu Asp Thr Lys Val
        500                 505                 510

Asn Ala Phe Asp Gly Arg Ile Thr Ala Leu Asp Ser Lys Val Glu Asn
            515                 520                 525

Gly Met Ala Ala Gln Ala Ala
530                 535

<210> SEQ ID NO 43
<211> LENGTH: 534
<212> TYPE: PRT
<213> ORGANISM: Moraxella catarrhalis

<400> SEQUENCE: 43

Ala Lys Asn Asp Ile Thr Leu Glu Asp Leu Pro Tyr Leu Ile Lys Lys
1               5                   10                  15

Ile Asp Gln Asn Glu Leu Glu Ala Asp Ile Gly Asp Ile Thr Ala Leu
            20                  25                  30

Glu Lys Tyr Leu Ala Leu Ser Gln Tyr Gly Asn Ile Leu Ala Leu Glu
        35                  40                  45

Glu Leu Asn Lys Ala Leu Glu Glu Leu Asp Glu Asp Val Gly Trp Asn
50                  55                  60

Gln Asn Asp Ile Ala Asn Leu Glu Asp Asp Val Glu Thr Leu Thr Lys
65                  70                  75                  80

Asn Gln Asn Ala Leu Ala Glu Gln Gly Glu Ala Ile Lys Glu Asp Leu
            85                  90                  95

Gln Gly Leu Ala Asp Phe Val Glu Gly Gln Glu Gly Lys Ile Leu Gln
        100                 105                 110

Asn Glu Thr Ser Ile Lys Lys Asn Thr Gln Arg Asn Leu Val Asn Gly
        115                 120                 125

Phe Glu Ile Glu Lys Asn Lys Asp Ala Ile Ala Lys Asn Asn Glu Ser
    130                 135                 140

Ile Glu Asp Leu Tyr Asp Phe Gly His Glu Val Ala Glu Ser Ile Gly
145                 150                 155                 160

Glu Ile His Ala His Asn Glu Ala Gln Asn Glu Thr Leu Lys Gly Leu
            165                 170                 175

Ile Thr Asn Ser Ile Glu Asn Thr Asn Asn Ile Thr Lys Asn Lys Ala
        180                 185                 190

Asp Ile Gln Ala Leu Glu Asn Asn Val Val Glu Glu Leu Phe Asn Leu
    195                 200                 205

Ser Gly Arg Leu Ile Asp Gln Lys Ala Asp Ile Asp Asn Asn Ile Asn
210                 215                 220
```

```
Asn Ile Tyr Glu Leu Ala Gln Gln Asp Gln His Ser Ser Asp Ile
225                 230                 235                 240

Lys Thr Leu Lys Lys Asn Val Glu Glu Gly Leu Leu Glu Leu Ser Gly
            245                 250                 255

His Leu Ile Asp Gln Lys Thr Asp Ile Ala Gln Asn Gln Ala Asn Ile
        260                 265                 270

Gln Asp Leu Ala Thr Tyr Asn Glu Leu Gln Asp Gln Tyr Ala Gln Lys
    275                 280                 285

Gln Thr Glu Ala Ile Asp Ala Leu Asn Lys Ala Ser Ser Glu Asn Thr
290                 295                 300

Gln Asn Ile Glu Asp Leu Ala Ala Tyr Asn Glu Leu Gln Asp Ala Tyr
305                 310                 315                 320

Ala Lys Gln Gln Thr Glu Ala Ile Asp Ala Leu Asn Lys Ala Ser Ser
            325                 330                 335

Glu Asn Thr Gln Asn Ile Glu Asp Leu Ala Ala Tyr Asn Glu Leu Gln
        340                 345                 350

Asp Ala Tyr Ala Lys Gln Gln Thr Glu Ala Ile Asp Ala Leu Asn Lys
    355                 360                 365

Ala Ser Ser Glu Asn Thr Gln Asn Ile Ala Lys Asn Gln Ala Asp Ile
370                 375                 380

Ala Asn Asn Ile Asn Asn Ile Tyr Glu Leu Ala Gln Gln Gln Asp Gln
385                 390                 395                 400

His Ser Ser Asp Ile Lys Thr Leu Ala Lys Ala Ser Ala Ala Asn Thr
            405                 410                 415

Asp Arg Ile Ala Lys Asn Lys Ala Ala Asp Ala Ser Phe Glu Thr
        420                 425                 430

Leu Thr Lys Asn Gln Asn Thr Leu Ile Glu Lys Asp Lys Glu His Asp
    435                 440                 445

Lys Leu Ile Thr Ala Asn Lys Thr Ala Ile Asp Ala Asn Lys Ala Ser
450                 455                 460

Ala Asp Thr Lys Phe Ala Ala Thr Ala Asp Ala Ile Thr Lys Asn Gly
465                 470                 475                 480

Asn Ala Ile Thr Lys Asn Ala Lys Ser Ile Thr Asp Leu Gly Thr Lys
            485                 490                 495

Val Asp Gly Phe Asp Ser Arg Val Thr Ala Leu Asp Thr Lys Val Asn
        500                 505                 510

Ala Phe Asp Gly Arg Ile Thr Ala Leu Asp Ser Lys Val Glu Asn Gly
    515                 520                 525

Met Ala Gln Ala Ala
    530

<210> SEQ ID NO 44
<211> LENGTH: 148
<212> TYPE: PRT
<213> ORGANISM: Moraxella catarrhalis

<400> SEQUENCE: 44

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp
```

```
                    50                  55                  60

Asn Gln Asn Asp Ile Ala Asn Leu Glu Asp Asp Val Glu Thr Leu Thr
 65                  70                  75                  80

Lys Asn Gln Asn Ala Leu Ala Glu Gly Glu Ala Ile Lys Glu Asp
                 85                  90                  95

Leu Gln Gly Leu Ala Asp Phe Val Glu Gln Glu Gly Lys Ile Leu
                100                 105                 110

Gln Asn Glu Thr Ser Ile Lys Lys Asn Thr Gln Arg Asn Leu Val Asn
                115                 120                 125

Gly Phe Glu Ile Glu Lys Asn Lys Asp Ala Ile Ala Lys Asn Asn Glu
                130                 135                 140

Ser Ile Glu Asp
145

<210> SEQ ID NO 45
<211> LENGTH: 154
<212> TYPE: PRT
<213> ORGANISM: Moraxella catarrhalis

<400> SEQUENCE: 45

Lys Asp Ala Ile Ala Lys Asn Asn Glu Ser Ile Glu Asp Leu Tyr Asp
  1               5                  10                  15

Phe Gly His Glu Val Ala Glu Ser Ile Gly Glu Ile His Ala His Asn
                 20                  25                  30

Glu Ala Gln Asn Glu Thr Leu Lys Gly Leu Ile Thr Asn Ser Ile Glu
                 35                  40                  45

Asn Thr Asn Asn Ile Thr Lys Asn Lys Ala Asp Ile Gln Ala Leu Glu
 50                  55                  60

Asn Asn Val Val Glu Glu Leu Phe Asn Leu Ser Gly Arg Leu Ile Asp
 65                  70                  75                  80

Gln Lys Ala Asp Ile Asp Asn Asn Ile Asn Asn Ile Tyr Glu Leu Ala
                 85                  90                  95

Gln Gln Gln Asp Gln His Ser Ser Asp Ile Lys Thr Leu Lys Lys Asn
                100                 105                 110

Val Glu Glu Gly Leu Leu Glu Leu Ser Gly His Leu Ile Asp Gln Lys
                115                 120                 125

Thr Asp Ile Ala Gln Asn Gln Ala Asn Ile Gln Asp Leu Ala Thr Tyr
                130                 135                 140

Asn Glu Leu Gln Asp Gln Tyr Ala Gln Lys
145                 150

<210> SEQ ID NO 46
<211> LENGTH: 510
<212> TYPE: PRT
<213> ORGANISM: Moraxella catarrhalis

<400> SEQUENCE: 46

Gln Ala Lys Asn Asp Ile Thr Leu Glu Asp Leu Pro Tyr Leu Ile Lys
  1               5                  10                  15

Lys Ile Asp Gln Asn Glu Leu Glu Ala Asp Ile Gly Asp Ile Thr Ala
                 20                  25                  30

Leu Glu Lys Tyr Leu Ala Leu Ser Gln Tyr Gly Asn Ile Leu Ala Leu
                 35                  40                  45

Glu Glu Leu Asn Lys Ala Leu Glu Glu Leu Asp Glu Asp Val Gly Trp
 50                  55                  60

Asn Gln Asn Asp Ile Ala Asn Leu Glu Asp Asp Val Glu Thr Leu Thr
```

-continued

```
                65                  70                  75                  80
Lys Asn Gln Asn Ala Leu Ala Glu Gln Gly Glu Ala Ile Lys Glu Asp
                    85                  90                  95
Leu Gln Gly Leu Ala Asp Phe Val Glu Gly Gln Glu Gly Lys Ile Leu
            100                 105                 110
Gln Asn Glu Thr Ser Ile Lys Lys Asn Thr Gln Arg Asn Leu Val Asn
            115                 120                 125
Gly Phe Glu Ile Glu Lys Asn Lys Asp Ala Ile Ala Lys Asn Asn Glu
    130                 135                 140
Ser Ile Glu Asp Leu Tyr Asp Phe Gly His Glu Val Ala Glu Ser Ile
145                 150                 155                 160
Gly Glu Ile His Ala His Asn Glu Ala Gln Asn Glu Thr Leu Lys Gly
                    165                 170                 175
Leu Ile Thr Asn Ser Ile Glu Asn Thr Asn Ile Thr Lys Asn Lys
                180                 185                 190
Ala Asp Ile Gln Ala Leu Glu Asn Asn Val Val Glu Glu Leu Phe Asn
            195                 200                 205
Leu Ser Gly Arg Leu Ile Asp Gln Lys Ala Asp Ile Asp Asn Asn Ile
    210                 215                 220
Asn Asn Ile Tyr Glu Leu Ala Gln Gln Gln Asp Gln His Ser Ser Asp
225                 230                 235                 240
Ile Lys Thr Leu Lys Lys Asn Val Glu Glu Gly Leu Leu Glu Leu Ser
                    245                 250                 255
Gly His Leu Ile Asp Gln Lys Thr Asp Ile Ala Gln Asn Gln Ala Asn
                260                 265                 270
Ile Gln Asp Leu Ala Thr Tyr Asn Glu Leu Gln Asp Gln Tyr Ala Gln
            275                 280                 285
Lys Gln Thr Glu Ala Ile Asp Ala Leu Asn Lys Ala Ser Ser Glu Asn
    290                 295                 300
Thr Gln Asn Ile Glu Asp Leu Ala Ala Tyr Asn Glu Leu Gln Asp Ala
305                 310                 315                 320
Tyr Ala Lys Gln Gln Thr Glu Ala Ile Asp Ala Leu Asn Lys Ala Ser
                    325                 330                 335
Ser Glu Asn Thr Gln Asn Ile Glu Asp Leu Ala Ala Tyr Asn Glu Leu
                340                 345                 350
Gln Asp Ala Tyr Ala Lys Gln Gln Thr Glu Ala Ile Asp Ala Leu Asn
            355                 360                 365
Lys Ala Ser Ser Glu Asn Thr Gln Asn Ile Ala Lys Asn Gln Ala Asp
    370                 375                 380
Ile Ala Asn Asn Ile Asn Asn Ile Tyr Glu Leu Ala Gln Gln Gln Asp
385                 390                 395                 400
Gln His Ser Ser Asp Ile Lys Thr Leu Ala Lys Ala Ser Ala Ala Asn
                    405                 410                 415
Thr Asp Arg Ile Ala Lys Asn Lys Ala Asp Ala Asp Ala Ser Phe Glu
                420                 425                 430
Thr Leu Thr Lys Asn Gln Asn Thr Leu Ile Glu Lys Asp Lys Glu His
            435                 440                 445
Asp Lys Leu Ile Thr Ala Asn Lys Thr Ile Asp Ala Asn Lys Ala
    450                 455                 460
Ser Ala Asp Thr Lys Phe Ala Ala Thr Ala Asp Ala Ile Thr Lys Asn
465                 470                 475                 480
Gly Asn Ala Ile Thr Lys Asn Ala Lys Ser Ile Thr Asp Leu Gly Thr
                    485                 490                 495
```

```
Lys Val Asp Gly Phe Asp Ser Arg Val Thr Ala Leu Asp Thr
            500                 505                 510

<210> SEQ ID NO 47
<211> LENGTH: 511
<212> TYPE: PRT
<213> ORGANISM: Moraxella catarrhalis

<400> SEQUENCE: 47

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp
    50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Gln Glu Gly Lys Ile Leu
            100                 105                 110

Gln Asn Glu Thr Ser Ile Lys Lys Asn Thr Gln Arg Asn Leu Val Asn
        115                 120                 125

Gly Phe Glu Ile Glu Lys Asn Lys Asp Ala Ile Ala Lys Asn Asn Glu
130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Ile Thr Lys Asn Lys
            180                 185                 190

Ala Asp Ile Gln Ala Leu Glu Asn Asn Val Val Glu Glu Leu Phe Asn
        195                 200                 205

Leu Ser Gly Arg Leu Ile Asp Gln Lys Ala Asp Ile Asp Asn Asn Ile
210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
            260                 265                 270

Ile Gln Asp Leu Ala Thr Tyr Asn Glu Leu Gln Asp Gln Tyr Ala Gln
        275                 280                 285

Lys Gln Thr Glu Ala Ile Asp Ala Leu Asn Lys Ala Ser Ser Glu Asn
    290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
            340                 345                 350

Gln Asp Ala Tyr Ala Lys Gln Gln Thr Glu Ala Ile Asp Ala Leu Asn
```

```
                355                 360                 365
Lys Ala Ser Ser Glu Asn Thr Gln Asn Ile Ala Lys Asn Gln Ala Asp
    370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
                405                 410                 415

Thr Asp Arg Ile Ala Lys Asn Lys Ala Asp Ala Asp Ala Ser Phe Glu
            420                 425                 430

Thr Leu Thr Lys Asn Gln Asn Thr Leu Ile Glu Lys Asp Lys Glu His
        435                 440                 445

Asp Lys Leu Ile Thr Ala Asn Lys Thr Ala Ile Asp Ala Asn Lys Ala
    450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser Ile Thr Asp Leu Gly Thr
                485                 490                 495

Lys Val Asp Gly Phe Asp Ser Arg Val Thr Ala Leu Asp Thr Lys
            500                 505                 510

<210> SEQ ID NO 48
<211> LENGTH: 490
<212> TYPE: PRT
<213> ORGANISM: Moraxella catarrhalis

<400> SEQUENCE: 48

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp
    50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Gln Glu Gly Lys Ile Leu
            100                 105                 110

Gln Asn Glu Thr Ser Ile Lys Lys Asn Thr Gln Arg Asn Leu Val Asn
        115                 120                 125

Gly Phe Glu Ile Glu Lys Asn Lys Asp Ala Ile Ala Lys Asn Asn Glu
    130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Asn Ile Thr Lys Asn Lys
            180                 185                 190

Ala Asp Ile Gln Ala Leu Glu Asn Asn Val Val Glu Glu Leu Phe Asn
        195                 200                 205

Leu Ser Gly Arg Leu Ile Asp Gln Lys Ala Asp Ile Asp Asn Asn Ile
    210                 215                 220
```

Asn Asn Ile Tyr Glu Leu Ala Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
            260                 265                 270

Ile Gln Asp Leu Ala Thr Tyr Asn Glu Leu Gln Asp Gln Tyr Ala Gln
        275                 280                 285

Lys Gln Thr Glu Ala Ile Asp Ala Leu Asn Lys Ala Ser Ser Glu Asn
    290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
            340                 345                 350

Gln Asp Ala Tyr Ala Lys Gln Gln Thr Glu Ala Ile Asp Ala Leu Asn
        355                 360                 365

Lys Ala Ser Ser Glu Asn Thr Gln Asn Ile Ala Lys Asn Gln Ala Asp
    370                 375                 380

Ile Ala Asn Asn Ile Asn Asn Ile Tyr Glu Leu Ala Gln Gln Asp
385                 390                 395                 400

Gln His Ser Ser Asp Ile Lys Thr Leu Ala Lys Ala Ser Ala Ala Asn
                405                 410                 415

Thr Asp Arg Ile Ala Lys Asn Lys Ala Asp Ala Asp Ala Ser Phe Glu
            420                 425                 430

Thr Leu Thr Lys Asn Gln Asn Thr Leu Ile Glu Lys Asp Lys Glu His
        435                 440                 445

Asp Lys Leu Ile Thr Ala Asn Lys Thr Ala Ile Asp Ala Asn Lys Ala
    450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser
                485                 490

<210> SEQ ID NO 49
<211> LENGTH: 535
<212> TYPE: PRT
<213> ORGANISM: Moraxella catarrhalis

<400> SEQUENCE: 49

Gln Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
                20                  25                  30

Leu Glu Lys Tyr Leu Ala Leu Ser Gln Tyr Gly Asn Ile Leu Ala Leu
            35                  40                  45

Glu Glu Leu Asn Lys Ala Leu Glu Glu Leu Asp Glu Asp Val Gly Trp
        50                  55                  60

Asn Gln Asn Asp Ile Ala Asn Leu Glu Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Gln Glu Gly Lys Ile Leu
            100                 105                 110

```
Gln Asn Glu Thr Ser Ile Lys Lys Asn Thr Gln Arg Asn Leu Val Asn
            115                 120                 125
Gly Phe Glu Ile Glu Lys Asn Lys Asp Ala Ile Ala Lys Asn Asn Glu
        130                 135                 140
Ser Ile Glu Asp Leu Tyr Asp Phe Gly His Glu Val Ala Glu Ser Ile
145                 150                 155                 160
Gly Glu Ile His Ala His Asn Glu Ala Gln Asn Glu Thr Leu Lys Gly
                165                 170                 175
Leu Ile Thr Asn Ser Ile Glu Asn Thr Asn Asn Ile Thr Lys Asn Lys
            180                 185                 190
Ala Asp Ile Gln Ala Leu Glu Asn Val Val Glu Glu Leu Phe Asn
        195                 200                 205
Leu Ser Gly Arg Leu Ile Asp Gln Lys Ala Asp Ile Asp Asn Asn Ile
210                 215                 220
Asn Asn Ile Tyr Glu Leu Ala Gln Gln Gln Asp Gln His Ser Ser Asp
225                 230                 235                 240
Ile Lys Thr Leu Lys Lys Asn Val Glu Glu Gly Leu Leu Glu Leu Ser
                245                 250                 255
Gly His Leu Ile Asp Gln Lys Thr Asp Ile Ala Gln Asn Gln Ala Asn
            260                 265                 270
Ile Gln Asp Leu Ala Thr Tyr Asn Glu Leu Gln Asp Gln Tyr Ala Gln
        275                 280                 285
Lys Gln Thr Glu Ala Ile Asp Ala Leu Asn Lys Ala Ser Ser Glu Asn
        290                 295                 300
Thr Gln Asn Ile Glu Asp Leu Ala Ala Tyr Asn Glu Leu Gln Asp Ala
305                 310                 315                 320
Tyr Ala Lys Gln Gln Thr Glu Ala Ile Asp Ala Leu Asn Lys Ala Ser
                325                 330                 335
Ser Glu Asn Thr Gln Asn Ile Glu Asp Leu Ala Ala Tyr Asn Glu Leu
            340                 345                 350
Gln Asp Ala Tyr Ala Lys Gln Gln Thr Glu Ala Ile Asp Ala Leu Asn
        355                 360                 365
Lys Ala Ser Ser Glu Asn Thr Gln Asn Ile Ala Lys Asn Gln Ala Asp
370                 375                 380
Ile Ala Asn Asn Ile Asn Asn Ile Tyr Glu Leu Ala Gln Gln Gln Asp
385                 390                 395                 400
Gln His Ser Ser Asp Ile Lys Thr Leu Ala Lys Ala Ser Ala Ala Asn
                405                 410                 415
Thr Asp Arg Ile Ala Lys Asn Lys Asp Ala Asp Ala Ser Phe Glu
            420                 425                 430
Thr Leu Thr Lys Asn Gln Asn Thr Leu Ile Glu Lys Asp Lys Glu His
        435                 440                 445
Asp Lys Leu Ile Thr Ala Asn Lys Thr Ala Ile Asp Ala Asn Lys Ala
        450                 455                 460
Ser Ala Asp Thr Lys Phe Ala Ala Thr Ala Asp Ala Ile Thr Lys Asn
465                 470                 475                 480
Gly Asn Ala Ile Thr Lys Asn Ala Lys Ser Ile Thr Asp Leu Gly Thr
                485                 490                 495
Lys Val Asp Gly Phe Asp Ser Arg Val Thr Ala Leu Asp Thr Lys Val
            500                 505                 510
Asn Ala Phe Asp Gly Arg Ile Thr Ala Leu Asp Ser Lys Val Glu Asn
        515                 520                 525
```

```
Gly Met Ala Ala Gln Ala Ala
    530                 535

<210> SEQ ID NO 50
<211> LENGTH: 534
<212> TYPE: PRT
<213> ORGANISM: Moraxella catarrhalis

<400> SEQUENCE: 50

Ala Lys Asn Asp Ile Thr Leu Glu Asp Leu Pro Tyr Leu Ile Lys Lys
1               5                   10                  15

Ile Asp Gln Asn Glu Leu Glu Ala Asp Ile Gly Asp Ile Thr Ala Leu
            20                  25                  30

Glu Lys Tyr Leu Ala Leu Ser Gln Tyr Gly Asn Ile Leu Ala Leu Glu
        35                  40                  45

Glu Leu Asn Lys Ala Leu Glu Glu Leu Asp Glu Asp Val Gly Trp Asn
    50                  55                  60

Gln Asn Asp Ile Ala Asn Leu Glu Asp Asp Val Glu Thr Leu Thr Lys
65                  70                  75                  80

Asn Gln Asn Ala Leu Ala Glu Gln Gly Glu Ala Ile Lys Glu Asp Leu
                85                  90                  95

Gln Gly Leu Ala Asp Phe Val Glu Gly Gln Glu Gly Lys Ile Leu Gln
            100                 105                 110

Asn Glu Thr Ser Ile Lys Lys Asn Thr Gln Arg Asn Leu Val Asn Gly
        115                 120                 125

Phe Glu Ile Glu Lys Asn Lys Asp Ala Ile Ala Lys Asn Asn Glu Ser
    130                 135                 140

Ile Glu Asp Leu Tyr Asp Phe Gly His Glu Val Ala Glu Ser Ile Gly
145                 150                 155                 160

Glu Ile His Ala His Asn Glu Ala Gln Asn Glu Thr Leu Lys Gly Leu
                165                 170                 175

Ile Thr Asn Ser Ile Glu Asn Thr Asn Asn Ile Thr Lys Asn Lys Ala
            180                 185                 190

Asp Ile Gln Ala Leu Glu Asn Asn Val Val Glu Glu Leu Phe Asn Leu
        195                 200                 205

Ser Gly Arg Leu Ile Asp Gln Lys Ala Asp Ile Asp Asn Asn Ile Asn
    210                 215                 220

Asn Ile Tyr Glu Leu Ala Gln Gln Asp Gln His Ser Ser Asp Ile
225                 230                 235                 240

Lys Thr Leu Lys Lys Asn Val Glu Glu Gly Leu Leu Glu Leu Ser Gly
                245                 250                 255

His Leu Ile Asp Gln Lys Thr Asp Ile Ala Gln Asn Gln Ala Asn Ile
            260                 265                 270

Gln Asp Leu Ala Thr Tyr Asn Glu Leu Gln Asp Gln Tyr Ala Gln Lys
        275                 280                 285

Gln Thr Glu Ala Ile Asp Ala Leu Asn Lys Ala Ser Ser Glu Asn Thr
    290                 295                 300

Gln Asn Ile Glu Asp Leu Ala Ala Tyr Asn Glu Leu Gln Asp Ala Tyr
305                 310                 315                 320

Ala Lys Gln Gln Thr Glu Ala Ile Asp Ala Leu Asn Lys Ala Ser Ser
                325                 330                 335

Glu Asn Thr Gln Asn Ile Glu Asp Leu Ala Ala Tyr Asn Glu Leu Gln
            340                 345                 350

Asp Ala Tyr Ala Lys Gln Gln Thr Glu Ala Ile Asp Ala Leu Asn Lys
        355                 360                 365
```

```
Ala Ser Ser Glu Asn Thr Gln Asn Ile Ala Lys Asn Gln Ala Asp Ile
        370                 375                 380

Ala Asn Asn Ile Asn Asn Ile Tyr Glu Leu Ala Gln Gln Gln Asp Gln
385                 390                 395                 400

His Ser Ser Asp Ile Lys Thr Leu Ala Lys Ala Ser Ala Ala Asn Thr
                405                 410                 415

Asp Arg Ile Ala Lys Asn Lys Ala Asp Ala Asp Ala Ser Phe Glu Thr
            420                 425                 430

Leu Thr Lys Asn Gln Asn Thr Leu Ile Glu Lys Asp Lys Glu His Asp
        435                 440                 445

Lys Leu Ile Thr Ala Asn Lys Thr Ala Ile Asp Ala Asn Lys Ala Ser
        450                 455                 460

Ala Asp Thr Lys Phe Ala Ala Thr Ala Asp Ala Ile Thr Lys Asn Gly
465                 470                 475                 480

Asn Ala Ile Thr Lys Asn Ala Lys Ser Ile Thr Asp Leu Gly Thr Lys
                485                 490                 495

Val Asp Gly Phe Asp Ser Arg Val Thr Ala Leu Asp Thr Lys Val Asn
            500                 505                 510

Ala Phe Asp Gly Arg Ile Thr Ala Leu Asp Ser Lys Val Glu Asn Gly
        515                 520                 525

Met Ala Ala Gln Ala Ala
    530

<210> SEQ ID NO 51
<211> LENGTH: 510
<212> TYPE: PRT
<213> ORGANISM: Moraxella catarrhalis

<400> SEQUENCE: 51

Ala Lys Asn Asp Ile Thr Leu Glu Asp Leu Pro Tyr Leu Ile Lys Lys
1               5                   10                  15

Ile Asp Gln Asn Glu Leu Glu Ala Asp Ile Gly Asp Ile Thr Ala Leu
            20                  25                  30

Glu Lys Tyr Leu Ala Leu Ser Gln Tyr Gly Asn Ile Leu Ala Leu Glu
        35                  40                  45

Glu Leu Asn Lys Ala Leu Glu Glu Leu Asp Glu Asp Val Gly Trp Asn
    50                  55                  60

Gln Asn Asp Ile Ala Asn Leu Glu Asp Asp Val Glu Thr Leu Thr Lys
65                  70                  75                  80

Asn Gln Asn Ala Leu Ala Glu Gln Gly Glu Ala Ile Lys Glu Asp Leu
                85                  90                  95

Gln Gly Leu Ala Asp Phe Val Glu Gly Gln Glu Gly Lys Ile Leu Gln
            100                 105                 110

Asn Glu Thr Ser Ile Lys Lys Asn Thr Gln Arg Asn Leu Val Asn Gly
        115                 120                 125

Phe Glu Ile Glu Lys Asn Lys Asp Ala Ile Ala Lys Asn Asn Glu Ser
    130                 135                 140

Ile Glu Asp Leu Tyr Asp Phe Gly His Glu Val Ala Glu Ser Ile Gly
145                 150                 155                 160

Glu Ile His Ala His Asn Glu Ala Gln Asn Glu Thr Leu Lys Gly Leu
                165                 170                 175

Ile Thr Asn Ser Ile Glu Asn Thr Asn Asn Ile Thr Lys Asn Lys Ala
            180                 185                 190

Asp Ile Gln Ala Leu Glu Asn Asn Val Val Glu Glu Leu Phe Asn Leu
```

|   |   |   |   |   |   |   |   |   |   |   |   |
|---|---|---|---|---|---|---|---|---|---|---|---|
|   |   |   |   | 195 |   |   |   | 200 |   |   | 205 |
| Ser | Gly | Arg | Leu | Ile | Asp | Gln | Lys | Ala | Asp | Ile | Asp | Asn | Asn | Ile | Asn |
|   |   | 210 |   |   |   |   | 215 |   |   |   |   | 220 |

Ser Gly Arg Leu Ile Asp Gln Lys Ala Asp Ile Asp Asn Asn Ile Asn
    210                 215                 220

Asn Ile Tyr Glu Leu Ala Gln Gln Asp Gln His Ser Ser Asp Ile
225                 230                 235                 240

Lys Thr Leu Lys Lys Asn Val Glu Glu Gly Leu Leu Glu Leu Ser Gly
                245                 250                 255

His Leu Ile Asp Gln Lys Thr Asp Ile Ala Gln Asn Gln Ala Asn Ile
            260                 265                 270

Gln Asp Leu Ala Thr Tyr Asn Glu Leu Gln Asp Gln Tyr Ala Gln Lys
        275                 280                 285

Gln Thr Glu Ala Ile Asp Ala Leu Asn Lys Ala Ser Ser Glu Asn Thr
    290                 295                 300

Gln Asn Ile Glu Asp Leu Ala Ala Tyr Asn Glu Leu Gln Asp Ala Tyr
305                 310                 315                 320

Ala Lys Gln Gln Thr Glu Ala Ile Asp Ala Leu Asn Lys Ala Ser Ser
                325                 330                 335

Glu Asn Thr Gln Asn Ile Glu Asp Leu Ala Ala Tyr Asn Glu Leu Gln
            340                 345                 350

Asp Ala Tyr Ala Lys Gln Gln Thr Glu Ala Ile Asp Ala Leu Asn Lys
        355                 360                 365

Ala Ser Ser Glu Asn Thr Gln Asn Ile Ala Lys Asn Gln Ala Asp Ile
    370                 375                 380

Ala Asn Asn Ile Asn Asn Ile Tyr Glu Leu Ala Gln Gln Gln Asp Gln
385                 390                 395                 400

His Ser Ser Asp Ile Lys Thr Leu Ala Lys Ala Ser Ala Ala Asn Thr
                405                 410                 415

Asp Arg Ile Ala Lys Asn Lys Ala Asp Ala Asp Ala Ser Phe Glu Thr
            420                 425                 430

Leu Thr Lys Asn Gln Asn Thr Leu Ile Glu Lys Asp Lys Glu His Asp
        435                 440                 445

Lys Leu Ile Thr Ala Asn Lys Thr Ala Ile Ala Asn Lys Ala Ser
    450                 455                 460

Ala Asp Thr Lys Phe Ala Ala Thr Ala Asp Ala Ile Thr Lys Asn Gly
465                 470                 475                 480

Asn Ala Ile Thr Lys Asn Ala Lys Ser Ile Thr Asp Leu Gly Thr Lys
                485                 490                 495

Val Asp Gly Phe Asp Ser Arg Val Thr Ala Leu Asp Thr Lys
            500                 505                 510

<210> SEQ ID NO 52
<211> LENGTH: 1563
<212> TYPE: DNA
<213> ORGANISM: Artificial Sequence
<220> FEATURE:
<223> OTHER INFORMATION: DNA sequence for MC-001 construct

<400> SEQUENCE: 52
atgcaggcca aaatgatat tacccctggaa gatctgccgt atctgatcaa aaaaatcgat      60
cagaacgaac tggaagccga tattggtgat attaccgcac tggaaaaata tctggcactg    120
agccagtatg aaatattct ggccctggaa gaactgaata agctctggga agagctggat    180
gaagatgtgg gttggaatca gaatgatatc gccaatctgg aagatgatgt tgaaaccctg    240
accaaaaatc agaatgcact ggcagaacag ggtgaagcaa ttaagaaga tctgcagggt    300

```
ctggcagatt tgttgaagg tcaggaaggc aaaattctgc agaacgaaac cagcatcaaa      360
aaaaacaccc agcgtaatct ggtgaatggc tttgaaattg aaaaaaacaa agatgccatt      420
gccaaaaaca acgaaagcat tgaagatctg tatgattttg gtcatgaagt tgccgaaagc      480
attggtgaaa ttcatgcaca taacgaagca cagaatgaaa ccctgaaagg tctgattacc      540
aacagcatcg aaaataccaa taacattacc aaaaacaaag cagatattca ggcgctggaa      600
aataatgttg tggaagaact gtttaatctg agcggtcgtc tgattgatca gaaagccgat      660
atcgataata acattaacaa catttatgaa ctggcacagc agcaggatca gcatagcagc      720
gatatcaaaa ccctgaaaaa aaacgttgaa gaaggtctgc tggaactgtc tggtcacctg      780
atcgatcaga aaactgatat tgcccagaat caggcaaata ttcaggatct ggccacctat      840
aatgaactgc aggatcagta tgcacagaaa cagaccgaag caattgatgc cctgaataaa      900
gcgagcagcg aaaacaccca gaatatcgaa gatctggcag catacaacga actgcaggat      960
gcctatgcaa acagcagac tgaagccatc gacgcactga acaaggcaag ctctgaaaac     1020
acgcagaaca ttgaagatct ggctgcctat aatgaattac aggatgcgta tgccaaacag     1080
cagaccgaag cgattgatgc gctgaacaaa gcctcttctg aaaatacaca gaatatcgcc     1140
aaaaatcagg ccgatattgc caacaatatc aataatatct atgaactggc ccagcagcag     1200
gatcagcact cttctgatat caaaacactg gcaaaagcaa gcgcagcaaa taccgatcgt     1260
attgcgaaaa caaagccga tgcagatgca agctttgaaa cactgacgaa aaaccagaac     1320
accctgattg aaaagataa agaacatgat aaactgatca ccgccaataa aaccgcaatt     1380
gatgcaaata aagccagcgc agataccaaa tttgcagcaa ccgcagatgc aattaccaaa     1440
aatggcaatg ccatcaccaa aaatgccaaa agcattaccg atctgggcac caaagttgat     1500
ggttttgata gccgtgtgac cgcactggat accaaagcaa gccatcatca tcaccaccac     1560
taa                                                                  1563
```

<210> SEQ ID NO 53
<211> LENGTH: 520
<212> TYPE: PRT
<213> ORGANISM: Artificial Sequence
<220> FEATURE:
<223> OTHER INFORMATION: Protein sequence for MC-001 construct

<400> SEQUENCE: 53

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
```

```
              130                 135                 140
Glu Ser Ile Glu Asp Leu Tyr Asp Phe Gly His Glu Val Ala Glu Ser
145                 150                 155                 160
Ile Gly Glu Ile His Ala His Asn Glu Ala Gln Asn Glu Thr Leu Lys
                165                 170                 175
Gly Leu Ile Thr Asn Ser Ile Glu Asn Thr Asn Asn Ile Thr Lys Asn
            180                 185                 190
Lys Ala Asp Ile Gln Ala Leu Glu Asn Asn Val Val Glu Glu Leu Phe
        195                 200                 205
Asn Leu Ser Gly Arg Leu Ile Asp Gln Lys Ala Asp Ile Asp Asn Asn
    210                 215                 220
Ile Asn Asn Ile Tyr Glu Leu Ala Gln Gln Gln Asp Gln His Ser Ser
225                 230                 235                 240
Asp Ile Lys Thr Leu Lys Lys Asn Val Glu Glu Gly Leu Leu Glu Leu
                245                 250                 255
Ser Gly His Leu Ile Asp Gln Lys Thr Asp Ile Ala Gln Asn Gln Ala
            260                 265                 270
Asn Ile Gln Asp Leu Ala Thr Tyr Asn Glu Leu Gln Asp Gln Tyr Ala
        275                 280                 285
Gln Lys Gln Thr Glu Ala Ile Asp Ala Leu Asn Lys Ala Ser Ser Glu
    290                 295                 300
Asn Thr Gln Asn Ile Glu Asp Leu Ala Ala Tyr Asn Glu Leu Gln Asp
305                 310                 315                 320
Ala Tyr Ala Lys Gln Gln Thr Glu Ala Ile Asp Ala Leu Asn Lys Ala
                325                 330                 335
Ser Ser Glu Asn Thr Gln Asn Ile Glu Asp Leu Ala Ala Tyr Asn Glu
            340                 345                 350
Leu Gln Asp Ala Tyr Ala Lys Gln Gln Thr Glu Ala Ile Asp Ala Leu
        355                 360                 365
Asn Lys Ala Ser Ser Glu Asn Thr Gln Asn Ile Ala Lys Asn Gln Ala
    370                 375                 380
Asp Ile Ala Asn Asn Ile Asn Asn Ile Tyr Glu Leu Ala Gln Gln Gln
385                 390                 395                 400
Asp Gln His Ser Ser Asp Ile Lys Thr Leu Ala Lys Ala Ser Ala Ala
                405                 410                 415
Asn Thr Asp Arg Ile Ala Lys Asn Lys Ala Asp Ala Asp Ala Ser Phe
            420                 425                 430
Glu Thr Leu Thr Lys Asn Gln Asn Thr Leu Ile Glu Lys Asp Lys Glu
        435                 440                 445
His Asp Lys Leu Ile Thr Ala Asn Lys Thr Ala Ile Asp Ala Asn Lys
    450                 455                 460
Ala Ser Ala Asp Thr Lys Phe Ala Ala Thr Asp Ala Ile Thr Lys
465                 470                 475                 480
Asn Gly Asn Ala Ile Thr Lys Asn Ala Lys Ser Ile Thr Asp Leu Gly
                485                 490                 495
Thr Lys Val Asp Gly Phe Asp Ser Arg Val Thr Ala Leu Asp Thr Lys
            500                 505                 510
Ala Ser His His His His His His
        515                 520

<210> SEQ ID NO 54
<211> LENGTH: 1539
<212> TYPE: DNA
<213> ORGANISM: Artificial Sequence
```

<220> FEATURE:
<223> OTHER INFORMATION: DNA sequence for MC-002 construct

<400> SEQUENCE: 54

| | |
|---|---|
| atgcaggcca aaaatgatat taccctggaa gatctgccgt atctgatcaa aaaaatcgat | 60 |
| cagaacgaac tggaagccga tattggtgat attaccgcac tggaaaaata tctggcactg | 120 |
| agccagtatg gaaatattct ggccctggaa gaactgaata agctctggga gagctggat | 180 |
| gaagatgtgg gttggaatca gaatgatatc gccaatctgg aagatgatgt tgaaccctg | 240 |
| accaaaaatc agaatgcact ggcagaacag ggtgaagcaa ttaaagaaga tctgcagggt | 300 |
| ctggcagatt ttgttgaagg tcaggaaggc aaaattctgc agaacgaaac cagcatcaaa | 360 |
| aaaacaccc agcgtaatct ggtgaatggc tttgaaattg aaaaaaacaa agatgccatt | 420 |
| gccaaaaaca cgaaagcat tgaagatctg tatgattttg gtcatgaagt tgccgaaagc | 480 |
| attggtgaaa ttcatgcaca taacgaagca cagaatgaaa ccctgaaagg tctgattacc | 540 |
| aacagcatcg aaaataccaa taacattacc aaaaacaaag cagatattca ggcgctggaa | 600 |
| aataatgttg tggaagaact gtttaatctg agcggtcgtc tgattgatca gaaagccgat | 660 |
| atcgataata acattaacaa catttatgaa ctggcacagc agcaggatca gcatagcagc | 720 |
| gatatcaaaa ccctgaaaaa aaacgttgaa gaaggtctgc tggaactgtc tggtcacctg | 780 |
| atcgatcaga aaactgatat tgcccagaat caggcaaata ttcaggatct ggccacctat | 840 |
| aatgaactgc aggatcagta tgcacagaaa cagaccgaag caattgatgc cctgaataaa | 900 |
| gcgagcagcg aaaacaccca gaatatcgaa gatctggcag catacaacga actgcaggat | 960 |
| gcctatgcaa acagcagac tgaagccatc gacgcactga acaaggcaag ctctgaaaac | 1020 |
| acgcagaaca ttgaagatct ggctgcctat aatgaattac aggatgcgta tgccaaacag | 1080 |
| cagaccgaag cgattgatgc gctgaacaaa gcctcttctg aaaatacaca gaatatcgcc | 1140 |
| aaaaatcagg ccgatattgc caacaatatc aataatatct atgaactggc cagcagcag | 1200 |
| gatcagcact cttctgatat caaaacactg gcaaagcaa gcgcagcaaa taccgatcgt | 1260 |
| attgcgaaaa acaaagccga tgcagatgca agctttgaaa cactgacgaa aaaccagaac | 1320 |
| accctgattg aaaaagataa agaacatgat aaactgatca ccgccaataa aaccgcaatt | 1380 |
| gatgcaaata agccagcgc agataccaaa tttgcagcaa ccgcagatgc aattaccaaa | 1440 |
| aatggcaatg ccatcaccaa aaatgccaaa agcattaccg atctgggcac caaagttgat | 1500 |
| ggttttgata gccgtgtgac cgcactggat accaaataa | 1539 |

<210> SEQ ID NO 55
<211> LENGTH: 512
<212> TYPE: PRT
<213> ORGANISM: Artificial Sequence
<220> FEATURE:
<223> OTHER INFORMATION: Protein sequence for MC-002 construct

<400> SEQUENCE: 55

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60
```

```
Trp Asn Gln Asn Asp Ile Ala Asn Leu Glu Asp Val Glu Thr Leu
 65                  70                  75                  80

Thr Lys Asn Gln Asn Ala Leu Ala Glu Gln Gly Glu Ala Ile Lys Glu
                 85                  90                  95

Asp Leu Gln Gly Leu Ala Asp Phe Val Glu Gly Gln Glu Gly Lys Ile
                100                 105                 110

Leu Gln Asn Glu Thr Ser Ile Lys Lys Asn Thr Gln Arg Asn Leu Val
                115                 120                 125

Asn Gly Phe Glu Ile Glu Lys Asn Lys Asp Ala Ile Ala Lys Asn Asn
            130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
                180                 185                 190

Lys Ala Asp Ile Gln Ala Leu Glu Asn Asn Val Val Glu Glu Leu Phe
            195                 200                 205

Asn Leu Ser Gly Arg Leu Ile Asp Gln Lys Ala Asp Ile Asp Asn Asn
210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
            275                 280                 285

Gln Lys Gln Thr Glu Ala Ile Asp Ala Leu Asn Lys Ala Ser Ser Glu
            290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
                340                 345                 350

Leu Gln Asp Ala Tyr Ala Lys Gln Gln Thr Glu Ala Ile Asp Ala Leu
            355                 360                 365

Asn Lys Ala Ser Ser Glu Asn Thr Gln Asn Ile Ala Lys Asn Gln Ala
            370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
            435                 440                 445

His Asp Lys Leu Ile Thr Ala Asn Lys Thr Ala Ile Asp Ala Asn Lys
            450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
```

485                 490                 495
Thr Lys Val Asp Gly Phe Asp Ser Arg Val Thr Ala Leu Asp Thr Lys
              500                 505                 510

<210> SEQ ID NO 56
<211> LENGTH: 1614
<212> TYPE: DNA
<213> ORGANISM: Artificial Sequence
<220> FEATURE:
<223> OTHER INFORMATION: DNA sequence for construct

<400> SEQUENCE: 56

| | | |
|---|---|---|
| atgcaggcca aaatgatat taccctggaa gatctgccgt atctgatcaa aaaaatcgat | 60 |
| cagaacgaac tggaagccga tattggtgat attaccgcac tggaaaaata tctggcactg | 120 |
| agccagtatg aaatattct ggccctggaa gaactgaata agctctgga agagctggat | 180 |
| gaagatgtgg gttggaatca gaatgatatc gccaatctgg aagatgatgt tgaaaccctg | 240 |
| accaaaaatc agaatgcact ggcagaacag ggtgaagcaa ttaaagaaga tctgcagggt | 300 |
| ctggcagatt ttgttgaagg tcaggaaggc aaaattctgc agaacgaaac cagcatcaaa | 360 |
| aaaaacaccc agcgtaatct ggtgaatggc tttgaaattg aaaaaaacaa agatgccatt | 420 |
| gccaaaaaca cgaaagcat tgaagatctg tatgattttg gtcatgaagt tgccgaaagc | 480 |
| attggtgaaa ttcatgcaca taacgaagca cagaatgaaa ccctgaaagg tctgattacc | 540 |
| aacagcatcg aaaataccaa taacattacc aaaaacaaag cagatattca ggcgctggaa | 600 |
| aataatgttg tggaagaact gtttaatctg agcggtcgtc tgattgatca gaaagccgat | 660 |
| atcgataata acattaacaa catttatgaa ctggcacagc agcaggatca gcatagcagc | 720 |
| gatatcaaaa ccctgaaaaa aaacgttgaa gaaggtctgc tggaactgtc tggtcacctg | 780 |
| atcgatcaga aaactgatat tgcccagaat caggcaaata ttcaggatct ggccacctat | 840 |
| aatgaactgc aggatcagta tgcacagaaa cagaccgaag caattgatgc cctgaataaa | 900 |
| gcgagcagcg aaaacaccca gaatatcgaa gatctggcag catacaacga actgcaggat | 960 |
| gcctatgcaa acagcagac tgaagccatc gacgcactga acaaggcaag ctctgaaaac | 1020 |
| acgcagaaca ttgaagatct ggctgcctat aatgaattac aggatgcgta tgccaaacag | 1080 |
| cagaccgaag cgattgatgc gctgaacaaa gcctcttctg aaaatacaca gaatatcgcc | 1140 |
| aaaaatcagg ccgatattgc caacaatatc aataatatct atgaactggc cagcagcag | 1200 |
| gatcagcact cttctgatat caaaacactg gcaaaagcaa gcgcagcaaa taccgatcgt | 1260 |
| attgcgaaaa caaagccga tgcagatgca agctttgaaa cactgacgaa aaaccagaac | 1320 |
| accctgattg aaaaagataa agaacatgat aaactgatca ccgccaataa accgcaatt | 1380 |
| gatgcaaata aagccagcgc agataccaaa tttgcagcaa ccgcagatgc aattaccaaa | 1440 |
| aatggcaatg ccatcaccaa aaatgccaaa agcattaccg atctgggcac caaagttgat | 1500 |
| ggttttgata gccgtgtgac cgcactggat accaaagtta atgcatttga tggtcgtatt | 1560 |
| accgctctgg atagtaaagt tgaaaatgga atggcagcac aagcagcaca ctaa | 1614 |

<210> SEQ ID NO 57
<211> LENGTH: 537
<212> TYPE: PRT
<213> ORGANISM: Artificial Sequence
<220> FEATURE:
<223> OTHER INFORMATION: Protein sequence for construct

<400> SEQUENCE: 57

-continued

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Ile Thr Lys Asn
            180                 185                 190

Lys Ala Asp Ile Gln Ala Leu Glu Asn Asn Val Val Glu Glu Leu Phe
            195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
```

```
                420             425             430
Glu Thr Leu Thr Lys Asn Gln Asn Thr Leu Ile Glu Lys Asp Lys Glu
            435                 440                 445

His Asp Lys Leu Ile Thr Ala Asn Lys Thr Ala Ile Asp Ala Asn Lys
        450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
            500                 505                 510

Val Asn Ala Phe Asp Gly Arg Ile Thr Ala Leu Asp Ser Lys Val Glu
        515                 520                 525

Asn Gly Met Ala Ala Gln Ala Ala His
        530                 535

<210> SEQ ID NO 58
<211> LENGTH: 1545
<212> TYPE: DNA
<213> ORGANISM: Artificial Sequence
<220> FEATURE:
<223> OTHER INFORMATION: DNA sequence for MC-004 construct

<400> SEQUENCE: 58
atgcaggcca aaatgatat taccctggaa gatctgccgt atctgatcaa aaaaatcgat      60
cagaacgaac tggaagccga tattggtgat attaccgcac tggaaaaata tctggcactg    120
agccagtatg aaatattct ggccctggaa gaactgaata agctctgga agagctggat      180 gaagatgtgg ttggaatca gaatgatatc gccaatctgg aagatgatgt tgaacccctg    240
accaaaaatc agaatgcact ggcagaacag ggtgaagcaa ttaaagaaga tctgcagggt    300
ctggcagatt tgttgaagg tcaggaaggc aaaattctgc agaacgaaac cagcatcaaa    360
aaaaacaccc agcgtaatct ggtgaatggc tttgaaattg aaaaaaacaa agatgccatt    420
gccaaaaaca cgaaagcat gaagatctg tatgattttg tcatgaagt tgccgaaagc      480 attggtgaaa ttcatgcaca taacgaagca cagaatgaaa ccctgaaagg tctgattacc    540
aacagcatcg aaataccaa taacattacc aaaaacaaag cagatattca ggcgctggaa    600
aataatgttg tggaagaact gtttaatctg agcggtcgtc tgattgatca gaaagccgat    660
atcgataata acattaacaa catttatgaa ctggcacagc agcaggatca gcatagcagc    720
gatatcaaaa ccctgaaaaa aaacgttgaa gaaggtctgc tggaactgtc tggtcacctg    780
atcgatcaga aaactgatat tgcccagaat caggcaaata ttcaggatct ggccacctat    840
aatgaactgc aggatcagta tgcacagaaa cagaccgaag caattgatgc cctgaataaa    900
gcgagcagcg aaaacaccca gaatatcgaa gatctggcag catacaacga actgcaggat    960
gcctatgcaa acagcagac tgaagccatc gacgcactga caaggcaag ctctgaaaac     1020 acgcagaaca ttgaagatct ggctgcctat aatgaattac aggatgcgta tgccaaacag    1080
cagaccgaag cgattgatgc gctgaacaaa gcctcttctg aaaatacaca gaatatcgcc    1140
aaaaatcagg ccgatattgc caacaatatc aataatatct atgaactggc ccagcagcag    1200
gatcagcact cttctgatat caaaacactg gcaaaagcaa gcgcagcaaa taccgatcgt    1260
attgcgaaaa acaagccga tgcagatgca agctttgaaa cactgacgaa aaaccagaac    1320
accctgattg aaaaagataa agaacatgat aaactgatca ccgccaataa aaccgcaatt    1380
```

```
gatgcaaata aagccagcgc agataccaaa tttgcagcaa ccgcagatgc aattaccaaa   1440
aatggcaatg ccatcaccaa aaatgccaaa agcattaccg atctgggcac caaagttgat   1500
ggttttgata gccgtgtgac cgcactggat accaaacatc attaa                   1545
```

<210> SEQ ID NO 59
<211> LENGTH: 514
<212> TYPE: PRT
<213> ORGANISM: Artificial Sequence
<220> FEATURE:
<223> OTHER INFORMATION: Protein sequence for MC-004 construct

<400> SEQUENCE: 59

```
Met Gln Ala Lys Asn Asp Ile Thr Leu Glu Asp Leu Pro Tyr Leu Ile
 1               5                  10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335
```

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
            500                 505                 510

His His

<210> SEQ ID NO 60
<211> LENGTH: 1500
<212> TYPE: DNA
<213> ORGANISM: Artificial Sequence
<220> FEATURE:
<223> OTHER INFORMATION: DNA sequence for MC-005 construct

<400> SEQUENCE: 60
atgcaggcca aaaatgatat taccctggaa gatctgccgt atctgatcaa aaaaatcgat      60
cagaacgaac tggaagccga tattggtgat attaccgcac tggaaaaata tctggcactg     120
agccagtatg gaaatattct ggccctggaa gaactgaata agctctctgga agagctggat    180 gaagatgtgg gttggaatca gaatgatatc gccaatctgg aagatgatgt tgaaaccctg    240
accaaaaatc agaatgcact ggcagaacag ggtgaagcaa ttaaagaaga tctgcagggt     300
ctggcagatt tgttgaagg tcaggaaggc aaaattctgc agaacgaaac cagcatcaaa      360
aaaaacaccc agcgtaatct ggtgaatggc tttgaaattg aaaaaaacaa agatgccatt    420
gccaaaaaca cgaaagcat tgaagatctg tatgattttg gtcatgaagt tgccgaaagc     480
attggtgaaa ttcatgcaca taacgaagca cagaatgaaa ccctgaaagg tctgattacc    540
aacagcatcg aaaataccaa taacattacc aaaaacaaag cagatattca ggcgctggaa    600
aataatgttg tggaagaact gtttaatctg gccggtcgtc tgattgatca aaagccgat    660 atcgataata acattaacaa catttatgaa ctggcacagc agcaggatca gcatagcagc    720
gatatcaaaa ccctgaaaaa aacgttgaa gaaggtctgc tggaactgtc tggtcacctg    780
atcgatcaga aaactgatat tgcccagaat caggcaaata ttcaggatct ggccaccctat   840 aatgaactgc aggatcagta tgcacagaaa cagaccgaag caattgatgc cctgaataaa    900
gcgagcagcg aaaacacccca gaatatcgaa gatctggcag catacaacga actgcaggat   960
gcctatgcaa acagcagac tgaagccatc gacgcactga acaaggcaag ctctgaaaac   1020

-continued

```
acgcagaaca ttgaagatct ggctgcctat aatgaattac aggatgcgta tgccaaacag    1080
cagaccgaag cgattgatgc gctgaacaaa gcctcttctg aaaatacaca gaatatcgcc    1140
aaaaatcagg ccgatattgc caacaatatc aataatatct atgaactggc ccagcagcag    1200
gatcagcact cttctgatat caaaacactg gcaaaagcaa gcgcagcaaa taccgatcgt    1260
attgcgaaaa acaaagccga tgcagatgca agctttgaaa cactgacgaa aaaccagaac    1320
accctgattg aaaagataa agaacatgat aaactgatca ccgccaataa aaccgcaatt    1380
gatgcaaata aagccagcgc agataccaaa tttgcagcaa ccgcagatgc aattaccaaa    1440
aatggcaatg ccatcaccaa aaatgccaaa agcgcaagcc atcatcatca ccaccactaa    1500
```

<210> SEQ ID NO 61
<211> LENGTH: 499
<212> TYPE: PRT
<213> ORGANISM: Artificial Sequence
<220> FEATURE:
<223> OTHER INFORMATION: Protein sequence for MC-005 construct

<400> SEQUENCE: 61

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285
```

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
450                 455                 460

Ala Ser Ala Asp Thr Lys Phe Ala Thr Ala Asp Ala Ile Thr Lys
465                 470                 475                 480

Asn Gly Asn Ala Ile Thr Lys Asn Ala Lys Ser Ala Ser His His His
                485                 490                 495

His His His

<210> SEQ ID NO 62
<211> LENGTH: 1476
<212> TYPE: DNA
<213> ORGANISM: Artificial Sequence
<220> FEATURE:
<223> OTHER INFORMATION: DNA sequence for MC-006 construct

<400> SEQUENCE: 62
atgcaggcca aaatgatat accctggaa gatctgccgt atctgatcaa aaaaatcgat      60
cagaacgaac tggaagccga tattggtgat attaccgcac tggaaaaata tctggcactg     120
agccagtatg aaatattct ggccctggaa gaactgaata agctctgga agagctggat     180 gaagatgtgg gttggaatca gaatgatatc gccaatctgg aagatgatgt tgaaaccctg     240
accaaaaatc agaatgcact ggcagaacag ggtgaagcaa ttaaagaaga tctgcagggt     300
ctggcagatt ttgttgaagg tcaggaaggc aaaattctgc agaacgaaac cagcatcaaa     360
aaaaacaccc agcgtaatct ggtgaatggc tttgaaattg aaaaaaacaa agatgccatt     420
gccaaaaaca cgaaagcat tgaagatctg tatgattttg gtcatgaagt tgccgaaagc     480
attggtgaaa ttcatgcaca taacgaagca cagaatgaaa ccctgaaagg tctgattacc     540
aacagcatcg aaaataccaa taacattacc aaaaacaaag cagatattca ggcgctggaa     600
aataatgttg tggaagaact gtttaatctg agcggtcgtc tgattgatca gaaagccgat     660
atcgataata acattaacaa catttatgaa ctggcacagc agcaggatca gcatagcagc     720
gatatcaaaa ccctgaaaaa aaacgttgaa gaaggtctgc tggaactgtc tggtcacctg     780
atcgatcaga aaactgatat tgcccagaat caggcaaata ttcaggatct ggccacctat     840

```
aatgaactgc aggatcagta tgcacagaaa cagaccgaag caattgatgc cctgaataaa      900
gcgagcagcg aaaacaccca gaatatcgaa gatctggcag catacaacga actgcaggat      960
gcctatgcaa aacagcagac tgaagccatc gacgcactga acaaggcaag ctctgaaaac     1020
acgcagaaca ttgaagatct ggctgcctat aatgaattac aggatgcgta tgccaaacag     1080
cagaccgaag cgattgatgc gctgaacaaa gcctcttctg aaaatacaca gaatatcgcc     1140
aaaaatcagg ccgatattgc caacaatatc aataatatct atgaactggc cagcagcag      1200 gatcagcact cttctgatat caaaacactg gcaaaagcaa gcgcagcaaa taccgatcgt     1260
attgcgaaaa acaaagccga tgcagatgca agctttgaaa cactgacgaa aaaccagaac     1320
accctgattg aaaagataa agaacatgat aaactgatca ccgccaataa aaccgcaatt      1380
gatgcaaata aagccagcgc agataccaaa tttgcagcaa ccgcagatgc aattaccaaa     1440
aatggcaatg ccatcaccaa aaatgccaaa agctaa                               1476
```

<210> SEQ ID NO 63
<211> LENGTH: 491
<212> TYPE: PRT
<213> ORGANISM: Artificial Sequence
<220> FEATURE:
<223> OTHER INFORMATION: Protein sequence for MC-006 construct

<400> SEQUENCE: 63

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
```

```
                     245                 250                 255
Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
            275                 280                 285

Gln Lys Gln Thr Glu Ala Ile Asp Ala Leu Asn Lys Ala Ser Ser Glu
        290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
            355                 360                 365

Asn Lys Ala Ser Ser Glu Asn Thr Gln Asn Ile Ala Lys Asn Gln Ala
        370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
            435                 440                 445

His Asp Lys Leu Ile Thr Ala Asn Lys Thr Ala Ile Asp Ala Asn Lys
        450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser
                485                 490

<210> SEQ ID NO 64
<211> LENGTH: 1635
<212> TYPE: DNA
<213> ORGANISM: Artificial Sequence
<220> FEATURE:
<223> OTHER INFORMATION: DNA sequence for MC-007 construct

<400> SEQUENCE: 64
atgcaggcca aaatgatat tacoctggaa gatctgccgt atctgatcaa aaaaatcgat      60
cagaacgaac tggaagccga tattggtgat attaccgcac tggaaaaata tctggcactg     120
agccagtatg aaatattct ggccctggaa gaactgaata agctctgga agagctggat       180 gaagatgtgg gttggaatca gaatgatatc gccaatctgg aagatgatgt tgaaaccctg     240
accaaaaatc agaatgcact ggcagaacag ggtgaagcaa ttaaagaaga tctgcagggt     300
ctggcagatt ttgttgaagg tcaggaaggc aaaattctgc agaacgaaac cagcatcaaa     360
aaaaacaccc agcgtaatct ggtgaatggc tttgaaattg aaaaaaacaa agatgccatt     420
gccaaaaaca cgaaagcat tgaagatctg tatgattttg tcatgaagt tgccgaaagc       480 attggtgaaa ttcatgcaca taacgaagca cagaatgaaa ccctgaaagg tctgattacc     540
aacagcatcg aaataccaa taacattacc aaaaacaaag cagatattca ggcgctggaa     600
aataatgttg tggaagaact gtttaatctg agcggtcgtc tgattgatca gaaagccgat     660
```

-continued

```
atcgataata acattaacaa catttatgaa ctggcacagc agcaggatca gcatagcagc    720
gatatcaaaa ccctgaaaaa aaacgttgaa gaaggtctgc tggaactgtc tggtcacctg    780
atcgatcaga aaactgatat tgcccagaat caggcaaata ttcaggatct ggccacctat    840
aatgaactgc aggatcagta tgcacagaaa cagaccgaag caattgatgc cctgaataaa    900
gcgagcagcg aaaacaccca gaatatcgaa gatctggcag catacaacga actgcaggat    960
gcctatgcaa aacagcagac tgaagccatc gacgcactga acaaggcaag ctctgaaaac   1020
acgcagaaca ttgaagatct ggctgcctat aatgaattac aggatgcgta tgccaaacag   1080
cagaccgaag cgattgatgc gctgaacaaa gcctcttctg aaaatacaca gaatatcgcc   1140
aaaaatcagg ccgatattgc caacaatatc aataatatct atgaactggc ccagcagcag   1200
gatcagcact cttctgatat caaaacactg gcaaaagcaa gcgcagcaaa taccgatcgt   1260
attgcgaaaa acaaagccga tgcagatgca agctttgaaa cactgacgaa aaaccagaac   1320
accctgattg aaaagataa agaacatgat aaactgatca ccgccaataa aaccgcaatt   1380
gatgcaaata agccagcgc agataccaaa tttgcagcaa ccgcagatgc aattaccaaa   1440
aatggcaatg ccatcaccaa aaatgccaaa agcattaccg atctgggcac caaagttgat   1500
ggttttgata gccgtgtgac cgcactggat accaaagtta atgcatttga tggtcgtatt   1560
accgctctgg atagtaaagt tgaaaatggt atggcagcac aggcagcagc aagccatcat   1620
catcaccacc actaa                                                    1635
```

<210> SEQ ID NO 65
<211> LENGTH: 544
<212> TYPE: PRT
<213> ORGANISM: Artificial Sequence
<220> FEATURE:
<223> OTHER INFORMATION: Protein sequence for MC-007 construct

<400> SEQUENCE: 65

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190
```

```
Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
        210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
            245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
            275                 280                 285

Gln Lys Gln Thr Glu Ala Ile Asp Ala Leu Asn Lys Ala Ser Ser Glu
        290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
            325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
            355                 360                 365

Asn Lys Ala Ser Ser Glu Asn Thr Gln Asn Ile Ala Lys Asn Gln Ala
        370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
            405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
        450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
            485                 490                 495

Thr Lys Val Asp Gly Phe Asp Ser Arg Val Thr Ala Leu Asp Thr Lys
            500                 505                 510

Val Asn Ala Phe Asp Gly Arg Ile Thr Ala Leu Asp Ser Lys Val Glu
            515                 520                 525

Asn Gly Met Ala Ala Gln Ala Ala Ala Ser His His His His His His
            530                 535                 540
```

<210> SEQ ID NO 66
<211> LENGTH: 1617
<212> TYPE: DNA
<213> ORGANISM: Artificial Sequence
<220> FEATURE:
<223> OTHER INFORMATION: DNA sequence for MC-008 construct

<400> SEQUENCE: 66
atgcaggcca aaaatgatat taccctggaa gatctgccgt atctgatcaa aaaaatcgat      60

| | |
|---|---|
| cagaacgaac tggaagccga tattggtgat attaccgcac tggaaaaata tctggcactg | 120 |
| agccagtatg aaatattct ggccctggaa gaactgaata aagctctgga agagctggat | 180 |
| gaagatgtgg gttggaatca gaatgatatc gccaatctgg aagatgatgt tgaaaccctg | 240 |
| accaaaaatc agaatgcact ggcagaacag ggtgaagcaa ttaaagaaga tctgcagggt | 300 |
| ctggcagatt ttgttgaagg tcaggaaggc aaaattctgc agaacgaaac cagcatcaaa | 360 |
| aaaacacccc agcgtaatct ggtgaatggc tttgaaattg aaaaaaacaa agatgccatt | 420 |
| gccaaaaaca cgaaagcat tgaagatctg tatgattttg gtcatgaagt tgccgaaagc | 480 |
| attggtgaaa ttcatgcaca taacgaagca cagaatgaaa ccctgaaagg tctgattacc | 540 |
| aacagcatcg aaaataccaa taacattacc aaaaacaaag cagatattca ggcgctggaa | 600 |
| aataatgttg tggaagaact gtttaatctg agcggtcgtc tgattgatca gaaagccgat | 660 |
| atcgataata acattaacaa catttatgaa ctggcacagc agcaggatca gcatagcagc | 720 |
| gatatcaaaa ccctgaaaaa aaacgttgaa gaaggtctgc tggaactgtc tggtcacctg | 780 |
| atcgatcaga aaactgatat tgcccagaat caggcaaata ttcaggatct ggccacctat | 840 |
| aatgaactgc aggatcagta tgcacagaaa cagaccgaag caattgatgc cctgaataaa | 900 |
| gcgagcagcg aaaacaccca gaatatcgaa gatctggcag catacaacga actgcaggat | 960 |
| gcctatgcaa acagcagac tgaagccatc gacgcactga caaggcaag ctctgaaaac | 1020 |
| acgcagaaca ttgaagatct ggctgcctat aatgaattac aggatgcgta tgccaaacag | 1080 |
| cagaccgaag cgattgatgc gctgaacaaa gcctcttctg aaaatacaca gaatatcgcc | 1140 |
| aaaaatcagg ccgatattgc caacaatatc aataatatct atgaactggc ccagcagcag | 1200 |
| gatcagcact cttctgatat caaaacactg gcaaaagcaa gcgcagcaaa taccgatcgt | 1260 |
| attgcgaaaa acaaagccga tgcagatgca agctttgaaa cactgacgaa aaaccagaac | 1320 |
| accctgattg aaaaagataa agaacatgat aaactgatca ccgccaataa aaccgcaatt | 1380 |
| gatgcaaata aagccagcgc agataccaaa tttgcagcaa ccgcagatgc aattaccaaa | 1440 |
| aatggcaatg ccatcaccaa aaatgccaaa agcattaccg atctgggcac caaagttgat | 1500 |
| ggttttgata gccgtgtgac cgcactggat accaaagtta atgcatttga tggtcgtatt | 1560 |
| accgctctgg atagtaaagt tgaaaatggt atggcagcac aggcagcaca ccactaa | 1617 |

<210> SEQ ID NO 67
<211> LENGTH: 538
<212> TYPE: PRT
<213> ORGANISM: Artificial Sequence
<220> FEATURE:
<223> OTHER INFORMATION: Protein sequence for MC-008 construct

<400> SEQUENCE: 67

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

```
Asp Leu Gln Gly Leu Ala Asp Phe Val Glu Gly Gln Glu Gly Lys Ile
                100                 105                 110

Leu Gln Asn Glu Thr Ser Ile Lys Lys Asn Thr Gln Arg Asn Leu Val
                115                 120                 125

Asn Gly Phe Glu Ile Glu Lys Asn Lys Asp Ala Ile Ala Lys Asn Asn
                130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Ile Thr Lys Asn
                180                 185                 190

Lys Ala Asp Ile Gln Ala Leu Glu Asn Asn Val Val Glu Glu Leu Phe
                195                 200                 205

Asn Leu Ser Gly Arg Leu Ile Asp Gln Lys Ala Asp Ile Asp Asn Asn
                210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
                260                 265                 270

Asn Ile Gln Asp Leu Ala Thr Tyr Asn Glu Leu Gln Asp Gln Tyr Ala
                275                 280                 285

Gln Lys Gln Thr Glu Ala Ile Asp Ala Leu Asn Lys Ala Ser Ser Glu
                290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
                340                 345                 350

Leu Gln Asp Ala Tyr Ala Lys Gln Gln Thr Glu Ala Ile Asp Ala Leu
                355                 360                 365

Asn Lys Ala Ser Ser Glu Asn Thr Gln Asn Ile Ala Lys Asn Gln Ala
                370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
                420                 425                 430

Glu Thr Leu Thr Lys Asn Gln Asn Thr Leu Ile Glu Lys Asp Lys Glu
                435                 440                 445

His Asp Lys Leu Ile Thr Ala Asn Lys Thr Ala Ile Asp Ala Asn Lys
                450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
                500                 505                 510
```

Val Asn Ala Phe Asp Gly Arg Ile Thr Ala Leu Asp Ser Lys Val Glu
      515                 520                 525

Asn Gly Met Ala Ala Gln Ala Ala His His
    530                 535

<210> SEQ ID NO 68
<211> LENGTH: 1614
<212> TYPE: DNA
<213> ORGANISM: Artificial Sequence
<220> FEATURE:
<223> OTHER INFORMATION: DNA sequence for MC-009 construct

<400> SEQUENCE: 68

| | | |
|---|---|---|
| atggcgaaaa atgatattac cctggaagat ctgccgtatc tgatcaaaaa aatcgatcag | 60 |
| aacgaactgg aagccgatat tggtgatatt accgcactgg aaaaatatct ggcactgagc | 120 |
| cagtatggaa atattctggc cctggaagaa ctgaataaag ctctggaaga gctggatgaa | 180 |
| gatgtgggtt ggaatcagaa tgatatcgcc aatctggaag atgatgttga accctgacc | 240 |
| aaaaatcaga atgcactggc agaacagggt gaagcaatta agaagatct gcagggtctg | 300 |
| gcagattttg ttgaaggtca ggaaggcaaa attctgcaga cgaaaccag catcaaaaaa | 360 |
| aacacccagc gtaatctggt gaatggcttt gaaattgaaa aaacaaaga tgccattgcc | 420 |
| aaaaacaacg aaagcattga agatctgtat gattttggtc atgaagttgc cgaaagcatt | 480 |
| ggtgaaattc atgcacataa cgaagcacag aatgaaaccc tgaaaggtct gattaccaac | 540 |
| agcatcgaaa ataccaataa cattaccaaa acaaagcag atattcaggc gctggaaaat | 600 |
| aatgttgtgg aagaactgtt taatctgagc ggtcgtctga ttgatcagaa agccgatatc | 660 |
| gataataaca ttaacaacat ttatgaactg gcacagcagc aggatcagca tagcagcgat | 720 |
| atcaaaaccc tgaaaaaaaa cgttgaagaa ggtctgctgg aactgtctgg tcacctgatc | 780 |
| gatcagaaaa ctgatattgc ccagaatcag gcaaatattc aggatctggc cacctataat | 840 |
| gaactgcagg atcagtatgc acagaaacag accgaagcaa ttgatgccct gaataaagcg | 900 |
| agcagcgaaa cacccagaa tatcgaagat ctggcagcat acaacgaact gcaggatgcc | 960 |
| tatgcaaaac agcagactga agccatcgac gcactgaaca aggcaagctc tgaaaacacg | 1020 |
| cagaacattg aagatctggc tgcctataat gaattacagg atgcgtatgc caaacagcag | 1080 |
| accgaagcga ttgatgcgct gaacaaagcc tcttctgaaa atacacagaa tatcgccaaa | 1140 |
| aatcaggccg atattgccaa caatatcaat aatatctatg aactggccca gcagcaggat | 1200 |
| cagcactctt ctgatatcaa aacactggca aaagcaagcg cagcaaatac cgatcgtatt | 1260 |
| gcgaaaaaca aagccgatgc agatgcaagc tttgaaacac tgacgaaaaa ccagaacacc | 1320 |
| ctgattgaaa agataaaga acatgataaa ctgatcaccg ccaataaaac cgcaattgat | 1380 |
| gcaaataaag ccagcgcaga taccaaattt gcagcaaccg cagatgcaat taccaaaaat | 1440 |
| ggcaatgcca tcaccaaaaa tgccaaaagc attaccgatc tgggcaccaa agttgatggt | 1500 |
| tttgatagcc gtgtgaccgc actggatacc aaagttaatg catttgatgg tcgtattacc | 1560 |
| gctctggata gtaaagttga aaatggtatg gcagcacagg cagcacacca ctaa | 1614 |

<210> SEQ ID NO 69
<211> LENGTH: 537
<212> TYPE: PRT
<213> ORGANISM: Artificial Sequence
<220> FEATURE:
<223> OTHER INFORMATION: Protein sequence for MC-009 construct

<400> SEQUENCE: 69

```
Met Ala Lys Asn Asp Ile Thr Leu Glu Asp Leu Pro Tyr Leu Ile Lys
 1               5                  10                  15

Lys Ile Asp Gln Asn Glu Leu Glu Ala Asp Ile Gly Asp Ile Thr Ala
             20                  25                  30

Leu Glu Lys Tyr Leu Ala Leu Ser Gln Tyr Gly Asn Ile Leu Ala Leu
         35                  40                  45

Glu Glu Leu Asn Lys Ala Leu Glu Glu Leu Asp Glu Asp Val Gly Trp
 50                  55                  60

Asn Gln Asn Asp Ile Ala Asn Leu Glu Asp Asp Val Glu Thr Leu Thr
 65                  70                  75                  80

Lys Asn Gln Asn Ala Leu Ala Glu Gln Gly Glu Ala Ile Lys Glu Asp
                 85                  90                  95

Leu Gln Gly Leu Ala Asp Phe Val Glu Gly Gln Glu Gly Lys Ile Leu
             100                 105                 110

Gln Asn Glu Thr Ser Ile Lys Lys Asn Thr Gln Arg Asn Leu Val Asn
             115                 120                 125

Gly Phe Glu Ile Glu Lys Asn Lys Asp Ala Ile Ala Lys Asn Asn Glu
         130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                 165                 170                 175

Leu Ile Thr Asn Ser Ile Glu Asn Thr Asn Asn Ile Thr Lys Asn Lys
             180                 185                 190

Ala Asp Ile Gln Ala Leu Glu Asn Val Val Glu Glu Leu Phe Asn
             195                 200                 205

Leu Ser Gly Arg Leu Ile Asp Gln Lys Ala Asp Ile Asp Asn Asn Ile
210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
             245                 250                 255

Gly His Leu Ile Asp Gln Lys Thr Asp Ile Ala Gln Asn Gln Ala Asn
             260                 265                 270

Ile Gln Asp Leu Ala Thr Tyr Asn Glu Leu Gln Asp Gln Tyr Ala Gln
         275                 280                 285

Lys Gln Thr Glu Ala Ile Asp Ala Leu Asn Lys Ala Ser Ser Glu Asn
         290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                 325                 330                 335

Ser Glu Asn Thr Gln Asn Ile Glu Asp Leu Ala Ala Tyr Asn Glu Leu
             340                 345                 350

Gln Asp Ala Tyr Ala Lys Gln Gln Thr Glu Ala Ile Asp Ala Leu Asn
             355                 360                 365

Lys Ala Ser Ser Glu Asn Thr Gln Asn Ile Ala Lys Asn Gln Ala Asp
         370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
                 405                 410                 415
```

```
Thr Asp Arg Ile Ala Lys Asn Lys Ala Asp Ala Asp Ala Ser Phe Glu
            420                 425                 430

Thr Leu Thr Lys Asn Gln Asn Thr Leu Ile Glu Lys Asp Lys Glu His
        435                 440                 445

Asp Lys Leu Ile Thr Ala Asn Lys Thr Ala Ile Asp Ala Asn Lys Ala
    450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser Ile Thr Asp Leu Gly Thr
                485                 490                 495

Lys Val Asp Gly Phe Asp Ser Arg Val Thr Ala Leu Asp Thr Lys Val
                500                 505                 510

Asn Ala Phe Asp Gly Arg Ile Thr Ala Leu Asp Ser Lys Val Glu Asn
            515                 520                 525

Gly Met Ala Ala Gln Ala Ala His His
    530                 535

<210> SEQ ID NO 70
<211> LENGTH: 1611
<212> TYPE: DNA
<213> ORGANISM: Artificial Sequence
<220> FEATURE:
<223> OTHER INFORMATION: DNA sequence for MC-010 construct

<400> SEQUENCE: 70
atgcaggcca aaatgatat taccctggaa gatctgccgt atctgatcaa aaaaatcgat      60
cagaacgaac tggaagccga tattggtgat attaccgcac tggaaaaata tctggcactg     120
agccagtatg aaatattct ggccctggaa gaactgaata agctctgga gagctggat       180 gaagatgtgg ttggaatca gaatgatatc gccaatctgg aagatgatgt tgaaaccctg     240
accaaaaatc agaatgcact ggcagaacag ggtgaagcaa ttaagaaga tctgcagggt     300 ctggcagatt tgttgaagg tcaggaaggc aaaattctgc agaacgaaac cagcatcaaa     360
aaaaacaccc agcgtaatct ggtgaatggc tttgaaattg aaaaaaacaa agatgccatt    420
gccaaaaaca cgaaagcat tgaagatctg tatgattttg tcatgaagt tgccgaaagc     480 attggtgaaa ttcatgcaca taacgaagca cagaatgaaa ccctgaaagg tctgattacc   540
aacagcatcg aaaataccaa taacattacc aaaaacaaag cagatattca ggcgctggaa   600 ataatgttg tggaagaact gtttaatctg agcggtcgtc tgattgatca gaaagccgat    660
atcgataata acattaacaa catttatgaa ctggcacagc agcaggatca gcatagcagc   720
gatatcaaaa ccctgaaaaa aaacgttgaa gaaggtctgc tggaactgtc tggtcacctg   780
atcgatcaga aaactgatat tgcccagaat caggcaaata ttcaggatct ggccaccctat  840 aatgaactgc aggatcagta tgcacagaaa cagaccgaag caattgatgc cctgaataaa   900
gcgagcagcg aaaacacccc agaatatcgaa gatctggcag catacaacga actgcaggat   960
gcctatgcaa acagcagac tgaagccatc gacgcactga caaggcaag ctctgaaaac    1020 acgcagaaca ttgaagatct ggctgcctat aatgaattac aggatgcgta tgccaaacag   1080
cagaccgaag cgattgatgc gctgaacaaa gcctcttctg aaaatacaca gaatatcgcc    1140
aaaaatcagg ccgatattgc caacaatatc aataatatct atgaactggc cagcagcag     1200 gatcagcact cttctgatat caaaacactg gcaaaagcaa gcgcagcaaa taccgatcgt   1260
attgcgaaaa acaaagccga tgcagatgca agctttgaaa cactgacgaa aaaccagaac   1320
accctgattg aaaaagataa agaacatgat aaactgatca ccgccaataa aaccgcaatt   1380
```

```
gatgcaaata aagccagcgc agataccaaa tttgcagcaa ccgcagatgc aattaccaaa    1440
aatggcaatg ccatcaccaa aaatgccaaa agcattaccg atctgggcac caaagttgat    1500
ggttttgata ccgtgtgac cgcactggat accaaagtta atgcatttga tggtcgtatt     1560
accgctctgg atagtaaagt tgaaaatggt atggcagcac aggcagcata a             1611
```

<210> SEQ ID NO 71
<211> LENGTH: 536
<212> TYPE: PRT
<213> ORGANISM: Artificial Sequence
<220> FEATURE:
<223> OTHER INFORMATION: Protein sequence for MC-010 construct

<400> SEQUENCE: 71

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320
```

```
Ala Tyr Ala Lys Gln Gln Thr Glu Ala Ile Asp Ala Leu Asn Lys Ala
            325                 330                 335

Ser Ser Glu Asn Thr Gln Asn Ile Glu Asp Leu Ala Ala Tyr Asn Glu
        340                 345                 350

Leu Gln Asp Ala Tyr Ala Lys Gln Gln Thr Glu Ala Ile Asp Ala Leu
    355                 360                 365

Asn Lys Ala Ser Ser Glu Asn Thr Gln Asn Ile Ala Lys Asn Gln Ala
370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
            405                 410                 415

Asn Thr Asp Arg Ile Ala Lys Asn Lys Ala Asp Ala Asp Ala Ser Phe
        420                 425                 430

Glu Thr Leu Thr Lys Asn Gln Asn Thr Leu Ile Glu Lys Asp Lys Glu
    435                 440                 445

His Asp Lys Leu Ile Thr Ala Asn Lys Thr Ala Ile Asp Ala Asn Lys
        450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
            485                 490                 495

Thr Lys Val Asp Gly Phe Asp Ser Arg Val Thr Ala Leu Asp Thr Lys
        500                 505                 510

Val Asn Ala Phe Asp Gly Arg Ile Thr Ala Leu Asp Ser Lys Val Glu
    515                 520                 525

Asn Gly Met Ala Ala Gln Ala Ala
530                 535

<210> SEQ ID NO 72
<211> LENGTH: 1560
<212> TYPE: DNA
<213> ORGANISM: Artificial Sequence
<220> FEATURE:
<223> OTHER INFORMATION: DNA sequence for MC-011 construct

<400> SEQUENCE: 72
atggcgaaaa atgatattac cctggaagat ctgccgtatc tgatcaaaaa aatcgatcag      60
aacgaactgg aagccgatat tggtgatatt accgcactgg aaaaatatct ggcactgagc     120
cagtatggaa atattctggc cctggaagaa ctgaataaag ctctggaaga gctggatgaa     180
gatgtgggtt ggaatcagaa tgatatcgcc aatctggaag atgatgttga aaccctgacc     240
aaaaatcaga tgcactggca gaacagggt gaagcaatta agaagatct gcagggtctg      300 gcagattttg ttgaaggtca ggaaggcaaa attctgcaga acgaaccag catcaaaaaa      360 aacacccagc gtaatctggt gaatggcttt gaaattgaaa aaacaaaga tgccattgcc      420 aaaaacaacg aaagcattga agatctgtat gattttggtc atgaagttgc cgaaagcatt     480
ggtgaaattc atgcacataa cgaagcacag aatgaaaccc tgaaaggtct gattaccaac     540
agcatcgaaa ataccaataa cattaccaaa aacaaagcag atattcaggc gctggaaaat      600
aatgttgtgg aagaactgtt taatctgagc ggtcgtctga ttgatcagaa agccgatatc     660
gataataaca ttaacaacat ttatgaactg gcacagcagc aggatcagca tagcagcgat     720
atcaaaaccc tgaaaaaaaa cgttgaagaa ggtctgctgg aactgtctgg tcacctgatc     780
gatcagaaaa ctgatattgc ccagaatcag gcaaatattc aggatctggc cacctataat     840
```

-continued

```
gaactgcagg atcagtatgc acagaaacag accgaagcaa ttgatgccct gaataaagcg    900
agcagcgaaa acacccagaa tatcgaagat ctggcagcat acaacgaact gcaggatgcc    960
tatgcaaaac agcagactga agccatcgac gcactgaaca aggcaagctc tgaaaacacg   1020
cagaacattg aagatctggc tgcctataat gaattacagg atgcgtatgc caaacagcag   1080
accgaagcga ttgatgcgct gaacaaagcc tcttctgaaa atacacagaa tatcgccaaa   1140
aatcaggccg atattgccaa caatatcaat aatatctatg aactggccca gcagcaggat   1200
cagcactctt ctgatatcaa aacactggca aaagcaagcg cagcaaatac cgatcgtatt   1260
gcgaaaaaca aagccgatgc agatgcaagc tttgaaacac tgacgaaaaa ccagaacacc   1320
ctgattgaaa aagataaaga acatgataaa ctgatcaccg ccaataaaac cgcaattgat   1380
gcaaataaag ccagcgcaga taccaaattt gcagcaaccg cagatgcaat taccaaaaat   1440
ggcaatgcca tcaccaaaaa tgccaaaagc attaccgatc tgggcaccaa agttgatggt   1500
tttgatagcc gtgtgaccgc actggatacc aaagcaagcc atcatcatca ccaccactaa   1560
```

<210> SEQ ID NO 73
<211> LENGTH: 519
<212> TYPE: PRT
<213> ORGANISM: Artificial Sequence
<220> FEATURE:
<223> OTHER INFORMATION: Protein sequence for MC-011 construct

<400> SEQUENCE: 73

```
Met Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
            20                  25                  30

Leu Glu Lys Tyr Leu Ala Leu Ser Gln Tyr Gly Asn Ile Leu Ala Leu
        35                  40                  45

Glu Glu Leu Asn Lys Ala Leu Glu Glu Leu Asp Glu Asp Val Gly Trp
    50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Gln Glu Gly Lys Ile Leu
            100                 105                 110

Gln Asn Glu Thr Ser Ile Lys Lys Asn Thr Gln Arg Asn Leu Val Asn
        115                 120                 125

Gly Phe Glu Ile Glu Lys Asn Lys Asp Ala Ile Ala Lys Asn Asn Glu
    130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Asn Ile Thr Lys Asn Lys
            180                 185                 190

Ala Asp Ile Gln Ala Leu Glu Asn Asn Val Val Glu Glu Leu Phe Asn
        195                 200                 205

Leu Ser Gly Arg Leu Ile Asp Gln Lys Ala Asp Ile Asp Asn Asn Ile
    210                 215                 220

Asn Asn Ile Tyr Glu Leu Ala Gln Gln Gln Asp Gln His Ser Ser Asp
225                 230                 235                 240
```

```
Ile Lys Thr Leu Lys Lys Asn Val Glu Glu Gly Leu Leu Glu Leu Ser
                245                 250                 255
Gly His Leu Ile Asp Gln Lys Thr Asp Ile Ala Gln Asn Gln Ala Asn
            260                 265                 270
Ile Gln Asp Leu Ala Thr Tyr Asn Glu Leu Gln Asp Gln Tyr Ala Gln
        275                 280                 285
Lys Gln Thr Glu Ala Ile Asp Ala Leu Asn Lys Ala Ser Ser Glu Asn
    290                 295                 300
Thr Gln Asn Ile Glu Asp Leu Ala Ala Tyr Asn Glu Leu Gln Asp Ala
305                 310                 315                 320
Tyr Ala Lys Gln Gln Thr Glu Ala Ile Asp Ala Leu Asn Lys Ala Ser
                325                 330                 335
Ser Glu Asn Thr Gln Asn Ile Glu Asp Leu Ala Ala Tyr Asn Glu Leu
            340                 345                 350
Gln Asp Ala Tyr Ala Lys Gln Gln Thr Glu Ala Ile Asp Ala Leu Asn
        355                 360                 365
Lys Ala Ser Ser Glu Asn Thr Gln Asn Ile Ala Lys Asn Gln Ala Asp
    370                 375                 380
Ile Ala Asn Asn Ile Asn Asn Ile Tyr Glu Leu Ala Gln Gln Gln Asp
385                 390                 395                 400
Gln His Ser Ser Asp Ile Lys Thr Leu Ala Lys Ala Ser Ala Ala Asn
                405                 410                 415
Thr Asp Arg Ile Ala Lys Asn Lys Ala Asp Ala Asp Ala Ser Phe Glu
            420                 425                 430
Thr Leu Thr Lys Asn Gln Asn Thr Leu Ile Glu Lys Asp Lys Glu His
        435                 440                 445
Asp Lys Leu Ile Thr Ala Asn Lys Thr Ala Ile Asp Ala Asn Lys Ala
    450                 455                 460
Ser Ala Asp Thr Lys Phe Ala Ala Thr Ala Asp Ala Ile Thr Lys Asn
465                 470                 475                 480
Gly Asn Ala Ile Thr Lys Asn Ala Lys Ser Ile Thr Asp Leu Gly Thr
                485                 490                 495
Lys Val Asp Gly Phe Asp Ser Arg Val Thr Ala Leu Asp Thr Lys Ala
            500                 505                 510
Ser His His His His His
        515

<210> SEQ ID NO 74
<211> LENGTH: 1893
<212> TYPE: DNA
<213> ORGANISM: Moraxella catarrhalis

<400> SEQUENCE: 74
atgaaaacca tgaaacttct ccctctaaaa atcgctgtaa ccagtgccat gattattggc      60
ttgggtgcgg catctactgc gaatgcgcag gctaaaaatg atataacttt agaggattta     120
ccatatttaa taaaaaagat tgaccaaaat gaattggaag cagatatcgg agatattact     180
gctcttgaaa agtatctagc acttagccag tatggcaata ttttagctct agaagagctc     240
aacaaggctc tagaagagct cgacgaggat gttggatgga tcagaatga tattgcaaac     300 ttggaagatg atgttgaaac gctcaccaaa aatcaaaatg ctttggctga caaggtgag     360 gcaattaaag aagatcttca agggcttgca gattttgtag aagggcaaga gggtaaaatt     420
ctacaaaatg aaacttcaat taaaaaaat actcagagaa accttgtcaa tgggtttgag     480
```

```
attgagaaaa ataaagatgc tattgctaaa acaatgagt ctatcgaaga tctttatgat      540
tttggtcatg aggttgcaga aagtataggc gagatacatg ctcataatga agcgcaaaat      600
gaaactctta aaggcttgat aacaaacagt attgagaata ctaataatat taccaaaaac      660
aaagctgaca tccaagcact tgaaaacaat gtcgtagaag aactattcaa tctaagcggt      720
cgcctaattg atcaaaaagc agatattgat aataacatca acaatatcta tgagctggca      780
caacagcaag atcagcatag ctctgatatc aaaacactta aaaaaaatgt cgaagaaggt      840
ttgttggagc taagcggtca cctaattgat caaaaaacag atattgctca aaaccaagct      900
aacatccaag atctgccac ttacaacgag ctacaagacc agtatgctca aaagcaaacc       960
gaagcgattg acgctctaaa taaagcaagc tctgagaata cacaaaacat cgaagatctg     1020
gccgcttaca acgagctaca agatgcctat gccaaacagc aaaccgaagc aattgacgct     1080
ctaaataaag caagctctga atacacaa acatcgaag atctggccgc ttacaacgag        1140
ctacaagatg cctatgccaa acagcaaacc gaagccattg acgctctaaa taaagcaagc     1200
tctgagaata cacaaaacat tgctaaaaac caagcggata ttgctaataa catcaacaat     1260
atctatgagc tggcacaaca gcaagatcag catagctctg atatcaaaac cttggcaaaa     1320
gcaagtgctg ccaatactga tcgtattgct aaaaacaaag ccgatgctga tgcaagtttt     1380
gaaacgctca ccaaaaatca aaatactttg attgaaaaag ataaagagca tgacaaatta     1440
attactgcaa acaaaactgc gattgatgcc aataaagcat ctgcggatac caagtttgca     1500
gcgacagcag acgccattac caaaaatgga aatgctatca ctaaaaacgc aaaatctatc     1560
actgatttgg gcactaaagt ggatggtttt gacagtcgtg taactgcatt agacaccaaa     1620
gtcaatgcct ttgatggtcg tatcacagct ttagacagta agttgaaaa cggtatggct      1680 gcccaagctg ccctaagtgg tctattccag ccttatagcg ttggtaagtt taatgcgacc     1740
gctgcacttg gtggctatgg ctcaaaatct gcggttgcta tcggtgctgg ctatcgtgtg     1800
aatccaaatc tggcgtttaa agctggtgcg gcgattaata ccagtggtaa taaaaaaggc     1860
tcttataaca tcggtgtgaa ttacgagttc taa                                  1893

<210> SEQ ID NO 75
<211> LENGTH: 44
<212> TYPE: DNA
<213> ORGANISM: Artificial Sequence
<220> FEATURE:
<223> OTHER INFORMATION: Primer sequence

<400> SEQUENCE: 75
gaattcttaa ttaacatatg caggccaaaa atgatattac cctg                       44

<210> SEQ ID NO 76
<211> LENGTH: 43
<212> TYPE: DNA
<213> ORGANISM: Artificial Sequence
<220> FEATURE:
<223> OTHER INFORMATION: Primer sequence

<400> SEQUENCE: 76
ggcgcgcctc gagttattat ttggtatcca gtgcggtcac acg                        43

<210> SEQ ID NO 77
<211> LENGTH: 43
<212> TYPE: DNA
<213> ORGANISM: Artificial Sequence
<220> FEATURE:
<223> OTHER INFORMATION: Primer sequence
```

```
<400> SEQUENCE: 77
ggcgcgcctc gagttagtgt ttggtatcca gtgcggtcac acg           43

<210> SEQ ID NO 78
<211> LENGTH: 46
<212> TYPE: DNA
<213> ORGANISM: Artificial Sequence
<220> FEATURE:
<223> OTHER INFORMATION: Primer sequence

<400> SEQUENCE: 78
ggcgcgcctc gagttagtgg tgtttggtat ccagtgcggt cacacg        46

<210> SEQ ID NO 79
<211> LENGTH: 66
<212> TYPE: DNA
<213> ORGANISM: Artificial Sequence
<220> FEATURE:
<223> OTHER INFORMATION: Primer sequence

<400> SEQUENCE: 79
ggcgcgcctc gagttagtgg tggtgatgat gatggcttgc gcttttggca ttttggtga   60 tggcat                                                             66

<210> SEQ ID NO 80
<211> LENGTH: 36
<212> TYPE: DNA
<213> ORGANISM: Artificial Sequence
<220> FEATURE:
<223> OTHER INFORMATION: Primer sequence

<400> SEQUENCE: 80
ccgctcgagc tagcttttgg cattttggt gatggc                    36

<210> SEQ ID NO 81
<211> LENGTH: 43
<212> TYPE: DNA
<213> ORGANISM: Artificial Sequence
<220> FEATURE:
<223> OTHER INFORMATION: Primer sequence

<400> SEQUENCE: 81
ggaattccat atggcgaaaa atgatattac cctggaagat ctg           43

<210> SEQ ID NO 82
<211> LENGTH: 46
<212> TYPE: DNA
<213> ORGANISM: Artificial Sequence
<220> FEATURE:
<223> OTHER INFORMATION: Primer sequence

<400> SEQUENCE: 82
ggcgcgcctc gagttagtgg tgtgctgcct gtgctgccat accatt        46

<210> SEQ ID NO 83
<211> LENGTH: 40
<212> TYPE: DNA
<213> ORGANISM: Artificial Sequence
<220> FEATURE:
<223> OTHER INFORMATION: Primer sequence

<400> SEQUENCE: 83
ggcgcgcctc gagttatgct gcctgtgctg ccataccatt              40
```

<210> SEQ ID NO 84
<211> LENGTH: 27
<212> TYPE: DNA
<213> ORGANISM: Artificial Sequence
<220> FEATURE:
<223> OTHER INFORMATION: Primer sequence

<400> SEQUENCE: 84

```
cagttcatta taggtggcca gatcctg                                              27
```

<210> SEQ ID NO 85
<211> LENGTH: 4
<212> TYPE: PRT
<213> ORGANISM: Artificial Sequence
<220> FEATURE:
<223> OTHER INFORMATION: N terminal amino acids of MC-001

<400> SEQUENCE: 85

Met Gln Ala Lys
1

<210> SEQ ID NO 86
<211> LENGTH: 11
<212> TYPE: PRT
<213> ORGANISM: Artificial Sequence
<220> FEATURE:
<223> OTHER INFORMATION: N terminal amino acid sequence

<400> SEQUENCE: 86

Ala Lys Asn Asp Ile Thr Leu Glu Asp Leu Pro
1               5                   10

<210> SEQ ID NO 87
<211> LENGTH: 1542
<212> TYPE: DNA
<213> ORGANISM: Artificial Sequence
<220> FEATURE:
<223> OTHER INFORMATION: DNA sequence for MC-003 Construct

<400> SEQUENCE: 87

```
atgcaggcca aaaatgatat taccctggaa gatctgccgt atctgatcaa aaaaatcgat          60
cagaacgaac tggaagccga tattggtgat attaccgcac tggaaaaata tctggcactg         120
agccagtatg aaatattct ggccctggaa gaactgaata agctctgga agagctggat           180
gaagatgtgg gttggaatca gaatgatatc gccaatctgg aagatgatgt tgaaaccctg         240
accaaaaatc agaatgcact ggcagaacag ggtgaagcaa ttaaagaaga tctgcagggt         300
ctggcagatt ttgttgaagg tcaggaaggc aaaattctgc agaacgaaac cagcatcaaa         360
aaaaacaccc agcgtaatct ggtgaatggc tttgaaattg aaaaaaacaa agatgccatt         420
gccaaaaaca cgaaagcat tgaagatctg tatgattttg gtcatgaagt tgccgaaagc          480
attggtgaaa ttcatgcaca taacgaagca cagaatgaaa ccctgaaagg tctgattacc         540
aacagcatcg aaaataccaa taacattacc aaaaacaaag cagatattca ggcgctggaa         600
aataatgttg tggaagaact gtttaatctg agcggtcgtc tgattgatca gaaagccgat         660
atcgataata acattaacaa catttatgaa ctggcacagc agcaggatca gcatagcagc         720
gatatcaaaa ccctgaaaaa aaacgttgaa gaaggtctgc tggaactgtc tggtcacctg         780
atcgatcaga aaactgatat tgcccagaat caggcaaata ttcaggatct ggccacctat         840
aatgaactgc aggatcagta tgcacagaaa cagaccgaag caattgatgc cctgaataaa         900
gcgagcagcg aaaacaccca gaatatcgaa gatctggcag catacaacga actgcaggat         960
```

```
gcctatgcaa aacagcagac tgaagccatc gacgcactga acaaggcaag ctctgaaaac    1020
acgcagaaca ttgaagatct ggctgcctat aatgaattac aggatgcgta tgccaaacag    1080
cagaccgaag cgattgatgc gctgaacaaa gcctcttctg aaaatacaca gaatatcgcc    1140
aaaaatcagg ccgatattgc caacaatatc aataatatct atgaactggc ccagcagcag    1200
gatcagcact tttctgatat caaaacactg gcaaaagcaa gcgcagcaaa taccgatcgt    1260
attgcgaaaa acaaagccga tgcagatgca agctttgaaa cactgacgaa aaaccagaac    1320
accctgattg aaaaagataa agaacatgat aaactgatca ccgccaataa accgcaatt     1380 gatgcaaata aagccagcgc agataccaaa tttgcagcaa ccgcagatgc aattaccaaa    1440
aatggcaatg ccatcaccaa aaatgccaaa agcattaccg atctgggcac caaagttgat    1500
ggttttgata gccgtgtgac cgcactggat accaaacact aa                      1542
```

<210> SEQ ID NO 88
<211> LENGTH: 513
<212> TYPE: PRT
<213> ORGANISM: Artificial Sequence
<220> FEATURE:
<223> OTHER INFORMATION: Protein sequence for MC-003 Construct

<400> SEQUENCE: 88

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
                245                 250                 255
```

```
                -continued

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
            325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
            355                 360                 365

Asn Lys Ala Ser Ser Glu Asn Thr Gln Asn Ile Ala Lys Asn Gln Ala
        370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
            405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
            485                 490                 495

Thr Lys Val Asp Gly Phe Asp Ser Arg Val Thr Ala Leu Asp Thr Lys
            500                 505                 510

His
```